United States Patent
Maciag et al.

(10) Patent No.: US 7,501,281 B2
(45) Date of Patent: Mar. 10, 2009

(54) COMPOSITIONS, METHODS AND KITS RELATED TO THROMBIN, NOTCH SIGNALING AND STAMATOGENESIS AND GROWTH OF STEM CELLS

(75) Inventors: Thomas Maciag, Portland, ME (US); Lori Maciag, legal representative, Portland, ME (US); Vihren Kolev, Arlington, MA (US); Joseph M. Verdi, Falmouth, ME (US)

(73) Assignee: Maine Medical Center Research Institute, Portland, ME (US)

( * ) Notice: Subject to any disclaimer, the term of this patent is extended or adjusted under 35 U.S.C. 154(b) by 310 days.

(21) Appl. No.: 11/209,137

(22) Filed: Aug. 22, 2005

(65) Prior Publication Data
US 2006/0063253 A1    Mar. 23, 2006

Related U.S. Application Data

(63) Continuation of application No. PCT/US2004/006762, filed on Mar. 5, 2004.

(60) Provisional application No. 60/542,399, filed on Feb. 6, 2004, provisional application No. 60/537,304, filed on Jan. 16, 2004, provisional application No. 60/503,363, filed on Sep. 15, 2003, provisional application No. 60/452,425, filed on Mar. 5, 2003.

(51) Int. Cl.
C12N 5/00 (2006.01)
C12N 5/06 (2006.01)
C12N 5/08 (2006.01)

(52) U.S. Cl. ................ 435/377; 435/325; 435/354; 435/365; 435/368

(58) Field of Classification Search ............... None
See application file for complete search history.

(56) References Cited

U.S. PATENT DOCUMENTS

| | | | |
|---|---|---|---|
| 5,223,483 A | 6/1993 | Thomas et al. | |
| 5,401,832 A | 3/1995 | Linemeyer et al. | |
| 6,136,952 A * | 10/2000 | Li et al. | 530/326 |
| 6,433,138 B1 | 8/2002 | Zimrin et al. | |
| 6,461,611 B1 * | 10/2002 | Bar-Shavit | 424/94.64 |

FOREIGN PATENT DOCUMENTS

| | | |
|---|---|---|
| WO | WO 97/45143 | 12/1997 |
| WO | WO 01/53461 | 7/2001 |
| WO | WO 03/018595 | 3/2003 |
| WO | WO 03/052378 | 6/2003 |

OTHER PUBLICATIONS

Guide to Peripheral and Cerebrovascular Intervention, D. Bhatt, Editor, Remedica Books, 2004, Chapter 14.*
DiCuccio et al., Exp. Hematol. Jul. 1996;24(8):914-918, Abstract only.*
Ananyeva et al., "Oxidized LDL Mediates the Release of Fibroblast Growth Factor-1," *Arterioscler. Thromb. Vasc. Biol.*, vol. 17, pp. 445-453, 1997.
Anderson, D. J., "Cellular and Molecular Biology of Neural Crest Cell Lineage Determination," *Trends Genet.*, vol. 13, pp. 276-280, 1997.
Andersson et al., "Transplantation of Cultured Type 1 Astrocyte Cell Suspensions into Young, Adult and Aged Rat Cortex: Cell Migration and Survival," *Int. J. Dev. Neurosci.*, vol. 11, pp. 555-568, 1993.
Artavanis-Tsakonas et al., Choosing a Cell Fate: A View from the Notch Locus, *Trends Genet.*, vol. 7(11/12), pp. 403-408, 1991.
Artavanis-Tsakonas et al., "Notch Signaling," *Science*, vol. 268(5208), pp. 225-232, 1995.
Bagala et al., "The Alternative Translation of Synaptotagmin 1 Mediates the Non-Classical Release of FGF1," *Biochem. Biophys. Res. Commun.*, vol. 310, pp. 1041-1047, 2003.
Bahou et al., "The Thrombin Receptor Extracellular Domain Contains Sites Crucial for Peptide Ligand-Induced Activation," *J. Clin. Invest.*, vol. 91, pp. 1405-1409, 1993.
Baker et al., "Spacing Differentiation in the Developing Drosophila Eye: A Fibrinogen-Related Lateral Inhibitor Encoded by Scabrous," *Science*, vol. 250(4986), pp. 1370-1377, 1990.
Baron, M., "An Overview of the Notch Signaling Pathway," *Seminars in. Cell and Developmental Biology*, vol. 14, pp. 113-119, 2003.
Bettenhausen et al., "Transient and Restricted Expression During Mouse Embryogenesis of Dll1, a Murine Gene Closely Related to Drosophila Delta," *Development*, vol. 121, pp. 2407-2418, 1995.
Bierkamp et al., "A Zebrafish Homologue of the Drosophila Neurogenic Gene Notch and its Pattern of Transcription During Early Embryogenesis," *Mech. Dev.*, vol. 43, pp. 87-100, 1993.
Bjorklund, Better Cells for Brain Repair, *Nature*, vol. 362, pp. 414-415, 1993.
Bjornson et al., "Turning Brain into Blood: A Hematopoietic Fate Adopted by Adult Neural Stem Cells in Vivo," *Science*, vol. 283(5401), pp. 534-538, 1999.

(Continued)

*Primary Examiner*—David S Romeo
*Assistant Examiner*—Daniel C Gamett
(74) *Attorney, Agent, or Firm*—Drinker Biddle & Reath, LLP

(57) ABSTRACT

The present invention relates to methods based on the interactions of thrombin as a biological regulator. More specifically, the invention relates to the interactions of thrombin with regard to Notch signaling, Jagged1, PAR1, and cellular effects mediated thereby. The invention relates to the discovery that thrombin cleaves Jagged1 to produce non-membrane soluble Jagged1 (sJ1). The soluble Jagged1 protein can affect Notch signaling and, among other things, mediate the release of FGF-1 and/or IL-1α from a cell. The invention further relates to the role(s) of thrombin and signaling via Notch proteins and the effect on thrombosis, angiogenesis, and/or differentiation, among other processes. Moreover, the invention relates to discovery that thrombin, sJ1, and TRAP mediate, inter alia, rapid non-classical release of FGF-1, and proteins associated therewith (e.g., p40 Syn1 and S100A13, among others), and the effect growth and proliferation of a stem cell without loss of differentiation potential. Thus, the present invention relates to methods of clonally expanding a pluripotent stem cell while preserving the differentiation potential of the cell, a process termed "stamatogenesis."

8 Claims, 28 Drawing Sheets

OTHER PUBLICATIONS

Blam et al., "Addition of Growth Hormone Secretion Signal to Basic Fibroblast Growth Factor Results in Cell Transformation and Secretion of Aberrant Forms of the Protein," *Oncogene*, vol. 3(2), pp. 129-136, 1988.

Blank et al., "NF-kB and Related Proteins: Rel/Dorsal Homologies Meet Anykyrin-Like Repeats," *TIBS*, vol. 17, pp. 135-140, 1992.

Bongarzone et al., "Platelet-Derived Growth Factor and Basic Fibroblast Growth Factor Regulate Cell Proliferation and the Expression of Notch-1 Receptor in a New Oligodendrocyte Cell Line,"*Journal of Neuroscience Research*, vol. 62, pp. 319-328, 2000.

Brass et al., "Receptor and G Protein-Mediated Responses to Thrombin in HEL Cells," *The Journal of Biological Chemistry*, vol. 266(2), pp. 958-965, 1991.

Bunnag et al., "Transformed Phenotype Conferred to NIH/3T3 Cells by Ectopic Expression of Heparin-Binding Growth Factor 1/Acidic Fibroblast Growth Factor," *In Vitro Cell Dev. Biol.*, vol. 27(1), pp. 89-96. 1991.

Burgar et al., "Association of the Signaling Adaptor FRS2 with Fibroblast Growth Factor Receptor 1 (Fgfr1) is Mediated by Alternative Splicing of the Juxtamembrane Domain," *J. Biol. Chem.*, vol. 277, pp. 4018-4023, 2002.

Burgess et al., "The Heparin-Binding (Fibroblast) Growth Factor Family of Proteins," *Annu. Rev. Biochem.* vol. 58, pp. 575-606, 1989.

Capobianco et al., "Neoplastic Transformation by Truncated Alleles of Human NOTCH1/TAN1 and NOTCH2," *Mol. Cell Biol.*, vol. 17(11), pp. 6265-6273, 1997.

Cau et al., "Hes Genes Regulate Sequential Stages of Neurogenesis in the Olfactory Epithelium," *Development*, vol. 127, pp. 2323-2332, 2000.

Cavaleri et al., Nanog: A New Recruit to the Embryonic Stem Cell Orchestra, *Cell*, vol. 113, pp. 551-557, 2003.

Chambers et al., "Functional Expression Cloning of Nanog, a Pluripotency Sustaining Factor in Embryonic Stem Cells," *Cell*, vol. 113, pp. 643-655. 2003.

Chan et al., "The Effect of Cholesterol Feeding on the Metabolism of Rabbit Cerebral Microvessels," *Microvascular Research*, vol. 18:353-369, 1979.

Cheng et al., "Spinal Cord Repair in Adult Paraplegic Rats: Partial Restoration of Hind Limb Function," *Science*, vol. 273(5274), pp. 510-513, 1996.

Chitnis et al., "Primary Neurogenesis in Xenopus Embryos Regulated by a Homologue of the Drosophila Neurogenic Gene Delta," *Nature*, vol. 375, pp. 761-766, 1995.

Coffman et al., "Xotch, the Xenopus Homolog of Drosophila Notch," *Science*, vol. 249(4975), pp. 1438-1441, 1990.

Coffman et al., "Expression of an Extracellular Deletion of Xotch Diverts Cell Fate in Xenopus Embryos," Cell, vol. 73:659-671, 1993.

Conlon et al., "Notch1 is Required for the Coordinate Segmentation of Somites," *Development*, vol. 121, pp. 1533-1545, 1995.

Connolly et al., "Role of the Thrombin Receptor in Development and Evidence for a Second Receptor," *Nature*, vol. 381, pp. 516-519, 1996.

Coughlin, "How the Protease Thrombin Talks to Cells," *Proc. Natl. Acad. Sci.*, vol. 96, pp. 11023-11027, 1999.

Danen et al., Fibronectin, Integrins, and Growth Control, *Journal of Cellular Physiology*, vol. 189, pp. 1-13, 2001.

Defer et al., "Long-Term Outcome of Unilaterally Transplanted Parkinsonian Patients," *Brain*, vol. 119, pp. 41-50, 1996.

Del Amo et al., "Expression Pattern of Motch, a Mouse Homolog of Drosophila Notch, Suggests and Important Role in Early Postimplantation Mouse Development," *Development*, vol. 115, pp. 737-744, 1992.

Dontu et al., "In Vitro Propagation and Transcriptional Profiling of Human Mammary Stem/Progenitor Cells," *Genes & Development*, vol. 17, pp. 1253-1270, 2003.

Dunwoodie et al., "Mouse Dll3: A Novel Divergent Delta Gene Which may Complement the Function of Other Delta Homologues During Early Pattern formation in the Mouse Embryo," *Development*, vol. 124, pp. 3065-3076, 1997.

Ellisen et al., "TAN-1, the Human Homolog of the Drosophila Notch Gene, is Broken by Chromosomal Translocation in T Lymphoblastic Neoplasms," *Cell*, vol. 66, pp. 649-661, 1991.

Erzurum et al., "R136K Fibroblast Growth Factor-1 Mutant Induces Heparin-Independent Migration of Endothelial Cells Through Fibrin Glue," *J. Vasc. Surg.*, vol. 37, pp. 1075-1081, 2003.

Faux et al., "Interactions Between Fibroblast Growth Factors and Notch Regulate Neuronal Differentiation," *J. Neurosci.*, vol. 21(15), pp. 5587-5596, 2001.

Ferrari et al., "Muscle Regeneration by Bone Marrow-Derived Myogenic Progenitors," *Science*, vol. 279(5356), pp. 1528-1530, 1998.

Fitzgerald et al., "Interchangeability of *Caenorhabditis Elegans* DSL Proteins and Intrinsic Signalling Activity of Their Extracellular Domains *In Vivo*," *Development*, vol. 121, pp. 4275-4282, 1995.

Folkman et al., "Angiogenic Factors" *Science*, vol. 235(4787), pp. 442-447, 1987.

Forough et al., Differential Transforming Abilities of Non-Secreted and Secreted Forms of Human Fibroblast Growth Factor-1,:*J. Biol. Chem.*, vol. 268, pp. 2960-2968, 1993.

Fortini et al., "Notch: Neurogenesis is Only Part of the Picture," *Cell*, vol. 75, pp. 1245-1247, 1993.

Freed et al., "Survival of Implanted Fetal Dopamine Cells and Neurologic Improvement 12 to 46 Months After transplantation for Parkinson's Disease," *N. Engl. J. Med.*, vol. 327, pp. 1549-1555, 1992.

Friedmann et al., "Injury-Induced Gelatinase and Thrombin-Like Activities in Regenerating and Nonregenerating Nervous Systems," :*FASEB J.*, vol. 13, p. 533-543, 1999.

Friesel et al., "Inhibition of Endothelial Cell Proliferation by Gamma-Interferon," *J. Cell Biol.*, vol. 104, pp. 689-696, 1987.

Friesel et al., "Molecular Mechanisms of Angiogenesis: Fibroblast Growth Factor Signal Transduction," *FASEB J.*, vol. 9, pp. 19-925, 1995.

Furukawa et al., "Rax, Hes1, and Notch1 Promote the Formation of Muller Glia by Postnatal Retinal Progenitor Cells," *Neuron*, vol. 26:383-394, 2000.

Gaiano et al., "Radial Glial Identity is Promoted by Notch1 Signaling in the Murine Forebrain," *Neuron*, vol. 26, pp. 395-404, 2000.

Glembotski, "Myocardial α-Thrombin Receptor Activation Induces Hypertrophy and Increases Atrial Natriuretic Factor Gene Expression," *J. Biol. Chem.*, vol. 268, pp. 20646-20652, 1993.

Grandbarbe et al., "Delta-Notch Signaling Controls the Generation of Neurons/Glia From Neural Stem Cells in a Stepwise Process," *Development*, vol. 130:1391-1402, 2003.

Gray et al., "Human Ligands of the Notch Receptor," *American Journal of Pathology*, vol. 154, pp. 785-794, 1999.

Greenwald et al., "Making a Difference: The Role of Cell-Cell Interactions in Establishing Separate Identities for Equivalent Cells," *Cell*, vol. 68, pp. 271-281, 1992.

Guidos, C. J., "Notch Signaling in Lymphocyte Development," *Seminars in Immunology*, vol. 14, pp. 395-404, 2002.

Gurdon, "The Generation of Diversity and Pattern in Animal Development," *Cell*, vol. 68, pp. 185-199, 1992.

Gussoni et al., "Dystrophin Expression in the Mdx Mouse Restored by Stem Cell Transplantation," *Nature*, vol. 401, pp. 390-394, 1999.

Hamada et al., "Mutation in Ankyrin Repeats of the Mouse Notch2 Gene Induces Early Embryonic Lethality," *Development.* vol. 126 pp. 3415-3424, 1999.

Harada et al., "Localization of Putative Stem Cells in Dental Epithelium and Their Association with Notch and FGF Signaling," *J. Cell Biol.*, vol. 147, pp. 105-120, 1999.

Hardy et al., "Construction of Adenovirus Vectors Through Cre-Lax Recombination," *J. Virol.*, vol. 71(3), pp. 1842-1849, 1997.

Henderson et al., "Lag-2 May Encode a Signaling Ligand for the GLP and LIN-12 Receptors of C. Elegans," *Development*, vol. 120, pp. 2913-2924, 1994.

Herbert et al., Thrombin Induces Endothelial Cell Growth via Both a Proteolytic and a Non-Proteolytic Pathway,: *Biochem. Journal*, vol. 303, pp. 227-231, 1994.

Hicks et al. "A Secreted Delta1-Fc Fusion Protein Functions Both as an Activator and Inhibitor of Notch1 Signaling," *Journal of Neuroscience Research*, vol. 68, pp. 655-667, 2002.

Hirata et al., "Hes1 and Hes3 Regulate Maintenance of the Isthmic Organizer and Development of the Mid/Hindbrain," *EMBO Journal*, vol. 20(16), pp. 4454-4466, 2001.

Hirose et al., "Activated Protein Reduces the Ischemi/Reperfusion-Induced Spinal Cord Injury in Rats by Inhibiting Neutrophil Activation," *Annals of Surgery*, vol. 232(2), pp. 272-280, 2000.

Hitoshi et al., "Notch Pathway Molecules are Essential for the Maintenance, but not the Generation, of Mammalian Neural Stem Cells," *Genes Dev.*, vol. 16, pp. 846-858, 2002.

HLA et al., "Isolation of Immediate-Early Differentiation mRNAs by Enzymatic Amplification of Subtracted cDNA from Human Endothelial Cells," *Biochem. Biophys. Res. Commun.*, vol. 167(2), pp. 637-643, 1990.

HLA et al., "An Abundant Transcript Induced in Differentiating Human Endothelial Cells Encodes a Polypeptide with Structural Similarities to G-Protein-Coupled Receptors," *J. Biol. Chem.*, vol. 265(16), pp. 9308-9313, 1990.

Hsieh et al., "Truncated Mammalian Notch1 Activates CBF1/RBPJk-Repressed Genes by a Mechanism Resembling that of Epstein-Barr Virus EBNA2," *Mol. Cell. Biol.*, vol. 16(3), pp. 952-959, 1996.

Hu et al., "F3/Contactin Acts as a Functional Ligand for Notch During Oligodendrocyte Maturation," *Cell*, vol. 115, pp. 163-175, 2003.

Hukriede et al., "A Dominant-Negative Form of Serrate Acts as a General Antagonist of Notch Activation," *Development*, vol. 124, pp. 3427-3437, 1997.

Ikeya et al., "Interplay of Notch and FGF Signaling Restricts Cell Fate and MAPK Activation in the Drosophila Trachea," *Development*, vol. 126, pp. 4455-4463, 1999.

Iso et al., "Notch Signaling in Vascular Development," *Arterioscler. Thromb. Vasc. Biol.*, vol. 23, pp. 543-553, 2003.

Jackson et al., "Heat Shock Induces the Release of Fibroblast Growth Factor 1 from NIH 3T3 Cells," *Proc. Natl. Acad. Sci. USA.* vol. 89, pp. 10691-10695, 1992.

Jaleco et al., "Differential Effects of Notch Ligands Delta-1 and Jagged-1 in Human Lymphoid Differentiation," *J. Exp. Med.*, vol. 194(7), pp. 991-1001, 2001.

Jarriault et al., "Signaling Downstream of Activated Mammalian Notch," *Nature*, vol. 377, pp. 355-358, 1995.

Jennings et al., The Notch Signaling Pathway is Required for Enhancer of Split bHLH Protein Expression During Neurogenesis in the Drosophila Embryo, *Development*, vol. 120, pp. 3537-3548, 1994.

Jiang et al., "Defects in Limb, Craniofacial, and Thymic Development in Jagged2 Mutant Mice," *Genes Dev.*, vol. 12, pp. 1046-1057, 1998.

Jouanneau et al., "Secreted or Nonsecreted Forms of Acidic Fibroblast Growth Factor Produced by Transfected Epithelial Cells Influence Cell Morphology, Motility, and Invasive Potential," *Proc. Natl. Acad. Sci. USA*, vol. 88, pp. 2893-2897, 1991.

Joutel et al., "Notch Signaling Pathway and Human Diseases," *Seminars in Cell and Development Biology*, vol. 9, pp. 619-625, 1998.

Kadesch, T., "Notch Signaling: A Dance of Proteins Changing Partners," *Exp. Cell. Res.*, vol. 260, pp. 1-8, 2000.

Kang et al., "Regulation of Dopamine Production by Genetically Modified Primary Fibroblasts," *J. Neurosci.*, vol. 13(12), pp. 5203-5211, 1993.

Kessler et al., "Myoblast Cell Grafting Into Heart Muscle: Cellular Biology and Potential Applications," *Annu. Rev. Physiol.*, vol. 61, pp. 219-242, 1999.

Klagsbrun et al., "A Dual Receptor System is Required for Basic Fibroblast Growth Factor Activity," *Cell*, vol. 67, pp. 229-231, 1991.

Kopan et al., "The Intracellular Domain of Mouse Notch: A Constitutively Activated Repressor of Myogenesis Directed at the Basic Helix-Loop-Helix Region of MyoD," *Development*, vol. 120, pp. 2385-2396, 1994.

Kopan et al., "Signal Transduction by Activated mNotch: Importance of Proteolytic Processing and its Regulation by the Extracellular Domain," *Proc. Natl. Acad. Sci. USA*, vol. 93, pp. 1683-1688, 1996.

Kordower et al., "Neuropathological Evidence of Graft Survival and Striatal Reinnervation After the Transplantation of Fetal Mesencephalic Tissue in a Patient with Parkinson's Disease," *N. Engl. J. Med.*, vol. 332, pp. 1118-1124, 1995.

Krause, D. S., "Regulation of Hematopoietic Stem Cell Fate," *Oncogene*, vol. 21, pp. 3262-3269, 2002.

Krebs et al., "Notch Signaling is essential for Vascular Morphogenesis in Mice," *Genes & Development*, vol. 14, pp. 1343-1352, 2000.

Kubu et al., "Identification of the Translational Initiation Codon in Human MAGED1," *Genomics*, vol. 70, pp. 150-152, 2000.

Labonne et al., "Induction and Patterning of the Neural Crest, a Stem Cell-Like Precursor Population," *J. Neurobiol.*, vol. 36, pp. 175-189, 1998.

Lai, "Keeping a Good Pathway Down: Transcriptional Repression of Notch Pathway Target Genes by CSL Proteins," *EMBO Reports*, vol. 3(9), pp. 840-845, 2002.

Landriscina et al., "S100A13 Participates in the Release of Fibroblast Growth Factor 1 in Response to Heat Shock In Vitro," *J. Biol. Chem.*, vol. 276, pp. 22544-22552, 2001.

Landriscina et al., "Copper Induces the Assembly of a Multiprotein Aggregate Implicated in the Release of Fibroblast Growth Factor 1 in Response to Stress," *J. Biol. Chem.*, vol. 276, pp. 25549-25557, 2001.

Lardelli et al., "Motch A and Motch B—Two Mouse Notch Homologues Coexpressed in a Wide Variety of Tissues," *Exp. Cell Res.*, vol. 204, pp. 364-372, 1993.

Lardelli et al., The Novel Notch Homologue Mouse Notch 3 Lacks Specific Epidermal Growth Factor-Repeats and is Expressed in Proliferating Neuroepithelium, *Mechanisms of Development*, vol. 46, pp. 123-136, 1994.

Lavallee et al., "Synaptotagmin-1 is Required for Fibroblast Growth Factor-1 Release," *J. Biol. Chem.*, vol. 273, pp. 22217-22223, 1998.

Li et al., "Alagille Syndrome is Caused by Mutations in Human Jagged1 Which Encodes a Ligand for - Notch1," *Nat. Genet.*, vol. 16, pp. 243-251, 1997.

Lindner et al., "Members of the Jagged-Notch Gene Families are Expressed in Injured Arteries and Regulate Cell Phenotype via Alterations in Cell Matrix and Cell-Cell Interaction," *Am J Pathol.*, vol. 159(3), pp. 875-917, 2001.

Lindsell et al., "Jagged: A Mammalian Ligand that Activates Notch1," *Cell*, vol. 80, pp. 909-917, 1995.

Lobb, R. R., "Thrombin Inactivates Acidic Fibroblast Growth Factor but not Basic Fibroblast Growth Factor," *Biochemistry*, vol. 27, pp. 2572-2578, 1988.

Lopez-Lozano et al., "Regression of Parkinsonian Fetal Ventral Mesencephalon Grafts Upon Withdrawal of Cyclosporine a Immunosuppression," Transp. Proc., vol. 29, pp. 977-980, 1997.

Maciag et al., "An Endothelial Cell Growth Factor from Bovine Hypothalamus: Identification and Partial Characterization," *Proc. Natl. Acad. Sci. USA*, vol. 76, pp. 5674-5678, 1979.

Maciag et al., "Serial Propagation of Human Endothelial Cells In Vitro," *Journal of Cell Biology*, vol. 91, pp. 420-426, 1981.

Maciag et al., "Organizational Behavior of Human Umbilical Vein Endothelial Cells," *J. Cell Biol.*, vol. 94, pp. 511-520, 1982.

Maciag et al., "Heparin Binds Endothelial Cell Growth Factor, the Principal Endothelial Cell Mitogen in Bovine Brain," *Science*, vol. 225(4665), pp. 932-935, 1984.

Madiai et al., "Characterization of the Entire Transcription Unit of the Mouse Fibroblast Growth Factor 1 (FGF-1) Gene," *J. Biol. Chem.*, vol. 274, pp. 11937-11944, 1999.

Maerz et al., "FGF4 Dissociates Anti-Tumorigenic from Differentiation Signals of Retinoic Acid in Human Embryonal Carcinomas," *Oncogene*, vol. 17, pp. 761-767, 1998.

Maier et al., "Cyclooxygenase is an Immediate-Early Gene Induced by Interleukin-1 in Human Endothelial Cells," *J. Biol. Chem.*, vol. 265, pp. 10805-10808, 1990.

Maier et al., "Extension of the Life-Span of Human Endothelial Cells by an Interleukin-1-α Antisense Oligomer." *Science*, vol. 249(4976), pp. 1570-1574, 1990.

Maillard et al., "From the Yolk Sac to the Spleen: New Roles for Notch in Regulating Hematopoiesis," *Immunity*, vol. 18, pp. 587-589, 2003.

Maillard et al, "Notch and the Immune System," *Immunity*, vol. 19, pp. 781-791, 2003.

Mandinov et al., Copper Chelation Represses the Vascular Response to Injury, *Proc. Natl. Acad. Sci.*, vol. 100(11), pp. 6700-6705, 2003.

Mandinova et al., "S100A13 Mediates the Copper-Dependent Stress-Induced Release of IL-1α from Both Human U937 and Murine NIH 3T3 Cells," *J. Cell Sci.*, vol. 116, pp. 2687-2696, 2003.

Martinez-Gonzalez et al., "Neuron-Derived Orphan Receptor-1 (NOR-1) Modulates Vascular Smooth Muscle Cell Proliferation," *Circ. Res.*, vol. 92, pp. 96-103, 2003.

Matsumoto et al., "p38 MAP Kinase Negatively Regulates Endothelial Cell Survival, Proliferation, and Differentiation in FGF-1-Stimulated Angiogenesis," *J. Cell Biol.*, vol. 156, pp. 149-160, 2002.

Matsuno et al., "Deltex Acts as a Positive Regulator of Notch Signaling Through Interactions with the Notch Ankyrin Repeats," *Development*, vol. 121, pp. 2633-2644, 1995.

McKay, "Stem Cells in the Central Nervous System," *Science*, vol. 276(5309), pp. 66-71, 1997.

McNamara et al., "Thrombin Stimulates Proliferation of Cultured Rat Aortic Smooth Muscle Cells by a Proteolytically Activated Receptor," *J. Clin. Invest.*, vol. 91, pp. 94-98, 1993.

Mello et al., "The Maternal Genes apx-1 and glp-1 and Establishment of Dorsal-Ventral Polarity in the Early C. Elegans Embryo," *Cell*, vol. 77, pp. 95-106, 1994.

Mishra-Gorur et al., "Down-Regulation of Delta by Proteolytic Processing," *J. Cell Biol.*, vol. 159, pp. 313-324, 2002.

Mitsui et al., "The Homeoprotein Nanog is Required for Maintenance of Pluripotency in Mouse Epiblast and ES Cells," *Cell*, vol. 113, pp. 631-642, 2003.

Molofsky et al., "Bmi-1 Dependence Distinguishes Neural Stem Cell Self-Renewal from Progenitor Proliferation," *Nature*, vol. 425, pp. 962-967, 2003.

Morimura et al., "Cell Cycle Arrest and Apoptosis Induced by Notch 1 in B Cells," *J. Biol. Chem.*, vol. 275(47), pp. 36523-36531, 2000.

Morrison et al., "Prospective Identification, Isolation by Flow Cytometry, and In Vivo Self-Renewal of Multipotent Mammalian Neural Crest Stem Cells," *Cell*, vol. 96, pp. 737-749, 1999.

Morrison et al., "Transient Notch Activation Initiates an Irreversible Switch from Neurogenesis to Gliogenesis by Neural Crest Stem Cells," *Cell*, vol. 101, pp. 499-510, 2000.

Morrison et al., "Neuronal Potential and Lineage Determination by Neural Stem Cells," *Curr. Opin. Cell. Biol.*, vol. 13, pp. 666-674, 2001.

Mouta Carreira et al., "S100A13 is Involved in the Regulation of Fibroblast Growth Factor-1 and p40 Synaptotamin-1 Release In Vitro," *J. Biol. Chem.*, vol. 273(35), pp. 22224-22231, 1998.

Mumm et al., "Notch Signaling: From the Outside In," *Developmental Biology*, vol. 228, pp. 151-165, 2000.

Nabel et al., "Recombinant Fibroblast Growth Factor-1 Promotes Intimal Hyperplasia and Angiogenesis in Arteries In Vivo," *Nature*, vol. 362, pp. 844-846, 1993.

Nickoloff et al., "Notch Signaling as a Therapeutic Target in Cancer: A New Approach to the Development of Cell Fate Modifying Agents," *Oncogene*, vol. 22, 6598-6608, 2003.

Nicolas et al., "Notch1 Functions as a Tumor Suppressor in Mouse Skin," *Nature Genetics*, vol. 33, pp. 416-421, 2003.

Niewiarowska et al., "Association of Fibronectin with the Platelet Cytoskeleton," *J. Biol. Chem.*, vol. 259(10), pp. 6181-6187, 1984.

Nofziger et al., "Notch Signaling Imposes two Distinct Blocks in the Differentiation of C2C12 Myoblasts," *Development*, vol. 126, pp. 1689-1702, 1999.

Nye et al., "An Activated Notch Suppresses Neurogenesis and Myogenesis but not Gliogenesis in Mammalian Cells," *Development*, vol. 120, pp. 2421-2430, 1994.

Nye et al., "Vertebrate Ligands for Notch," *Current Biology*, vol. 5(9), pp. 966-969, 1995.

Olson, "Regeneration in the Adult Central Nervous System: Experimental Repair Strategies," *Nature Med.*, vol. 3(12), pp. 1329-1335, 1997.

Oyama et al., "Two Distinct Anti-Allergic Drugs, Amlexanox and Cromolyn, Bind to the Same Kinds of Calcium Binding Proteins, Except Calmodulin, in Bovine Lung Extract," *Biochem. Biophys. Res. Commun.*, vol. 240, pp. 341-347, 1997.

Ozawa et al., "An Alternatively Spliced Fibroblast Growth Factor (FGF)-5 mRNA is Abundant in Brain and Translates into a Partial Agonist/Antagonist for FGF-5 Activity," *J. Biol. Chem.*, vol. 273(44), pp. 29262-29271, 1998.

Pan et al., "Stem Cell Pluripotency and Transcription Factor $Oct_4$," *Cell Research*, vol. 12, pp. 321-329, 2002.

Panek et al., "In Vitro Biological Characterization and Antiangiogenic Effects of PD 166866, a Selective Inhibitor of the FGF-1 Receptor Tyrosine Kinase," *J. Pharmacol. Exp. Ther.*, vol. 286(1), pp. 569-577, 1998.

Park et al., "Bmi1, Stem Cells, and Senescence Regulation," *The Journal of Clinical Investigation*, vol. 113(2), pp. 175-179, 2004.

Pendurthi et al., "Acidic and Basic Fibroblast Growth Factors Suppress Transcriptional Activation of Tissue Factor and Other Inflammatory Genes in Endothelial Cells," *Arterioscler. Thromb. Vasc. Biol.*, vol. 17, pp. 940-946, 1997.

Pereira et al., "Cultured Adherent Cells from Marrow can Serve as Long-Lasting Precursor Cells for Bone, Cartilage, and Lung in Irradiated Mice," *Proc. Natl. Acad. Sci. USA*, vol. 92, pp. 4857-4861, 1995.

Peterson et al., "one Marrow as a Potential Source of Hepatic Oval Cells," *Science*, vol. 2841(5417), pp. 168-170, 1999.

Peterson et al., "Thrombin Induces Endothelial Cell-Surface Exposure of the Plasminogen Receptor Annexin 2," *J. Cell. Sci.*, vol. 116, pp. 2399-2408, 2003.

Pittenger et al., "Multilineage Potential of Adult Human Mesenchymal Stem Cells," *Science*, vol. 284(5411), pp. 143-147, 1999.

Prockop, "Marrow Stromal Cells as Stem Cells for Nonhematopoietic Tissues," *Science*, vol. 284(5309), pp. 71-74, 1997.

Prudovsky et al., "The Intracellular Translocation of the Components of the Fibroblast Growth Factor 1 Release Complex Precedes Their Assembly Prior to Export," *J. Cell. Biol.*, vol. 158, pp. 201-208, 2002.

Qi et al., "Processing of the Notch Ligand Delta by the Metalloprotease Kuzbanian," *Science*, vol. 283(5398), pp. 91-94, 1999.

Raaphorst, F. M., "Self-Renewal of Hematopoietic and Leukemic Stem Cells: A Central Role for the Polycomb-Group Gene Bmi-1," *Trends Immunol.*, vol. 24, pp. 522-524, 2003.

Radtke et al., "The Role of Notch in Tumorigenesis: Oncogene or Tumour Suppressor?" *Nat. Rev. Cancer.* vol. 3, pp. 756-767, 2003.

Rae et al., "Novel Association of a Diverse Range of Genes with Renal Cell Carcinoma as Identified by Differential display," *Int. J. Cancer*, vol. 88, pp. 726-732, 2000.

Rangarajan et. al., "Notch Signaling is a Direct Determinant of Keratinocyte Growth Arrest and Entry into Differentiation," *EMBO J.*, vol. 20(13), pp. 3427-3436, 2001.

Rasmussen et al., "cDNA Cloning and Expression of a Hamster α-Thrombin Receptor Coupled to $Ca^{2+}$ Mobilization," *FEBS Lett.*, vol. 288(1-2), pp. 123-128, 1991.

Reaume et al., "Expression Analysis of a Notch Homologue in the Mouse Embryo," *Developmental Biology*, vol. 154, pp. 377-387, 1992.

Renaud et al., "Up-Regulation of aFGF Expression in quiescent Cells is Related to Cell Survival," *Journal of Cellular Physiology*, vol. 158, pp. 435-443, 1994.

Reynolds et al., "A multipotent EGF-Responsive Striatal Embryonic Progenitor Cell Produces Neurons and Astrocytes," *The Journal of Neuroscience*, vol. 12, pp. 4565-4574, 1992.

Reynolds et al., "Generation of Neurons and Astrocytes from Isolated Cells of the Adult Mammalian Central Nervous System," *Science*, vol. 255(5502), pp. 1707-1710, 1992.

Rietze et al., "Purification of a Pluripotent Neural Stem cell from the Adult Mouse Brain," *Nature*, vol. 412, pp. 736-739, 2001.

Rifkin et al., Recent Developments in the Cell Biology of Basic Fibroblast Growth Factor, *J. Cell Biol.*, vol. 109, pp. 1-6, 1989.

Robey et al., "An Activated Form of Notch Influences the Choice Between CD4 and CD8 T Cell Lineages," *Cell*, vol. 87, pp. 483-492, 1996.

Rogelj et al., "Basic Fibroblast Growth Factor Fused to a Signal Peptide Transforms Cells," *Nature*, vol. 331, pp. 173-175, 1988.

Rohn et al., Transduction of Notch2 in Feline Leukemia Virus-Induced Thymic Lymphoma, *J. Virol.*, vol. 70, pp. 8071-8080, 1996.

Rosengart et al., "Heparin Protects Heparin-Binding Growth Factor-1 from Proteolytic Inactivation In Vitro," *Biochem. Biophys. Res. Commun.*, vol. 152(1), pp. 432-440, 1988.

Rosenstein, "Why do Neural Transplants Survive?" *Experimental Neurology*, vol. 33, pp. 1-6, 1995.

Sanberg et al., "Testis-Derived Sertoli Cells have a Trophic Effect on Dopamine Neurons and Alleviate Hemiparkinsonism in Rats," *Nature Med.*, vol. 3, pp. 1129-1132, 1997.

Scarborough et al., "Tethered Ligand Agonist Peptides," *The Journal of Biological Chemistry*, vol. 267, pp. 13146-13149, 1992.

Schwartz et al., "Vascular Wall Growth Control: The Role of the Endothelium," *Arteriosclerosis, Thrombosis, and Vascular Biology*, vol. 1, pp. 107-126, 1981.

Schwartz, "Locating Ligand-Binding Sites in 7TM Receptors by Protein Engineering," *Current Opin. Biotechnol.*, vol. 5, pp. 434-444, 1994.

Schweisguth et al., "Suppressor of Hairless, the Drosophila Homolog of the Mouse Recombination Signal-Binding Protein Gene, Controls Sensory Organ Cell Fates," *Cell*, vol. 69, pp. 1199-1212, 1992.

Sestan et al., "Contact-Dependent Inhibition of Cortical Neurite Growth Mediated by Notch Signaling," *Science*, vol. 286, pp. 741-746, 1999.

Shah et al., "Alternative Neural Crest Cell Fates are Instructively Promoted by TGFβ Superfamily Members," *Cell*, vol. 85, pp. 331-343, 1996.

Shah et al., "Integration of Multiple Instructive Cues by Neural Crest Stem Cells Reveals Cell-Intrinsic Biases in Relative Growth Factor Responsiveness," *Proc. Natl. Acad. Sci. U.S.A*, vol. 94, pp. 11369-11374, 1997.

Shawber et al., "Notch Signaling Inhibits Muscle Cell Differentiation Through a CBF-1-Independent Pathway," *Development*, vol. 122, pp. 3765-3773, 1996.

Shawber et al., "Jagged2: A Serrate-Like Gene Expressed During Rat Embryogenesis," *Developmental Biology*, vol. 180, pp. 370-376, 1996.

Shi et al., "A Carboxyl-Terminal Domain in Fibroblast Growth Factor (FGF)-1 Inhibits FGF-1 Release in Response to Heat Shock In Vitro," *J. Biol, Chem.*, vol. 272(2), pp. 1142-1147, 1997.

Shih et al., "Passage of Phenotypes of Chemically Transformed Cells via Transfection of DNA and Chromatin," *Proc. Natl. Acad. Sci. USA*, vol. 76(11), pp. 5714-5718, 1979.

Shimizu et al., "Binding of Delta1, Jagged1, and Jagged2 to Notch2 Rapidly Induces Cleavage, Nuclear Translocation, and Hyperphosphorylation of Notch2," *Molecular and Cellular Biology,.* vol. 20(18): pp. 6913-6922, 2000.

Shimizu et al., "Integrity of Intracellular Domain of Notch Ligand is Indispensable for Cleavage Required for Release of the Notch2 Intracellular Domain," *The EMBO Journal*, vol. 21(3), pp. 294-302, 2002.

Shin et al., "Serum-Starvation Induces the Extracellular Appearance of FGF-1," *Biochimica et Biophysica* Acta, vol. 1312, pp. 27-38, 1996.

Shutter et al., "Dll4, a Novel Notch Ligand Expressed in Arterial Endothelium," *Genes and Development*, vol. 14, pp. 1313-1318, 2000.

Small et al., "Soluble Jagged 1 Represses the Function of Its Transmembrane Form to Induce the Formation of the Src-dependent Chord-like Phenotype," *The Journal of Biological Chemistry*, vol. 276(34), pp. 32022-32030, 2001.

Small et al., "Notch Activation Suppresses Fibroblast Growth Factor-dependent Cellular Transformation," *The Journal of Biological Chemistry*, vol. 278(18), pp. 16405-16413, 2003.

Sommer et al. "Neural Stem Cells and Regulation of Cell Number," *Progress in Neurobiology*, vol. 66, pp. 1-8, 2002.

Spencer et al., "Unilateral Transplantation of Human Fetal Mesencephalic Tissue into the Caudate Nucleus of patients with Parkinson's Disease," *The New England Journal of Medicine*, vol. 327(22), pp. 1541-1548, 1992.

Spinner et al., "Jagged1 Mutations in Alagille Syndrome," *Human Mutation*, vol. 17, pp. 18-33, 2001.

Sriuranpong et al., "Notch Signaling Induces Cell Cycle Arrest in Small Cell Lung Cancer Cells," *Cancer Research*, vol. 61, pp. 3200-3205, 2001.

Stemple et al., "Isolation of a Stem Cell for Neurons and Glia from the Mammalian Neural Crest," *Cell*, vol. 71, pp. 973-985, 1992.

Sun et al., "Secreted Forms of Delta and Serrate Define Antagonists of notch Signaling in *Drosophila*," *Development*, vol. 124, pp. 3439-3448, 1997.

Talarico et al., "The K-*fgf/hst* Oncogene Induces Transformation through an Autocrine Mechanism That Requires Extracellular Stimulation of the Mitogenic Pathway," *Molecular and Cellular Biology*, vol. 11(2), pp. 1138-1145, 1991.

Talora et al., "Specific Down-Modulation of Notch1 Signaling in Cervical Cancer Cells is Required for Sustained HPV-E6E7 Expression and Late Steps of Malignant Transformation," *Genes Development*, vol. 16, pp. 2252-2263, 2002.

Tanigaki et al., "Notch1 and Notch3 Instructively Restrict bFGF-Responsive Multipotent Neural Progenitor Cells to an Astroglial Fate," *Neuron*, vol. 29, pp. 45-55, 2001.

Tarantini et al., "The Precursor but Not the Mature Form of IL1α Blocks the Release of FGF1 in Response to Heat Shock," *The Journal of Biological Chemistry*, vol. 276(7), pp. 5147-5151, 2001.

Tarantini et al., "The Extravesicular Domain of Synaptotagmin-1 Is Released with the Latent Fibroblast Growth Factor-1 Homodimer in Response to Heat Shock," *The Journal of Biological Chemistry*, vol. 273(35), pp. 22209-22216, 1998.

Thomas et al., "The *Drosophila* Gene *Serrate* Encodes an EGF-Like Transmembrane Protein with a Complex Expression Pattern in Embryos and Wing Discs," *Development*, vol. 111, pp. 749-761, 1991.

Thompson et al., "Site Directed Neovessel Formation in Vivo," *Science*, vol. 241(4871), pp. 1349-1352, 1988.

Trifonova et al., "The Non-Transmembrane Form of Delta1, but Not of Jagged1, Induces Normal Migratory Behavior Accompanied by Fibroblast Growth Factor Receptor 1-Dependent Transformation," *The Journal of Biological Chemistry*, vol. 279(14), pp. 13285-13288, 2004.

Tropepe et al., "Direct Neural Fate Specification from Embryonic Stem Cells: A Primitive Mammalian Neural Stem Cell Stage Acquired through a Default Mechanism," *Neuron*, vol. 30, pp. 65-78, 2001.

Tsai et al., "A Nucleolar Mechanism Controlling Cell Proliferation in Stem Cells and Cancer Cells," *Genes and Development*, vol. 16, pp. 2991-3003, 2002.

Turner et al., "Scientific and Ethical Concerns in Neural Fetal Tissue Transplantation," *Neurosurgery*, vol. 33(6), pp. 1031-1037, 1993.

Varnum-Finney et al., "Immobilization of Notch Ligand, Delta-1, is required for Induction of Notch Signaling," *Journal of Cell Science*, vol. 113, pp. 4313-4318, 2000.

Vas et al., "Soluble Jagged-1 is Able to Inhibit the Function of Its Multivalent Form to Induce Hematopoietic Stem Cell Self-renewal in a Surrogate in Vitro Assay," *J Leukoc Biol.*, vol. 75(4), pp. 714-720, 2004.

Verdi et al., "Neurotrophins Regulate Sequential Changes in Neurotrophin Receptor Expression by Sympathetic Neuroblasts," *Neuron*, vol. 13, pp. 1359-1372, 1994.

Verdi et al., "A Reciprocal Cell-Cell Interaction Mediated by NT-3 and Neuregulins Controls the Early Survival and Development of Sympathetic Neuroblasts," *Neuron*, vol. 16, pp. 515-527, 1996.

Vu et al., "Molecular Cloning of a Functional Thrombin Receptor Reveals a Novel Proteolytic Mechanism of Receptor Activation," *Cell*, vol. 64, pp. 1057-1068, 1991.

Walker et al., "The Notch/Jagged Pathway Inhibits Proliferation of Human Hematopoietic Progenitors In Vitro," *Stem Cells*, vol. 17, pp. 162-171, 1999.

Wang et al., "Up a Notch: Instructing Gliogenesis," *Neuron*, vol. 27, pp. 197-200, 2000.

Weijzen et al., "Activation of Notch-1 Signaling Maintains the Neoplastic Phenotype in Human Ras-Transformed Cells," *Nat. Med.*, vol. 8(9), pp. 979-986, 2002.

Weinmaster et al., "A Homolog of *Drosophila Notch* Expressed During Mammalian Development," *Development*, vol. 113, pp. 199-205, 1991.

Weintraub, "The MyoD Family and Myogenesis: Redundancy, Networks, and Thresholds," *Cell*, vol. 75, pp. 1241-1244, 1993.

Weissman et al., "Stem and Progenitor Cells: Origins, Phenotypes, Lineage Commitments, and Transdifferentiations," *Annu. Rev. Cell Dev. Biol.*, vol. 17, pp. 387-403, 2001.

White et al., "In Vivo Transplantation of mammalian Neural Crest Cells into Chick Hosts Reveals a New Automatic Sublineage Restriction," *Development*, vol. 126, pp. 4351-4363, 1999.

White et al., "Neural Crest Stem Cells Undergo Cell-Intrinsic Developmental Changes in Sensitivity to Instructive Differentiation Signals," *Neuron*, vol. 29, pp. 57-71, 2001.

Wong et al., "A Non-Transmembrane Form of Jagged-1 Regulates the Formation of Matrix-Dependent Chord-Like Structures," *Biochemical and Biophysical Research Communications*, vol. 268, pp. 853-859, 2000.

Xue et al., "Embryonic Lethality and Vascular Defects in Mice Lacking the Notch Ligand Jagged1," *Human Molecular Genetics*, vol. 8(5), pp. 723-730, 1999.

Yan et al., "Exon Switching and Activation of Stromal and Embryonic Fibroblast Growth Factor (FGF)-FGF Receptor Genes in Prostate Epithelial Cells Accompany Stromal Independence and Malignancy," *Molecular and Cellular Biology*, vol. 13(8), pp. 4513-4522, 1993.

Zagouras et al., "Alterations in Notch Signaling in Neoplastic Lesions of the Human Cervix," *Proc. Natl. Acad. Sci. USA*, vol. 92, pp. 6414-6418, 1995.

Zhan et al., "Long Term Growth Factor Exposure and Differential Tyrosine Phosphorylation Are Required For DNA Synthesis In BALB/c 3T3 Cells," *The Journal of Biological Chemistry*, vol. 268(13), pp. 9611-9620, 1993.

Zhong et al., "Molecular Cloning of the Rat Vascular Smooth Muscle Thrombin Receptor," *The Journal of Biological Chemistry*, vol. 267(24), pp. 16975-16979, 1992.

Zimrin et al., "Models of In Vitro Angiogenesis: Endothelial Cell Differentiation on Fibrin but not Matrigel is Transciptionally Dependent," *Biochemical and Biophysical Research Communications*, vol. 213(2), pp. 630-638, 1995.

Zimrin et al., "Progress Towards a Unifying Hypothesis for Angiogenesis," *J. Clin. Invest.*, vol. 97(6), pp. 1359, 1996.

Zimrin et al., "An Antisense Oligonucleotide to the Notch Ligand Jagged Enhances Fibroblast Growth Factor-Induced Angiogenesis In Vitro," *The Journal of Biological Chemistry*, vol. 271(51), pp. 32499-32502, 1996.

\* cited by examiner

FIG. 8C-1

MRSPRTRGRSGRPLSLLLALLCALRAKVCGASGQFELEILSMQNVNGEL
QNGNCCGGARNPGDRKCTRDECDTYFKVCLKEYQSRVTAGGPCSFGSGS
TPVIGGNTFNLKASRGNDRNRIVLPFSFAWPRSYTLLVEAWDSSNDTVQ
PDSIIEKASHSGMINPSRQWQTLKQNTGVAHFEYQIRVTCDDYYYGFGC
NKFCRPRDDFFGHYACDQNGNKTCMEGWMGPECNRAICRQGCSPKHGSC
KLPGDCRCQYGWQGLYCDKCIPHPGCVHGICNEPWQCLCETNWGGQLCD
KDLNYCGTHQPCLNGGTCSNTGPDKYQCSCPEGYSGPNCEIAEHACLSD
PCHNRGSCKETSLGFECECSPGWTGPTCSTNIDDCSPNNCSHGGTCQDL
VNGFKCVCPPQWTGKTCQLDANECEAKPCVNAKSCKNLIASYYCDCLPG
WMGQNCDININDCLGQCQNDASCRDLVNGYRCICPPGYAGDHCERDIDE
CASNPCLNGGHCQNEINRFQCLCPTGFSGNLCQLDIDYCEPNPCQNGAQ
CYNRASDYFCKCPEDYEGKNCSHLKDHCRTTPCEVIDSCTVAMASNDTP
EGVRYISSNVCGPHGKCKSQSGGKFTCDCNKGFTGTYCHENINDCESNP
CRNGGTCIDGVNSYKCICSDGWEGAYCETNINDCSQNPCHNGGTCRDLV
NDFYCDCKNGWKGKTCHSRDSQCDEATCNNGGTCYDEGDAFKCMCPGGW
EGTTCNIARNSSCLPNPCHNGGTCVVNGESFTCVCKEGWEGPICAQNTN
DCSPHPCYNSGTCVDGDNWYRCECAPGFAGPDCRININECQSSPCAFGA
TCVDEINGYRCVCPPGHSGAKCQEVSGRPCITMGSVIPDGAKWDDDCNT
CQCLNGRIACSKVWCGPRPCLLHKGHSECPSGQSCIPILDDQCFVHPCT
GVGECRSSSLQPVKTKCTSDSYYQDNCANITFTFNKEMMSPGLTTEHIC
SELRNLNILKNVSAEYSIYIACEPSPSANNEIHVAISAEDIRDDGNPIK
EITDKIIDLVSKRDGNSSLIAAVAEVRVQRRPLKNRTDFLVPLLSSVLT
VAWICCLVTAFYWCLRKRRKPGSHTHSASEDNTTNNVREQLNQIKNPIE
KHGANTVPIKDYENKNSKMSKIRTHNSEVEEDDMDKHQQKARFGKQPAY
TLVDREEKPPNGTPTKHPNWTNKQDNRDLESAQSLNRMEYIV

FIG. 8C-2

```
MRSPRTRGRSGRPLSLLLALLCALRAKVCGASGQFELEILSMQNVNGEL
QNGNCCGGARNPGDRKCTRDECDTYFKVCLKEYQSRVTAGGPCSFGSGS
TPVIGGNTFNLKASRGNDRNRIVLPFSFAWPRSYTLLVEAWDSSNDTVQ
PDSIIEKASHSGMINPSRQWQTLKQNTGVAHFEYQIRVTCDDYYYGFGC
NKFCRPDDFFGHYACDQNGNKTCMEGWMGPECNRAICRQGCSPKHGSC
KLPGDCRCQYGWQGLYCDKCIPHPGCVHGICNEPWQCLCETNWGGQLCD
KDLNYCGTHQPCLNGGTCSNTGPDKYQCSCPEGYSGPNCEIAEHACLSD
PCHNRGSCKETSLGFECECSPGWTGPTCSTNIDDCSPNNCSHGGTCQDL
VNGFKCVCPPQWTGKTCQLDANECEAKPCVNAKSCKNLIASYYCDCLPG
WMGQNCDININDCLGQCQNDASCRDLVNGYRCICPPGYAGDHCERDIDE
CASNPCLNGGHCQNEINRFQCLCPTGFSGNLCQLDIDYCEPNPCQNGAQ
CYNRASDYFCKCPEDYEGKNCSHLKDHCRTTPCEVIDSCTVAMASNDTP
EGVRYISSNVCGPHGKCKSQSGGKFTCDCNKGFTGTYCHENINDCESNP
CRNGGTCIDGVNSYKCICSDGWEGAYCETNINDCSQNPCHNGGTCRDLV
NDFYCDCKNGWKGKTCHSRDSQCDEATCNNGGTCYDEGDAFKCMCPGGW
EGTTCNIARNSSCLPNPCHNGGTCVVNGESFTCVCKEGWEGPICAQNTN
DCSPHPCYNSGTCVDGDNWYRCECAPGFAGPDCRININECQSSPCAFGA
TCVDEINGYRCVCPPGHSGAKCQEVSGRPCITMGSVIPDGAKWDDDCNT
CQCLNGRIACSKVWCGPRPCLLHKGHSECPSGQSCIPILDDQCFVHPCT
GVGECRSSSLQPVKTKCTSDSYYQDNCANITFTFNKEMMSPGLTTEHIC
SELRNLNILKNVSAEYSIYIACEPSPSANNEIHVAISAEDIRDDGNPIK
EITDKIIDLVSKRDGNSSLIAAVAEVRVQRRPLKNRTD
```

FIG. 8D-1 atgcgttccccacggacrcgcggccggtccgggcgcccctaagcctcc
tgctcgccctgctctgtgcctgcgagccaaggtgtgtggggcctcggg
tcagttcgagttggagatcctgtccatgcagaacgtgaacggggagctg
cagaacgggaactgctgcggcggcgcccggaacccgggagaccgcaagt
gcaccgcgacgagtgtgacacatacttcaaagtgtgcctcaaggagta
tcagtcccgcgtcacggccggggggcctgcagcttcggctcagggtcc
acgcctgtcatcgggggcaacaccttcaacctcaaggccagccgcggca
acgaccgcaaccgcatcgtgctgcctttcagtttcgcctggccgaggtc
ctatacgttgcttgtggaggcgtgggattccagtaatgacaccgttcaa
cctgacagtattattgaaaaggcttctcactcgggcatgatcaaccca
gccggcagtggcagacgctgaagcagaacacgggcgttgcccactttga
gtatcagatccgcgtgacctgtgatgactactatggctttggctgy
aataagttctgccgccccagagatgacttctttggacactatgcctgtg
accagaatggcaacaaaacttgcatggaaggctggatgggccccgaatg
taacagagctatttgccgacaaggctgcagtcctaagcatgggtcttgc
aaactcccaggtgactgcaggtgccagtayggctggcaaggcctgtact
gtgataagtgcatcccacacccgggatgcgtccacggcatctgtaatga
gccctggcagtgcctctgtgagaccaactggggcggccagctctgtgac
aaagatctcaattactgtgggactcatcagccgtgtctcaacggggggaa
cttgtagcaacacaggccctgacaaatatcagtgttcctgccctgaggg
gtattcaggacccaactgtgaattgctgagcacgcctgcctctctgat
ccctgtcacaacagaggcagctgtaaggagacctccctgggctttgagt
gtgagtgttccccaggctggaccggccccacatgctctacaaacattga
tgactgttctcctaataactgttcccacgggggcacctgccaggacctg
gttaacggatttaagtgtgtgtgcccccacagtggactgggaaaacgt
gccagttagatgcaaatgaatgtgaggccaaaccttgtgtaaacgccaa
atcctgtaagaatctcattgccagctactgcgactgtcttcccggc
tggatgggtcagaattgtgacataaatattaatgactgccttggccagt
gtcagaatgacgcctcctgtcgggatttggttaatggttatcgctgtat
ctgtccacctggctatgcaggcgatcactgtgagagagacatcgatgaa
tgtgccagcaaccctgtttgaatgggggtcactgtcagaatgaaatca
acagattccagtgtctgtgtcccactggtttctctggaaacctctgtca
gctggacatcgattattgtgagcctaatccctgccagaacggtgcccag
tgctacaaccgtgccagtgactatttctgcaagtgccccgaggactatg
agggcaagaactgctcacacctgaaagaccactgccgcacgacccctg
tgaagtgattgacagctgcacagtggccatggcttccaacgacacct
gaagggtgcggtatatttcctccaacgtctgtggtcctcacgggaagt

FIG. 8D-2

```
gcaagagtcagtcgggaggcaaattcacctgtgactgtaacaaaggctt
cacgggaacatactgccatgaaatattaatgactgtgagagcaaccct
tgtagaaacggtggcacttgcatcgatggtgtcaactcctacaagtgca
tctgtagtgacggctgggagggggcctactgtgaaccaatattaatga
ctgcagccagaacccctgccacaatgggggcacgtgtcgcgacctggtc
aatgacttctactgtgactgtaaaatgggtggaaggaaagacctgcc
actcacgtgacagtcagtgtgatgaggccacgtgcaacaacggtggcac
ctgctatgatgaggggatgcttttaagtgcatgtgtcctggcggctgg
gaaggaacaacctgtaacatagcccgaaacagtagctgcctgcccaacc
cctgccataatgggggcacatgtgtggtcaacggcgagtcctttacgtg
cgtctgcaaggaaggctgggagggggcccatctgtgctcagaataccaat
gactgcagccctcatcctgttacaacagcggcacctgtgtggatggag
acaactggtaccggtgcgaatgtgccccgggttttgctgggcccgactg
cagaataaacatcaatgaatgccagtcttccttgtgcctttggagcg
acctgtgtggatgagatcaatggctaccggtgtgtctgccctccagggc
acagtggtgccaagtgccaggaagtttcagggagaccttgcatcaccat
ggggagtgtgataccagatggggccaaatgggatgatgactgtaatacc
tgccagtgcctgaatggacggatcgcctgctcaaaggtctggtgtggcc
ctcgaccttgcctgctccacaaagggcacagcgagtgcccagcgggca
gagctgcatccccatcctggacgaccagtgcttcgtccacccctgcact
ggtgtgggcgagtgtcggtcttccagtctccagccggtgaagacaaagt
gcacctctgactcctattaccaggataactgtgcgaacatcacatttac
ctttaacaaggagatgatgtcaccaggtcttactacggagcacatttgc
agtgaattgaggaatttgaatattttgaagaatgtttccgctgaatatt
caatctacatcgcttgcgagccttcccttcagcgaacaatgaaataca
tgtggccatttctgctgaagatatacgggatgatgggaacccgatcaag
gaaatcactgacaaataatcgatcttgttagtaaacgtgatggaaaca
gctcgctgattgctgccgttgcagaagtaagagttcagaggcggcctct
gaagaacagaacagatttccttgttcccttgctgagctctgtcttaact
gtggcttggatctgttgcttggtgacggccttctactggtgcctgcgga
agcggcggaagccgggcagccacacactcagcctctgaggacaacac
caccaacaacgtgcgggagcagctgaaccagatcaaaaacccattgag
aaacatggggccaacacggtccccatcaaggattacgagaacaagaact
ccaaaatgtctaaataaggacacacaattctgaagtagaagaggacga
catggacaaacaccagcagaaagcccggtttggcaagcagccggcgtat
acgctggtagacagagaagagaagccccccaacggcacgccgacaaaac
acccaaactggacaaacaaacaggacaacagagacttggaaagtgccca
gagcttaaaccgaatggagtacatcgtatag
```

FIG. 8D-3

```
atgcgttccccacggacrcgcggccggtccgggcgcccctaagcctcc
tgctcgccctgctctgtgccctgcgagccaaggtgtgtggggcctcggg
tcagttcgagttggagatcctgtccatgcagaacgtgaacggggagctg
cagaacgggaactgctgcggcggcgcccggaacccgggagaccgcaagt
gcacccgcgacgagtgtgacacatacttcaaagtgtgcctcaaggagta
tcagtcccgcgtcacggccggggggccctgcagcttcggctcaggtcc
acgcctgtcatcgggggcaacaccttcaacctcaaggccagccgcggca
acgaccgcaaccgcatcgtgctgcctttcagtttcgcctggccgaggtc
ctatacgttgcttgtggaggcgtgggattccagtaatgacaccgttcaa
cctgacagtattattgaaaaggcttctcactcgggcatgatcaacccca
gccggcagtggcagacgctgaagcagaacacgggcgttgcccactttga
gtatcagatccgcgtgacctgtgatgactactatggctttggctgy
aataagttctgccgccccagagatgacttctttggacactatgcctgtg
accagaatggcaacaaaacttgcatggaaggctggatgggccccgaatg
taacagagctatttgccgacaaggctgcagtcctaagcatgggtcttgc
aaactcccaggtgactgcaggtgccagtayggctggcaaggcctgtact
gtgataagtgcatcccacacccgggatgcgtccacggcatctgtaatga
gccctggcagtgcctctgtgagaccaactggggcggccagctctgtgac
aaagatctcaattactgtgggactcatcagccgtgtctcaacggggga
cttgtagcaacacaggccctgacaaatatcagtgttcctgccctgaggg
gtattcaggacccaactgtgaaattgctgagcacgcctgcctctctgat
ccctgtcacaacagaggcagctgtaaggagacctccctgggctttgagt
gtgagtgttccccaggctggaccggccccacatgctctacaaacattga
tgactgttctcctaataactgttccacggggggcacctgccaggacctg
gttaacggatttaagtgtgtgtgccccacagtggactgggaaaacgt
gccagttagatgcaaatgaatgtgaggccaaaccttgtgtaaacgccaa
atcctgtaagaatctcattgccagctactactgcgactgtcttcccggc
tggatgggtcagaattgtgacataaatattaatgactgccttggccagt
gtcagaatgacgcctcctgtcgggatttggttaatggttatcgctgtat
ctgtccacctggctatgcaggcgatcactgtgagagagacatcgatgaa
tgtgccagcaaccctgtttgaatgggggtcactgtcagaatgaaatca
acagattccagtgtctgtgtcccactggtttctctggaaacctctgtca
gctggacatcgattattgtgagcctaatccctgccagaacggtgcccag
tgctacaaccgtgccagtgactatttctgcaagtgccccgaggactatg
agggcaagaactgctcacacctgaaagaccactgccgcacgacccctg
tgaagtgattgacagctgcacagtggccatggcttccaacgacacacct
gaaggggtgcggtatatttcctccaacgtctgtggtcctcacgggaagt
```

FIG. 8D-4

```
gcaagagtcagtcgggaggcaaattcacctgtgactgtaacaaaggctt
cacgggaacatactgccatgaaatattaatgactgtgagagcaaccct
tgtagaaacggtggcacttgcatcgatggtgtcaactcctacaagtgca
tctgtagtgacggctgggaggggcctactgtgaaccaatattaatga
ctgcagccagaacccctgccacaatggggcacgtgtcgcgacctggtc
aatgacttctactgtgactgtaaaatgggtggaaggaaagacctgcc
actcacgtgacagtcagtgtgatgaggccacgtgcaacaacggtggcac
ctgctatgatgaggggatgcttttaagtgcatgtgtcctggcggctgg
gaaggaacaacctgtaacatagcccgaaacagtagctgcctgcccaacc
cctgccataatgggggcacatgtgtggtcaacggcgagtcctttacgtg
cgtctgcaaggaaggctgggagggcccatctgtgctcagaataccaat
gactgcagccctcatccctgttacaacagcggcacctgtgtggatggag
acaactggtaccggtgcgaatgtgccccgggttttgctgggcccgactg
cagaataaacatcaatgaatgccagtcttccttgtgcctttggagcg
acctgtgtggatgagatcaatggctaccggtgtgtctgccctccagggc
acagtggtgccaagtgccaggaagtttcagggagaccttgcatcaccat
ggggagtgtgataccagatggggccaatgggatgatgactgtaatacc
tgccagtgcctgaatggacggatcgcctgctcaaaggtctggtgtggcc
ctcgaccttgcctgctccacaaagggcacagcgagtgccccagcgggca
gagctgcatccccatcctggacgaccagtgcttcgtccacccctgcact
ggtgtgggcgagtgtcggtcttccagtctccagccggtgaagacaaagt
gcacctctgactcctattaccaggataactgtgcgaacatcacatttac
ctttaacaaggagatgatgtcaccaggtcttactacggagcacatttgc
agtgaattgaggaatttgaatattgaagaatgtttccgctgaatatt
caatctacatcgcttgcgagccttcccttcagcgaacaatgaaataca
tgtggccatttctgctgaagatacgggatgatgggaacccgatcaag
gaaatcactgacaaataatcgatcttgttagtaaacgtgatggaaaca
gctcgctgattgctgccgttgcagaagtaagagttcagaggcggcctct
gaagaacagaacagat
```

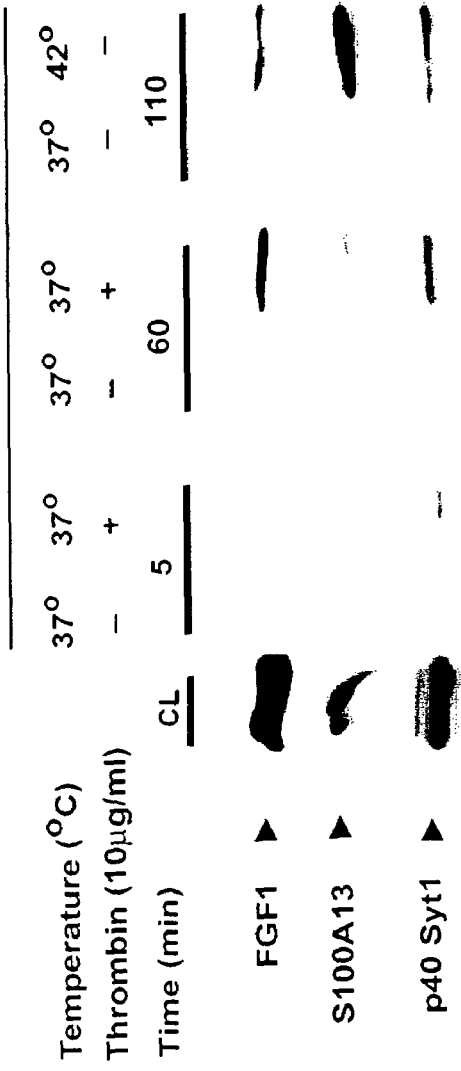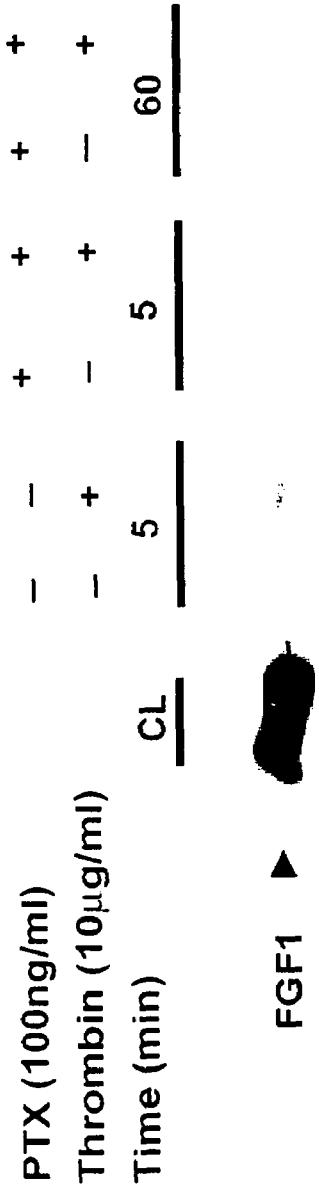
FIG. 9A
FIG. 9B

COMPOSITIONS, METHODS AND KITS RELATED TO THROMBIN, NOTCH SIGNALING AND STAMATOGENESIS AND GROWTH OF STEM CELLS

CROSS-REFERENCE TO RELATED APPLICATIONS

The present application is a continuation of International Patent Application No. PCT/US04/06762, filed on Mar. 5, 2004, now published as WO2004/078944, which is entitled to priority under 35 U.S.C. § 119(e) to U.S. Provisional Patent Application No. 60/542,399, filed Feb. 6, 2004, U.S. Provisional Patent Application No. 60/537,304, filed Jan. 16, 2004, U.S. Provisional Patent Application No. 60/503,363, filed Sep. 15, 2003, and U.S. Provisional Patent Application No. 60/452,425, filed Mar. 5, 2003, each of which application is hereby incorporated herein by reference in its entirety.

STATEMENT REGARDING FEDERALLY SPONSORED RESEARCH OR DEVELOPMENT

This invention was supported in part by US Government funds (National Institutes of Health grant Nos. HL32348, HL35627, HL70865, RR15555, and RR18789), and the US Government may therefore have certain rights in the invention.

BACKGROUND OF THE INVENTION

During the aging process, the number and multipotentiality of quiescent stem cell populations and their representation in developed tissues diminishes (Sommer et al., 2002, Prog. Neurobiol. 66:1-18). A major goal of modem biology is to understand the molecular mechanisms that underlie stem cell self-renewal in hopes of either facilitating the long-term expansion of adult stem cell populations ex vivo without a loss of phenotypic multipotentiality for either therapeutic transplantation strategies or activation and the expansion of stem cell populations to modulate tissue homeostasis in vivo. Attempts to experimentally define molecular phenotypes underlying "stemness" have applied cell and genetic approaches to identify several genes that may affect the self-renewal process including Nanog (Cavaleri et al., 2003, Cell 113:551-552; Chambers et al., 2003, Cell 113:643-655; Hirata et al., 2001, EMBO J. 20:4454-4466; Mitsui et al., 2003, Cell 113:631-642), Nucleostemin (Tsai et al., 2002, Genes Dev. 16:2991-3003), Oct4 (Chambers et al., 2003, Cell 113:643-655; Pan et al., 2002, Cell Res. 12:321-329) and Bmi1 (Park et al., 2004, J. Clin. Invest. 113:175-179). However, the mechanisms that underlie stem cell self-renewal remain to be determined.

Notch signaling plays a key role in normal development through diverse effects on differentiation, survival, and proliferation and these events are highly dependent on signal strength and cellular context (Artavanis-Tsakonas et al., 1995, Science 268:225-232; Kadesch, T., 2000, Exp. Cell. Res. 260:1-8). In the canonical pathway, four Notch transmembrane receptor genes, Notch1-4 (Kadesch, T., 2000, Exp. Cell. Res. 260:1-8), and three transmembrane ligand gene families: Jagged1-3 (Lindsell et al., 1995, Cell 80:909-917; Shawber et al., 1996, Dev. Biol. 180:370-376), Delta1-4 (Bettenhausen et al., 1995, Development 121:2407-2418; Dunwoodie et al., 1997, Development 124:3065-3076; Shutter et al., 2000, Genes Dev. 14:1313-1318) and F3/Contactin (Hu et al., 2003, Cell 115:163-175) have been described to date (Mumm et al., 2000, Dev. Biol. 228:151-165), and these transmembrane ligands activate Notch receptors on neighboring cells (Artavanis-Tsakonas et al., 1995, Science 268:225-232; Iso et al., 2003, Arterioscler. Thromb. Vasc. Biol. 23:543-553; Kimble et al., 1997, Annu. Rev. Cell Dev. Biol. 13:333-361). Notch signaling involves the proteolytic cleavage of Notch which generates an intracellular domain that is able to translocate to the nucleus (Baron, M., 2003, Semin. Cell Dev. Biol. 14:113-119; Radtke et al., 2003, Nat. Rev. Cancer. 3:756-767) and activate CSL1 (for CBF-1/RBPJk/KBF2 in mammals; Su(H) in *Drosophila* and *Xenopus*; and Lag-2 in *C. elegans*) family of transcription factors-dependent transcription (Lai, 2002, EMBO Rep. 3:840-845). In contrast, soluble forms of functional Notch ligands that contain only the extracellular domain have also been described (Hicks et al., 2002, J. Neurosci. Res. 68: 655-667; Qi et al., 1999, Science 283:91-94; Zimrin et al., 1996, J. Biol. Chem. 271:32499-32502). Notch receptors have also been reported to regulate cellular processes through CSL-independent pathways that may involve interactions with other signaling molecules such as NF-κB and Src (Nofziger et al., 1999, Development 126: 1689-1702; Small et al., 2001, J. Biol. Chem. 276:32022-32030; Shawber et al. 1996, Development 122: 3765-3773). Phenotypic analysis of mice null for Notch receptors or their ligands emphasizes the requirement for proper Notch signaling not only during development but in the adult as well (Conlon et al. 1995, Development 121: 1533-1545; Hamada et al., 1999, Development 126: 3415-3424; Jiang et al., 1998, Genes Dev. 12: 1046-1057; Krebs et al., 2000, Genes Dev. 14: 1343-1352; Xue et al., 1999 Hum. Mol. Genet. 8: 723-730). Indeed, aberrant Notch signaling has been implicated in several human pathological conditions including the development of the CADASIL (Joutel et al. 1996, Nature 383: 707-710) and Alagille syndromes (Li et al., 1997, Nat. Genet. 16: 243-251; Li et al., 1997, Nat. Genet. 16: 243-251) and the formation of neoplasias in mice and humans (Rae et al., 2000, Int. J. Cancer 88: 726-732; Rohn et al. 1996, J. Virol. 70: 8071-8080; Zagouras et al., 1995, Proc. Natl. Acad. Sci. USA 92: 6414-6418).

Because perturbations in the regulation of Notch signaling have been implicated in malignant transformation (Maillard et al., 2003, Immunity 19:781-791; Radtke et al., 2003, Nat. Rev. Cancer. 3:756-767) and tumor suppression function (Nicolas et al., 2003, Nat. Genet. 33:416-421; Radtke et al., 2003, Nat. Rev. Cancer. 3:756-767), similar Notch signals may potentially contribute to the expansion of undifferentiated stem cells (Hitoshi et al., 2002, Genes Dev. 16:846-858; Nickoloff et al., 2003, Oncogene 22:6598-6608; Tropepe et al., 2001, Neuron 30:65-78).

The regulation of Notch signaling is vital in the genesis, ontogeny and lineage specification of neural stem cell (NSC) populations (Morrison et al., 2001, Curr. Opin. Cell. Biol. 13:666-672). In the central nervous system, a two-step requirement for Notch signaling in gliogenic differentiation has been proposed (Grandbarbe et al., 2003, Development 130:1391-1402), and these events are required for the maintenance but not formation of neural stem cells (Hitoshi et al., 2002, Genes Dev. 16:846-858). Indeed, populations of NSC have been generated independent of Notch signaling using embryonic stem cells from null mice (Hitoshi et al., 2002, Genes Dev. 16:846-858), and these cells are quickly depleted in the early embryonic brains of mice with diminished Notch signaling capacity as exhibited by RBP-Jkappa(−/−), Notch1 (−/−) and presenillin1 (−/−) mice (Hitoshi et al., 2002, Genes Dev. 16:846-858). However, later in development, Notch signaling is required for astrocytic differentiation of NSC populations (Tanigaki et al., 2001, Neuron 29:45-55). In the peripheral nervous system, the addition of a soluble non-transmembrane form of the Notch ligand, Delta1, to clonally-derived populations of neural crest stem cells (NCSC) leads to an immediate and irreversible loss of neurogenic potential including differentiation into glia (Morrison et al., 2001, Curr. Opin. Cell. Biol. 13:666-672). Interestingly, this response can also be reproduced in NCSC populations by the expression of a constitutively active form of Notch1 (Morrison et al., 2001, Curr. Opin. Cell. Biol. 13:666-672). Therefore, numerous gain-of-function Notch signaling events may contribute to instructive gliogenic NSC differentiation (Wang et al., 2000, Neuron 27:197-200), but the consequences of suppressing endogenous Notch signaling in these oells have not been studied.

Neurological damage in a mammal having as its genesis trauma, tumor formation or a genetic or other component, is very difficult to treat and/or reverse in the mammal. One treatment for neurological damage to the central nervous system is neurotransplantation. Over the last few decades, neurotransplantation has been used to explore the development, plasticity, and regeneration of the central nervous system (McKay, 1997, Science 276:66-71). Also, neurotransplantation has been used to effect the repair and functional restoration of diseased and damaged nervous tissues (Bjorklund, 1993, Nature 362:414-415; Olson, 1997, Nature Med. 3:1329-1335; Spencer et al., 1992, N. Engl. J. Med. 327: 1541-1548: Freed et al., 1992, N. Engl. J. Med. 327:1549-1555; Kordower et al., 1995, N. Engl. J. Med. 332:1118-1124; Defer et al., 1996, Brain 119:41-50; Lopez-Lozano et al., 1997, Transp. Proc. 29:977-980; Rosenstein, 1995, Exp. Neurol. 33:106; Turner et al., 1993, Neurosurg. 33:1031-1037; Kang et al., 1993, J. Neurosci. 13:5203-5211; Andersson et al., 1993, Int. J. Dev. Neurosci. 11:555-568; Sanberg et al., 1997, Nature Med. 3:1129-1132).

In particular, a series of human patients with Parkinson's disease have been treated by neurotransplantation of mesencephalic cells obtained from 6 to 9 week old abortuses of human fetuses (Spencer et al., 1992, N. Engl. J. Med. 327: 1541-1548: Freed et al., 1992, N. Engl. J. Med. 327:1549-1555; Kordower et al., 1995, N. Engl. J. Med. 332:1118-1124; Defer et al., 1996, Brain 119:41-50; Lopez-Lozano et al., 1997, Transp. Proc. 29:977-980). Some of the patients exhibited significant improvement both in clinical symptoms and in the synthesis of dopamine, as assessed by fluorodopa uptake using positron-emission tomography (Spencer et al., 1992, N. Engl. J. Med. 327:1541-1548; Freed et al., 1992, N. Engl. J. Med. 327:1549-1555; Kordower et al., 1995, N. Engl. J. Med. 332:1118-1124; Defer et al., 1996, Brain 119:41-50). However, the process of obtaining fetal tissue for therapeutic uses has presented major logistic and ethical barriers (Rosenstein, 1995, Exp. Neurol. 33:106; Turner et al., 1993, Neurosurg. 33:1031-1037). Also, only about 5 to 10% of dopaminergic neurons survive, apparently because of adverse immune reaction to the same (Lopez-Lozano et al., 1997, Transp. Proc. 29:977-980) and because the fetal tissue is primarily dependent on lipid instead glycolytic metabolism (Rosenstein, 1995, Exp. Neurol. 33:106). For these reasons, attempts have been made to develop alternative cells such as fibroblasts (Kang et al., 1993, J. Neurosci. 13:5203-5211), fetal astrocytes (Andersson et al., 1993, Int. J. Dev. Neurosci. 11:555-568), and sertoli cells (Sanberg et al., 1997, Nature Med. 3:1129-1132) which are suitable for neurotransplantation.

In order to treat diseases, disorders, or conditions of the central nervous system, such as for example brain tumors, brain trauma, Huntington's disease, Alzheimer's disease, Parkinson's disease, and spinal cord injury, by transplantation, donor cells should be easily available, capable of rapid expansion in culture, immunologically inert, capable of long term survival and integration in the host brain tissue, and amenable to stable transfection and long-term expression of exogenous genes (Bjorklund, 1993, Nature 362:414-415; Olson, 1997, Nature Med. 3:1329-1335). Thus, there is a long-felt and acute need for methods for clonally expanding a stem cell, and stem cells produced thereby, for use in regenerative medicine, or therapeutic cloning. Therefore, there is a long-felt need for methods to create pluripotent stem cells that are genetically matched to a patient in order to generate personalized tissues that would combat the ravages of aging and disease without organ rejection or other complications that plague conventional transplant therapy.

The advantage of using autologous adult stem cells for regenerative medicine lies in the fact that they are derived from and returned to the same patient, and are therefore not subject to immune-mediated rejection. The major drawback is that these cells lack the plasticity and pluripotency of ES cells and thus their potential is uncertain. To overcome this hurdle, much attention has been directed towards bone marrow cells, which can differentiate into such diverse tissues as bone, cartilage, and muscle (Pittenger et al., 1999, Science 284:143-147). It has also been shown that mouse bone marrow cells, when injected directly into infracted mouse hearts, can develop into myocytes and vascular structures (Orlic et al., 2001, Nature 410:701-705). Similar experiments have shown that mouse bone marrow cells delivered intravascularly are able to migrate to the central nervous system and eventually exhibit neuron-like phenotypes (Brazelton et al., 2000, Science 290:1775-1779; Mezey et al., 2000, Science 290:1779-1782).

The regenerative capacity of adult cells is not limited to those stem cells obtained derived from bone marrow. That is, neural stem cells are capable of differentiating into blood cells when transplanted into bone marrow (Bjornson et al., 1999, Science 283:534-537). However, although these results are promising, the number of pluripotent bone marrow and neural stem cells is limited. Although the ability to produce large number of pluripotent stem cells would have immediate clinical applications, such as the generation of lines from patients (e.g., cancer, cardiovascular diseases, and neurodegenerative diseases) which would provide cell-based therapy to cure these diseases, the clonal expansion of these cells has not been possible. Thus, there is an acute need for methods for clonally expanding pluripotent human stem cells without loss of pluripotency, and cells produced thereby for use in numerous therapies, and the present invention meets these needs.

The functional integrity of the human vascular system is maintained by the endothelial cell which monitors the non-thrombogenic interface between blood and tissue in vivo. Thus, factors that influence human endothelial cell function may contribute significantly to the regulation and maintenance of homeostasis (see Maciag, 1984, In: Progress in Hemostasis and Thrombosis, pp. 167-182, Spaet, ed., A. R. Liss, New York; Folkman and Klagsburn, 1987, Science 235: 442-447; Burgess and Maciag, 1989, Annu. Rev. Biochem. 58:575-606). Likewise, events that perturb this complex equilibrium are relevant to the pathophysiology of human disease states in which cellular components of the vascular tree are active participants including, e.g., atherogenesis, coronary insufficiency, hypertension, rheumatoid arthritis, solid tumor growth and metastasis, and wound repair.

Since the endothelium is present in all organs and tissues, endothelial cell function is also fundamental to the physiology and integration of these multicellular systems. This includes the ability to monitor and interface with repair systems that employ the tightly regulated inflammatory, angiogenic and neurotropic responses. Indeed, biochemical signals that are responsible for the modification of these responses have been well characterized as polypeptide growth factors and cytokines; however, their mechanisms of operation have, prior to the present invention, been poorly understood, impeding their acceptance as valuable tools in clinical management.

During the past decade, differential cDNA cloning methods, including e.g., conventional subtractive hybridization (Hla and Maciag, 1990, Biochem. Biophys. Res. Commun. 167:637-643), differential polymerase chain reaction (PCR)-oriented hybridization (Hla and Maciag, 1990, J. Biol. Chem. 265:9308-9313), and more recently, a modification of the differential display (Zimrin et al., 1995, Biochem. Biophys. Res. Commun. 213:630-638) were used to identify genes induced during the process of human umbilical vein endothelial cell (HUVEC) differentiation in vitro. Very early studies disclosed that HUVEC populations are able to generate capillary-like, lumen-containing structures when introduced into a growth-limited environment in vitro (Maciag et al., 1982, J. Cell Biol. 94:511-520). These studies permitted the identification and characterization of protein components of the extracellular matrix as inducers of this differentiation process, while at the same time defining the capillary-like structures as non-terminally differentiated (Maciag, 1984, In: Progress in Hemostasis and Thrombosis, pp. 167-182, Spaet, ed., A. R. Liss, New York). Additional experiments have elucidated the importance of polypeptide cytokines, such as IL-1 (Maier et al., 1990, J. Biol. Chem. 265:10805-10808) and IFNγ (Friesel et al., 1987, J. Cell Biol. 104:689-696), as inducers of HUVEC differentiation in vitro, and ultimately lead to an understanding that the precursor form of IL-1α was responsible for the induction of HUVEC senescence in vitro (Maciag et al., 1981, J. Cell Biol. 91:420-426; Maier et al., 1990, Science 249:1570-1574).

Recent research has employed differential cDNA cloning methods, which permits the identification of new and very interesting genes. However, until very recently, establishing their identity did not provide insight into the mechanism of HUVEC differentiation. Current research has focused upon the fibroblast growth factor (FGF) and interleukin (IL)-1 gene families as regulators of the angiogenesis process, both in vitro and in vivo (Friesel et al., 1995, FASEB J. 9:919-925; Zimrin et al., 1996, J. Clin. Invest. 97:1359). The human umbilical vein endothelial cell (HUVEC) has proven to be an effective model for studying the signal pathways utilized by FGF-1 to initiate HUVEC migration and growth, the role of IL-1α as an intracellular inhibitor of FGF-1 function and modifier of HUVEC senescence, and the interplay between the FGF and the IL-1 gene families as key effectors of HUVEC differentiation in vitro. Such insight has enabled the present inventors to use modem molecular methods to identify a key regulatory ligand-receptor signaling system, which is able to both induce capillary endothelial cell migration and repress large vessel endothelial cell migration.

Because members of the fibroblast growth factor (FGF) family are also known as potent regulators of developmental, physiological and pathophysiologic events in mammals, the FGF family has been the subject of numerous comprehensive reviews related to the field of cellular differentiation. (See, e.g., Burgess and Maciag, 1989, Annu. Rev. Biochem. 58: 575-606; Friesel and Maciag, 1995, FASEB J. 9: 919-925; Rifkin and Moscatelli, 1989, J. Cell Biol. 109: 1-6; Klagsbrun and Baird, 1991, Cell 67: 229-231. The best characterized members of the FGF family are FGF-1 (acidic FGF) and FGF-2 (basic FGF). These two proteins are unusual growth factors in that they lack a classical signal sequence to direct their secretion through the conventional endoplasmic reticulum (ER)-Golgi apparatus. Ligation of a signal sequence to the FGF prototypes yields functional extracellular ligands with potent transforming potential in vitro and the ability to induce exaggerated angiogenic and neurotropic phenomena in vivo including the generation of atheroma-like lesions.

Because the mitogenic activities of FGF-1 and FGF-2 are mediated by a high affinity receptor at the plasma membrane surface, it has been proposed that a tightly regulated, yet unconventional, export pathway exists to regulate the export of these growth factors. Consequently, the regulation of human endothelial cell growth and the role of FGF-1 in mediating this process in vivo has been the subject of a number of studies. See, e.g., Maciag et al., 1979, Proc. Natl. Acad. Sci. USA 76: 5674-5678; Maciag et al., 1981, J. Cell Biol. 91: 420-426; Maciag et al., 1982, J. Cell Biol. 94: 511-520; Maciag et al., 1984, Science 225: 932-935).

The addition of a signal sequence (ss) to either FGF-1 or FGF-2 established the function of genes encoding these modified FGF proteins as transforming genes in a variety of target cells. See, e.g., Rogelj et al., 1988, Nature 331: 173-175; Blam et al., Oncogene. 3: 129-136); Jouanneau et al., 1991, Proc. Natl. Acad. Sci. USA 88: 2893-2897; Talarico and Basilico, 1991, Mol. Cell. Biol. 11:1138-1145; Forough et al., 1993, J. Biol. Chem. 268: 2960-2968). In vivo expression studies in the porcine iliac artery using a liposome:vector gene transfer method demonstrate an exaggerated hypertrophic response to the presence of extracellular FGF-1 including the formation of a prominent neointima containing numerous capillary and aorta-like structures (Nabel et al., 1993, Nature 362: 844-846). In a similar manner, a transgene expressing a FGF-44$_{(ss)}$:FGF-1 chimera under control of the α-crystallin promoter, which is active during lens development in the eye, induces a hypertrophic response that includes inappropriate formation of blood vessels and nerve bundles in the lens (Overbeek et al., 1994, Development).

In both studies, the transfer of the wild-type FGF-1 cDNA failed to yield pathologic consequences. Prior studies (e.g., Thompson et al., 1988, Science 241: 1349-1352) have suggested that FGF-1 may have evolved without a functional signal sequence because expression would be accompanied by inappropriate export during certain situations, resulting in the formation of exaggerated vascular and neuronal structures. Thus, it appears that the pathway for FGF-1 export is tightly regulated in order to control the angiogenic and neurogenic activities of the protein.

Thrombin is also known to play a role in angiogenesis, as well as modulation of cell growth and differentiation. Thrombin is able to elicit many cellular responses, including those that are thrombotic, inflammatory, proliferative and atherosclerotic. Such thrombin-mediated cellular responses are mediated by proteolytic activation of a specific cell surface receptor known as the thrombin receptor, which is a tethered ligand receptor (Vu et al., 1991, Cell 64: 1057-1068; Rasmussen et al., 1991, FEBS Lett. 288: 123-128; Zhong et al., 1992, J. Biol. Chem. 267: 16975-16979; Bahou et al., 1993, J. Clin. Invest. 91: 1405-1413; McNamara et al., 1993, J. Clin. Invest. 91: 94-98; Glembotski, 1993, J. Biol. Chem. 268: 20646-20652; and Park et al., 1994, Cardiovasc. Res. 28: 1263-1268). The thrombin receptor has seven transmembrane-spanning domains and belongs to the family of G-protein coupled receptors (Vu et al., 1991, Cell 64: 1057-1068 and Schwartz, 1994, Current Opin. Biotechnol. 5: 434-444). Activation of the receptor occurs by thrombin cleavage of an extracellular N-terminal domain. The new N-terminus—through intramolecular interaction—activates the receptor (Vu et al., 1991, Cell 64: 1057-1068; Coughlin, 1993, Thromb. Haemostas. 70: 184-187; Van Obberghen-Schilling and Pouyssegur, 1993, Thromb. Haemostas. 70: 163-167; Brass et al., 1994, Ann. NY Acad. Sci. 714: 1-12).

Thrombin is also known to have a variety of activities in different cell types and thrombin receptors are known to be present in such cell types as human platelets, vascular smooth muscle cells, endothelial cells and fibroblasts. For example, thrombin is important in periodontal wound healing and associated inflammatory processes by promoting the growth and contraction of gingival fibroblasts (Chang et al., 2001, J. Periodontol. 72:303-13). Such periodontal stimulatory effects of thrombin are associated with its protease activation of thrombin receptors. It follows that substances with the ability to mediate the function of thrombin may be useful in the treatment of thrombotic, inflammatory, atherosclerotic and fibroproliferative disorders, as well as other disorders in which thrombin and its receptor play a pathological role.

In addition to the thrombin and FGF-1 signaling systems, the Jagged/Serrate/Delta-Notch/Lin/Glp signaling system, originally described during the development of *C. elegans* and *Drosophila*, is a cell signaling system with a critical role in cellular growth and differentiation. The Jagged/Serrate/Delta-Notch/Lin/Glp signaling system, instrumental in cell fate decisions, has been found to be highly conserved in mammalian cells (Nye and Kopan, 1995, Curr. Biol. 5:966-969). Notch proteins comprise a family of closely-related transmembrane receptors initially identified in embryologic studies in *Drosophila* (Fortini and Artavanis-Tsakonas, 1993, Cell 75:1245-1247). The genes encoding the Notch receptor show a high degree of structural conservation, and contain multiple EGF repeats in their extracellular domains (Coffinan et al., 1990, Science 249:1438-1441; Ellisen et al., 1991, Cell 66:649-661; Weinmaster et al., 1991, Development 113:199-205; Weinmaster et al., 1992, Development 116:931-941; Franco del Amo et al., 1992, Development 115:737-744; Reaume et al., 1992, Dev. Biol. 154:377-387; Lardelli and Lendahi, 1993, Mech. Dev. 46:123-136; Bierkamp and Campos-Ortega, 1993, Mech. Dev. 43:87-100; Lardelli et al., 1994, Exp. Cell Res. 204:364-372). In addition to the thirty-six EGF repeats within the extracellular domain of Notch 1, there is a cys-rich domain composed of three Notch Lin Glp (NLG) repeats, which is important for ligand function, followed by a cys-poor region between the transmembrane and NLG domain.

The intracellular domain of Notch 1 contains six ankyrin/Cdc10 repeats positioned between two nuclear localization sequences (NLS) (Artavanis-Tsakonas et al., 1995, Science 268:225-232). This motif is found in many functionally diverse proteins (see, e.g., Bork, 1993, Proteins 17:363-374), including members of the Rel/NF-κB family (Blank et al., 1992, TIBS 17:135-140), and is thought to be responsible for protein-protein interactions. Notch has been shown to interact with a novel ubiquitously distributed cytoplasmic protein deltex through its ankyrin repeats, a domain shown by deletion analysis to be necessary for activity (Matsuno et al., 1995, Development 121:2633-2644).

Several Notch ligands have been identified in vertebrates, including Delta, Serrate and Jagged. The Notch ligands are also transmembrane proteins, having highly conserved structures. These ligands are known to signal cell fate and pattern formation decisions through the binding to the Lin-12/Notch family of transmembrane receptors (Muskavitch and Hoffmann, 1990, Curr. Top. Dev. Biol. 24:289-328; Artavanis-Tsakonas and Simpson, 1991, Trends Genet. 7:403-408; Greenwald and Rubin, 1992, Cell 68:271-281; Gurdon, 1992, Cell 68:185-199; Fortini and Artavanis-Tsakonas, 1993, Cell 75:1245-1247; and Weintraub, 1993, Cell 75:1241-1244). A related protein, the Suppressor of hairless (Su(H)), when co-expressed with Notch in *Drosophila* cells, is sequestered in the cytosol, but is translocated to the nucleus when Notch binds to its ligand Delta (Fortini and Artavanis-Tsakonas, 1993, Cell 75:1245-1247). Studies with constitutively activated Notch proteins missing their extracellular domains have shown that activated Notch suppresses neurogenic and mesodermal differentiation (Coffinan et al., 1993, Cell 73:659-671; Nye et al., 1994, Development 120:2421-2430).

The Notch signaling pathway, which is activated by Jagged1 in the endothelial cell, involves cleavage of the intracellular domain by a protease, followed by nuclear trafficking of the Notch fragment and the interaction of this fragment with the $KBF_2/RBP-J_k$ transcription factor (Jarriault et al., 1995, Nature 377:355-358; Kopan et al., 1996, Proc. Natl. Acad. Sci. USA 93:1683-1688), a homolog of the *Drosophila* Suppressor of hairless gene (Schweisguth et al., 1992, Cell 69:1199-1212), a basic helix-loop-helix transcription factor involved in Notch signaling in insects (Jennings et al., 1994, Development 120:3537-3548) and in the mouse (Sasai et al., 1992, Genes Dev. 6:2620-2634). This effector is able to repress the transcriptional activity of other genes encoding transcription factors responsible for entry into the terminal differentiation program (Nye et al., 1994; Kopan et al., 1994, J. Cell. Physiol. 125:1-9).

The Jagged1 gene encodes a transmembrane protein which is directed to the cell surface by the presence of a signal peptide sequence (Lindsell et al., 1995, Cell 80:909-917). While the intracellular domain contains a sequence with no known homology to intracellular regions of other transmembrane structures, the extracellular region of the ligand contains a cys-rich region, 16 epidermal growth factor (EGF) repeats, and a DSL (Delta Serrate Lag) domain. The DSL domain as well as the EGF repeats, are found in other genes including the *Drosophila* ligands, Serrate (Baker et al., 1990, Science 250:1370-1377; Thomas et al., 1991, Development 111:749-761) and Delta (Kopczynski et al., 1988, Genes Dev. 2:1723-1735), and *C. elegans* genes Apx-1 (Henderson et al., 1994, Development 120:2913-2924; Mello et al., 1994, Cell 77:95-106) and Lag-2 (Tax et al., 1994, Nature 368:150-154).

Until the discovery of the invention disclosed in International Application WO 97/45143 (the disclosure of which is incorporated by reference herein in its entirety), human Jagged1 remained undefined and the function and relationship, if any, of the human ligand to Notch remained unknown in the art. The human Jagged1 gene and soluble forms thereof have now been cloned, isolated and defined, and the Jagged1-Notch role in endothelial cell differentiation and/or migration has been elucidated. The novel Jagged1-Notch signaling pathway produces disparate effects on the migration of large and small vessel endothelial cells, providing what appears to be the first demonstration of a signaling difference between large and small vessel endothelial cells both in degree and direction. This highlights the potential function of a previously unknown ligand-receptor signaling pathway in the endothelial cell which is modulated during the migratory phase of angiogenesis. WO 97/45143 also discloses the previously unresolved phenomenon in which endothelial cells have been shown to reproducibly differentiate into a non-terminal and completely reversible tubular-like cell phenotype in vitro (Maciag et al., 1982, J. Cell Biol. 94:511-520). Further, the WO 97/45143 also discloses a method for preventing the undesirable migration of specific cell types into large blood vessels following angioplastic surgery to control restenosis.

It is desirable to identify the bases of cellular differentiation, with the ultimate goal of gaining the understanding and ability to provide targeted, precise therapy to patients in need of therapy for differentiation-related disorders, such as those affecting inflammatory responses, atherogenic responses, and neurotropic responses. For example, in view detrimental effects that may ensue as a result of FGF-1 export, effective regulation is needed. International Patent Publication No. WO 03/018595A2 of Maciag et al. (incorporated by reference herein in its entirety) discloses that FGF-1 is exported in response to various stimuli, including stressors (such as temperature stress), as an FGF-1 complex comprising, inter alia, p40 Syn1 and S100A13. Formation of the FGF-1 complex may also be cofactor-mediated, and complexation of FGF-1 with Syn-1 may occur under "non-stress" conditions as well. Further, complexes including FGF-1 and Syn-1 may be involved in processes of FGF-1 export and regulation.

Characterization of FGF-1 as a potent promoter of angiogenesis when elaborated into the extracellular milieu in vivo links FGF-1 to physiologic regulation of FGF-1 export (see, e.g., Folkman et al., 1987, Science 235:442-447) associated with numerous disease processes. There is a long-term unfulfilled need to develop therapeutics for such disease processes as inflammation, thrombosis, and to regulate angiogenesis, and to provide treatment, and even preventative therapy, to patients in need thereof. The present invention fills these needs.

BRIEF SUMMARY OF THE INVENTION

The invention includes a method for producing a population of pluripotent stem cells. The method comprises expanding a stem cell wherein the cell is contacted with an effective amount of a factor selected from the group consisting of thrombin, soluble Jagged1 (sJ1), and thrombin receptor-activated peptide (TRAP), and combinations thereof, thereby producing a population of pluripotent stem cells.

In one aspect, the stem cell is selected from the group consisting of a neural stem cell and a neural crest stem cell.

The invention includes a method for expanding a pluripotent stem cell without detectable loss of pluripotency. The method comprises contacting a pluripotent stem cell with a differentiation inhibiting amount of at least one factor selected from the group consisting of thrombin, soluble Jagged1 (sJ1), and thrombin receptor-activated peptide (TRAP), thereby expanding a pluripotent stem cells without detectable loss of pluripotency.

The invention also includes a method for clonally expanding a stem cell. The method comprising administering a differentiation inhibiting amount of at least one inhibitor of Notch-signaling selected from the group consisting of thrombin, soluble Jagged1 (sJ1), and thrombin receptor-activated peptide (TRAP) to a stem cell under conditions wherein the cell proliferates, thereby clonally expanding the stem cell.

The invention includes a method for producing a population of multipotent stem cells. The method comprises contacting a multipotent stem cell with a differentiation inhibiting amount of a factor selected from the group consisting of thrombin, sJ1, and TRAP, under conditions wherein the cell proliferates, thereby producing a population of multipotent stem cells.

The invention includes a method for inducing the rapid release of fibroblast growth factor 1 (FGF-1) from a cell. The method comprises contacting the cell with an effective amount of thrombin, thereby inducing the rapid release of FGF-1 from the cell.

The invention includes a method for inducing the rapid release of a complex comprising fibroblast growth factor 1 (FGF-1) from a cell. The method comprises contacting the cell with an effective amount of thrombin, thereby inducing the rapid release of a complex comprising FGF-1 from the cell.

In one aspect, the complex further comprises S100A13.

In another aspect, the complex further comprises p40 synaptotagmin 1.

The invention includes a method for expanding a multipotent stem cell without detectable loss of multipotentiality. The method comprises growing a multipotent stem cell wherein the cell is contacted with a differentiation inhibiting amount of thrombin, thereby expanding a multipotent stem cell without detectable loss of multipotentiality.

In one aspect, the method further comprises contacting the cell with a differentiation inhibiting amount of sJ1.

In another aspect, the method further comprises contacting the cell with a differentiation inhibiting amount of TRAP.

In yet another aspect, the method further comprises contacting the cell with a differentiation inhibiting amount of TRAP.

The invention includes a method for producing a population of undifferentiated stem cells. The method comprises culturing a stem cell in medium comprising an effective amount of at least one factor selected from the group consisting of thrombin, sJ1, and TRAP, wherein the factor inhibits differentiation of the cell, thereby producing a population of undifferentiated stem cells.

The invention includes a method for producing a population of pluripotent stem cells. The method comprises culturing a stem cell in medium comprising an effective amount of at least one factor selected from the group consisting of thrombin, sJ1, and TRAP, wherein the factor inhibits differentiation of the cell, thereby producing a population of pluripotent stem cells.

The invention includes a method for releasing soluble Jagged1 from a cell. The method comprises contacting a cell expressing Jagged1 with a cleaving agent in an amount sufficient to release the soluble Jagged1 from the cell, thereby releasing soluble Jagged1 from the cell.

In one aspect, the cleaving agent is thrombin, or an active portion thereof.

In another aspect, the soluble Jagged1 is released by cleavage of Jagged1 by the thrombin, or an active portion thereof.

The invention includes a method for cleaving Jagged1 to produce soluble Jagged1. The method comprises contacting a Jagged1 with a cleaving agent in an amount sufficient to cleave the Jagged1 to release the soluble Jagged1, thereby producing soluble Jagged1.

In one aspect, the cleaving agent is thrombin, or an active portion thereof.

In another aspect, the soluble Jagged1 comprises amino acids 1-1067 of Jagged1.

The invention includes a method for inducing FGF-1 export from a cell. The method comprises contacting a cell with a cleaving agent in an amount sufficient to induce export of FGF-1 from a cell, wherein the cleaving agent cleaves Jagged1 to release soluble Jagged1, and further wherein the soluble Jagged1 binds a Notch receptor on the cell, thereby inducing FGF-1 export from the cell.

In one aspect, the cleaving agent is thrombin.

In another aspect, the FGF-1 export occurs within about one hour.

In yet another aspect, the cleaving agent cleaves a thrombin receptor on the cell.

The invention includes a method for inhibiting thrombosis. The method comprises administering a cleaving agent in an amount sufficient to cleave Jagged1 to release soluble Jagged1, wherein the soluble Jagged1 binds a Notch receptor, thereby inhibiting Notch signaling, thereby inhibiting thrombosis.

In one aspect, the cleaving agent is thrombin.

The invention includes a method for affecting angiogenesis. The method comprises administering a cleaving agent in an amount sufficient to cleave Jagged1 to release soluble Jagged1, wherein the soluble Jagged1 binds a Notch receptor, thereby affecting angiogenesis in the cell.

In one aspect, the cleaving agent is thrombin.

In another aspect, the Jagged1 is expressed on a cell.

In yet another aspect, the soluble Jagged1 binding with the Notch receptor inhibits Notch signaling in the cell and further wherein the signaling is required for angiogenesis.

The invention includes a method for inhibiting interleukin alpha 1 (IL-1α) release from a cell. The method comprises administering a cleaving agent in an amount sufficient to cleave Jagged1 to release soluble Jagged1, wherein the soluble Jagged1 binds a Notch receptor on the cell thereby inhibiting Notch signaling in the cell, and further wherein the signaling is required for IL-1α release, thereby inhibiting IL-1α release from the cell.

In one aspect, the cleaving agent is thrombin.

In another aspect, the thrombin cleaves a thrombin receptor.

The invention includes a method for inducing fibroblast growth factor 1 (FGF-1) mRNA expression in a cell. The method comprises administering a cleaving agent in an amount sufficient to cleave Jagged1 to release soluble Jagged1, wherein the soluble Jagged1 binds a Notch receptor on the cell and further wherein the binding of soluble Jagged1 with the Notch receptor induces expression of FGF-1 mRNA in the cell, thereby inducing FGF-1 mRNA expression in the cell.

In one aspect, the cleaving agent is thrombin.

The invention includes a method for inhibiting Notch receptor signaling in a cell. The method comprises administering a cleaving agent in an amount sufficient cleave Jagged1 to release soluble Jagged1, wherein the soluble Jagged1 binds a Notch receptor on the cell, thereby inhibiting Notch receptor signaling in the cell.

In one aspect, the cleaving agent is thrombin.

The invention includes a method for inhibiting expression of type I collagen in a cell, the method comprising administering a cleaving agent in an amount sufficient to cleave Jagged1 to release soluble Jagged1, wherein the soluble Jagged1 binds a Notch receptor and further wherein binding of the soluble Jagged1 with the Notch receptor inhibits type I collagen expression, thereby inhibiting expression of type I collagen in the cell.

The invention includes a method for inhibiting cleavage of Jagged1 in a cell. The method comprises contacting the cell with an effective amount of a cleavage inhibitor, thereby inhibiting cleavage of Jagged1 in the cell.

In one aspect, the cleavage of Jagged1 is mediated by thrombin to produce soluble Jagged1.

In another aspect, the cleavage inhibitor binds with thrombin to inhibit the protease activity of the thrombin.

In yet another aspect, the cleavage inhibitor binds with Jagged1 and wherein the binding inhibits thrombin cleavage of the Jagged1.

The invention includes a method for inhibiting production of soluble Jagged1 by a cell. The method comprises contacting a cell expressing Jagged1 with a cleavage-inhibiting amount of a cleavage inhibitor, thereby inhibiting production of soluble Jagged1 in the cell.

In one aspect, the cleavage inhibitor inhibits cleavage of Jagged1 by thrombin.

In another aspect, the cleavage inhibitor is a thrombin protease inhibitor.

The invention includes a kit for producing a population of pluripotent stem cells. The kit comprises an effective amount of at least one factor selected from the group consisting of thrombin, sJ1, and TRAP. The kit further comprises an applicator and an instructional material for the use of the kit.

In one aspect, the factor is thrombin.

In another aspect, the kit further comprises sJ1.

The invention includes a kit for expanding a pluripotent stem cell without detectable loss of pluripotency. The kit comprises a differentiation inhibiting amount of at least one factor selected from the group consisting of thrombin, soluble Jagged1 (sJ1), and thrombin receptor-activated peptide (TRAP). The kit further comprises an applicator and an instructional material for the use of the kit.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIGS. 2A and 2B, demonstrates the requirement of FGF1 signaling and Notch repression in anchorage-independent growth.

FIG. 3, comprising FIGS. 3A-1 through 3A-4 and FIGS. 3B-1 through 3B-4, demonstrates that the expression of activated notch suppressed spheroid formation and colony growth in soft agar in hst-β(FGF4):FGF1 NIH 3T3 cell transfectants. FIGS. 3A-1 through 3A-4 depict colony formation in soft agar exhibited by hst-β(FGF4):FGF1 NIH 3T3 cell transfectants adenovirally transduced with either lacZ (FIG. 3A-1), dnFGFR1 (FIG. 3A-2), caN1 (FIG. 3A-3) or caN2 (FIG. 3A-4). Positive colonies were visualized by staining with p-iodonitrotetrazolium violet two weeks after plating. FIGS. 3B-1 through 3B-4B depicts phase-contrast photomicrographs of hst-β(FGF4):FGF1 NIH 3T3 cell transfectants adenovirally transduced with either lacZ (FIG. 3B-1), dnF-GFR1 (FIG. 3B-12, caN1 (FIG. 3B-3) or caN2 (FIG. 3B-4).

FIG. 4, comprising FIGS. 4A-4B, demonstrates the regulation of FGF/FGFR gene expression by soluble Jagged1.

FIG. 4B depicts the expression of FGFR family members in vector control and sJ1 NIH 3T3 stable transfectants as determined by RT-PCR using primers and conditions as described elsewhere herein. Each primer set was designed to detect both the 2 and 3-IG loop forms for FGFR1, FGFR2 and FGFR3 as well as the VT− and VT+ isoforms of FGFR1.

FIG. 5, comprising FIGS. 5A-5B, demonstrates that the inhibition of Notch induced secretion of FGF1 under normal growth conditions.

FIG. 6, comprising FIGS. 6A-6C demonstrates that FGF1 suppressed caN1/CSL-activated transcription.

FIG. 8 comprising FIGS. 8A-8D demonstrates the cleavage of Jagged1 by thrombin.

FIG. 8C-1 depicts the amino acid sequence of full-length human Jagged1 (SEQ ID NO:1). FIG. 8C-2 depicts the amino acid sequence of soluble Jagged1 (sJ1, [SEQ ID NO:3]), comprising from residue number 1 through number 1067, corresponding to amino acid residues of full-length human Jagged1 (SEQ ID NO:1).

FIGS. 8D-1 through 8D-2 set forth the nucleotide sequence of a nucleic acid encoding full-length human Jagged1 (SEQ ID NO:2). FIGS. 8D-3 through 8D-4 sets forth the nucleotide sequence of a nucleic acid encoding human soluble Jagged1 (SEQ ID NO:4), corresponding to the nucleic acid encoding amino acid residues 1-1067 relative to full-length human Jagged1.

FIG. 9, comprising FIGS. 9A-9C, demonstrates non-classical release of FGF1 induced by thrombin. FIG. 9A is an image depicting an immunoblot analysis demonstrating the rapid release of FGF1, S100A13, p40 Syt1 at 37° C. induced by thrombin. FGF1, Myc and Syt1 immunoblot analysis was used to identify the presence of FGF1R136K, S100A13:Myc and p40Syt1 in media conditioned by FGF1R136K NIH 3T3 cell transfectants adenovirally transduced with either S100A13:Myc or p40 Syt1 at 37° C. following the addition of 10 μg/ml α-thrombin for 5 and 60 minutes. Analysis of the medium conditioned in the absence of α-thrombin or by heat shock (42° C., 110 minutes) served as controls. Cell lysates (CL) from these cells are shown in the left panel. FIG. 9B demonstrates that the thrombin-induced release of FGF1 is blocked by pertussis toxin (PTX). FIG. 9B depicts an FGF1 immunoblot analysis of media conditioned by FGF1R136K NIH cell transfectants after 1 hour of pretreatment in the presence and absence of 10 μg/ml α-thrombin. PTX (100 ng/ml) and/or thrombin treatment did not affect the cytosolic levels of FGF1 and a representative cell lysate (CL) is shown in the left panel. FIG. 9C depicts an FGF1 immunoblot analysis of media conditioned by FGF1R136K NIH 3T3 cell transfectants in response to the addition of 5 μM TRAP for 5 and 60 minutes. The release of FGF1R136K in response to heat shock in the absence of TRAP is also shown as well as a representative cell lysate (left panel). FIG. 9D depicts an FGF1 immunoblot analysis media conditioned by PAR1 null cells 5 and 60 minutes after the addition of 10 μg/ml of α-thrombin. FGF1 immunoblot analysis of media conditioned by heat shock served as a positive control.

FIG. 10, comprising FIGS. 10A-10C, demonstrates FGF1 transcription is induced by soluble Jagged1 and thrombin.

FIG. 11, comprising FIGS. 11A-11D, demonstrates that the thrombin-induced release of FGF1 is suppressed by the activation of Notch1 signaling.

FIG. 12, comprising FIGS. 12A-12D, demonstrates that sJ1 and thrombin mediates FGF1.A transcript expression and clonogenic activity.

FIG. 13, comprising FIGS. 13A and 13D, demonstrates that the expansion of neural stem cells is enhanced in the presence of sJ1 and thrombin.

FIG. 14, comprising FIGS. 14A and 14B, demonstrates a role for sJ1 and thrombin in the stamatogenic expansion of NCSC populations. Secondary NCSC population were generated from founder NCSC clones after 13 days of growth in Morrison media supplemented either with 7.5 nM sJ1 (▲-▲), 5 μg/ml α-thrombin (▼-▼), 5 μM TRAP (♦-♦) or no additive (control; ■-■) and compared to freshly isolated populations of NCSC (●-●).

DETAILED DESCRIPTION OF THE INVENTION

Figure 1:
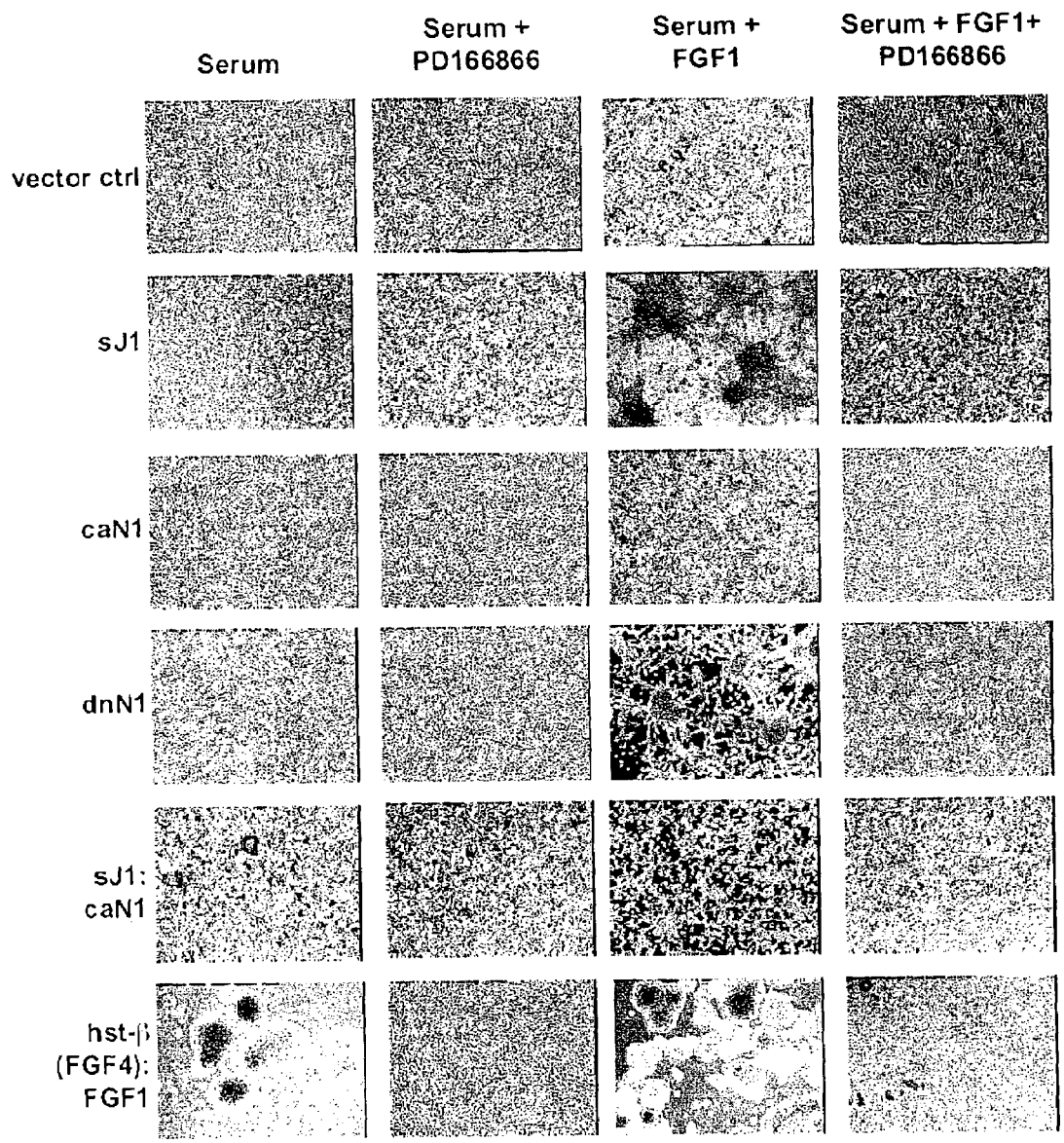
FIG. 1 is a series of images demonstrating the role of FGF1 and the Notch pathway in spheroid formation. Briefly, NIH 3T3 cell transfectants were grown in media containing either 10% BCS or 10% BCS with the addition of FGF1 (10 ng/ml) and heparin (10 U/ml), or 1 µM PD166866 as indicated. The images are phase-contrast photomicrographs of the cells three days after plating.

While it is known that the processes of thrombosis, angiogenesis and inflammation are related, the mechanism linking the three processes was heretofore unknown. The present invention discloses, for the first time, that thrombosis, angiogenesis and inflammation are related by way of thrombin. More specifically, thrombin simultaneously affects thrombosis, angiogenesis and inflammation by way of thrombin-mediated proteolysis of the transmembrane protein Jagged1 and by way of thrombin-mediated proteolysis of the thrombin receptor. The understanding of the thrombin-based relationship among thrombosis, angiogenesis and inflammation as set forth more fully herein provides novel methods of treating disorders related to the Jagged1-Notch-FGF-1 signaling pathways.

That is, the present invention demonstrates that thrombin-mediated proteolysis of Jagged1 occurs on the extracellular domain of Jagged1, and releases soluble Jagged 1, a truncated form of the transmembrane full-length form of Jagged 1. Descriptions of Jagged1 and soluble Jagged1 (sJ1) can be found in U.S. Pat. No. 6,433,138 to Maciag, and in International Patent Publication No. WO 97/45143, both of which are incorporated herein by reference in their entirety. Accordingly, the present invention features methods of identifying, modulating, and altering the interaction of thrombin with Jagged1, in order to increase or decrease the production of soluble Jagged1, thereby modulating Jagged1/Notch interactions and FGF-1 release.

Additionally, the invention relates to the novel discovery that thrombin mediates the release of FGF-1 from a cell. Further, the novel invention relates to the discovery that thrombin cleaves Jagged1 to produce soluble Jagged1 which, in turn, binds the Notch receptor. Binding of soluble Jagged1 with the Notch receptor inhibits Notch signaling. Further, cleavage of Jagged1 to release soluble Jagged1 mediates the rapid release of FGF-1 from the cell.

The invention particularly features the interaction of thrombin with membrane-bound Jagged1. Thrombin cleaves Jagged1 to release soluble Jagged1. As a result of the release of soluble Jagged1, the soluble form of Jagged1 binds to the Notch receptor, and consequently represses Notch signaling. As a result of the repression of Notch signaling, the transcription of FGF-1 mRNA is increased in the cell and the release of IL-1α from the cell is decreased.

The present invention also includes methods encompassing the modulation of thrombin-mediated non-classical release of FGF-1 into the extracellular compartment, whereby FGF-1 can function as a mitogen. Thrombin-mediated release of FGF-1 occurs upon cleavage of the thrombin receptor by thrombin. Non-classical release of FGF-1 into the extracellular compartment occurs rapidly upon thrombin cleavage of the thrombin receptor, reaching a maximum extracellular concentration of FGF-1 within one hour after the cell is contacted with thrombin, with the extracellular concentration of FGF-1 beginning to decrease one hour after the onset of thrombin-mediated induction. The thrombin-mediated non-classical release of FGF-1 is distinct from, for example, the stress-mediated non-classical release of FGF-1 into the extracellular milieu. Discussion of the stress-mediated release of FGF-1 can be found in, for example, Prudovsky et al. (2002, J. Cell Biol. 158:201-208), Mouta Carreira et al. (2001, Growth Factors 18:277-285), Lansriscina et al. (2001, J. Biol. Chem. 276:25549-25557), Tarantini et al. (2001, J. Biol. Chem. 276:5147-5151), and Shi et al. (1997, J. Biol. Chem. 272:1142-1147).

The present invention encompasses the treatment of Jagged1-Notch-FGF-1 signaling system-related disorders, including, but not limited to disorders of angiogenesis, thrombosis, and inflammation. Disorders of angiogenesis, thrombosis, and inflammation that can benefit from an increase in extracellular FGF-1 can be ameliorated by the administration of thrombin to a patient in need thereof. Similarly, disorders that can benefit from a decrease in the extracellular levels of IL-1α may be ameliorated by the administration of thrombin to a patient in need thereof.

The present invention also encompasses the treatment of Jagged1-Notch-FGF-1 related disorders that arise due to an increased extracellular level of FGF-1. By way of a non-limiting example, such disorders include protooncogenic conditions. Disorders that can benefit from a decrease in extracellular levels of FGF-1 can be ameliorated or treated by administration of an inhibitor of the thrombin-Jagged1 interaction or an inhibitor of the proteolytic cleavage of Jagged1 by thrombin.

Additionally, the invention relates to the discovery that thrombin, as well as sJ1, TRAP, and combinations thereof, mediate clonal expansion of pluripotent stem cells without loss of pluripotentiality, a process referred to herein as "stamatogenesis." Further, thrombin, sJ1, TRAP, and combinations thereof, induce rapid non-classical release of FGF-1, and proteins associated therewith, into the extracellular compartment. And the invention encompasses various methods compositions and kits relating to these discoveries.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Angiogenesis," as used herein, means the formation of new blood vessels and encompasses the development of angiogenic tissue and/or altered cell or tissue morphology typical of angiogenic tissue development. One skilled in the art would appreciate, based upon the disclosure provided herein, that the level of angiogenesis can be assessed using, for example but not limited to, a CAM assay, a nude mouse in vivo assay, an endothelial cell migration assay to assess sprout formation, the development of chord-like structures, and other methods known in the art.

"Antisense nucleic acid sequence," "antisense sequence," "antisense DNA molecule" or "antisense gene" refer to pseudogenes which are constructed by reversing the orientation of the gene with regard to its promoter, so that the antisense strand is transcribed. The term also refers to the antisense strand of RNA or of cDNA which compliments the strand of DNA encoding the protein or peptide of interest. In either case, when introduced into a cell under the control of a promoter, the anti-sense nucleic acid sequence inhibits the synthesis of the protein of interest from the endogenous gene. The inhibition appears to depend on the formation of an RNA-RNA or cDNA-RNA duplex in the nucleus or in the cytoplasm. Thus, if the antisense gene is stably introduced into a cultured cell, the normal processing and/or transport is affected if a sense-antisense duplex forms in the nucleus; or if antisense RNA is introduced into the cytoplasm of the cell, the expression or translation of the endogenous product is inhibited.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

Antisense nucleic acid sequences can further include modifications which can affect the biological activity of the antisense molecule, or its manner or rate of expression. Such modifications can also include, e.g., mutations, insertions, deletions, or substitutions of one or more nucleotides that do not affect the function of the antisense molecule, but which may affect intracellular localization. Modifications include, but are not limited to, 5-fluorouracil, 5-bromouracil, 5-chlorouracil, 5-iodouracil, hypoxanthine, xanthine, 4-acetylcytosine, 5-(carboxyhydroxymethyl uracil, 5-carboxyhydroxymethyl-2-thiouridine, 5-carboxymethylaminomethyl uracil, dihydrouracil, beta-D-galactosylqueosine, inosine, N6-isopentyladenine, 1-methylguanine, 1-methylinosine, 2,2 dimethylguanine, 2-methyladenine, 2-methylguanine, 3-methylcytosine, 5-methylcytosine, N6-adenine, 7-methylguanine, 5-methylaminomethyluracil, 5-methylaminomethyl-2-thioracil, beta-D-mannosylqueosine, 5'-methoxycarboxymethyluracil, 5-methyluracil, 2-methylthio-N-6-isopentenyladenine, uracil-5 oxyacetic acid, wybutoxosine, pseudouracil, queosine, 2-thiocytosine, 5-methyl-2-thiouracil, 2-thiouracil, 4-thiouracil, 5-methyluracil, uracil-5-oxy-acetic acid methylester, uracil-5-oxyacetic acid, 5-methy-2-thiouracil, 3-(3-amino-3-N-2-carboxypropyl) uracil, and 2,6-diaminopurine.

The antisense nucleic acid sequence can determine an uninterrupted antisense RNA sequence or it can include one or more introns. The antisense Jagged1 molecule(s) of the present invention are referred to as "γ-Jagged1."

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

By the term "applicator," as the term is used herein, is meant any device including, but not limited to, a hypodermic syringe, a pipette, and the like, for administering the compounds and compositions of the invention.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The use of the term "DNA encoding" should be construed to include the DNA sequence which encodes the desired protein and any necessary 5' or 3' untranslated regions accompanying the actual coding sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

One skilled in the art would appreciate, based upon the disclosure provided herein, that such amount depends on the nature of the cell or tissue from which the cell is obtained, and the amount of endogenous type I collagen expression in the cell prior to or in the absence of administration of soluble Jagged1.

The skilled artisan would further appreciate, based upon the disclosure provided herein, that there are a number of assays, several of which are disclosed elsewhere herein, useful for assessing the level of type I collagen expression, or the level of expression of a stem cell marker, a differentiation marker, a therapeutic protein, and the like, in a cell such as a differential display method (e.g., SAGE analysis), antibody-based detection of type I collagen gene translation product in a cell (e.g., immunoblotting, ELISA, immunoprecipitation, and the like), and detection of nucleic acid encoding type I collagen (e.g., Southern blotting, Northern blotting, PCR-based assays, and the like), as well as assays to be developed in the future.

A "therapeutic" treatment is a treatment administered to a patient who exhibits signs of pathology for the purpose of diminishing or eliminating those signs and/or decreasing or diminishing the frequency, duration and intensity of the signs.

An "effective amount" of a compound is that amount of compound which is sufficient to provide a detectable effect to a cell to which the compound is administered when compared to an otherwise identical cell to which the compound is not administered.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

The instructional material of the kit may, for example, be affixed to a container that contains the compound and/or composition (e.g., thrombin, Jagged1, sJ1, TRAP, and the like) of the invention or be shipped together with a container which contains the compound and/or composition. Alternatively, the instructional material may be shipped separately from the container with the intention that the recipient uses the instructional material and the compound cooperatively.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

A first region of an oligonucleotide "flanks" a second region of the oligonucleotide if the two regions are adjacent to one another or if the two regions are separated by no more than about 1000 nucleotide residues, and preferably no more than about 100 nucleotide residues.

By the term "DNA segment" is meant a molecule comprising a linear stretch of nucleotides wherein the nucleotides are present in a sequence that encodes, through the genetic code, a molecule comprising a linear sequence of amino acid residues that is referred to as a protein, a protein fragment, or a polypeptide.

"Gene," as used herein, refers to a single polypeptide chain or protein, and as used herein includes the 5' and 3' ends. The polypeptide can be encoded by a full-length sequence or any portion of the coding sequence, so long as the functional activity of the protein is retained.

A "complementary DNA" or "cDNA" gene includes recombinant genes synthesized by reverse transcription of messenger RNA ("mRNA") lacking intervening sequences (introns).

By the term "gel electrophoresis," is meant assay to assess the size of particular DNA fragments. More specifically, the most common technique (although not the only one) to determine the size of a nucleic acid fragment, is agarose gel electrophoresis, which is based on the principle that DNA molecules migrate through the gel as though it were a sieve that retards the movement of the largest molecules to the greatest extent, and the movement of the smallest molecules to the least extent. The fractionated molecules can be visualized by staining, permitting the DNA fragments of a genome to be visualized. Such techniques are well-known in the art and the gel matrix can be comprised of a variety of substances including, but not limited to, agarose, acrylamide, and the like, as described in, e.g., Sambrook and Russell (2001, Molecular Cloning, A Laboratory Approach, Cold Spring Harbor Press, Cold Spring Harbor, N.Y.), Ausubel et al. (2002, Current Protocols in Molecular Biology, John Wiley & Sons, NY), and other standard treatises.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

In addition, when the term "homology" is used herein to refer to the nucleic acids and proteins, it should be construed to be applied to homology at both the nucleic acid and the amino acid levels.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web site of the National Library of Medicine (NLM) at the National Institutes of Health (NIH) using the BLAST program. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. These programs are publicly available at, e.g., the website for the National Center for Biotechnology Information (NCBI) world wide web site of the National Library of Medicine at the National Institutes of Health.

The percent identity between two sequences can be determined using techniques similar to those described above, with or without allowing gaps. In calculating percent identity, typically exact matches are counted.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions. For example, a cDNA encoding a soluble form of a membrane-bound protein of the invention, Jagged1, can be isolated based on its hybridization with a nucleic acid molecule encoding all or part of the membrane-bound form. Likewise, a cDNA encoding a membrane-bound form can be isolated based on its hybridization with a nucleic acid molecule encoding all or part of the soluble form.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "ligand," as used herein, refers to any protein or proteins that can interact with a receptor binding domain, thus having a "binding affinity" for such domain. Ligands can be soluble or membrane bound, and they can be a naturally occurring protein, or synthetically or recombinantly produced. The ligand can also be a nonprotein molecule that acts as ligand when it interacts with the receptor binding domain. Interactions between the ligand and receptor binding domain include, but are not limited to, any covalent or non-covalent interactions. The receptor binding domain is any region of the receptor molecule, e.g., Notch, that interacts directly or indirectly with the ligand, e.g., Jagged1. If the Notch-Jagged1 interaction acts as an on-off switch, Jagged1 can provide the receptor binding domain, and Notch or a component produced as a result of the Notch-Jagged1 interaction can act as the ligand.

"Mutants," "derivatives," and "variants" of the peptides of the invention (or of the DNA encoding the same) are peptides which may be altered in one or more amino acids (or in one or more base pairs) such that the peptide (or nucleic acid) is not identical to the sequences recited herein, but has the same property as the soluble Jagged1 peptides disclosed herein, in that the peptide has the property of inducing expression of certain genes as assessed using SAGE analysis (e.g., enhancer of split groucho, type IV collagenase, connexin 32, cathepsin D, and vimentin; mediating reduced level of expression of certain genes (e.g., pro-α-2(I) collagen, FGFR-1, and IkB-β, affecting endothelial sprout formation, affecting angiogenesis, the ability to develop angiogenic tissue masses in nude mice, the ability to induce angiogenesis in a CAM angiogenesis model, the ability to be cleaved by thrombin, the ability to mediate clonal expansion of stem cells without a detectable loss of pluripotency, and the like.

A "variant" or "allelic or species variant" of a protein or nucleic acid is meant to refer to a molecule substantially similar in structure and biological activity to either the protein or nucleic acid. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell.

"Neural cell" is used herein to refer to a cell that exhibits morphology, function, and phenotypic characteristics similar to that of glial cells and neurons derived from the central nervous system and/or the peripheral nervous system.

"Neuron-like cell" is used herein to refer to a cell that exhibits morphology similar to that of a neuron and detectably expresses a the neuron-specific markers, such as, but not limited to, MAP2, neurofilament 200 kDa, neurofilament-L, neurofilament-M, synaptophysin, β-tubulin III (TUJ1), Tau, NeuN, a neurofilament protein, and a synaptic protein.

As used herein, "non-classical release" of an FGF means the release of an FGF from a cell, wherein FGF transport from the cell is not mediated by a signal sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

By the term "exogenous nucleic acid" is meant that the nucleic acid has been introduced into a cell or an animal using technology which has been developed for the purpose of facilitating the introduction of a nucleic acid into a cell or an animal.

The term "expression of a nucleic acid" as used herein means the synthesis of the protein product encoded by the nucleic acid. More specifically, expression is the process by which a structural gene produces a polypeptide. It involves transcription of the gene into mRNA, and the translation of such mRNA into a polypeptide.

By "multipotential stem cell", "multipotent neural stem cell," or "pluripotent stem cell," as used interchangeably herein, is meant a cell that has the potential of differentiating into at least two cell types (e.g., a glial cell, a neuron, an oligodendrocyte, a chondrocyte, an adipocyte, a hepatocyte, a cardiac cell, a pancreatic cell, a smooth muscle cell, and the like) and which exhibits self-renewal. Self-renewal, in turn, means that at least one of the two daughter cells resulting from cell division, must also be a stem cell. The term multipotential stem cell or multipotent neural cell does not require that the stem cell be derived from neural tissue, only that it can differentiate into, among other things, a neural cell (e.g., a Schwann cell, a glial cell, an astrocyte, a neuron, an oligodendrocyte, and the like).

A stem cell is "multipotent" in that its progeny can differentiate into a least two different cell types, including, but not limited to, a skin cell, a fat cell, a smooth muscle cell, a hematopoietic cell, a pancreatic cell, a skeletal muscle cell, a cardiac cell, a liver cell, a pancreatic cell, among many others.

A "portion" of a polynucleotide means at least about twenty sequential nucleotide residues of the polynucleotide. It is understood that a portion of a polynucleotide may include every nucleotide residue of the polynucleotide.

A "polynucleotide" means a single strand or parallel and anti-parallel strands of a nucleic acid. Thus, a polynucleotide may be either a single-stranded or a double-stranded nucleic acid.

By a "population of cells" is meant a collection of at least ten cells. Preferably, the collection comprises at least about twenty cells, even more preferably, at least about 30 cells, even more preferably, at least about 100 cells, more preferably, at least about 1,000 cells, even more preferably, at least about 10,000 cells, yet more preferably, at least about 100,000 cells, even more preferably, at least about a million cells, yet more preferably, at least about 5 million cells, even more preferably, a least about 10 million cells.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "oligonucleotide or oligomer", as used herein, refers to a molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A cell that comprises an exogenous nucleic acid is referred to as a "recombinant cell." Such a cell may be a eukaryotic cell or a prokaryotic cell. A gene which is expressed in a recombinant cell wherein the gene comprises a recombinant polynucleotide, produces a "recombinant polypeptide."

By the term "specifically binds," as used herein, is meant a compound, e.g., a protein, a nucleic acid, an antibody, and the like, which recognizes and binds a specific molecule, but does not substantially recognize or bind other molecules in a sample.

A "substantially pure" protein or nucleic acid is a protein or nucleic acid preparation that is generally lacking in other cellular components with which it is normally associated in vivo. That is, as used herein, the term "substantially pure" describes a compound, e.g., a nucleic acid, protein or polypeptide, which has been separated from components which naturally accompany it. Typically, a compound is substantially pure when at least about 10%, preferably at least about 20%, more preferably at least about 50%, still more preferably at least about 75%, even more preferably at least about 90%, and most preferably at least about 99% of the total material (by volume, by wet or dry weight, or by mole percent or mole fraction) in a sample is the compound of interest. Purity can be measured by any appropriate method, e.g., by column chromatography, gel electrophoresis or HPLC analysis.

A compound, e.g., a nucleic acid, a protein or polypeptide is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state, e.g., a DNA fragment which has been removed from the sequences which are normally adjacent to the fragment in a genome in which it naturally occurs.

Similarly, a "substantially pure" preparation of a protein or a polypeptide, as used herein, refers to a protein or polypeptide which has been purified from components with which it is normally associated in its naturally occurring state. A substantially pure peptide can be purified by following known procedures for protein purification, wherein an immunological, enzymatic or other assay is used to monitor purification at each stage in the procedure. Protein purification methods are well known in the art, and are described, for example in Deutscher et al. (1990, In: Guide to Protein Purification, Harcourt Brace Jovanovich, San Diego).

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an anti-myc-monoclonal antibody affinity matrix, a glutathione-S-transferase tag epitope, and a maltose binding protein (MBP) tag epitope, which can induce binding between a protein comprising such an epitope and a glutathione- or maltose-Sepharose column, respectively. Production of proteins comprising such tag epitopes is well known in the art and is described in standard treatises, such as Sambrook and Russell (2001, Molecular Cloning, A Laboratory Approach, Cold Spring Harbor Press, Cold Spring Harbor, N.Y.), and Ausubel et al. (2002, Current Protocols in Molecular Biology, John Wiley & Sons, NY). Likewise, antibodies to the tag epitope (e.g., anti-HA, anti-myc antibody 9E10, and the like) allow detection and localization of the fusion protein in, for example, Western blots, ELISA assays, and immunostaining of cells.

A "therapeutic protein," as used herein, refers to protein that improves or maintains the health of the cell expressing the protein or that of a cell in proximity to the cell expressing the protein. Numerous exemplary therapeutic proteins are widely-known in the art and are not listed here since they are well-known to the artisan.

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

To "treat" a disease as the term is used herein, means to reduce the frequency of the disease or disorder reducing the frequency with which a symptom of the one or more symptoms disease or disorder is experienced by an animal.

By the term "type I collagen," as used herein, is meant any collagen known to be a type I collagen, e.g., pro-α1(I) collagen, pro-α2(I) collagen, and the like, as well as other collagens identified as type I collagen in the future according to criteria that are well-known in the art.

Description

The present invention encompasses methods based on the interactions of thrombin with Jagged1 proteins, methods based on the role of thrombin on signaling via Notch proteins and the subsequent effect on thrombosis, angio genesis, and/or differentiation, and methods based on the thrombin-mediated export of FGF-1 from a cell.

The clinical importance of the disparate effect of the Jagged1-Notch signaling pathway on the macro- and micro-diameter blood vessels is significant, offering a solution to many aspects of vascular pathophysiology. For example, the morbidity and mortality from hypertension is clearly based on the disease of the large vessels (atherosclerosis and stroke), but in the major forms of hypertension, the actual cause for elevated blood pressure lies in the peripheral vascular beds (arterioles and microvasculature) (Chobanian et al., 1986, Hypertension 8:15-21). The presently defined methods relate to the interplay between thrombin and Jagged1, as well as the interplay between the thrombin-Jagged1 pathway and the thrombin-mediated non-classical release of FGF-1 into the extracellular compartment. Such methods as disclosed herein may resolve the previously unanswered question of how hypertension could be directly related to the aortic intima and atherosclerosis, and vice versa, how known atherogenic risk factors could affect the microvascular endothelium (Chan et al., 1979, Microvasc. Res. 18:353-369).

Moreover, the presently embodied compositions and methods are useful for the modification of a post-angioplastic situation, when one or more large coronary vessel have been stripped of their endothelial cell lining. One of the most serious complications limiting the value of the angioplastic procedure is the occurrence of restenosis or the rapid migration and proliferation of smooth muscle cells, monocytes/macrophages, platelets, and endothelium at the wound site resulting in a reocclusion of the vessel that may be more extensive than before treatment (see numerous review articles on the subject, e.g., Schwartz et al., 1981, Atherosclerosis 1:107-161). However, treating the wounded or injured area with a therapeutic amount of additional thrombin, or a functionally equivalent drug or protein having the ability to modulate Notch signaling, will prevent or inhibit reocclusion by increasing the migration of the large vessel endothelial cells on the borders of the lesion into the denuded area to cover the lesion, while also decreasing emergence of the micro-vascular cells (smooth muscle, endothelial, macrophage, etc.) from the vaso vasorum and providing the nutrient microvessels or sprouts to supply the proliferating smooth muscle cells.

Methods of Producing Soluble Jagged1

Figures 1, 3A:
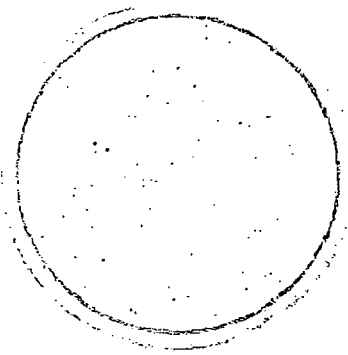
Figures 2, 3A:
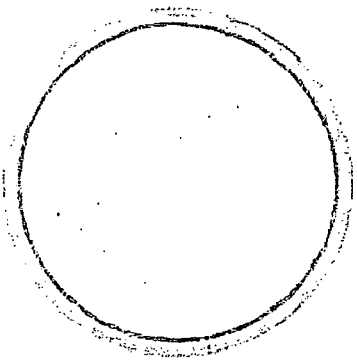
Figures 3, 3A:
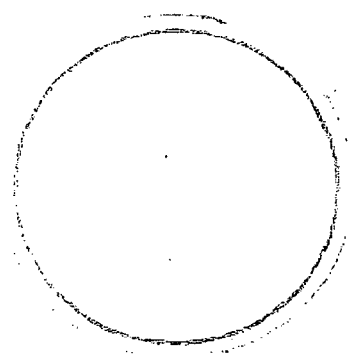
Figures 3, 3A, 4:
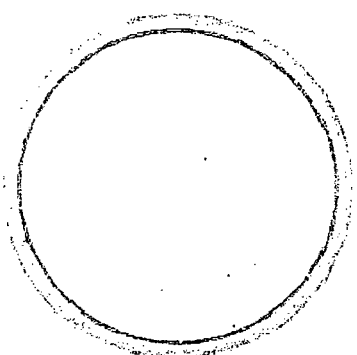

The present invention includes a method of releasing soluble Jagged1 from a cell. U.S. Pat. No. 6,433,138 to Maciag et al., incorporated herein by reference in its entirety, discusses in detail the Jagged1 protein, as well as the role of the Jaggedl protein in cellular signaling by way of the Notch receptor and the Notch receptor signaling pathway. Jagged1 is a transmembrane protein which is directed to the cell surface by the presence of a signal peptide sequence (Lindsell et al., 1995, Cell 80:909-917). While the intracellular domain contains a sequence with no known homology to intracellular regions of other transmembrane structures, the extracellular region of the ligand contains a cys-rich region, 16 epidermal growth factor (EGF) repeats, and a DSL (Delta Serrate Lag) domain. The amino acid sequence of the full-length Jagged1 protein is set forth in FIG. 8C-1 (SEQ ID NO:1), and is encoded by the nucleotide sequence set forth in FIGS. 8D-1 and 8D-2 (SEQ ID NO:2). A more extensive discussion of Jagged1-Notch signaling and interactions can be found in, for example, Lindner et al. (Am J Pathol., 2001, 159:875-883), Zimmin et al. (J Biol. Chem., 1996, 271:32499-32502), and data disclosed herein. Soluble Jagged1 (sJ1) comprises amino acid residues from about 1 to 1067 (SEQ ID NO:3) of full-length Jagged1 (SEQ ID NO:1) as set forth in FIGS. 8C and 8D.

Soluble Jagged1 has been shown to bind to the Notch receptor and to repress type I collagen expression. Further, soluble Jagged1 plays a role in cell regulation and cell differentiation by way of the interaction of soluble Jagged1 binding to the Notch receptor. To date, however, it was not understood whether soluble Jagged1 was released in vivo or, if so, how it was produced from full-length Jagged1.

The present invention provides a method of cleaving full-length Jagged1 to produce soluble Jagged1. This is because it has now been discovered that thrombin cleaves full-length Jagged1 to produce and release soluble Jagged1. In one embodiment of the invention, thrombin is contacted with a cell comprising transmembrane full-length Jagged1. Thrombin acts to proteolytically cleave an extracellular portion of Jagged1 from transmembrane Jagged1, thereby releasing soluble Jagged1. As set forth elsewhere herein, and as would be known to one of skill in the art based on the disclosure provided herein, soluble Jagged1 released from transmembrane Jagged1 by thrombin interacts with the Notch receptor, thereby suppressing Notch signaling.

As disclosed elsewhere herein (e.g., Example 1; Small et al., 2003, J. Biol. Chem. 278:16405-16413), suppression of Notch receptor signaling in NIH-3T3 cells results in the appearance of an exaggerated fibroblast growth factor (FGF)-dependent transformed phenotype characterized by anchorage-independent growth in soft agar. It was demonstrated previously that the Notch receptor plays a critical role in cellular differentiation, including, but not limited to angiogenesis and neurogenesis. Therefore, suppression of Notch receptor signaling as discussed herein may be achieved by methods disclosed in and contemplated by the present invention.

As will be understood by one of skill in the art, thrombin cleavage of Jagged1 according to the methods of the present invention can produce soluble Jagged1 (sJ1), the sequence of which is characterized by amino acid residues 1-1067 (SEQ ID NO:3) of the amino acid sequence of full-length Jagged1 (SEQ ID NO:1) depicted in FIG. 8C. However, one of skill in the art will also understand that allelic variants, mutants, and homologs of full-length Jagged1 exist, and furthermore, that such variants, mutants, and homologs can be created using recombinant DNA technologies well known to one of skill in the art. Therefore, the present invention also encompasses production of soluble Jagged1 by thrombin cleavage of any form of Jagged1 that, when proteolytically cleaved by thrombin, will release soluble Jagged1, where soluble Jagged1 is any portion of Jagged1 that is less than full length. Preferably, soluble Jagged1 comprises amino acids 1-1067 of full-length Jagged1 (SEQ ID NO:1). Soluble Jagged1 also refers to a Jagged1 molecule that is less than full-length and is not membrane-associated.

The present invention also provides methods encompassing variants, mutants and homologs of soluble Jagged1 (sJ1) as characterized by amino acid residues 1-1067 of the amino acid sequence of human Jagged1 (SEQ ID NO:1) set forth in FIG. 8C. As will be understood by one of skill in the art, allelic variants, mutants, and homologs of full-length Jagged1, when acted upon by thrombin as disclosed herein, can produce soluble Jagged1 that is a variant, mutant or homolog of soluble Jagged1 as characterized by amino acid residues 1-1067 of the amino acid sequence set forth in FIGS. 8C. Such variants, mutants, and homologs of soluble Jagged1 retain some or all of the properties of soluble Jagged1 as characterized by amino acid residues 1-1067 (SEQ ID NO:3) of the amino acid sequence set forth in FIG. 8C-1. By way of a non-limiting example, one such property of soluble Jagged1 is the ability to bind to the Notch receptor and repress Notch signaling, and/or the characteristic that the protein is not membrane-associated and/or lacks a transmembrane domain, among the characteristics as would be understood by the skilled artisan once armed with the teaches provided herein.

The "biological activity" of a soluble Jagged1 produced by a method of the present invention includes the ability of soluble Jagged1 to bind to the Notch receptor. Therefore, any variant, fragment or homolog of Jagged1 that has the ability to bind to the Notch receptor is a "soluble Jagged1" according to the present invention. Further, the ability of soluble Jagged1 to bind to the Notch receptor provides that the biological activity of a soluble Jagged1 produced by a method of the present invention encompasses at least one of the ability to repress Notch signaling in a cell comprising a Notch receptor, the ability to upregulate transcription of FGF-1 mRNA in a cell comprising a Notch receptor, and the ability to inhibit the release of IL-1α from a cell comprising a Notch receptor.

Further biological activity of sJ1 includes, but is not limited to, mediating the rapid non-classical release of a complex comprising, inter alia, FGF-1, p40 Syn1, and S100A13, as well as the ability to preserve the differentiation potential of a multipotent stem cell thereby enabling the clonal expansion of such cells without loss of pluripotential of the stem cell, a process termed "stamatogenesis."

As disclosed elsewhere herein, because the Jaggedl/Notch signaling pathway is involved in angiogenesis and vasculogenesis, the biological activity of soluble Jagged1 produced by a method of the present invention includes the ability to modulate angiogenesis and vasculogenesis. For example, another biological activity of soluble Jagged1 produced by a method of the present invention is the ability to affect the level of expression of various nucleic acids enhancing expression of certain genes (e.g., enhancer of split groucho, type IV collagenase, connexin 32, cathepsin D, and vimentin), while mediating reduced levels of expression of other genes (e.g., pro-α-2(I) collagen, FGFR-1, and IkB-β), as determined using serial analysis of gene expression (SAGE) analysis (see International Application WO 97/45143, incorporated by reference herein in its entirety).

Further, the activity of soluble Jagged1 produced by a method of the present invention includes, but is not limited to, affecting endothelial sprout formation, affecting angiogenesis, affecting development of angiogenic tissue masses in nude mice, and affecting angiogenesis in a CAM angiogenesis model. Additionally, the biological activity of a soluble Jagged1 produced by a method of the present invention includes the ability to repress type I collagen expression, which is extremely important in the regulation of fibrotic disease.

The present invention particularly features methods of using thrombin to cleave Jagged1. In an embodiment of the invention, thrombin is used as a cleaving agent to cleave Jagged1 to produce soluble Jagged1 since it has been discovered that surprisingly, thrombin cleaves Jagged1 to produce soluble Jagged1.

The function of thrombin as a serine protease is well-documented in the prior art, and will not be discussed here, as one of ordinary skill in the art will be well-versed in the role of thrombin as a serine protease, the conditions suitable for thrombin activity, and the numerous ways in which to assay thrombin activity. For example, one of skill in the art would understand that thrombin protease activity as disclosed in the methods of the present invention can be assayed in numerous ways, including detecting an increase in the level of soluble Jagged1, detecting a decrease in the level of full-length or non-soluble Jagged1, detecting a specific amino or carboxy terminal sequence present in soluble Jagged1, and detecting an interaction between soluble Jagged1 and a Notch receptor, among others.

Methods useful in the analysis of thrombin-mediated cleavage of Jagged1 as disclosed in the present invention include, but are not limited to, gel electrophoresis, antibody-based detection of soluble and/or full-length Jagged1, mass spectrometry, microcalorimetry, analytical ultracentrifugation, UV-visible spectrometry, column and/or batch chromatography, affinity chromatography, fluorimetry, and radiography. As known to one of skill in the art, numerous protease assays are well-described and commercially available and can be used to assess the levels of thrombin-mediated cleavage of Jagged1 to release soluble Jagged1.

The present invention also provides for methods comprising analogs of a protein or peptide which comprises thrombin as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine;

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are thrombin polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of thrombin (or of the DNA encoding the same) which mutants, derivatives and variants are thrombin polypeptides which are altered in one or more amino acids (or, when referring to the nucleotide sequence encoding the same, are altered in one or more base pairs) such that the resulting peptide (or DNA) is not identical to the thrombin sequences of human thrombin, for example, but has the same biological property as wild type human thrombin, in that the peptide has biological/biochemical properties of thrombin as known to one of skill in the art. A biological property of a thrombin includes, but is not limited to include, the ability of the peptide to cleave Jagged1 to release soluble Jagged1. Further, another biological activity of thrombin is the ability to proteolytically cleave the thrombin receptor. Further, the activities of thrombin include, but are not limited to, the ability to proteolytically cleave the thrombin receptor and initiate a G-protein mediated, pertussis toxin-sensitive signal which mediates a non-classical release of FGF-1 into the extracellular compartment. Additionally, the biological activity of thrombin includes the ability to cleave Jagged1 to release soluble Jagged1, whereby the soluble Jagged1 subsequently leads to repression of type I collagen expression, which is extremely important in the regulation of all fibrotic diseases. Further, an activity of thrombin includes the ability to mediate the rapid release of FGF-1 from a cell which is mediated by, or associated with, thrombin cleavage of Jagged1 to produce soluble Jagged1.

Further, the invention should be construed to include naturally occurring variants or recombinantly derived mutants or fragments of thrombin, which variants, mutants or fragments render the protein encoded thereby either more, less, or just as biologically active as the full-length proteins and/or the truncated proteins of the invention.

In addition, the skilled artisan would appreciate that changes can be introduced by mutation of the nucleic acid encoding the protein thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

To generate variant proteins, an isolated nucleic acid molecule encoding a variant protein can be created by introducing one or more nucleotide substitutions, additions or deletions into the nucleotide sequence of any thrombin, such that one or more amino acid residue substitutions, additions or deletions are introduced into the encoded thrombin protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

One skilled in the art would appreciate, based upon the disclosure provided herein, that a mutant polypeptide that is a variant of thrombin can be assayed for the following activity, including, but not limited to, the ability to induce expression of certain genes (e.g., enhancer of split groucho, type IV collagenase, connexin 32, cathepsin D, and vimentin); the ability to reduce expression of various genes (e.g., pro-α-2(I) collagen, FGFR-1, and IkB-β); the ability to induce sprout formation; the ability to induce angiogenesis in a CMA model; the ability to induce formation of angiogenic tissue masses in nude mice; and the ability to repress type I collagen expression, which is extremely important in the regulation of all fibrotic diseases; the ability to cleave Jagged1 to produce soluble Jagged1; the ability to cleave a thrombin receptor; the ability to affect Notch signaling; the ability to affect FGF-1 release from a cell; the ability to affect IL-1α from a cell; the ability to mediate clonal expansion of stem cells without loss of pluripotency, and the like.

The "biological activity of a thrombin polypeptide" useful in a method of the present invention includes, but is not limited to, the ability of thrombin to cleave Jagged1 to from soluble Jagged1, wherein soluble Jagged1 subsequently binds the Notch receptor. Therefore, any variant, fragment or homolog of thrombin that has the ability to produce soluble Jagged1, which soluble Jagged1 has the ability to bind to the Notch receptor, is a thrombin polypeptide useful in the present invention. Further, the ability of thrombin to produce soluble Jagged1, wherein the soluble Jagged1 binds to the Notch receptor, provides that the biological activity of a thrombin polypeptide useful in a method of the present invention encompasses the ability to repress Notch signaling in a cell comprising a Notch receptor, thus affecting any process mediated by Notch signaling, e.g., transcription of FGF-1 mRNA in a cell, the ability to repress the release of IL-1α from a cell, and the like.

As disclosed elsewhere herein, because the Jagged1/Notch signaling pathway is involved in angiogenesis and vasculogenesis, the biological activity of a thrombin polypeptide that cleaves Jagged1 to produce soluble Jagged1 includes the ability to modulate angiogenesis and vasculogenesis. Another biological activity of a thrombin useful in a method of the present invention is a thrombin molecule that can produce soluble Jagged1, which soluble Jagged1 has the ability to affect the level of expression of various nucleic acids enhancing expression of certain genes (e.g., enhancer of split groucho, type IV collagenase, connexin 32, cathepsin D, and vimentin), while mediating reduced levels of expression of other genes (e.g., pro-α-2(I) collagen, FGFR-1, and IkB-β), as determined using serial analysis of gene expression (SAGE) analysis, can therefore be use to affect expression of such genes.

Further still, the activities of a thrombin polypeptide useful in a method of the present invention include, but are not limited to, to affect endothelial sprout formation, to affect angiogenesis, to induce development of angiogenic tissue masses in nude mice, and the ability to affect angiogenesis in a CAM angiogenesis model. Additionally, the biological activity of a thrombin polypeptide useful in a method of the present invention includes the ability of thrombin to repress type I collagen expression, which is extremely important in the regulation of all fibrotic diseases. As set forth in greater detail elsewhere herein, thrombin mediates the aforementioned activities by cleavage of soluble Jagged1 from Jagged1, wherein soluble Jagged1 binds to a Notch receptor.

It is also well described in the prior art that the mitogenic activity of thrombin is due, in part, to the ability of thrombin to proteolytically cleave its high affinty G protein-coupled receptor, the thrombin receptor. Cleavage of the thrombin receptor by thrombin involves the cleavage of the N-terminal domain of the thrombin receptor, which reveals a new N-terminal domain of the receptor. The new N-terminal domain acts as a tethered peptide ligand that binds to the thrombin receptor. This tethered ligand-thrombin receptor subsequently effects transmembrane signaling via autoactivation of the thrombin receptor. For example, it is known that thrombin cleavage of the thrombin receptor plays a part in platelet activation (Coughlin, 1999, Proc. Natl. Acad. Sci. 96:11023-11027).

In the present application, it is disclosed for the first time that thrombin cleavage of the thrombin receptor is responsible for a G-protein mediated, pertussis toxin-sensitive non-classical release of FGF-1 into the extracellular compartment. Therefore, the present invention features methods of releasing FGF-1 into the extracellular compartment using thrombin-mediated cleavage of the thrombin receptor. FGF-1 release into the extracellular compartment is useful to obtain the mitogenic effects of FGF-1.

In an embodiment of the present invention, FGF-1 is released into the extracellular compartment by a method comprising contacting a cell expressing a thrombin receptor with thrombin. Cleavage of the thrombin receptor by thrombin results in the surprisingly non-classical and rapid release of FGF-1 into the extracellular compartment. As discussed in detail elsewhere herein, the release of FGF-1 into the extracellular compartment is useful for obtaining the mitogenic effects of FGF-1 and it had not been previously demonstrated or suggested that thrombin mediated such an effect.

In another aspect of the present invention, a method is provided wherein a cell that contains Jagged1, Notch, and a thrombin receptor is contacted with thrombin. Upon contacting the cell with thrombin, thrombin proteolytically cleaves Jagged1 to release soluble Jagged1, which binds to Notch, inhibiting Notch signaling. As discussed in greater detail elsewhere herein, Notch signaling inhibition induces the expression of FGF-1 mRNA and inhibits the release of IL-1α. Concurrently upon contacting the cell with thrombin, thrombin cleaves a thrombin receptor, inducing the non-classical release of FGF-1 into the extracellular compartment. Thus, the methods of the invention can e used to produce soluble Jagged 1, as well as FGF-1.

The present invention also features a method of cleaving a Jagged1 polypeptide to produce a soluble Jagged1 polypeptide. In an embodiment of the invention, full-length Jagged1 polypeptide is contacted with thrombin, whereupon thrombin proteolytically cleaves the full-length Jagged1 polypeptide (SEQ ID NO:1) to produce soluble Jagged1 (sJ1; SEQ ID NO:3). As discussed more fully elsewhere herein, soluble Jagged1 produced by thrombin action in this embodiment of the invention can comprise amino acid residues from about 1-1067 of the amino acid sequence set forth in FIGS. 8C, or may comprise a variant, mutant or homolog thereof.

In one aspect of the invention, soluble Jagged1 produced by cleavage of Jagged1 comprises amino acid residues 1 to 1067 of the amino acid sequence set forth in FIG. 8C. A soluble Jagged1 produced by methods of the present invention is exemplified in that it is not associated with a cell membrane, and is less than full-length when compared to full-length transmembrane Jagged1 (FIG. 8C), and further, that the soluble Jagged1 is soluble in aqueous solution.

As will be understood by one of ordinary skill in the art, the size and/or amino acid sequence of soluble Jagged1 can be elucidated by any one of a number of well-known protein analytical techniques, including, but not limited to automated amino acid sequencing, Edman degradation, mass spectrometry, gel electrophoresis, and the like. Further, the identity of a soluble Jagged1 fragment produced by a thrombin-based method of the present invention can be ascertained by the use of proteolytic or mass spectrometric fragment analysis. For example, isolation of a soluble Jagged1, fragmentation of the isolated soluble Jagged1, and comparison of the size and/or sequence of the resulting soluble Jagged1 polypeptide fragments, will enable one of skill in the art, when armed with the amino acid sequence of the full-length Jagged1 set forth in FIG. 8C herein, to deduce the amino acid sequence of the isolated soluble Jagged1.

The present invention also provides methods of using thrombin to cleave any form of Jagged1 to produce a soluble portion of Jagged1. As will be understood by one of skill in the art, a polypeptide "comprising at least the soluble portion of Jagged1" may be a Jagged1 polypeptide that is comprised of fewer amino acids than the Jagged1 polypeptide set forth in FIG. 8C. Thus, the present invention includes methods comprising the thrombin-mediated cleavage of soluble Jagged1 from a mutant, variant or homolog of Jagged1, such mutants, variants and homologs set forth in greater detail elsewhere herein.

In an embodiment of the invention, full-length Jagged1 or a polypeptide comprising at least the soluble portion of Jagged1, from which thrombin can proteolytically cleave soluble Jagged1, is integrated in the membrane of a cell. In another embodiment, full-length Jagged1 or a polypeptide comprising at least the soluble portion of Jagged1, from which thrombin can proteolytically cleave soluble Jagged1, is associated with a cell membrane. In yet another embodiment, full-length Jagged1 or a polypeptide comprising at least the soluble portion of Jagged1, from which thrombin can proteolytically cleave soluble Jagged1, exists in solution associated with one or more additional moieties selected from the group consisting of a polypeptide, a carbohydrate, a nucleic acid, a mineral, and a salt. In still another embodiment, full-length Jagged1 or a polypeptide comprising at least the soluble portion of Jagged1, from which thrombin can proteolytically cleave soluble Jagged1, exists free in solution, or in sufficient aqueous medium that thrombin can effect the cleavage thereof.

Methods of Inhibiting Cleavage of Jagged1

The present invention features methods of inhibiting cleavage of Jagged1 in a cell comprising Jagged1. As set forth in detail elsewhere herein, the cleavage of Jagged1 produces soluble Jagged1, which then interacts with the Notch receptor, inhibiting Notch signaling. Therefore, one of skill in the art would understand, based on the disclosure herein, that inhibition of the cleavage of Jagged1 will repress the production of soluble Jagged1. The repression of soluble Jagged1 production is useful for the prevention of any conditions or disorders associated with repression of Notch signaling. For example, as disclosed in detail elsewhere herein, repression of Notch signaling induces a rapid, non-classical release of FGF-1 from a cell. Because in certain specific situations, FGF-1 (and other FGFs) are known to be protooncogeneic, the repression of soluble Jagged1 production will repress inhibition of Notch signaling, subsequently repressing the rapid, soluble Jagged 1-induced release of FGF-1 into the extracellular compartment and thereby inhibit angiogenesis.

In an embodiment of the present invention, a cell containing Jagged1 is contacted with an agent capable of inhibiting the cleavage of Jagged1. As will be understood by one of skill in the art, an agent capable of inhibiting cleavage of Jagged1, i.e., an inhibitor of soluble Jagged1 production, can be identified using methods well known in the art. By way of a non-limiting example, an inhibitor of Jagged1 cleavage can be identified by monitoring the cleavage of Jagged1 in a first system in which a Jagged1-cleaving agent is provided in the presence of a putative Jagged1 cleavage inhibitor, and comparing the results obtained in the first system with the results obtained from a second system in which the same Jagged 1-cleaving agent is provided in the absence any Jagged1 cleavage inhibitor. Inhibition of the cleavage of Jagged1 in the first system can be identified using numerous methods of analysis, including those methods of identification of Jagged1 cleavage/soluble Jagged1 production set forth in extensive detail elsewhere herein, followed by a differential comparison of the results obtained in the first and second experimental systems described immediately above. The presence of a lesser amount of soluble Jagged1 in the putative Jagged1 cleavage inhibitor-containing system than in the system devoid of any Jagged1 cleavage inhibitor is an indication that the putative Jagged1 cleavage inhibitor functions to inhibit the cleavage of Jagged1 and the production of soluble Jagged1.

One embodiment of the invention provides a method of inhibiting the cleavage of Jagged1, wherein thrombin is the Jagged1-cleaving agent. Inhibition of the thrombin-mediated cleavage of Jagged1 is confirmed using any method set forth herein for the analysis of the inhibition of Jagged1 cleavage. Inhibition of the thrombin-mediated cleavage of Jagged1 may occur in a number of ways. In one aspect of the invention, thrombin cleavage of Jagged1 may be inhibited by an agent that binds to thrombin, thereby preventing the interaction of thrombin with Jagged1 by preventing direct contact of thrombin with Jagged1. In another aspect of the invention, thrombin cleavage of Jagged1 may be inhibited by an agent that binds to thrombin and alters the structure of thrombin, thereby preventing the interaction of thrombin with Jagged1. In yet another aspect of the invention, thrombin cleavage of Jagged1 may be inhibited by an agent that binds to thrombin and inhibits the proteolytic activity of thrombin, thereby preventing proteolytic action of thrombin on Jagged1.

Another embodiment of the invention provides a method of inhibiting the thrombin-mediated cleavage of Jagged1, wherein the interaction of thrombin and Jagged1 is prevented by way of an agent that binds to Jagged1. In one aspect of the invention, thrombin cleavage of Jagged1 may be inhibited by an agent that binds to Jagged1, thereby preventing the interaction of thrombin with Jagged1 by preventing direct contact of thrombin with Jagged1. In another aspect of the invention, thrombin cleavage of Jagged1 may be inhibited by an agent that binds to Jagged1 and alters the structure of Jagged1, thereby preventing the interaction of thrombin with Jagged1.

The present invention also includes a method of identifying a compound capable of affecting the interaction of thrombin with Jagged1. The method comprises contacting a first reaction mixture containing Jagged1 and thrombin with a test compound, then assaying the first reaction mixture for the appearance of soluble Jagged1. A lower level of soluble Jagged1 in the first reaction mixture, when compared with a second reaction mixture containing Jagged1 and thrombin without the test compound, is indicative of a compound capable of affecting the interaction of thrombin with Jagged1. Such a compound is defined herein as inhibiting the interaction of thrombin with Jagged1, as the lower level of soluble Jagged1 is indicative of a decreased proteolysis of Jagged1 by thrombin. The invention includes any compound identified by the methods disclosed herein.

The present invention therefore also includes a method of identifying a compound capable of enhancing the interaction of thrombin with Jagged1. The method comprises contacting a first reaction mixture containing Jagged1 and thrombin with a test compound, then assaying the first reaction mixture for the appearance of soluble Jagged1. A higher level of soluble Jagged1 in the first reaction mixture, when compared with a second reaction mixture containing Jagged1 and thrombin without the test compound, is indicative of a compound capable of enhancing the interaction of thrombin with Jagged1. Such a compound is defined herein as enhancing the interaction of thrombin with Jagged1, as the higher level of soluble Jagged1 is indicative of a increased proteolysis of Jagged1 by thrombin. The invention includes any compound identified by this method.

The present invention also features a method of inhibiting production of soluble Jagged1 by a cell. In an embodiment of the invention, a cell is contacted with a cleavage-inhibiting amount of a cleavage inhibitor, thereby inhibiting cleavage of Jagged1 to produce soluble Jagged1. A "cleavage-inhibiting amount" of a cleavage inhibitor is defined herein as an amount of the cleavage inhibitor sufficient to produce a lower level of soluble Jagged1 in a reaction mixture containing thrombin, Jagged1, and the cleavage inhibitor, in comparison to the level of soluble Jagged1 in a reaction mixture that does not contain the cleavage inhibitor. A detectably lower level of soluble Jagged1 in the mixture comprising the inhibitor compared with the mixture that does not comprise it is an indication that the cleavage inhibitor inhibits cleavage of Jagged1 by thrombin.

In an aspect of the invention, the cleavage inhibitor is an agent that binds with thrombin, thereby preventing the interaction of thrombin with Jagged1 by preventing direct contact of thrombin with Jagged1. In another aspect of the invention, the cleavage inhibitor is an agent that binds to thrombin and alters the structure of thrombin, thereby preventing the interaction of thrombin with Jagged1. In yet another aspect of the invention, the cleavage inhibitor is an agent that binds to thrombin and inhibits the proteolytic activity of thrombin, thereby preventing proteolytic action of thrombin on Jagged1. In yet another aspect of the invention, the cleavage inhibitor is an agent that binds to Jagged 1, thereby preventing the interaction of thrombin with Jagged1 by preventing direct contact of thrombin with Jagged1. In still another aspect of the invention, the cleavage inhibitor is an agent that binds to Jagged1 and alters the structure of Jagged1, thereby preventing the interaction of thrombin with Jagged1.

The present invention also features a cleavage inhibitor that is an inhibitor of the proteolytic activity of thrombin. Compounds having the ability to inhibit protease activity, i.e., protease inhibitors, are well-known in the art, and accordingly, one of skill in the art would recognize and know how to use a compound that is a protease inhibitor. Further, protease inhibitors specific to serine proteases such as thrombin are well-known in the art, and are therefore not discussed herein.

Methods of Inhibiting Notch Receptor Signaling

The present invention also provides methods of inhibition of Notch signaling in a cell. As discussed elsewhere herein, the inhibition of Notch signaling plays a role in mediating differentiation in a cell. Therefore, it is a feature of the present invention to provide methods of mediating cellular differentiation, among other processes involving Notch signaling.

In an embodiment of the invention, a system capable of Notch receptor signaling is inhibited by the administration of thrombin to the system. Jagged1 is cleaved by thrombin, releasing soluble Jagged1, which binds to the Notch receptor, repressing Notch receptor signaling, and subsequently repressing events dependent upon Notch receptor signaling, such as, but not limited to neurogenesis and angiogenesis. This is because, as demonstrated for the first time herein, thrombin cleaves Jagged1 to release soluble Jagged1. Thus, soluble Jagged1, which inhibits Notch signaling, can be produced by administering sufficient thrombin to mediate cleavage of Jagged1. The amount of thrombin to be administered can be readily determined by assaying for the release of soluble Jagged1, the effect on Notch signal, and the like.

Methods of Inducing FGF-1 Transcript and FGF-1 Protein

The present invention features a method of inducing FGF-1 mRNA expression in a cell. In an embodiment of the invention, a cell comprising Jagged1 and Notch is contacted with thrombin. This is because, as demonstrated for the first time herein, thrombin cleaves Jagged1 to release soluble Jagged1. Upon cleavage and release of soluble Jagged1 from Jagged1 by thrombin, soluble Jagged1 binds with the Notch receptor, repressing Notch signaling. As a result of the repression of Notch signaling, cellular expression of FGF-1 mRNA is induced.

Numerous methods are available for quantitating the level of FGF-1 mRNA upregulated in the cell, and methods of detection of increased transcript levels are well known to the skilled artisan. Inducing the levels of FGF-1 mRNA can be beneficial in a system were increased expression of FGF-1 is desired. As discussed elsewhere herein, increased levels of FGF-1 are beneficial when the mitogenic properties of FGF-1 are desired and such instances would be readily appreciated by the skilled artisan.

While not wishing to be bound by any particular theory, increased levels of FGF-1 mRNA can provide a benefit when an increased release of FGF-1 into the extracellular compartment is desired. It is therefore a feature of the present invention to contact a cell comprising Jagged1, more preferably, further comprising Notch, and even more preferably, further comprising a thrombin receptor, with thrombin. Upon contacting the cell with thrombin, thrombin proteolytically cleaves Jagged1 to form soluble Jagged1, soluble Jagged1 binds to Notch, inhibiting Notch signaling and therefore, upregulating the production of FGF-1 mRNA. Concomitantly, thrombin cleaves the thrombin receptor, leading to the autoactivation of the thrombin receptor, which induces the rapid release of the FGF-1 from the cell into the extracellular compartment. The skilled artisan would know, based on the disclosure herein, that the cellular release of FGF-1 is beneficial when the mitogenic properties of FGE-1 are desired.

The present invention also provides methods for regulating FGF-1 export from cells, which offers many related advantages. That is, FGF-1 can be useful in a variety of biological and clinical contexts and has been recognized for potentially beneficial effects in a wide variety of cell and tissue type. (see, e.g., Burgess and Maciag, 1989, Annu. Rev. Biochem. 58:575-606; Friesel and Maciag, 1995, FASEB J. 9:919-925; Rifkin and Moscatelli, 1989, J. Cell Biol. 109:1-6; Klagsbrun and Baird, 1991, Cell 67:229-231). For instance, an amount of thrombin that increases FGF-1 export refers to an amount of thrombin that stimulates sufficient FGF-1 export to produce detectable levels of extracellular FGF-1 that are effective to bring about a desired effect. For example, by way of illustration and not limitation, regulated FGF-1 export can provide approaches for promoting the repair and healing of soft tissue injuries including burns, lacerations, and cutaneous ulcerations, as well as injuries to the cornea. The up-regulation of FGF-1 also can promote the healing of bone fractures, damaged/injured ligaments, damaged/injured tendons and inflammation of, among other things, bursae. Similarly, stimulation of FGF-1 release facilitates the regeneration of cartilage, cartilaginous tissue, or both. Enhanced FGF-1 release also may have a beneficial or therapeutic effect in the amelioration of vascular injury, as FGF-1 plays a role in vascular tissue repair and the growth of new blood vessels (i.e., angiogenesis). Other beneficial effects of increased FGF-1 production are discussed in U.S. Pat. Nos. 5,223,483 and 5,401,832, disclosures of which are hereby incorporated by reference in their entirety. These and other benefits of regulating FGF-1 export by cells will be appreciated by those familiar with the art and are not intended to be limited by the examples provided herein.

Determination of FGF-1 export by cells may be accomplished using any method for detecting FGF-1 known in the art, including those exemplified herein. In preferred embodiments the method for detecting FGF-1 further permits quantification of FGF-1 exported by cells. Well known methods for determining FGF-1 in soluble components of cell conditioned media may include (but need not be limited to) immunochemical methods using antibodies that specifically bind to FGF-1, such as radioimmunoassay (RIA), enzyme linked immunosorbent assay (ELISA), immunoprecipitation analysis or "western" immunoblot analysis. Other methods for determining FGF-1 may include biochemical analyses based on known structural and binding properties of FGF such as heparin binding, or biological assays quantifying, for example, cellular responses to FGF-1 present in a sample. These and other methods for determining FGF-1 will be known to those familiar with the art and the examples provided herein shall not be limiting.

As an example of a model system for upregulating FGF-1 export from cells, NIH 3T3 cells are transfected with a gene encoding FGF-1 to produce FGF-1-NIH 3T3 transfectants that release FGF-1 into culture medium as a response to cleavage of the thrombin receptor by thrombin. The thrombin-mediated release of FGF-1 by the cell is distinguished from the stress-mediated release of FGF-1 from the cell, as the thrombin-mediated release of FGF-1 occurs more rapidly than release of FGF-1 mediated by heat shock (e.g., 42° C. for two hours). The thrombin-mediated release of FGF-1 reaches maximum levels of release within one hour of contact of the cell with thrombin.

Methods of the present invention useful for inducing thrombin-mediated/thrombin receptor cleavage-mediated ("thrombin-mediated") release of FGF-1 into the extracellular compartment can be distinguished from stress-induced release of FGF-1 into the extracellular compartment, which is discussed in greater detail elsewhere herein. For example, the thrombin-mediated release of detectable FGF-1 occurs almost instantaneously upon thrombin-mediated cleavage of the thrombin receptor, and maximum local extracellular levels of FGF-1 are reached within one hour of the cell being contacted with thrombin. After one hour, the thrombin-induced extracellular levels of FGF-1 rapidly decrease, at which time stress-induced extracellular FGF-1 levels are beginning to increase. In contrast, the stress-induced release of FGF-1 occurs more slowly, and the extracellular levels of FGF-1 appearing due to a stress response do not reach an appreciable level until about two hours post stress-induction, thereby being distinguishable from the surprising FGF-1 release mediated by thrombin.

Therefore, the present invention features a method of inducing a rapid, short-duration cellular release of FGF-1. Such export of FGF-1 is useful when the mitogenic properties of FGF-1 are desired in more of a controlled manner than can be obtained by way of the stress-induced FGF-1 release pathway discussed elsewhere herein. In an embodiment of the invention, a cell comprising Jagged1, Notch and a thrombin receptor is contacted with thrombin. Jagged1 is cleaved by thrombin, releasing soluble Jagged1, which binds to the Notch receptor, repressing Notch receptor signaling and upregulating transcription of FGF-1 mRNA. Concomitantly, thrombin cleaves the N-terminal domain of the thrombin receptor, and mediating the non-classical release of FGF-1 into the extracellular compartment, which is rapid and of short-duration compared with the stress-induced release of FGF-1.

Methods of Affecting Cell Growth and Development

The present invention also includes a method of affecting angiogenesis in a system capable of angiogenesis. As more fully set forth elsewhere herein in discussing methods of using thrombin, or a functionally equivalent derivative or allelic or species variant thereof, thrombin can be used to affect angiogenesis due to the role of the Jagged1-Notch signaling pathway in angiogenesis and the newly discovered effect of thrombin in cleaving Jagged1 to produce soluble Jagged1, and the effects mediated by such soluble Jagged1.

In an embodiment of the invention, a method of affecting angiogenesis comprises contacting a cell comprising Jagged1 and Notch with thrombin. Upon contacting the cell with thrombin, thrombin cleaves Jagged1 to form soluble Jagged1 and soluble Jagged1 binds to the Notch receptor, inhibiting Notch signaling, thereby affecting angiogenesis.

One skilled in the art would appreciate, based upon the disclosure provided herein, that the ability of a thrombin-released soluble Jagged1 protein to affect angiogenesis can be measured not only by the aforementioned assays but by any similar assay now available or which is developed in the future to measure angiogenic potential and/or angiogenesis.

Further, one skilled in the art would appreciate that angiogenesis can be affected not only by the addition of exogenous thrombin to produce soluble Jagged1 protein in vivo, but can also be affected by the introduction of an exogenous nucleic acid encoding thrombin into a cell where it is expressed, and/or by the introduction into a mammal of cells which express the protein which is encoded by a thrombin nucleic acid. Thus, the method of the present invention is not limited to any particular manner in which thrombin is provided to a cell or to a mammal; rather, the invention encompasses various methods whereby a thrombin, and/or a portion thereof, is administered to a cell or to a mammal.

As more fully set forth elsewhere herein, a thrombin protein can be administered to a mammal via a variety of routes. Further, the dosage and amounts administered depend on numerous factors which are discussed more fully elsewhere herein. Pharmaceutical compositions and other relevant methods for administering thrombin are known in the art and are described, for instance, in Genaro, ed. (1985, Remington's Pharmaceutical Sciences, Mack Publishing Co., Easton, Pa.), which is incorporated herein by reference.

The amount of thrombin administered, whether it is administered as protein or as nucleic acid or as a cell expressing thrombin, is sufficient to detectably effect a Jagged1/Notch signaling response. The pharmaceutical compositions useful for practicing the invention can be administered to deliver a dose of between about 1 nanogram per kilogram and about 100 milligrams per kilogram of thrombin protein per patient body weight. Suitable amounts of the thrombin for administration include doses which are high enough to have the desired effect without concomitant adverse effects.

When the thrombin administered is a protein or peptide, a preferred dosage range is from about 1 pg to about 100 mg of protein or peptide per kg of patient body weight. When the thrombin is administered in the form of DNA encoding the same contained within a recombinant virus vector, an effective dosage of plaque forming units of virus per kilogram of patient body weight can be used. When naked DNA encoding the thrombin is to be administered as the pharmaceutical composition, a dosage of between about 1 pg to about 100 mg of DNA per kilogram of patient body weight can be readily determined. Further, when the thrombin is administered in the form of a cell expressing a nucleic acid encoding the same, the dosage of cells per kilogram of patient body weight can be assessed depending on the amount of thrombin expressed by the cells and the level desired as disclosed previously elsewhere herein.

When thrombin is administered by administering a nucleic acid encoding the protein, the nucleic acid can be administered "naked" (e.g., substantially free of any other substance with which a nucleic acid is typically associated such as protein, and the like). Alternatively, the nucleic acid can be encapsulated or otherwise associated with another substance capable of facilitating the introduction of the nucleic acid into a cell. Such nucleic acid delivery techniques are described elsewhere herein and are well-known in the art and are described in, for example, Sambrook et al., supra, and Ausubel et al., supra.

An "angiogenic effective amount" can be readily determined using any of the angiogenesis assays disclosed herein as well as methods well-known in the art. That is, the angiogenic effect of a thrombin administered to a cell and/or to an organism or assay system, can be assessed by, for example, measuring the effect of thrombin on expression of various genes (e.g., using differential display analyses such as SAGE analysis), migration of cells in culture, formation of chords by cells grown on plastic or on collagen matrices, assessing the level of repression of type I collagen expression, measuring the angiogenic potential using a CAM assay and/or measuring the in vivo growth of the cell using transplant studies in various murine models. However, the present invention is not limited to these assays to detect effects of thrombin on angiogenesis, or to determine an angiogenic effective amount; rather, similar assays, which are now known or which are developed in the future, may be used to determine the effect of thrombin on angiogenesis.

The invention also includes a method of affecting differentiation of a cell. The method comprises contacting a cell with an effective amount of a substantially purified thrombin. One skilled in the art would appreciate, based upon the disclosure provided herein, that contacting a cell with thrombin mediates signaling via the Jagged1/Notch pathway such that cell differentiation, angiogenesis, and other cellular processes, are affected as demonstrated by the data disclosed herein.

One skilled in the art would further appreciate, based upon the disclosure provided herein, that a cell should preferably express Jagged1 protein, a Jagged1 receptor, e.g., Notch, and comprise all necessary components of the Jagged1/Notch signaling pathway such that Jagged1/Notch interactions involved in differentiation can be affected by contacting the cell with thrombin. Cells that express Jagged1 protein and a Jagged1 receptor that can be used for such an assay include, but are not limited to, any mesodermal-derived cell, any endodermal-derived cell, any ectodermal-derived cell, and any neurodermal-derived cell, and the like. In addition to cells that naturally express Jagged1 protein and an endogenous Jagged1 receptor, the present invention encompasses cells that have been manipulated such that they express Jagged1 protein and/or a Jagged1 receptor and comprise the necessary Jagged1/Notch signaling pathway so that the effect of thrombin upon differentiation can be assessed in the cell.

A "differentiation effective amount" of thrombin can be readily determined by assessing the effect(s) of contacting a cell with thrombin or a fragment thereof. Such methods include, but are not limited to, those disclosed herein which include measuring the effect of thrombin on expression of various genes (e.g., using differential display analyses such as SAGE analysis) including repression of type I collagen expression, growth of cells on plastic or on collagen matrices, formation of chords and/or tubes by cells grown on plastic or on collagen matrices, measuring the angiogenic potential using a CAM assay and/or measuring the in vivo growth of the cell using transplant studies in various murine models. However, the present invention is not limited to these assays to detect effects of thrombin on cell differentiation; rather, similar assays which are now known or which are developed in the future may be used to determine the effect of thrombin on differentiation.

The subjects, animals, or patients, as referred to herein, treated in accordance with the present invention include any vertebrate organism; more preferably any mammal; most preferably a human. The only limiting factor is that the organism produces Jagged1 and Notch and/or the toporythmic genes which modulate binding to Notch.

By providing methods of affecting angiogenesis by modulating the thrombin-Notch-Jagged1 signal pathway, the present invention provides methods and compositions which affect a number of physiologic and pathologic conditions, including placental development, wound healing, rheumatoid arthritis, diabetic retinopathy and solid tumor growth and metastasis and motor neuron disorders. The referenced wound healing includes healing of any injury or lesion in the skin, tissue, vasculature, or nervous system of the subject, and includes cell migration and differentiation of cells comprising the mesoderm, endoderm, ectoderm and/or neuroderm. The wound or injury can be the result of surgery, trauma, and/or disease or condition. Such disease and/or conditions include ischemic lesions resulting from a lack of oxygen to the cell or tissue, e.g., cerebral or cardiac infarction or ischemia, malignant lesions, infectious lesions, e.g., abscess, degenerative lesions, lesions related to nutritional disorders, neurological lesions associated with systemic diseases, e.g., diabetic neuropathy and retinopathy, systemic lupus erythematosus, carcinoma or sarcoidosis, and lesions caused by toxins, e.g., alcohol, lead, etc. Motor neuron disorders may include, e.g., amylotrophic lateral sclerosis, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and hereditary Motorsensory Neuropathy (Charcot-Marie-Tooth disease).

Methods of Inhibiting Cytokine Release from a Cell

The present invention also features methods of inhibiting interleukin alpha 1 (IL-1α) release from a cell. Methods of inhibiting interleukin alpha 1 (IL-1α) release from a cell are useful for the reduction of inflammation and for mediating the inflammatory response. For example, the neointima development is a natural response of the arterial wall to injury, and is based on time-dependent infiltration of the arterial wall with inflammatory cells as well as on up-regulation of growth factors and inflammatory cytokines. This leads to migration of vascular smooth muscle cells (SMC) from the vessel media to the intima where they continue to proliferate and deposit extracellular matrix. IL1α, the prototype member of the IL1 gene family, is well recognized for its receptor-dependent inflammatory activities in vitro and in vivo. IL1α as an extracellular protein may be significant to restenosis due to its multiple roles as both a proinflammatory cytokine and as a regulator of endothelial cell behavior. It is through IL1α function as an inflammatory agent that it can recruit macrophages, which are the richest cellular source of FGF-1 in the body, to sites of inflammation and/or physiological stress. The role of IL-1α in various diseases is discussed in International Publication No. WO 03/018595 of Maciag et al. and in Mandinov et al. (2003, Proc. Natl. Acad. Sci. 100:6700-6705), each of which is incorporated by reference herein in its entirety.

In an embodiment of the present invention, thrombin is administered to a subject to repress the release of IL-1α from a cell in the subject. The administration of thrombin cleaves Jagged1, releasing soluble Jagged1, which binds to the Notch receptor, repressing Notch receptor signaling and repressing the release of IL-1α into the extracellular compartment. In an aspect of the invention, thrombin is administered to a subject to modulate inflammation in the subject. As the skilled artisan will understand based on the present disclosure, administration of thrombin represses the release of IL-1α into the extracellular compartment, thereby modulating inflammation in the subject.

Methods of Inhibiting Collagen Expression

The invention also includes a method of inhibiting expression of type I collagen in a cell. The method comprises administering an expression inhibiting amount of thrombin to a cell, thereby inhibiting expression of type I collagen. This is because, as demonstrated for the first time herein, thrombin cleavage of Jagged1 releases soluble Jagged1 and further inhibits expression of type I collagen. One skilled in the art would understand that various type I collagens (e.g., pro-α-1(I) collagen, pro-α-2(I) collagen, and the like) are encompassed by the invention, which is not limited to any particular type I collagen.

One skilled in the art would also appreciate, based upon the disclosure provided herein, that thrombin can be administered to a cell via a variety of methods including, but not limited to, administering a nucleic acid encoding thrombin, a vector encoding thrombin, and an isolated thrombin. The important feature is not how the thrombin is delivered to the cell but, rather, that thrombin be administered to the cell in sufficient quantity to affect thrombin-mediated Jagged1/Notch interactions involved in Jagged1/Notch signaling so as to repress expression of a type I collagen gene. That is, the thrombin is administered such that it can cleave Jagged1 expressed by the cell, thereby releasing soluble Jagged1.

The level of thrombin required to inhibit type I collagen expression can be readily determined using the assays disclosed herein or other assays well-known in the art and/or based from the assays disclosed elsewhere herein. For example, such assays include, but are not limited to, assessing the level of type I collagen gene expression using SAGE analysis and/or other nucleic-acid based assays (e.g., Southern blotting, Northern blotting, slot-blots, PCR-based methods, and the like). In addition, type I collagen expression can be determined by assessing the production of a specific type I collagen domain, e.g., the amino-terminal peptide portion of pro-α-1(I), and the like, using antibody-based detection methods, which are well-known in the art and/or disclosed elsewhere herein (e.g., immunoblotting, ELISA, immunoprecipitation, and such). Methods of inhibiting type I collagen expression are of crucial importance in the development of therapeutics for a plethora of fibrotic diseases associated with production of type I collagen for which there is currently no effective treatment. Therefore, the present invention provides important potential novel therapeutic methods based on the newly discovered cleavage of Jagged1 by thrombin to release soluble Jagged1.

Methods of Clonally Expanding a Stem Cell

The invention includes a method of producing a population of pluripotent stem cells. The method comprises obtaining at least one stem cell and expanding the cell under conditions where the pluripotential of the stem cell is maintained. Preferably, the cell is contacted with an amount of a factor selected from thrombin, soluble Jagged1 (sJ1), and thrombin receptor-activated peptide (TRAP), and any combinations thereof. This is because the data disclosed herein demonstrate, for the first time, that surprisingly, when a stem cell is contacted with at least one such factor, it grows and divides without detectable, or substantial, loss in pluripotency. More particularly, the stem cell retains the ability to grow and divide while retaining the ability to differentiate into various cell lineages. Further, as demonstrated elsewhere herein, the stem cell continues to express markers associated with a stem cell and does not detectably express markers associated with differentiation of the cell into a cell lineage.

One skilled in the art would appreciate, based upon the disclosure provided herein, that the present invention is not limited in any way to derivation of a stem cell from any particular tissue or source. Rather, the invention encompasses a wide plethora of methods either known in the art, or to be developed, for obtaining a population of cells containing at least one multipotent stem cell. Methods for obtaining stem cells from a wide variety of sources are well known in the art and include, e.g., isolation of stem cells from bone marrow, skin, hematopoietic tissue. Such methods include, but are not limited to, isolation of bone marrow-derived stem cells (i.e., stromal cells or mesenchymal stem cells) as described previously (see, e.g., Prockop, 1997, Science 284:71-74; Pereira et al., 1995, Proc. Natl. Acad. Sci. USA 92:4857-4861; Ferrari et al., 1998, Science 279:1528-1530; Gussoni et al., 1999, Nature 401:390-394; Peterson et al., 1999, Science 284: 1168-1170; Kessler and Byrne, 1999, Annu. Rev. Physiol.

61:219-242; Pittenger et al., 1999, Science 284:143-147). Additionally, multipotent stem cells, including multipotent neural stem cells, have been isolated from peripheral tissues, such as, but not limited to, tongue, skin and olfactory epithelium (International Patent Publication No. WO 01/53461, the disclosure of which is incorporated by reference in its entirety herein). Such multipotent neural stem cells can differentiate into neurons, astrocytes, Schwann cells, oligodendrocytes, and/or non-neural cells (e.g., cardiac cells, pancreatic cells, smooth muscle cells, adipocytes, hepatocytes, cartilage cells, bone cells, and the like). Thus, there are numerous sources of starting material from which to isolate a stem cell for use in the methods of the invention.

Regardless of the source of the multipotential stem cell, one skilled in the art, based upon the disclosure provided herein, would understand that the cell can be induced to differentiate into a wide plethora of cell types. This is because numerous signals, methods, and/or conditions are known in the art to direct differentiation of a stem cell to produce a desired cell type or types. Such signals and conditions include, but are not limited to, those known to induce neural crest-derived stem cells to become melanocytes, cartilage, smooth muscle cells, or bone (as reviewed in LaBonne et al., 1998, J. Neurobiol. 36:175-189; Sieber-Blum, 2000, Intl. Rev. Cytol. 197:1-33). Thus, once provided with the teachings disclosed herein, the skilled artisan can readily grow large numbers of stem cells, which can be induced to differentiate into a wide number of different, or the same, cell type.

Additionally, as would be understood by one skilled in the art, based upon the disclosure provided herein, the stem cells produced using the methods of the invention can be administered into a recipient, and the route and method of administration would be well-known to the artisan for providing cell based or gene therapy to the recipient. This is because it is known that stem cells administered to an animal can "home-in" to a particular site or tissue and there, perhaps due to factors in the tissue milieu, the cell can differentiate into a cell type of the tissue where it is located. Thus, the present invention provides multipotent stem cells that can be administered to an animal, including a human, without first differentiating the cell.

Moreover, the invention encompasses cell-based and gene-based therapeutic modalities comprising the clonally expanded stem cells produced according to the methods of the invention. That is, the expanded stem cell of the invention can be differentiated into a neural cell and administered to a patient in need thereof where the patient suffers a disease or condition where providing neural cells would treat or ameliorate the disease or condition. Such disease or condition includes, but is not limited to, spinal chord injury, stroke, trauma, ischemia, Parkinson's disease, and the like. The skilled artisan would readily appreciate that in such cell-therapy, stem cells can be obtained from the patient in need of treatment, expanded using the methods of the invention, and then the clonally expanded cells are administered (in the absence of or following directed differentiation) to the patient, such that the autologous transplant obviates any immune rejection of the cells.

Additionally, the present invention includes methods comprising introducing into the cell, at any point during clonal expansion, an exogenous nucleic acid encoding a therapeutic protein. Therefore, in this gene-therapy approach, the recombinant cells are administered to the patient and can express the protein, which was either not expressed, expressed in insufficient amount, or a defective form was expressed, in the recipient prior to administration of the recombinant cell. Once again, the cell can be differentiated into a desire cell type, or can be administered to the recipient as a multipotential stem cell that can differentiate into a desired cell type, or not, after it is administered to the patient. The invention also encompasses delivery of the cells produced as disclosed herein in a microcapsule or other device such that the cells are place in a site where expresion of a therapeutic protein can provide a benefit to the recipient.

The invention includes contacting a stem cell with a factor selected from thrombin, soluble Jagged1, and TRAP, or any combination thereof. This is because the data disclosed herein demonstrate that, surprisingly, contacting a stem cell with an effective amount of such factor enhances self-renewal of the cell such that the cell proliferates without detectable loss of pluripotential. That is, the data disclosed herein demonstrate that stem cells cultured in medium comprising sJ1 retain neurogenic potential as demonstrated using an art-recognized assay. For instance, as exemplified herein, the stem cell can be assessed for immunoreactivity with an antibody specific for GFAP (glial fibrillary acidic protein), which is a marker of the onset of glial-specific clonogenic differentiation. However, one skilled in the art, once armed with the teachings provided herein, would readily appreciate that a wide plethora of assays known in the art, and those to be developed in the future, for assessing the differentiation or other potential of a stem cell can be used to determine whether the stem cell retains its pluripotential or not. Such assays include methods based on detecting the level of expression of a stem cell marker, many of which are known in the art, and also include methods of assessing the onset of expression of a marker associated with a differentiated cell lineage.

Stem cell markers are well-known in the art and include, but are not limited to, nestin, p75, nucleostemin, Bmi1, among many others. Markers that can indicate the loss or decrease of pluripotential and the onset of differentiation into a differentiated cell lineage include, but are not limited to, GFAP for glial cells and astrocytes, neurofilament 160 (NF-160), MAP-2, βIII tubulin, and NeuN for neurons, and galactocerebroside and O-4 for oligodendrocytes, and myelin protein ($P_0$). The invention includes contacting a cell with sJ1, thrombin, TRAP, or a any combination thereof, because the data disclosed herein that thrombin induces the rapid non-classical release of FGF-1 by a cell, wherein the FGF-1 is present in a complex comprising, among other proteins, S100A13 and p40 Syt1. TRAP mimics thrombin in also inducing such export of GFG-1. Further, thrombin activated PAR1 signaling and enhanced FGF1.A transcription. Furthermore, the data disclosed herein demonstrate that contacting a multipotent stem cell (e.g., neural crest stem cell) with thrombin or sJ1 or TRAP induced expression of the FGF1.A transcript. Additionally, thrombin or sJ1, or both combined, enhanced multipotent stem cell self-renewal (e.g., clonogenic expansion, stemness, retention of neurogenecity, retention of neurogenic potential, retention of multipotentiality, retention of trifatent potential, maintenance of undifferentiated pluripotency, stamatogenesis, among others). That is, expansion of multipotent stem cells in growth medium comprising thrombin or sJ1 induced continued expression of markers associated with stem cells, reduced or inhibited detectable expression of markers associated with differentiation or loss of multipotentiality, preserved neurogenic capacity (e.g., a single cell gave rise to glial, neuron and neuron colonies containing either smooth muscle or glial markers), preserved sensitivity to instructive differentiation factors, maintained ability to generate trifatent clones (e.g., clones from a single colony were able to produce neuron, glial, and smooth muscle cell progeny), among other things.

One skilled in the art, based upon the disclosure provided herein, would understand that soluble Jagged1 can be administered to a cell, or contacted therewith, by administering full-length Jagged1 and thrombin, this is because, as disclosed elsewhere herein, it has been demonstrated that thrombin cleaves Jagged 1 to produce sJ1. Thus, where administration of sJ1 is required or desired, Jagged1 and thrombin can be administered in its stead, but only where the presence of thrombin is either required, or does not otherwise affect the process sought to be affected. The skilled artisan would, once armed with the teachings provided herein, be able to readily determine when thrombin and Jagged1 can be administered to a cell, tissue, or organism, instead of, or along with, sJ1.

These data amply support methods of growing, producing and expanding a stem cell while preserving the pluripotential of the cell. Thus, the present invention provides novel, and crucial, methods for the growth, culture and expansion of pluripotent stem cells. Once provided with these valuable cells, the skilled artisan would readily appreciate the numerous therapeutic approaches made possible by having large numbers of stem cells available. That is, one skilled in the art, once armed with the teachings of the present invention, can obtain a pluripotent stem cell from an animal and readily expand the stem cell which can then be induced to differentiate into a cell lineage of interest. This is especially valuable where large numbers of that differentiated cell cannot be obtained because, for instance, such cells cannot be expanded in vitro or otherwise (e.g., non-dividing cells such as neural cells, and the like).

Thus, the present invention makes possible the removal of a biological sample from a patient, wherein the sample comprises a pluripotent stem cell, and the production of large numbers of pluripotent stem cells in vitro. The pluripotent stem cell can then be administered to the patient thereby enabling ex vivo cell therapy where providing the stem cell to the patient provides a benefit. Moreover, the expanded pluripotent stem cells can be modified such that an exogenous nucleic acid encoding a protein of interest, e.g., a therapeutic protein, can be expressed by the cells. Methods for introducing an exogenous nucleic acid to a cell, or for activating expression of an endogenous nucleic acid not previously expressed in a cell, are well-known in the art, and include those disclosed herein, as well as methods discussed in, e.g., Sambrook and Russell (2001, Molecular Cloning, A Laboratory Approach, Cold Spring Harbor Press, Cold Spring Harbor, N.Y.), Ausubel et al. (2002, Current Protocols in Molecular Biology, John Wiley & Sons, NY), and other standard treatises. Thus, numerous gene therapy approaches are provided by the methods of the invention. Further, the unmodified or genetically modified pluripotent stem cells produced according to the method of the invention can be induced to differentiate into a wide plethora of cell types, and these cells can be administered to the patient. All of these methods obviate the risks of transplantation since the cells are administered to the original donor and such autologous transplant regimes do not generate an immune response against the cells.

One skilled in the art would appreciate, one provided with the teachings set forth herein, that the present invention, which provides methods for manipulating cell processes related to Notch-Jagged signaling and affected by thrombin activity, and for the production of a virtually endless supply of self-renewing multipotential cells has broad implications for numerous fields, including, but not limited to, regenerative, reparative, developmental, transplantation, and other fields where control of cell fate plays a role. Moreover, virtually all cells, if not each and every human cell, comprise Jagged/Notch signaling pathways, and the present invention provides a method of manipulating such pathway to affect cell processes. Accordingly, based upon the disclosure provided herein, the skilled artisan would readily appreciate that the present invention includes methods not only of clonally expanding stem cells without loss of multipotentiality. Rather, skilled artisan would understand that the present invention includes the inverse methods whereby, by affecting the pathways disclosed herein (e.g., by inhibiting thrombin cleavage of Jagged1, by inhibiting production of TRAP, by inhibiting interaction of thrombin with PAR1, by inhibiting thrombin-mediated Jagged/Notch signaling) in a cell, the cell can be induced to undergo terminal differentiation, and potentially apoptosis, thereby providing novel therapies related to control of unwanted cell growth (e.g., cancer) associated with a wide plethora of diseases, disorders and conditions associated with, or mediated by, such unwanted growth.

The present invention includes a method of expanding a pluripotent stem cell without detectable loss of pluripotency. The method comprises contacting a stem cell with an effective amount of thrombin, sJ1, TRAP, and combinations thereof. This is because, as demonstrated herein, contacting a pluripotent stem cell with these factors, or combinations thereof, mediates the clonal expansion, or growth and division, of a pluripotent cell without detectable loss of stem cell characteristics. The skilled artisan, based on the disclosure provided herein, would readily appreciate that an "effective amount" of sJ1, thrombin, TRAP, or any combination thereof, can be easily assessed using the assays disclosed herein, which evaluate, inter alia, rapid non-classical release of FGF-1 from a cell at issue, increased level of FGF1.A mRNA, cell growth and division without loss of a stem cell-associated marker and/or without detectable level of differentiation-associated marker, trifatency, production of multipotential progeny, and the like.

The method encompasses comparing the stem cell contacted with the factor with an otherwise identical stem cell which is not contacted with the factor to assess and compare the loss, if any, of pluripotency in the cell contacted with the factor. Thus, as amply disclosed elsewhere herein, an effective amount of a factor that mediates expansion of a pluripotent stem cell without detectable loss of pluripotency, can be readily determined based upon the disclosure provided herein, as well as the knowledge in the art, where assays for assessing the multipotential of a stem cell are widely available, and where other useful assays may be developed in the future, and all these techniques are encompassed by the present invention.

This is because the data disclosed herein demonstrate, for the first time, that contacting a pluripotent (i.e., multipotent) stem cell with sJ1, thrombin, TRAP, and combinations thereof, allows the proliferation of the cell without detectable loss of the multipotentiality of the cell. That is, the expanded stem cell is able to self-renew to produce at least one daughter cell in each cell division that is also a stem cell.

Further, the progeny cells do not exhibit detectable level of expression of a marker associated with a differentiated cell, and/or the daughter cells maintain the same, or greater, level of expression of a known stem cell marker compared with the level of expression of that stem cell marker in mother cell. The data disclosed herein demonstrate that when a multipotent stem cell was in cultured in medium comprising sJ1, thrombin, or both, and, optionally, TRAP, the cell continued to express the stem cell marker proteins p75, nestin, nucleostemin, and Bmi1, but did not express detectable levels of $P_0$ or GFAP, or other marker indicating the onset of differentiation unlike control, but otherwise identical stem cells that were not treated with sJ1, thrombin, or TRAP. Moreover, the data disclosed herein demonstrate that contacting the multipotential stem cell with sJ1 and/or thrombin preserves the trifatent potential of the cell in that the cell is then able to differentiate into three cell types, i.e., neuron (N), glial (G) and smooth muscle (Sm). Thus, the invention provides a novel method for clonally expanding a multipotential stem cell without loss of, among other things, the trifatent ability (i.e., the ability of progeny of each clone to develop into three difference cell types, such as, but not limited to, glial, neuronal and smooth muscle) of the clones.

The invention also encompasses a method of clonally expanding a stem cell, where the method comprises administering a differentiation inhibiting amount of thrombin, sJ1, TRAP, and combinations thereof. Again, the method is amply supported by the data disclosed herein demonstrating that a stem cell contacted with thrombin, sJ1, TRAP, or a combination thereof, can be clonally expanded to produce progeny that retains pluripotential in that the cells retain the ability of the mother cell to differentiate into at least two different cell types.

A "differentiation inhibiting amount," means any amount of thrombin, sJ1, TRAP, or a combination thereof, that detectably inhibits the loss of pluripotency of the stem cell in that the progeny cells retain the ability to self-renew and to differentiate into a least two different cell types, or retain the ability to a detectably greater extent than an otherwise identical cell that is not contacted with the factor.

The invention encompasses a method of clonally expanding a stem cell where the method comprises administering a differentiation inhibiting amount of at least one inhibitor of Notch-signaling to a stem cell under conditions wherein the cell proliferates. An inhibitor of Notch-signaling includes, but is not limited to, thrombin, sJ1 and TRAP, and combinations thereof. This is because the data disclosed elsewhere herein amply demonstrate that inhibition of Notch-signaling mediates clonogenic expansion of a multipotent stem cell such that the progeny of the stem cell do not undergo detectable loss of multipotential compared with the mother cell. Thus, the progeny cells retain, among numerous other things, the ability to produce progeny of various cell types (e.g., neuron, glial, and smooth muscle expressing cells), the ability to express cell markers known to be associated with stem cells, do not exhibit detectable expression of cell markers known to be associated with differentiated cells, retain sensitivity to instructive differentiation factors, and many other characteristics associated with stem cells.

One skilled in the art would appreciate, based upon the disclosure provided herein, that other inhibitors of Notch-signaling, including those developed in the future, are encompassed in the invention. This is because the data disclosed herein demonstrate, for the first time, that inhibition of Notch-signaling, using, among other things, thrombin, sJ1, or both, prevent the loss of differentiation potential of a pluripotent stem cell when the cell is grown and expanded in vitro. This discovery makes possible numerous potential stem cell-based therapeutics by making available large quantities of these cells which were previously not available.

Preferably, a multipotent stem cell is contacted with an effective amount of thrombin. Alternatively, the cell is contacted with sJ1. Preferably, the cell is contacted with TRAP. Even more preferably, the cell is contacted with thrombin and sJ1. Further, any combination of the three can be employed in the method of the invention, and the skilled artisan, once armed with the teachings provided herein, would readily ascertain a desirable combination, or the use of a single factor, in the method of the invention.

The present invention encompasses a method of producing a population of multipotent stem cells comprising contacting a multipotent stem cell with a differentiation inhibiting amount of thrombin, sJ1, TRAP, and any combination thereof. This is because, as more fully discussed previously elsewhere herein, the data disclosed herein amply support that a multipotent cell contacted by such factor retains its pluripotential thereby allowing the production of a population of such cells, which can then be used in myriad potential therapeutic uses. Also, the amount of the factor can be readily determined based upon the disclosure provided herein which sets forth numerous assays that can be used to determine the amount, as well as the stem cell characteristics of the cells, and which provides extensive reduction to practice. Among the variables to be considered in determining a differentiation inhibiting amount are, inter alia, the type of cell and culture conditions employed, and the skilled artisan is well versed in such techniques and therefore these are not discussed further herein.

The invention encompasses a method of inducing rapid release of FGF-1 from a cell where the method comprises contacting the cell with an effective amount of thrombin. This method is amply supported by the disclosure which demonstrates that a cell contacted with thrombin demonstrates the rapid non-classical release of FGF-1. These surprising results provide potentially therapeutic benefits in that the rapid release of FGF-1 is associated with, or mediates, numerous cell responses, including, among many others, an effect on differentiation, angiogenesis, thrombogenesis, and many others. Thus, the method provides numerous useful modalities relating to a plethora of diseases or conditions that can be treated or ameliorated by the rapid non-classical release of FGF-1 from a cell.

The "rapid release", as used herein, relates to the surprising discovery disclosed herein that contacting a cell with thrombin mediates the non-classical release of FGF-1 with remarkable kinetics, including, within minutes of contacting a cell with the factor. That is, typically, the release requires at least about ninety minutes of exposure to stress (e.g., elevated temperature, and the like), but a cell contacted with thrombin released detectable FGF-1 into the extracellular compartment at 37° C., and the release occurred substantially faster than 90 minutes after exposure to thrombin. Indeed, detectable extracellular FGF-1 was present after only 5 minutes in cells contacted with thrombin, as well as in cells contacted with TRAP, and cells contacted with sJ1, all disclosed elsewhere herein. Therefore, the rapid release of FGF-1 from cells can be mediated by contacting the cell with an effective amount of thrombin, TRAP, sJ1, and combinations thereof, without the need to elevate the temperature of the cell, or otherwise subject the cell to stress conditions. The rapid release mediates, in turn, various responses thereby providing useful methods for treating or alleviating diseases, disorders or conditions that are affected by the rapid release of FGF-1 from a cell, such as those disclosed or discussed elsewhere herein, and those that would be appreciated by the skilled artisan armed with the teachings provided herein.

Further, the invention encompasses inducing the rapid release of a complex comprising FGF-1 from a cell. The method comprises contacting the cell with an effective amount of at least one of thrombin, sJ1, TRAP, and combinations thereof, thereby inducing the rapid release. As discussed previously, the data disclosed herein demonstrate that contacting a cell with thrombin, sJ1, or TRAP, or combinations thereof, mediates the rapid non-classical release of FGF-1 from a cell. The release is rapid in that the kinetics are much faster than the typical release of FGF-1 from the cell in response to stress (e.g., an elevated temperature of about 42° C.). Moreover, as demonstrated herein, the release of FGF-1 is mediated by release of a complex comprising, among other things, S100A13 and p40 Syn1, such that these other proteins are also rapidly released from a cell along with FGF-1 upon contacting the cell with thrombin, sJ1, TRAP, or combination thereof. Accordingly, methods for the rapid release of any of the members of the FGF-1 containing complex are encompassed in the present invention. Such methods provide useful therapeutics for treatment or amelioration of disease, disorder or condition where the release of such molecules to the extracellular compartment would be useful as would be understood by one skilled in the art armed with the teachings provided herein.

The invention includes a method of producing a population of undifferentiated stem cells, wherein the method comprises culturing a stem cell in a medium comprising an effective amount of at least one factor selected from the group consisting of thrombin, sJ1, TRAP, and any combination thereof. This is because, as more fully disclosed elsewhere herein, the present invention demonstrates, for the first time, that contacting a stem cell with one, or combination, of these factors, preserves the differentiation potential of the stem cell as it divides in culture in that the factor inhibits differentiation as assayed by numerous methods to determine the stamatogenic potential of a cell. The skilled artisan would appreciate that culture conditions for growth of stem cells in culture are well known. Additionally, the present invention provides a factor (e.g., thrombin, sJ1, TRAP), which when added to the culture, preserves the stem cell characteristics and attributes of the cell as it grown and divides, thus providing ample numbers of undifferentiated stem cells as demonstrated herein.

The invention encompasses a method of producing a population of pluripotent stem cells. The method comprises culturing a stem cell in a medium comprising an effective amount of at least one factor selected from the group consisting of thrombin, sJ1, TRAP, and any combination thereof. This is because, as discussed elsewhere herein, the present invention demonstrates, for the first time, that contacting a stem cell with one, or combination, of these factors, preserves the differentiation potential (i.e., the "stamatogenic potential") of the stem cell as it divides in culture. That is, as demonstrated by the data disclosed herein, the factor inhibits differentiation as assessed by numerous methods to determine the stem cell-like attributes of a cell. The skilled artisan would appreciate that culture conditions for growth of stem cells in culture are well known. Additionally, the present invention provides a factor (e.g., thrombin, sJ1, TRAP), which when added to the culture, preserves the stem cell characteristics and attributes of the cell as it grown and divides, thus providing ample numbers of pluripotent stem cells as demonstrated herein.

Kits

The invention includes various kits which comprise a protein of the invention, and/or a nucleic acid encoding the protein, an applicator, and instructional materials which describe use of the kit to perform the methods of the invention. Although exemplary kits are described below, the contents of other useful kits will be apparent to the skilled artisan in light of the present disclosure. Each of these kits is included within the invention.

In one aspect, the invention includes a kit for producing a population of pluripotent stem cells. The kit is used pursuant to the methods disclosed in the invention. Briefly, the kit may be used to administer a factor to a stem cell, which factor preserves, or inhibits the loss of, the pluripotential of the stem cell. As demonstrated elsewhere herein, contacting a pluripotent stem cell with an effective amount of thrombin, sJ1, TRAP, and any combination thereof, mediates a plethora of effects as disclosed herein. These effects include, but are not limited to, the rapid non-classical release of FGF-1 from the cell, and the clonal expansion of the cell without detectable loss in the pluripotential of the cell. Thus, the kit comprises an effective amount of at least one of thrombin, sJ1, and TRAP. The kit further comprises an applicator and an instructional material for the use of the kit.

In one aspect, the kit comprises thrombin. This is because, as disclosed elsewhere herein, contacting a stem cell with thrombin can mediate the clonal expansion of the stem cell without loss of pluripotential ("stemness"). The kit can further comprise sJ1, and this is because the data disclosed herein demonstrate that the combination of thrombin and sJ1 can mediate the desired clonal expansion of stem cells while preserving their potential to differentiate.

The particular applicator included in the kit will depend on, e.g., the method used to administer the protein, and/or nucleic acid encoding the same, as well as the animal or cell to which the protein and/or nucleic acid of the invention is to be administered, and such applicators are well-known in the art and may include, among other things, a pipette, a syringe, a dropper, and the like. Moreover, the kit comprises an instructional material for the use of the kit. These instructions simply embody the disclosure provided herein.

The kit can include a pharmaceutically-acceptable carrier. The composition is provided in an appropriate effective amount as set forth elsewhere herein. Further, the route of administration and the frequency of administration are as previously set forth elsewhere herein.

The invention also includes a kit for expanding a pluripotent stem cell without detectable loss of pluripotency. The kit comprises a differentiation inhibiting amount of at least one of thrombin, soluble Jagged1 (sJ1), and thrombin receptor-activated peptide (TRAP). The kit further comprises an applicator and an instructional material for the use of the kit. The kit is used pursuant to the methods disclosed in the invention.

Other kits, useful for practicing the invention as disclosed herein, are encompassed herein. The above discussed kits are exemplary and other kits as would be readily appreciated by the skilled artisan, based upon the disclosure provided herein, are included in the invention.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Notch Activation Suppresses FGF-Dependent Cellular Transformation

Aberrant activations of the Notch and FGFR signaling pathways have been correlated with neoplastic growth in humans and other mammals. The data disclosed herein demonstrate that the suppression of Notch signaling in the NIH 3T3 cell either by the expression of the extracellular domain of the Notch ligand Jagged1 (i.e., nonmembrane or soluble Jagged1, sJ1) or dominant-negative forms of Notch1 (dnN1)

and Notch2 (dnN2) results in the appearance of an exaggerated FGF-dependent transformed phenotype characterized by anchorage-independent growth in soft agar. Anchorage-independent growth exhibited by Notch-repressed NIH 3T3 cells may result from prolonged FGFR stimulation caused by both an increase in the expression of prototypic and oncogenic FGF gene family members and the nonclassical export of FGF1 into the extracellular compartment. Interestingly, FGF exerts a negative effect on Notch by signaling CSL-dependent transcription and the ectopic expression of constitutively active forms of Notch1 or Notch2 abrogate FGF1 release and the phenotypic effects of FGFR stimulation. These data suggest that communication between the Notch and FGFR pathways may represent an important reciprocal autoregulatory mechanism for the regulation of normal cell growth.

Jagged1 is an FGF response gene in human endothelial cells undergoing differentiation on fibrin clots (Zimrin et. al, 1996, J. Biol. Chem. 271: 32499-32502). Since several of the phenotypic characteristics displayed by Notch-repressed cells were dependent on the activity of the FGFR effector molecule Src (Small et al., 2001, J. Biol. Chem. 276:32022-32030), it was examined whether communication between Notch and FGFR signaling pathways can also represent an important mechanism regulating cellular behavior in fibroblasts. While several studies report that the expression of Notch and/or its ligands was correlated with activation of the FGFR signaling pathway (Bongarzone et al., 2000, J. Neurosci. Res. 62: 319-328; Faux et. al, 2001, J. Neurosci. 21: 5587-5596; Matsumoto et al., 2002, J. Cell Biol. 156: 149-160.) and vice versa (Ikeya et al., 1999, Development 126: 4455-4463), little is known about how interactions between these two important and ubiquitous pathways influence cellular phenotype, including growth. In order to address this question, the effects of FGFR stimulation in combination with Notch repression or activation in NIH 3T3 cells was examined. These interactions were examined using the NIH 3T3 cell because phenotypic characteristics associated with the downregulation of Notch signaling (Small et al., 2001, J. Biol. Chem. 276:32022-32030) were examined previously in this cell type and because the NIH 3T3 cell represents a relatively simple system in that the NIH 3T3 cell primarily expresses transcripts encoding Notch1 and Notch2 but not Notch3 and Notch4. In addition, aberrant activations of both Notch (Rae et al., 2000, Int. J. Cancer 88: 726-732; Rohn et al. 1996, J. Virol. 70: 8071-8080; Zagouras et al., 1995, Proc. Natl. Acad. Sci. USA 92: 6414-6418) and FGFR (Forough et al., 1993, J. Biol. Chem. 268: 2960-2968; Maerz et al., 1998, Oncogene 17: 761-767; Yan et al., 1993 Mol. Cell Biol. 13: 4513-4522) signaling pathways have been found to be associated with neoplastic growth and the NIH 3T3 cell is uniquely sensitive to oncogene-mediated transformation (Shih et al., 1979, Proc. Natl. Acad. Sci. USA 76: 5714-5718).

The data disclosed herein demonstrate that that antagonistic interactions between the Notch and FGFR signaling pathways regulate anchorage-independent growth in murine fibroblasts. Stimulation of the FGFR pathway by exogenous FGF1 causes Notch-repressed cells to grow as detached spheroids in tissue culture and to aggressively form colonies in soft agar, phenotypic characteristics associated with cellular transformation (reviewed in Danen et al., 2001, J. Cell Physiol. 189: 1-13). The transformed phenotype exhibited by Notch-repressed cells may be attributed to their maintenance of FGFR generated signals generated by an increase in both the expression and release of FGF family members.

Further, FGF1 has an inhibitory effect on Notch/CSL-dependent transcription. In contrast, the expression of caN1 or caN2 protects the NIH 3T3 cell from FGF-induced anchorage-independent growth and suppresses the release of FGF1 under normal growth conditions. These results suggest that crosstalk between the Notch and FGFR signaling pathways may represent an important autoregulatory mechanism that is involved in the regulation of cell growth.

The Materials and Methods are now set forth.

Generation of Stable NIH 3T3 Transfectants

Stable NIH 3T3 transfectants for vector control, sJ1, dnN1, dnN2, caN1 and caN2 were obtained and screened for expression as previously described (Small et al., 2001, J. Biol. Chem. 276:32022-32030). The FGF1 mutant containing the 3' signal peptide sequence of FGF4 (hst-β (FGF4):FGF1), and FGF1 (pXZ38) stable transfectants were obtained and screened for expression as described in (Forough et al., 1993, J. Biol. Chem. 268: 2960-2968). Stably transfected constitutively active Ras (caRas) clonal populations were obtained by previously described methods (Small et al., 2001, J. Biol. Chem. 276:32022-32030) using the activated H-Ras pUSE-amp plasmid (Upstate Biotechnology).

Colony Formation in Soft Agar

Clonal populations of NIH 3T3 cells stably transfected with vector control, soluble Jagged1 (sJ1), constitutively active Notch1 (caN1), constitutively active Notch2 (caN2), dominant negative Notch 1 (dnN1), dominant negative Notch 2 (dnN2), an oncogenic mutant of FGF1 engineered with the FGF4 signal peptide sequence (hst-β (FGF4):FGF1), or constitutively active oncogenic Ras construct (caRas), were plated on 6 cm tissue culture dishes with 0.5% agar in an overlay containing DMEM (Gibco BRL) media, 10% bovine calf serum (BCS; Hyclone), and 0.33% agar at $1.5 \times 10^3$ cells/dish. As indicated, some dishes were also treated with 1 μM of the FGFR1-specific inhibitor, PD166866 (Panek et al., 1998, J. Pharmacol. Exp. Ther. 286: 569-577) and/or 10 ng/ml recombinant human FGF1 and 10 U/ml heparin (Sigma). Cells were fed with 0.5 ml of media with or without FGF1 and/or the FGFR1-specific inhibitor every 3 days as indicated. Twenty days after plating, colonies were stained with p-iodonitrotetrazolium violet (Sigma) for visualization. Quantitation of colony formation was achieved by counting all p-iodonitrotetrazolium violet-stained colonies consisting of more than 4 cells under a Zeiss Stemi SVII Apo dissecting microscope.

Analysis of FGF1-Induced Spheroid Formation

Clonal populations of NIH 3T3 stable transfectants were resuspended and grown in media containing 10% BCS, 10% BCS containing 1 μM PD166866, 10% BCS containing 10 ng/ml recombinant human FGF1 and 10 U/ml heparin or 10% BCS containing 10 ng/ml recombinant human FGF1, 10 U/ml heparin and 1 μM PD166866 as indicated in the figure legend. Approximately $2 \times 10^5$ cells were plated per well (6-well dish) and three days after plating, phase-contrast micrographs of the cells were taken.

Analysis of Spheroid Formation and Soft Agar Colony Growth in Hst-β(FGF4):FGF1 Transfectants Following Adenoviral Transduction Hst-β(FGF4):FGF1 stable transfectants were transduced with either adenovirus expressing lacZ, dnFGFR, caN1 or caN2 as described below. After 24 hours, the cells were plated on 6-well dishes at concentration $10^5$ cells/well and three days after plating, phase-contrast micrographs of the cells were taken. For colony formation in the soft agar assay, the hst-β(FGF4):FGF1 transfectants were transduced with the indicated recombinant adenoviral vectors, and plated into 0.33% agar 24 hours after the transduction. Two weeks after plating, colonies were visualized by staining with p-iodonitrotetrazolium violet.

Analysis of the Expression of the FGF/FGFR Gene Family Members

Total RNA from vector control, sJ1, caN1 and dnN1 stable transfectants was isolated using Tri Reagent™ (Sigma) according to the manufacturer's protocol. cDNA was obtained from 5 µg total RNA with SuperScript™ (Invitrogen) reverse transcriptase using an oligo dT primer (Invitrogen). The following specific primers were purchased from IDT and used for RT-PCR analysis. Sense primers are indicated by (s); Antisense primers are indicated by (as):

```
                                    (SEQ ID NO:5)
FGF1(s)
5'-ATGGCTGAAGGGGAGATCACAACC-3';

(SEQ ID NO:6)
FGF1(as)
5'-CGCGCTTACAGCTCCCGTTC-3';

(SEQ ID NO:7)
FGF2(s)
5'-ATGGCTGCCAGCGGCATCAC-3';

(SEQ ID NO:8)
FGF2(as)
5'-GAAGAAACAGTATGGCCTTCTGTCC-3';

(SEQ ID NO:9)
FGF3(s)
5'GCCTGATCTGGCTTCTGCTGC-3';

(SEQ ID NO:10)
FGF3(as)
5'-GCAGCTGGGTGCTTGGAGGTGG-3';

(SEQ ID NO:11)
FGF4(s)
5'-ACCACAGGGACGACTG-3';

(SEQ ID NO:12)
FGF4(as)
5'-CATACCGGGGTACGCGTAGG-3';

(SEQ ID NO:13)
FGF6(s)
5'-GGGCCATTAATTCTGACCACGTGCCTG-3';

(SEQ ID NO:14)
FGF6(as)
5'GGTCCTTATATCCTGGGGAGGAAGTGAGTG-3';

(SEQ ID NO:15)
FGF7(s)
5'-CACGGATCCTGCCAACTCTGC-3';

(SEQ ID NO:16)
FGF7(as)
5'-CCACAATTCCAACTGCCACGGTC-3';

(SEQ ID NO:17)
FGF8(s)
5'-CTCTGCCTCCAAGCCAGGTAAG-3';

(SEQ ID NO:18)
FGF8(as)
5'-GCTGATGCTGGCGCGTCTTGGAG-3';

(SEQ ID NO:19)
FGF9(s)
5'-GGTGAAGTTGGGAGCTATTTCG-3';

(SEQ ID NO:20)
FGF9(as)
5'-CATAGTATCTCCTTCCGGTGTCCAC-3';
```

```
                                    (SEQ ID NO:21)
FGF10(s)
5'-CACATTGTGCCTCAGCCTTTC-3';

(SEQ ID NO:22)
FGF10(as)
5'-CCTCTATTCTCTCTTTCAGCTTAC-3';

(SEQ ID NO:23)
FGFR1(s)
5'-AGGCCAGCCCCAACCTTG-3';

(SEQ ID NO:24)
FGFR1(VT + as)
5'-GGAGTCAGCTGACACTGTTAC-3';

(SEQ ID NO:25)
FGFR1(VT - as)
5'-CACTGGAGTCAGCTGACACC-3';

(SEQ ID NO:26)
FGFR2(s)
5'-TCCTTCAGTTTAGTTGAGGATAC-3';

(SEQ ID NO:27)
FGFR2(as)
5'-GCAGCTTTCAGAACCTTGAGG-3';

(SEQ ID NO:28)
FGFR3(s)
5'-CAAGTGCTAAATGCCTCCCAC-3';

(SEQ ID NO:29)
FGFR3(as)
5'-GCAGAGTATCACAGCTGC-3'.
```

PCR amplification was performed for 45 cycles as follows: 40 seconds at 94° C., 40 seconds at 50° C. (for FGF2, FGF3, FGF4 and FGFR3) or at 55° C. (for FGF1, FGF6, FGF7, FGF8, FGF9, FGF10, FGFR1 and FGFR2), 1 minute at 72° C. For FGF5, RT-PCR analysis was performed as described (Ozawa et al., 1998, J. Biol. Chem. 273: 29262-29271) and all amplified DNA was visualized with ethidium bromide on 1.5% agarose gels.

Analysis of FGF1 Release in Stable NIH 3T3 Cell Transfectants

Adenovirus vector expressing lacZ, FGF1, caN1, dnN1, caN2 or dnN2 was prepared as described (Hardy et al., 1997, J. Virol. 71: 1842-1849) at a titer of approximately $10^{12}$ viral particles/ml. For adenoviral transduction, NIH 3T3 stable transfectants were incubated in serum-free medium with approximately 103 viral particles/cell in the presence of poly-D-lysine hydrobromide (Sigma) ($5 \times 10^3$ molecules/viral particle) for two hours at 37° C., after which the adenovirus-containing media was removed and replaced with serum-containing medium (10% BCS) for an additional 24 hours. The transduced cells were harvested by trypsin digestion and seeded for the heat shock experiments as previously described (Jackson et al., 1992, Proc. Natl. Acad. Sci. USA 89: 10691-10695). After heat shock, the conditioned media from cells exposed to either 37° C. (normal conditions) or 42° C. (heat shock conditions) were treated with 0.1% DTT for 2 hours at 37° C., adsorbed to heparin-Sepharose and eluted from the column with 1.5 M NaCl. The eluants were resolved by 15% (w/v) SDS-PAGE and evaluated by FGF1 immunoblot analysis as described (Jackson et al., 1992, Proc. Natl. Acad. Sci. USA 89: 10691-10695).

Transient Transfection Assays of CSL-Regulated Transcription

NIH 3T3 cells were plated onto fibronectin-coated (10 µg/cm2) 12-well tissue culture dishes and transiently transfected at approximately 80% confluency with 500 ng of a Luciferase construct activated by 4 tandem copies of the CSL (CBF1) response element (Hsieh et al. 1996, Mol. Cell. Biol. 16: 952-959), 100 ng of the TK *Renilla* (Promega) construct as an internal control for transfection efficiency, and 500 ng of either vector control, sJ1 or caN1 constructs using Fugene 6 (Roche) per manufacturer's instructions. For analysis of caN1 activity in the background of NIH 3T3 stable lines, vector control, caN1, sJ1 and hst-β(FGF4):FGF1 stable transfectants were plated onto fibronectin-coated (10 μg/cm2) 12-well tissue culture dishes and transiently transfected with 500 ng of the CSL-Luciferase construct, 100 ng of the TK *Renilla* (Promega) construct as an internal control for transfection efficiency, and 200 ng of caN1. For all experiments, the media was replaced 24 hours after transfection with fresh DMEM (Gibco BRL) supplemented with 10% BCS or with 10% BCS containing 1, 2.5, 5 or 10 ng/ml of recombinant human FGF1 and 10 U/ml heparin as indicated in the legend for each figure described in the Brief Description of the Drawings elsewhere herein. The cells were harvested 48 hours after the media change and Luciferase/*Renilla* activity was measured using Promega's Dual-Luciferase Reporter Assay System. The efficiency of transcription was measured and normalized in relationship to the activity of pRL-TK *Renilla* and the activity is reported as the ratio of Luciferase/*Renilla* activity. Each experiment was done in triplicate and error bars represent the standard error of the mean.

Analysis of Jagged1 Expression

Vector control, SJ1, CaN1, J1, Hstβ(FGF4):FGF1 and sJ1: caN1 stable NIH 3T3 cell transfectants were plated on tissue culture dishes in either normal growth media (DMEM (Gibco BRL) media, 10% bovine calf serum (BCS; Hyclone)) or normal growth media containing 10 ng/ml recombinant FGF1 and 10 U/ml heparin. Cells were harvested at confluency (based on status of vector control cells grown in normal growth media).

Because hst-β(FGF4):FGF1 stable transfectants and the sJ1 transfectants grown in FGF1-containing media form spheroids, all cells were harvested by scraping in the presence of the growth media dn then the cells/growth media was collected into sterile 15 ml conical tubes. Cells were pelleted by centrifugation at 800×g for 5' at 4° C. After centrifugation, the supernatant was removed and the cell pellets were washed 3× with 1×PBS. Cells were lysed in 500 μl in 20 mM tris, pH 7.5 containing 300 mM sucrose, 60 mM KCl, 15 mM NaCl, 0.5 mM EDTA, 0.5% (v/v) Triton X-100 1 mM Phenymethyl sulfonyl flouride, 0.1% SDS, 2 μg/ml aprotinin, 10 μg/ml aprotinin, 10 μg/ml leupeptin, and 1 mM sodium orthovanadate for 15 minutes on ice. Cell lysates were pelleted and the supernatant containing soluble proteins removed.

Samples were normalized to protein concentration using the BCA Protein Assay Kit (Pierce). Equal protein loads were resolved by 8% acrylamide (w/v) SDS PAGE, transferred to Hybond C (Amersham) and immunoblotted with the Jagged1 (c20) antibody (Santa Cruz). Jagged1 was visualized using a horseradish peroxidase-conjugated antibody against goat IgG (Sigma) and the ECL detection system (Amershan).

The Results of the Experiments disclosed herein are now described.

Stimulation of the FGFR Pathway Potentiates a Transformed Phenotype in Notchrepressed Fibroblasts To determine how interactions between the Notch and FGFR signaling pathways regulate cellular processes, the response of Notch-activated and Notch-repressed NIH 3T3 cells to the addition of recombinant FGF1 to the growth media was examined (FIG. 1). Surprisingly, NIH 3T3 cells in which endogenous Notch signaling was repressed (sJ1, dnN1) formed multicellular, spheroid-like structures similar to those observed in NIH 3T3 cells stably expressing an oncogenic mutant of FGF1 engineered with the FGF4 signal peptide sequence (hst-β(FGF4):FGF1) to force constitutive secretion of FGF1 through the conventional ER-Golgi pathway (Forough et al., 1993, J. Biol. Chem. 268: 2960-2968). The cells contained within the spheroid structures were viable as they continued to proliferate over time and also grew as a monolayer when replated onto fresh tissue culture dishes in the absence of recombinant FGF1 in the growth media. In contrast, vector control and caN1 NIH 3T3 cells stable transfectants did not form spheroids but instead continued to grow as a monolayer in the presence of recombinant FGF1. Spheroid formation was a specific response to FGF1 as treatment with the FGFR1-specific inhibitor PD166866 (Panek et al., 1998, J. Pharmacol. Exp. Ther. 286: 569-577) completely abolished FGF1-induced spheroid formation in sJ1, dnN1 and hst-β (FGF4):FGF1 stable transfectants.

Figure 2A:
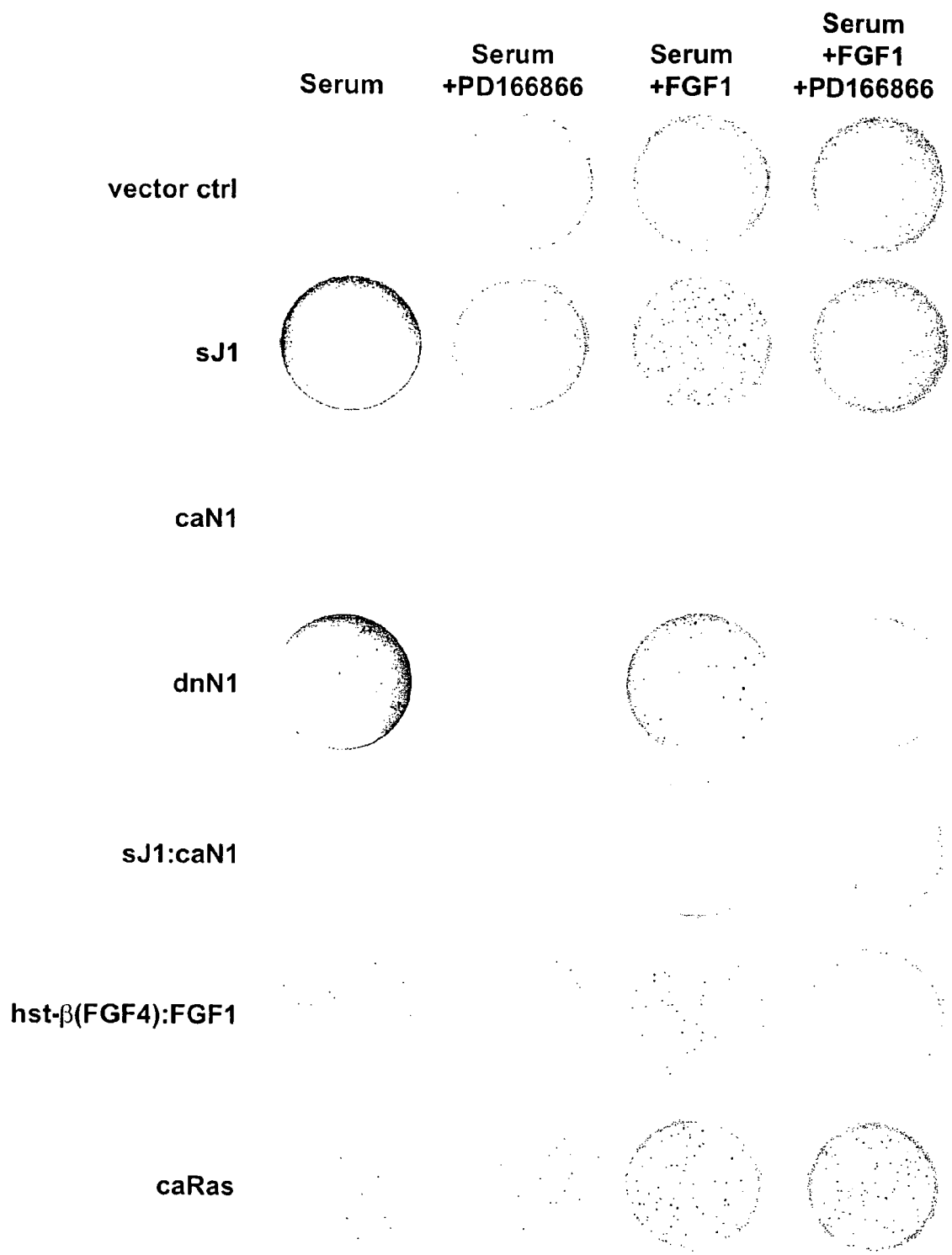
FIG. 2A depicts cells grown in soft agar as described elsewhere herein with some dishes treated with 1 µM of the FGFR1-specific inhibitor, PD166866, and/or 10 ng/ml recombinant human FGF1 and 10 U/ml heparin. Cells were fed every 3 days and the colony number was quantified after 20 days.
Figure 2B:
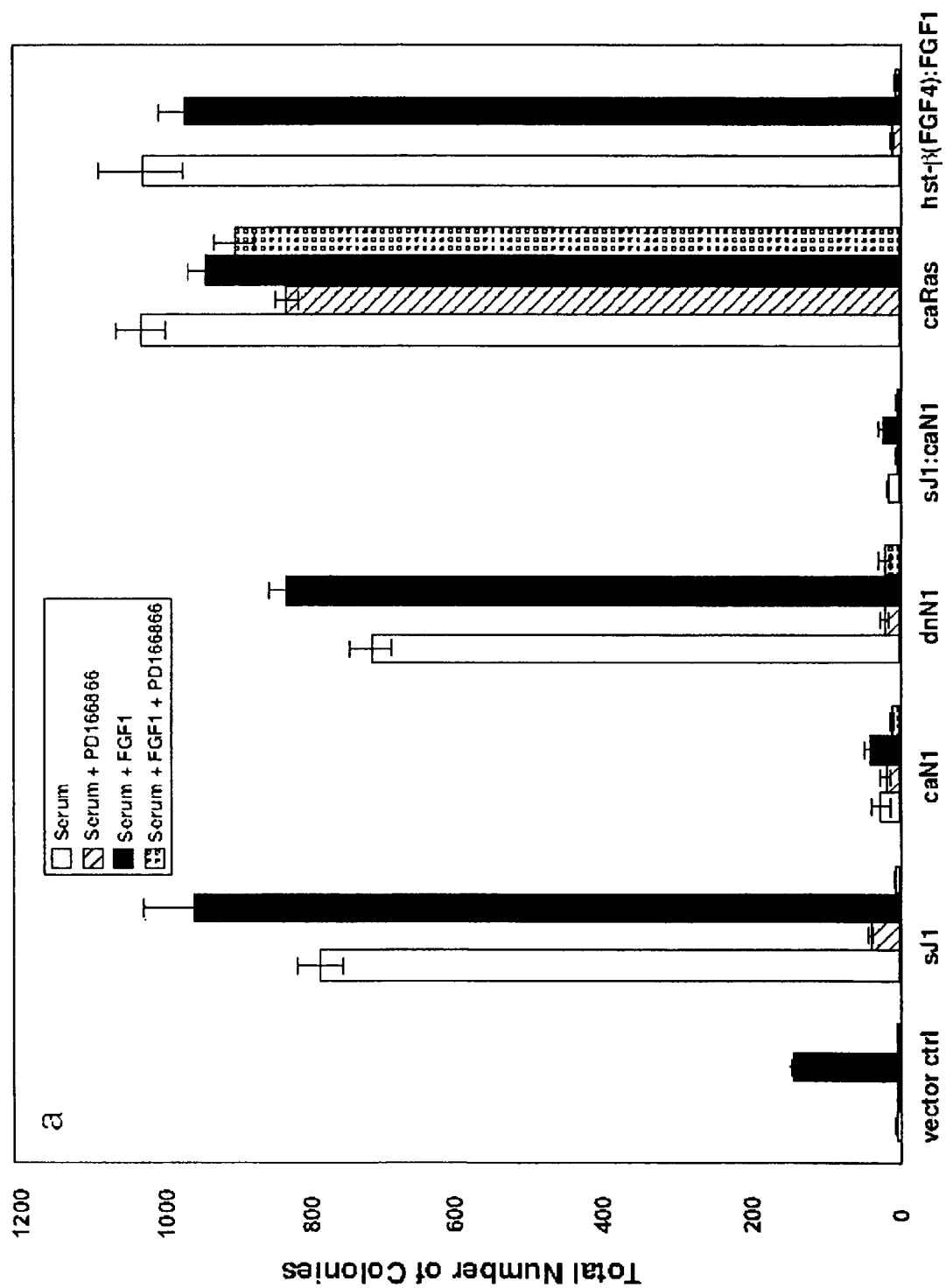
FIG. 2B is a histogram demonstrating the number of colonies quantified by counting all stained colonies from two plates for each experimental condition with a mean +/− standard error. Error bars represent the standard error of the mean and the data reflects a representation of one of several soft agar experiments conducted.

Cellular proliferation despite detachment from the extracellular matrix is indicative of anchorage-independent growth in most cell types and is an in vitro signature of the NIH 3T3 cell transformed phenotype (Shih et al., 1979, Proc. Natl. Acad. Sci. USA 76: 5714-5718). Therefore, Notch-activated and Notch-repressed cell lines were examined for anchorage-independent growth in soft agar both in the presence and absence of exogenously added recombinant FGF1 (FIGS. 2A and 2B). Although it was previously reported that sJ1 NIH 3T3 stable transfectants do not form colonies in soft agar when plated at low seed densities (100 cells/6 cm dish) in growth media containing 10% BCS (Wong et al., 2000, Biochem. Biophys. Res. Commun. 268: 853-859), the data disclosed herein demonstrate that sJ1 and dnN1 transfectants do form small, pinpoint-sized colonies in soft agar when plated at seed densities greater than 1500 cells/6 cm dish. The addition of FGF1 to the growth media greatly exaggerated the size of the colonies formed by sJ1 and dnN1 transfectants so that they were clearly visible to the eye, although the number of colonies did not significantly increase. Indeed, the intensity of the transformed phenotype induced by FGF1 in the Notch-repressed NIH 3T3 cells resembled that exhibited by NIH 3T3 cells stably expressing either an oncogenic Ras construct (caRas) or an oncogenic mutant of FGF1(hst-β(FGF4): FGF1). Interestingly, the size of the colonies also increased at seed densities of 5,000 to 10,000/6 cm dish even in the absence of exogenously added recombinant FGF1.

In contrast, the addition of FGF1 had either no effect or only resulted in the formation of sparse and very small colonies in the caN1 and vector control transfectants. These transfectants also do not form colonies regardless of plating concentration in the absence of FGF1. NIH 3T3 cells stably expressing dnN2 but not caN2 also formed small colonies whose size was dramatically increased in the presence of FGF1. Similar to spheroid formation, FGF potentiation of soft agar growth in NIH 3T3 cell growth was a specific response to FGFR stimulation since the addition of the FGFR1 inhibitor PD166866 substantially reduced FGF1-mediated colony formation in sJ1, dnN1 and the hst-β (FGF4): FGF1 transfectants, but had no effect on colony formation in the caRas cells. Treatment with PD166866 also inhibited small colony growth exhibited by sJ1 and dnN1 in the absence of FGF1. These data suggest that repression of endogenous Notch signaling sensitizes the NIH 3T3 cell to FGFR-mediated cellular transformation and that activation of the Notch signaling pathway may protect the NIH 3T3 cell from abnormal growth.

Activation of Notch Inhibits FGFR-Mediated Transformation

To further explore the possibility that Notch signaling may protect the NIH 3T3 cell from FGF-mediated anchorage independent growth, the ability of sJ1 NIH 3T3 stable transfectants cotransfected with caN1 to form colonies was assessed both in the presence and absence of FGF1. Expression of caN1 in the sJ1 NIH 3T3 background dramatically inhibited, in terms of both number and size, colony formation that occurred in the presence or absence of FGF1. Indeed, the number of colonies formed by the sJ1:caN1 cotransfectants was similar to that observed in vector control and caN1 stable lines (FIGS. 2A and 2B).

Figures 1, 3B:
Figures 2, 3B:
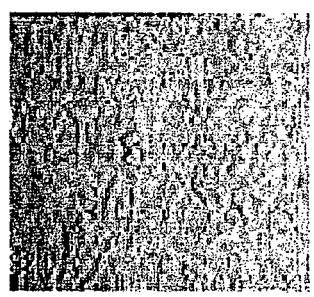
Figures 3, 3B:
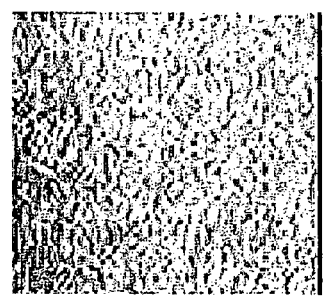
Figures 3, 3B, 4:
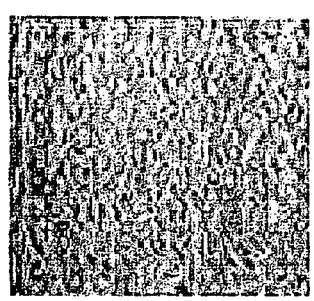

Unlike sJ1 single transfectants, sJ1:caN1 cotransfectants did not form spheroids in the presence of FGF1. However, these cells were less adherent to the tissue culture dish than the vector control or caN1 cells (FIG. 1). Although analysis of several different clonal cell lines of the various stable transfectants used in these studies yielded similar results, experiments were performed to confirm that constitutively active Notch could repress FGFR-mediated transformation by transducing hst-β(FGF4):FGF1 stable transfectants with adenovirus expressing either caN1 or caN2. Adenoviral expression of either caN1 or caN2, but not a lacZ control, reduced the number of colonies formed in soft agar to a level similar to that observed in the hst-β(FGF4):FGF1 NIH 3T3 cell transfectants transduced with a dominant negative FGFR1 construct (FIG. 3A) and completely abolished spheroid formation (FIG. 3B). These data support the novel finding that activation of the Notch pathway protects the NIH 3T3 cell from FGFR-mediated transformation.

Notch Signaling Regulates the Expression of the FGF Gene Family

Figure 4A:
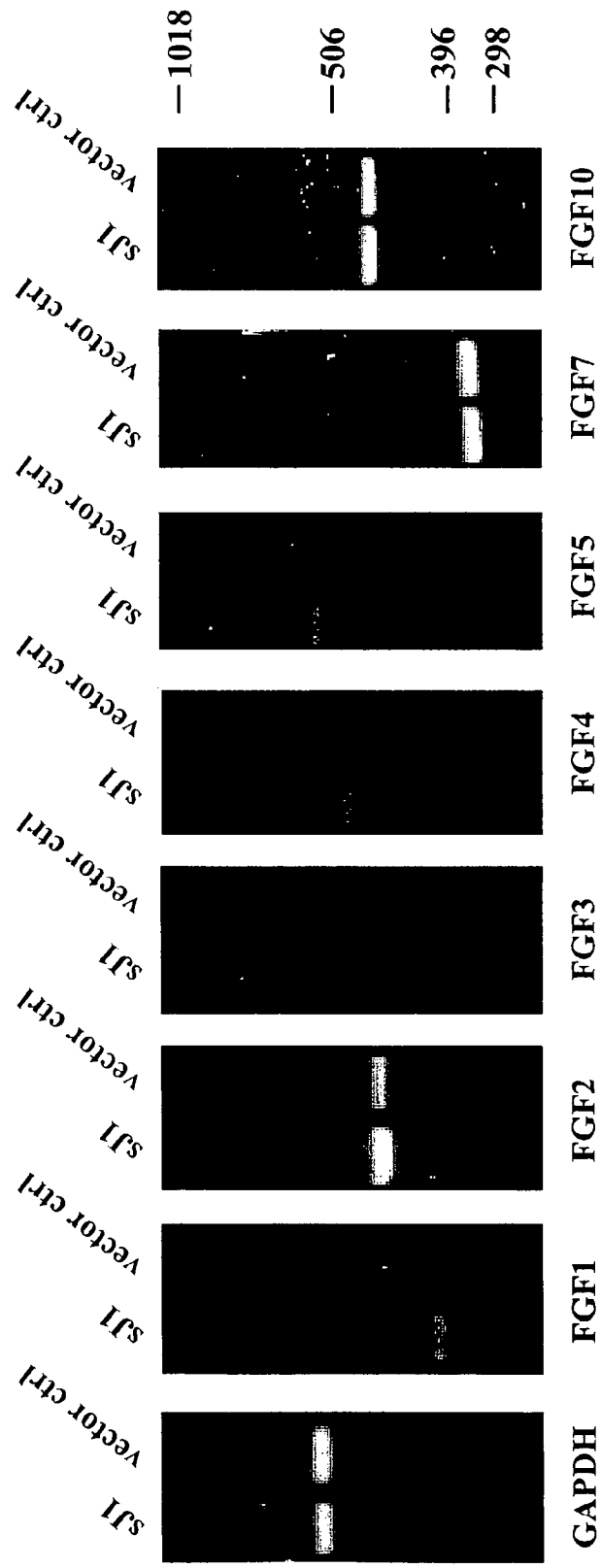
FIG. 4A depicts the expression of the FGF family members in vector control and sJ1 stable NIH 3T3 transfectants as determined by RT-PCR using primers and conditions as described elsewhere herein. RT-PCR using primers specific for murine GAPDH was performed as a control for cDNA synthesis.
Figure 4B:
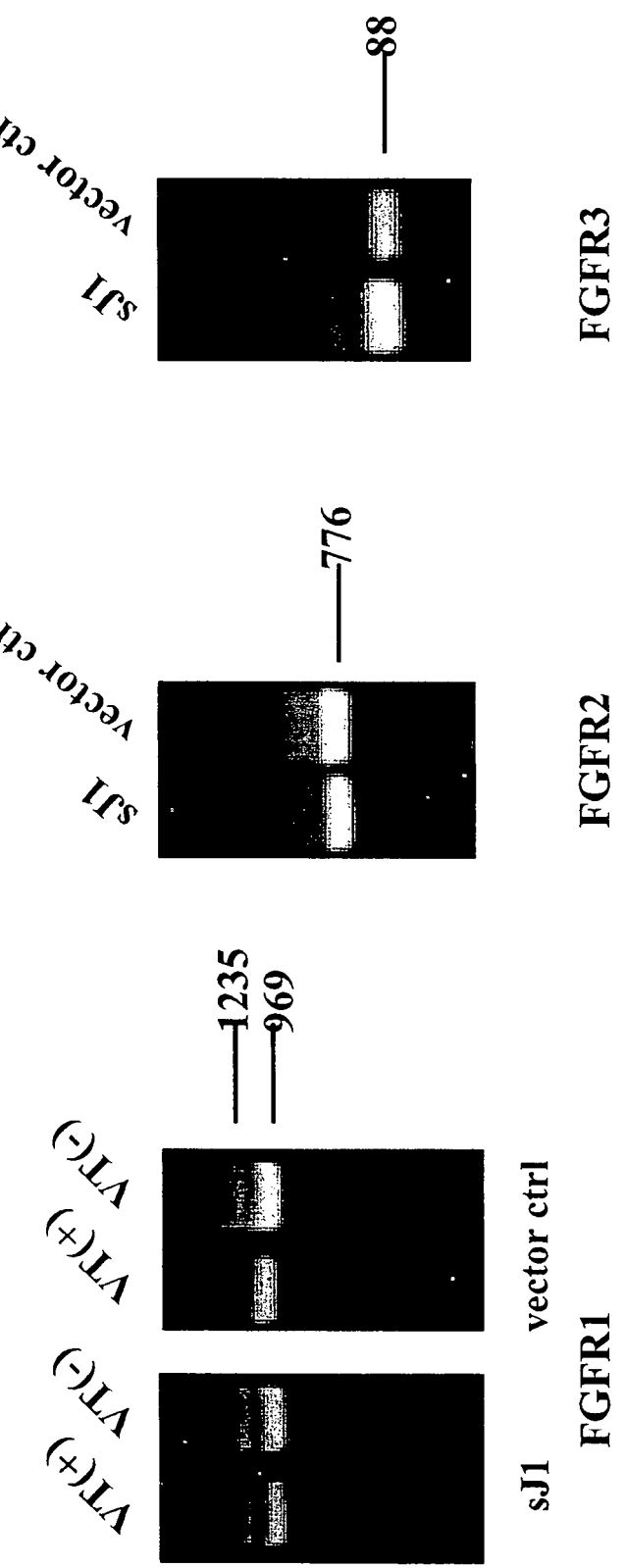

It was previously reported that Notch-repressed cells exhibit a pattern of tyrosine phosphorylation similar to that observed in NIH 3T3 cells stimulated by FGF I (Small et al., 2001, J. Biol. Chem. 276:32022-32030). The data disclosed herein demonstrate that sJ1 and dnN1 cells form small, PD166866-sensitive colonies in soft agar even in the absence of exogenous FGF1. Taken together, these observations suggested that Notch-repressed transfectants were releasing FGF into the extracellular compartment. Therefore, vector control and sJ1 cells were examined for expression of the first 10 of the 23 known members of the FGF gene family, including the prototypes FGF1 and FGF2 by using RT-PCR (FIG. 4A). While transcripts for FGF2, FGF7, and FGF10 are expressed in all the cell lines examined, expression of mRNAs encoding FGF1, FGF3, FGF4, and FGF5 is limited to the sJ1 stable transfectants. In contrast, the pattern of FGF gene family expression in caN1 transfectants is the same as that seen in the vector control lines. Transcripts encoding FGF6, 8 and 9 were not found in any of the cell lines examined by RT-PCR. No differences were found in the expression pattern of the FGFRs as all cell lines examined expressed both the 2 and 3-Ig loop isoforms of FGFR1, 2 and 3 as well as the VT− and VT+ isoforms (Burgar et al. 2002, J. Biol. Chem. 277: 4018-4023) of FGFR1 (FIG. 4B). These data indicate that sJ1-mediated repression of endogenous Notch signaling regulates the FGFR signaling pathway by a mechanism that includes changes in FGF, but not FGFR, mRNA expression.

Repression of Notch Signaling Induces FGF1 Release

Although most of the FGF family members contain signal peptides that facilitate their secretion through the classical ER-Golgi exocytosis pathway, it is well established that the prototype members of the FGF gene family (FGF1 and FGF2) do not contain a signal peptide and are instead released by non-classical mechanisms. While the pathway utilized by FGF2 to gain access to the extracellular compartment is not known, FGF1 is released in response to environmental stress as a component of a copper-dependent, multi-protein aggregate that includes the p40 extravesicular domain of p65 Synaptotagmin-1 and S100A13 (Landriscina et al., 2001, J. Biol. Chem. 276: 25549-25557; Landriscina et al., 2001, J. Biol. Chem. 276: 22544-22552; LaVallee et al., 1998, J. Biol. Chem. 273: 22217-22223; Mouta Carreira et al. 1998, J. Biol. Chem. 273: 22224-22231). Given that FGF1 but not FGF2 is differentially expressed in the sJ1 stable transfectants (FIG. 4A), these cells were assessed for FGF1 release.

Figure 5A:
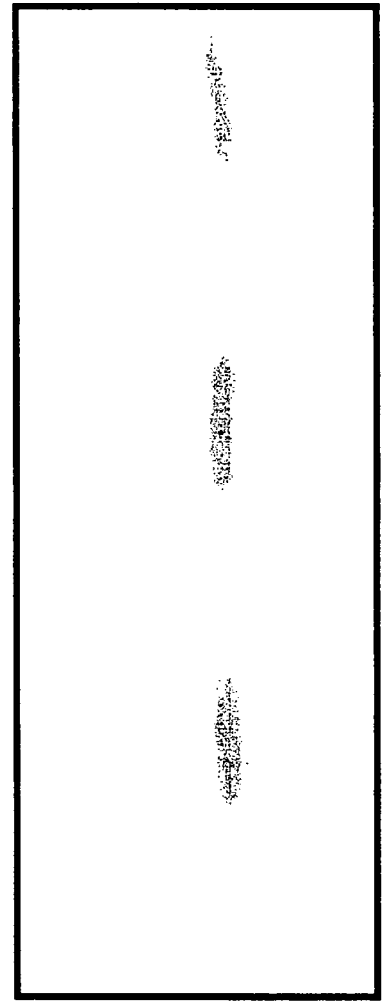
FIG. 5A is an immunoblot analysis of FGF1 export into the extracellular compartment in pMEX-neo, sJ1 and sJ1:caN1 stable transfectants transduced with FGF1 adenovirus and subsequently subjected to heat shock (42° C., 2 h) or maintained under normal growth conditions (37° C., 2 h).

Because the expression of FGF1 steady-state translation product in the NIH 3T3 cell is undetectable (Jackson et al., 1992, Proc. Natl. Acad. Sci. USA 89: 10691-10695) and is very low in sJ1 transfectants, vector control, sJ1, caN1, dnN1, caN2 and dnN2 transfectants were examined for the release of adenovirally transduced FGF1 under normal (37° C.) and heat shock (42° C.) conditions (FIG. 5). While vector control, sJ1 and sJ1:caN1 transfectants were able to export FGF1 at similar levels into the extracellular compartment in response to temperature stress, a significant release of FGF1 at 37° C. was observed only in the sJ1 cells. Expression of caN1 into the sJ1 background (sJ1:caN1) significantly reduced FGF1 release at 37° C., but not 42° C., indicating that activation of Notch attenuates FGF1 release under normal but not heat shock conditions.

Figure 5B:
FIG. 5B is an immunoblot analysis of FGF1 export into media conditioned by stable FGF1 NIH 3T3 cell transfectants adenovirally transduced with either LacZ, caN1, dnN1, caN2 or dnN2 and maintained under normal growth conditions (37° C., 2 h) or subjected to heat shock conditions (42° C., 2 h).

A role for Notch as a regulator of FGF export was further substantiated by the reverse experiment in which NIH 3T3 cells stably transfected with FGF1 were transduced with either the lacZ, caN1, dnN1, caN2, or dnN2 expressing adenovirus (FIG. 5B). Under these conditions, FGF1 was also released into the extracellular compartment in response to heat shock in all cell lines examined, but its release at 37° C. was limited to those cells expressing either dnN1 or dnN2.

Exogenous FGF1 Represses CSL-Dependent Signaling

Figure 6A:
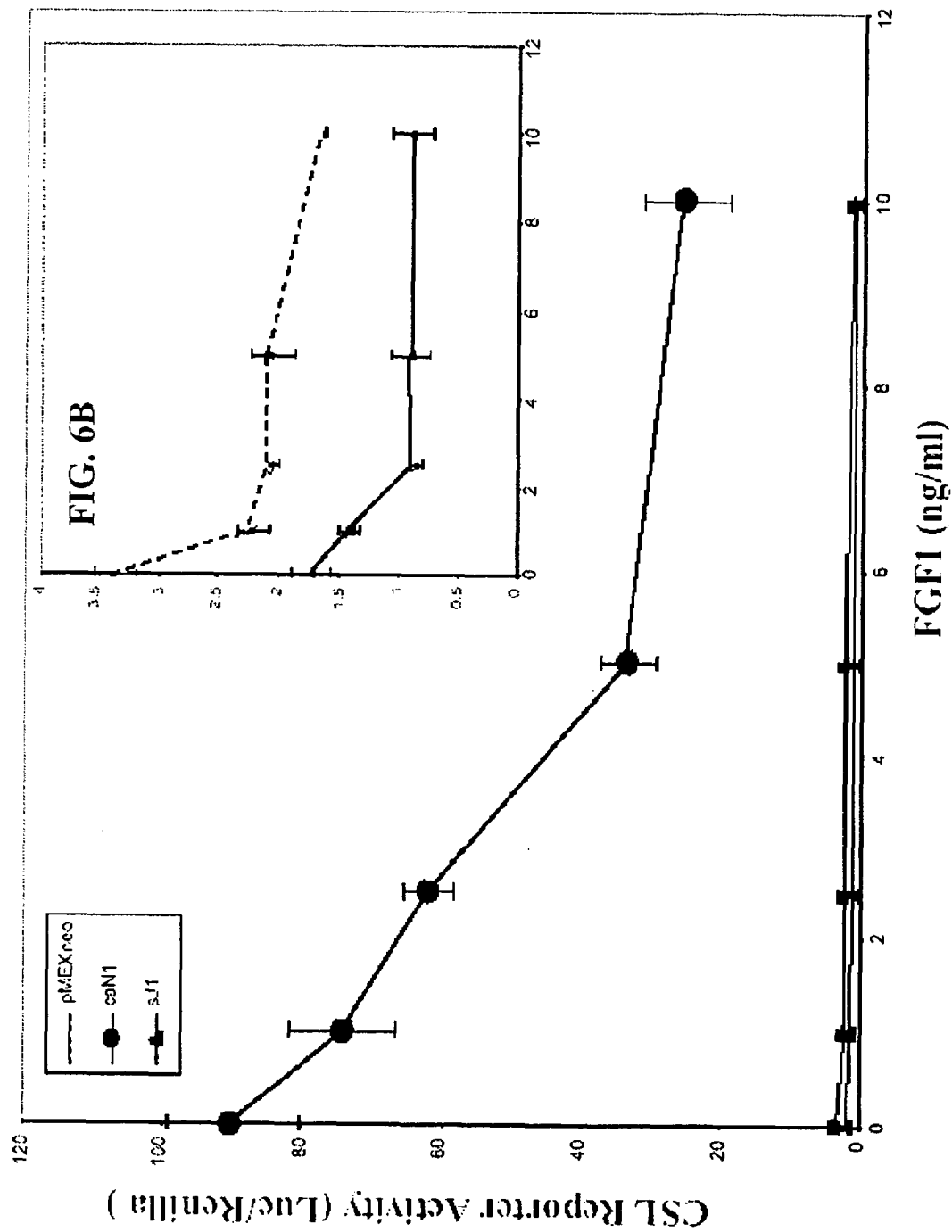
FIG. 6A is a graph depicting a dose-response curve of endogenous CSL-activated transcription in the presence of increasing concentrations of recombinant human FGF1 in vector control, caN1 and sJ1 transfectants. Reporter activity is represented as the ratio of Luciferase/*Renilla* activity.
Figure 6B:
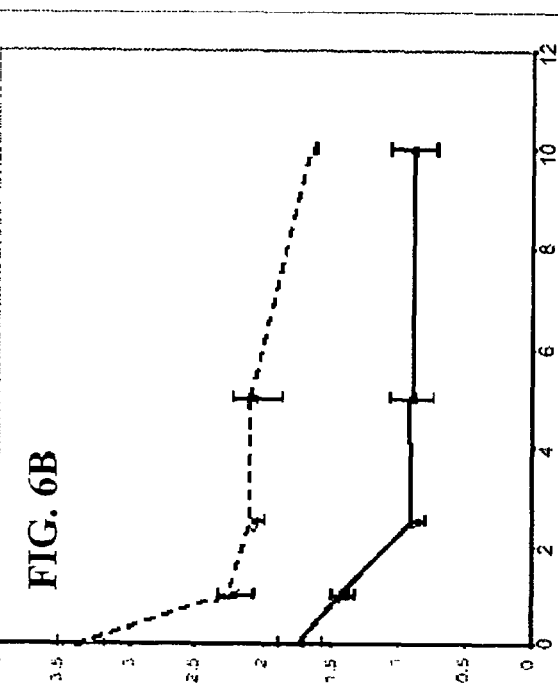
FIG. 6B is an insert highlighting the FGF1 dose response curve of CSL-activated transcription in vector control and sJ1 NIH 3T3 cell transfectants shown in FIG. 6A.
Figure 6C:
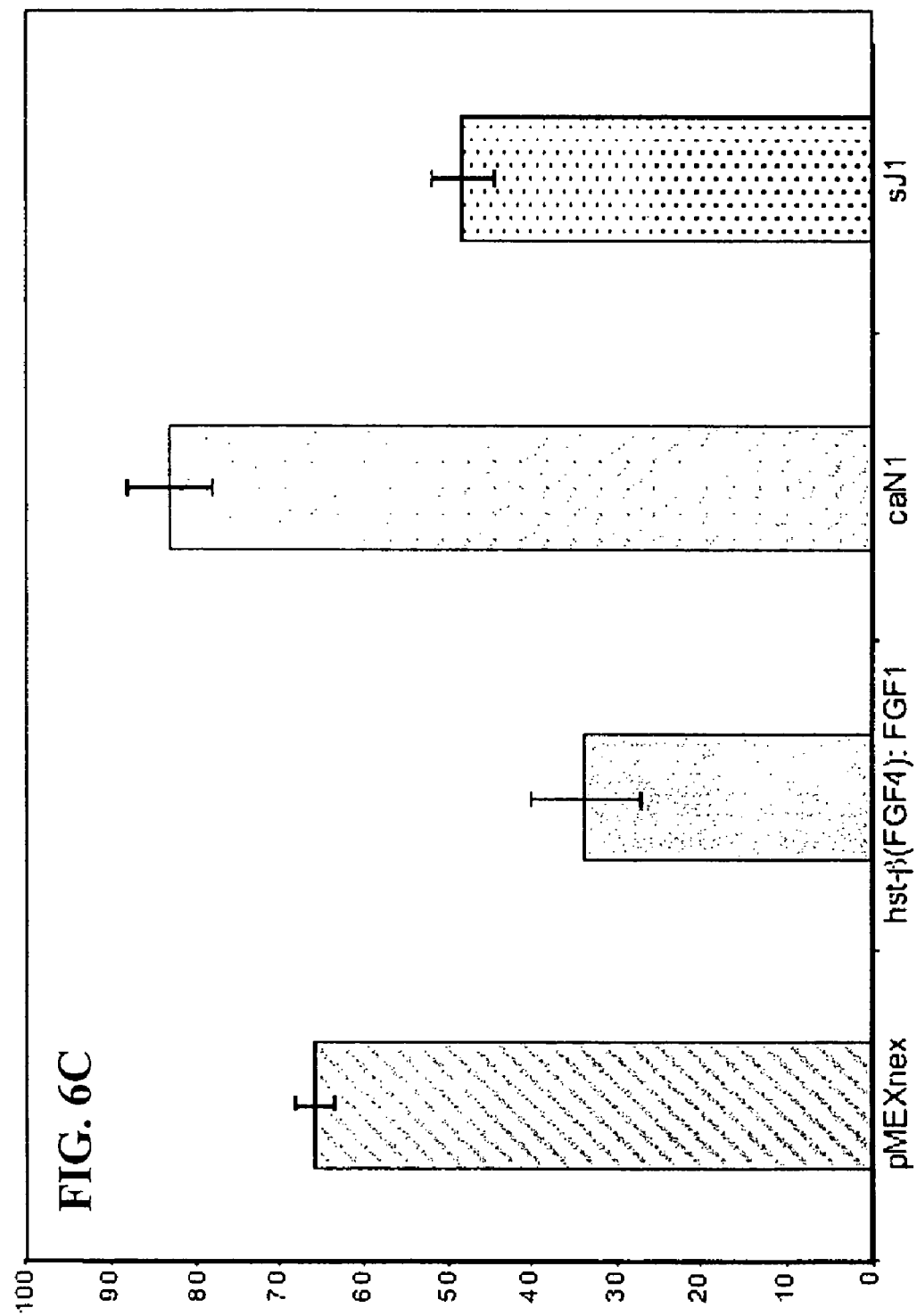
FIG. 6C is a histogram depicting CSL-activated transcription in vector control, hst-β(FGF4):FGF1, caN1 and sJ1 NIH 3T3 stable transfectants transiently transfected with caN1.

Previously, it had been observed that the ability of caN1 to upregulate a CSL-Luciferase reporter construct is significantly diminished in sJ1 stable transfectants in comparison to vector control cells (FIG. 6, Small et al., 2001, J. Biol. Chem. 276:32022-32030). As FGF release appears to be upregulated in Notch-repressed cells, it was examined whether caN1/CSL-mediated transcription was negatively correlated with activation of the FGFR signaling pathway. The ability of caN1 to stimulate transcription of a CSL-Luciferase reporter in hst-β(FGF4):FGF1 transfectants was significantly reduced in comparison to its activity in vector control and caN1 stable transfectants (FIG. 6A). In addition, exogenous FGF1 also repressed caN1/CSL transcription in a dose-dependent fashion in caN1 transfectants (FIG. 6B). The low levels of endogenous CSL transcription in vector control and sJ1 NIH transfectants also displayed a dose response to exogenous FGF1, although the magnitude of the FGF1 effect was less than that achieved in the caN1 transfectants (FIGS. 6B and 6C). However, while caN1/CSL-dependent transcriptional activation is significantly repressed by FGF1, this repression is not complete. These results are interesting since the vector control cells (FIGS. 2A and 2B) still do not proliferate in response to exogenous FGF1 under conditions of soft agar growth. Therefore, without wishing to be bound by any particular theory, it is possible that this relatively low level of conventional CSL-dependent activity is sufficient to repress the ability of the NIH 3T3 cell to respond to exogenous FGF1 as an agent of cell transformation.

FGF1 Upregulates the Expression of JAGGED1

Figure 7:
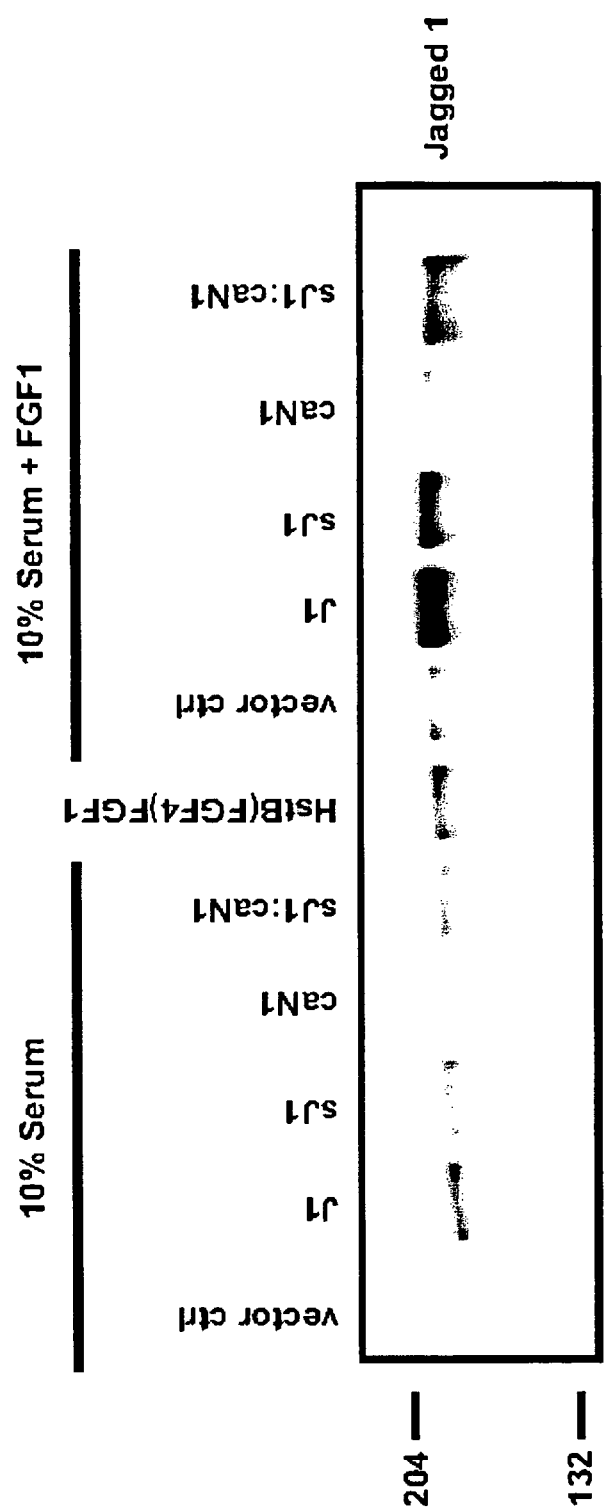
FIG. 7 demonstrates that FGF1 upregulated the steady-state level of Jagged1 expression. The expression of endogenous Jagged1 was determined by immunoblot analysis as described elsewhere herein in vector control, sJ1, caN1 and sJ1:caN1 stable transfectants plated in normal growth media (10% Serum) or in normal growth media containing 10 ng/ml FGF1 and 10 U/ml heparin (10% Serum+FGF 1). As a control for the J1 immunoblot, cell lysates obtained from NIH 3T3 cells stably transfected with a full length, human Jagged1 construct were also included in the immunoblot analysis. The expression of J1 was determined in hst-β(FGF4):FGF1 stable transfectants plated in normal growth serum, only.

Jagged1 has been demonstrated to be an FGF-response gene in human endothelial cells, such that the NIH 3T3 stable transfectants used in this study were assayed for expression of Jagged1 by immunoblot analysis using an antibody directed against an epitope located within the intracellular C-terminal domain of full-length Jagged1 (FIG. 7). The data disclosed herein demonstrate that Jagged1 expression was more pronounced in sJ1 and hst-β(FGF4):FGF1 transfectants than in vector control, and caN1 grown in normal growth medium (10% Serum). The presence of FGF1 in the growth media increased Jagged1 expression in all stable lines examined, with caN1 still displaying the lowest level of expression. NIH 3T3 cells do not express detectable levels of other Notch ligands, including Jagged2, Delta1, Delta3 or Delta4, either in the absence or presence of FGF1 in the growth media. In addition, the data demonstrate that steady state levels of mRNA encoding Notch1 and Notch2 appear to be unchanged as determined by RT-PCR, although slight differences in the expression of these transcripts detectable by more sensitive assays can not be ruled out.

Discussion

While both the Notch and FGFR signaling pathways have long been recognized as important regulators of cell fate determination events in a variety of cell types, little is still known about how interactions between these two major signaling pathways impact cellular processes. The data disclosed herein demonstrate, for the first time, the existence of an important cellular mechanism that may be involved in balancing the signals generated by these signaling pathways. Interestingly, whereas the stimulation of the FGFR by FGF1 exerts a negative regulatory effect on Notch signaling by repressing Notch-mediated CSL transcription, Notch, in turn, tempers FGF-generated signals by regulating the extracellular appearance of FGF gene family members. In addition, while activated Notch also represses the effects of FGFR stimulation through an as yet identified mechanism other than FGF export, the perturbation of endogenous Jagged1/Notch signaling disrupts the equilibrium between the Notch and FGFR pathways and leads to the manifestation of a transformed phenotype.

The results disclosed herein indicate that endogenous Jagged1/Notch signaling may regulate the FGFR signaling pathway by controlling the availability of FGF in the extracellular compartment. Indeed, the detection of mRNA encoding FGF1 and the protooncoproteins FGF3, FGF4, and FGF5 in sJ1 but not vector control nor caN1 stable NIH 3T3 transfectants indicates that interference with endogenous Jagged1/Notch signaling alters the expression pattern of FGF gene family members. While a Notch-responsive element, such as a CSL-binding site, has yet to be identified in any of the FGF gene family members, it is known that during the development of the *Drosophila* tracheal system, conventional Notch signaling negatively regulates the transcription of the FGF homologue, branchless, resulting in an attenuation in the activity of breathless, the FGFR homologue (Ikeya et al., 1999, Development 126: 4455-4463). Therefore, without wishing to be bound by any particular theory, there may be a similar regulatory mechanism in vertebrates.

In addition to regulating the expression of FGF gene family members, the data disclosed herein also suggest that Notch may act as a gatekeeper that represses the non-classical release of FGF1 under normal growing conditions. It has been previously reported that the export of FGF1 only occurs in the NIH 3T3 cell under conditions of cellular stress such as heat shock or hypoxia through a copper-dependent mechanism that requires the formation of a multiprotein complex consisting of FGF1, S100A13 and the p40 extravesicular domain of Synaptotagmin-1 (Landriscina et al., 2001, J. Biol. Chem. 276: 25549-25557; Landriscina et al., 2001, J. Biol. Chem. 276: 22544-22552; LaVallee et al., 1998, J. Biol. Chem. 273: 22217-22223; Mouta Carreira et al. 1998, J. Biol. Chem. 273: 22224-22231). Therefore, it was surprising to find that NIH 3T3 cells with suppressed Notch signaling released FGF1 not only during heat shock, but under normal growth conditions as well. While the possibility that caN1 inhibits FGF1 release under normal growth conditions by interacting directly with the FGF1 secretory complex cannot be dismissed, the observation that caN1 and caN2 stable transfectants continue to release FGF1 under heat shock conditions to the same extent as vector control transfectants argues against this possibility. Instead, it is more likely that repression of Notch in the sJ1, dnN1 and dnN2 stable transfectants induces a stress/survival response that enables FGF1 export.

Since expression of caN1 or caN2 strongly inhibited FGFR-mediated anchorage-independent growth in hst-β(FGF4):FGF1 transfectants, it is likely that activated Notch1/Notch2 interferes with FGFR-mediated cellular transformation at a level other than its regulation of FGF release. Although aberrant expression of FGFRs and their isoforms has also been associated with cellular transformation (Yan et al., 1993 Mol. Cell Biol. 13: 4513-4522; Abbass et. al., 1997, J. Clin. Endocrinol. Metab. 82: 1160-1166; Leung et. al., 1997, Oncogene 15: 1115-1120), this is probably not a contributing factor in the system disclosed herein since the expression of FGFR mRNA, including those transcripts that represent splice variants, is similar in all of the NIH 3T3 stable lines examined in this study.

Although it is currently unknown which other signaling pathways are involved in facilitating crosstalk between Notch and FGFR, it is possible that suppression of FGF-mediated anchorage-independent growth by caN1 and caN2 may occur through its regulation of Activator Protein (AP)-1-dependent transcription. In fibroblasts, continuous exposure to FGF1 increases the transcription of fos (LaVallee et al., 1998, J. Biol. Chem. 273: 22217-22223), a polypeptide component of the AP-1 complex. Notch activation has been reported to inhibit AP1-mediated transcription in HeLa and human erythroleukemia cell line K562 (Chu et. al., 2002, J. Biol. Chem. 277: 7587-7597) and caN1 suppression of AP-1 may be the underlying mechanism behind its inhibition of HPV-induced transformation in cervical carcinoma cells (Talora et. al., 2002, Genes Dev. 16: 2252-2263).

The surprising observation that FGF1 suppresses Notch1/CSL-mediated transcription suggests that Notch may also protect the NIH 3T3 cell from abnormal growth through the transcriptional regulation of Notch/CSL-responsive genes. FGF export would then reinforce the inhibition of Notch/CSL activation already present in Notch-repressed cells. This novel mechanism is consistent with the requirement for Notch/CSL-dependent induction of p21waf/cip for growth arrest and entry into keratinocyte differentiation, a cell that requires exogenous FGF for cell division (Rangarajan et. al., 2001, EMBO J. 20: 3427-3436). However, this regulatory mechanism may also contain a cell- and tissue-specific, as well as an age-dependent component since in the developing tooth bud, FGF10 is able to induce the Notch/CSL-dependent transcription of HES1 (Mustonen et al., 2002, Dev. Biol. 248: 281-293), and this may be complicated by an additional level of specificity for some but not all of the 23 members of the FGF gene family.

The upregulation of Jagged1 by FGF in the NIH 3T3 cell agrees with previous results in which Jagged1 expression was upregulated in human endothelial cells undergoing FGF but not VEGF-induced tube formation (Zimrin et. al, 1996, J. Biol. Chem. 271: 32499-32502). These results are also consistent with those of Matsumoto et al., who found Jagged1 to be upregulated by FGF2 in bovine capillary endothelial cells (Matsumoto et al., 2002, J. Cell Biol. 156: 149-160). In addition, several other studies have also correlated the expression of polypeptide components of the Notch-signaling pathway with FGFR stimulation. For example, FGF2 increases the expression of Notch1 in immortalized mouse oligodendrocytes (Bongarzone et al., 2000, J. Neurosci. Res. 62: 319-328) as do both FGF prototypes in murine neuroepithelial precursor cells (Faux et. al, 2001, J. Neurosci. 21: 5587-5596). Further, FGF10 also induces the Notch signal modifier lunatic fringe in the murine developing tooth bud (Harada et al., 1999, J. Cell Biol. 147: 105-120) suggesting a role for the cooperativity between FGFR and Notch signaling in the development of cell fate by lateral specification, and this is consistent with the report by Ikeya and Hayashi, 1999 that the interplay between Notch and FGFR (breathless) signaling regulates cell fate in vivo (Harada et al., 1999, J. Cell Biol. 147: 105-120). Thus, the newly discovered upregulation of Notch signaling components including Jagged1 disclosed herein may represent a negative autoregulatory mechanism to balance the FGFR mitogenic response in the NIH 3T3 cell.

The aggressive transformed phenotype displayed by Notch-repressed cells in the presence of exogenous FGF1 was unexpected. Indeed, only those FGF family members that contain a classical signal peptide and are secreted through the traditional ER-Golgi apparatus have been considered oncogenes, indicating that FGF must be continuously released by a cell to become oncogenic (Forough et al., 1993, J. Biol. Chem. 268: 2960-2968; Bunnag et al., 1991, In Vitro Cell Dev. Biol. 27: 89-96). Removal of the signal peptide from FGF4 decreases its transforming potential (Talarico et al., 1991, Mol. Cell Biol. 11: 1138-1145), while constitutive secretion of an oncogenic mutant of FGF1 engineered with the FGF4 signal peptide sequence (hst-β (FGF4):FGF1) induces a transformed phenotype in NIH 3T3 cells in vitro (Forough et al., 1993; FIGS. 1A, 2A and 2B) and produces aggressive, metastatic tumors in vivo (Forough et al., 1993, J. Biol. Chem. 268: 2960-2968). It is possible that continuous exposure to low levels of endogenous FGF may "prime" the Notch-repressed cells such that any additional FGFR stimulation results in aggressive and uncontrolled growth.

The protooncoprotein Src is an FGFR downstream effector molecule whose activity is increased in Notch-repressed cells (Small et al., 2001, J. Biol. Chem. 276:32022-32030), and it is possible that further potentiation of Src signaling by FGFR stimulation may be the primary mechanism driving FGF-mediated anchorage-independent growth in these cells. However, it has not been possible thus far to inhibit FGF-mediated soft agar colony growth or spheroid formation through the expression of a dominant-negative mutant of Src, indicating that another as yet identified pathway may be a contributing factor to the exaggerated transformed phenotype mediated by exogenous FGF1 in Notch-repressed cells.

Numerous studies have demonstrated that the activity of Notch is highly dependent on cell type and environmental context, and this is particularly true for the activity of soluble ligands, and for Notch regulation of cell growth. In the NIH 3T3 cell, it has been suggested that the soluble, non-transmembrane form of Jagged1 acts to inhibit Notch signaling, possibly by interfering with endogenous transmembrane ligand interaction with Notch receptors. Naturally occurring soluble forms of the Notch ligands arising from proteolytic cleavage (Qi et al., 1999, Science 283: 91-94) or perhaps differential mRNA processing (Li et al., 1997, Nat. Genet. 16: 243-251; Zimrin et. al, 1996, J. Biol. Chem. 271: 32499-32502) have been identified, yet the functional activities of these modified ligands are not clear. The observation that soluble forms of Notch ligands have been demonstrated to be both agonists (Li et al., 1997, Nat. Genet. 16: 243-251; Sestan et al., 1999, Science 286: 741-746; Morrison et al., 2000, Cell 101: 499-510) or antagonists of Notch signaling (Sun et al., 1997, Development 124: 3439-3448; Chitnis et al., 1995, Nature 375: 761-766; Fitzgerald et al., 1995, Development 121: 4275-4282; Hukriede et al., 1997, Development 124: 3427-3437) may be due to factors including oligomerization or immobilization of ligands (Shimizu et al., 2000, Mol. Cell Biol. 20: 6913-6922; Shimizu et al., 2002, EMBO J. 21: 294-302; Varnum-Finney et al., 2000, J. Cell Sci. 113 Pt 23: 4313-4318). While it is possible that proteolytic cleavage of Notch ligands generates non-functional soluble fragments that reduce endogenous ligand availability (Mishra-Gorur et al., 2002, J. Cell Biol. 159: 313-324), the data disclosed herein support a model where soluble ligands have significant activity in regulating Notch signaling. In addition, a preponderance of the human Jagged1 mutations found in individuals afflicted with Alagille syndrome results in the production of soluble ligands (Spinner et al., 2001, Hum. Mutat. 17: 18-33), suggesting a functional consequence in human disease. Without wishing to be bound by any particular theory, the generation of soluble ligands can represent an immediate cellular response to downregulate Notch signaling events.

Although aberrant activation, not inhibition, of Notch signaling pathways, have been reported to be associated with neoplastic growth in mammals (Gray et al., 1999, Am. J. Pathol. 154: 785-794; Zagouras et al., 1995, Proc. Natl. Acad. Sci. USA 92: 6414-6418; Ellisen et al., 1991, Cell 66: 649-661; Weijzen et al., 2002, Nat. Med. 8: 979-986), it is clear that the influence of Notch on cellular decisions, including growth, is dependent on cell type and environmental context (Rangarajan et. al., 2001, EMBO J. 20: 3427-3436; Morrison et al., 2000, Cell 101: 499-510; Capobianco et al., 1997, Mol. Cell Biol. 17: 6265-6273; Robey et al., 1996, Cell 87: 483-492). Indeed, Notch has also been reported by several groups to be a suppressor of cellular growth. For example, activation of Notch1 causes the arrest of cell cycle progression in the chicken B-cell line, DT40 (Morimura et al., 2000, J. Biol. Chem. 275: 36523-36531), in small cell lung cancer cells (Sriuranpong et al., 2001, Cancer Res. 61: 3200-3205), and prevents myeloid cell proliferation but not erythroid cell proliferation in the absence of polypeptide mitogens (Walker et al. 1999, Stem. Cells 17: 162-171). Further, downregulation, not upregulation, of Notch1 signaling is required for progression into the late stages of HPV-induced cervical carcinogenesis (Talora et. al., 2002, Genes Dev. 16: 2252-2263). Since both Notch and FGF are important regulators of many common physiological processes, including neurogenesis and angiogenesis, further elucidation of the cellular mechanisms mediating communication between the Notch and FGFR pathways will be important for understanding of pathological conditions mediated by these signaling pathways.

Example 2

Thrombin Enables Stamatogenesis, the Clonal Expansion of Stem Cells Without Loss of Pluripotency The non-transmembrane form of Jagged1 represses Notch-mediated CSL1-dependent transcription by facilitating the non-classical release of FGF1. To further define this pathway, the mechanism responsible for the appearance of the non-transmembrane form of Jagged1 was examined. Interestingly, the data disclosed herein surprisingly demonstrate thrombin was able to cleave Jagged1 and to enable the induction of FGF1.A transcription, as well as the rapid non-classical release of FGF1 into the extracellular compartment. FGF1 release also underlies the known mitogenic activity of thrombin since thrombin is ineffective in promoting cell proliferation in cells expressing a dominant-negative form of FGFR1. In addition, remarkably, thrombin enabled the clonal expansion of both peripheral and central nervous system stem cells without a loss of pluripotency. These data suggest that while Notch signaling directs differentiation, Notch antagonists, such as thrombin and the non-transmembrane form of Jagged1, repress this outcome and maintain cells in a self-renewing state termed stamatogenesis. They also provide novel methods of producing stem cells without loss of pluripotency which has long been needed in the art.

The data disclosed elsewhere herein (e.g., Example 1, Small et al., 2003, J. Biol. Chem. 278:16405-16413) demonstrate that the suppression of Notch-mediated signaling by the ectopic expression of either the extracellular domains of Notch1 and Notch2 or the soluble (s) non-transmembrane form of the Notch ligand, Jagged1 (sJ1) induces the nonclassical release of FGF1. In addition, sJ1 expression leads to a FGFR1-dependent decrease in classical Notch signaling, an increase in FGF1 transcription, and the formation of a FGFR1-dependent transformed phenotype (Small et al., 2003, J. Biol. Chem. 278:16405-16413). Further, cooperativity between the FGFR and Notch signaling pathways has been observed in a variety of biological systems (Bongarzone et al., 2000, J. Neurosci. Res. 62:319-328; Faux et al., 2001, J. Neurosci. 21:5587-5596; Ikeya et al., 1999, Development 126:4455-4463; Matsumoto et al., 2002, J. Cell. Biol. 156: 149-160). In contrast, the expression of the soluble non-transmembrane form of Delta1 (sDl1) does not lead to the induction of the FGF1 gene; rather it induces the expression of the FGF3, FGF4, and FGF9 transcripts which results in the formation of a FGFR1-mediated transformed phenotype and the repression of classical Notch signaling in vitro (Trifonova et al., 2004, J. Biol. Chem. In Press).

Because Notch-mediated signaling events are instrumental in the differentiation outcomes of neural stem cells (Wang et al., 2000, Neuron 27:197-200), antagonists of Notch signaling, such as sJ1 and sDl1 (Hicks et al., 2002, J. Neurosci. Res. 68: 655-667) may be important regulators of neural stem cell function and may play a causal role in mediating the undifferentiated expansion of either stem cell populations or undifferentiated progenitor pools during development.

Interest in thrombin as a potential modifier of Jagged1 evolved from previous studies on non-classical ER-Golgi-independent protein export (Jackson et al., 1992, Proc. Natl. Acad. Sci. U.S.A. 89:10691-10695; Landriscina et al., 2001, J. Biol. Chem. 276:25549-25557; Landriscina et al., 2001, J. Biol. Chem. 276:22544-22552; LaVallee et al., 1998, J. Biol. Chem. 273:22217-22223; Mouta et al., 2001, Growth Factors 18:277-285; Tarantini et al., 1998, J. Biol. Chem. 273:22209-22216). Previously, it had been demonstrated that the signal peptide-less protein, FGF1, is released into the extracellular compartment in response to cellular stress as a FGF1: S100A13 heterotetramer non-covalently complexed to the non-transmembrane extravesicular domain of Synaptotagmin (Syt)1 (Landriscina et al., 2001, J. Biol. Chem. 276: 25549-25557). The assembly of this complex requires the function of intracellular copper (Landriscina et al., 2001, J. Biol. Chem. 276:25549-25557), and this occurs near the inner surface of the plasma membrane (Prudovsky et al., 2002, J. Cell. Biol. 158:201-208). Because (i) intracellular S100A13 is known to be associated with annexin 2 (Oyama et al., 1997, Biochem. Biophys. Res. Commun. 240:341-347), (ii) thrombin is able to translocate annexin 2 from the inner to the outer leaflet of the plasma membrane (Peterson et al., 2003, J. Cell. Sci. 116:2399-2408), (iii) the expression of sJ1 mediates the release of FGF1 under non-stressed conditions (Small et al., 2003, J. Biol. Chem. 278:16405-16413), (iv) thrombin is a well described mitogen for a variety of FGF-responsive diploid cells (Algermissen et al., 1999, Exp. Dermatol. 8:193-198; Gordon et al., 1986, Ann. N.Y. Acad. Sci. 485:249-263; Paris et al., 1991, Ann. N.Y. Acad. Sci. 638:139-148), (v) the enzymatic activity of thrombin has been implicated in tissue repair functions (Fenton et al., 1998, Thromb Hemost 24:87-91) including the central (Cheng et al., 1996, Science 273: 510-513; Hirose et al., 2000, Ann. Surg. 232:272-280) and peripheral nervous systems (Friedmann et al., 1999, FASEB J. 13:533-543), (vi) mutant non-transmembrane forms of human Jagged1 expressed as a result of Alagille Syndrome exhibit spontaneous bleeding (Joutel et al., 1998, Semin. Cell. Dev. Biol. 9:619-625) and (vii) FGF1 is well recognized as an inducer of the tissue plasminogen activator gene (Pendurthi et al., 1997, Arterioscler. Thromb. Vasc. Biol. 17:940-946), it was assessed whether thrombin can facilitate the release of FGF1 into the extracellular compartment under non-stressed conditions by proteolytically generating a non-transmembrane form of Jagged1. This premise was examined because the mitogenic activity of thrombin may also be linked to the ability of sJ1 to induce the non-classical release of FGF1. Indeed, the data disclosed herein demonstrate, for the first time, that thrombin enables the transcription of the FGF1.A gene as well as the rapid release of FGF1 into the extracellular compartment using S100A13 and Syt1, components previously described as critical for the non-classical stress-induced FGF1 release pathway (Landriscina et al., 2001b, J. Biol. Chem. 276:22544-22552; LaVallee et al., 1998, J. Biol. Chem. 273:22217-22223).

Remarkably, exposure of either NCSC populations or cortical neurospheres to either sJ1 or thrombin allows the clonal expansion of the neural stem cell pool and the mitogenic activity of thrombin as well as the clonal expansion of NCSC populations by either thrombin or sJ1 are both lost by the expression of a dominant-negative form of FGFR1. Lastly, serial subcloning experiments demonstrate that secondary and tertiary stem cell populations maintain their full multi-potentiality without a change in the sensitivity to instructive differentiation signals. These data suggest that "stamatogenesis" (classical Greek: Stamato, "stem without change"), clonal stem cell self-renewal without the loss of pluripotency, utilizes the repression of differentiation induced by sJ1 and/or thrombin. The data disclosed herein suggest that these events may permit FGFR-dependent cell cycle progression and symmetric cell division leading to clonal expansion of stem cell populations without changes in their sensitivity to factors that instruct cellular differentiation.

The materials and methods disclosed in these experiments are now set forth.

Cell Culture

Murine NIH 3T3 (ATCC), Swiss 3T3 (ATCC), sJ1 NIH 3T3 cell transfectants were all disclosed elsewhere herein (e.g., Example 1), FGF1 NIH 3T3 transfectants (Jackson et al., 1992, Proc. Natl. Acad. Sci. U.S.A. 89:10691-10695) and PAR1 null mouse embryonic fibroblasts (a gift from Dr. S. Coughlin) were grown in Dulbecco's modified Eagle's medium (DMEM; Life Technologies) supplemented with 10% bovine calf serum (BCS; Hyclone) and 1× antibiotic/ antimycotic (Life Technologies). All stable NIH 3T3 cell transfectant cultures were further supplemented with 0.4 g/L Geneticin (GIBCO). Cells used in FGF1 release experiments were grown on human fibronectin-coated cell culture dishes (10 µg/cm$^2$) as previously described (Jackson et al., 1992, Proc. Natl. Acad. Sci. U.S.A. 89:10691-10695). The preparations of sDl1 and sJ1 were generous gifts from G. Weinmaster and M. Bhatia, respectively.

Clonogenic assays were performed as described (Stemple et al., 1992, Cell 71:973-985). Briefly, populations of murine NCSC were plated at a clonal density and maintained for a maximum of 14 days in Morrison media supplemented with 15% chick embryo extract (Morrison et al., 1999, Cell 96:737-749). The resulting clones were fixed in an acetic acid:ethanol solution (2:1) and stained with antibodies against peripherin (Chemicon) to detect neurons, smooth muscle actin (Sigma) to detect myofibroblasts, and GFAP (Chemicon) to detect Schwann cells. Clones were scored based on the appearance of just one phenotypic representative. The number and percentage of clones containing neurons only (N), Schwann cells only (S), myofibroblasts only (M), N+S, N+M, N+S+M, and S+M were scored at day 14 unless otherwise stated. The production of each representative phenotype in each individual clone was also scored to complement the clonal population assay.

In order to generate secondary NCSC populations, founder clones originating from differentiating E10 clones at distinct time points during NCSC differentiation (days 2 through 18) were treated with trypsin and replated at a cell clonal density using methods previously described (Kubu et al., 2000, Genomics 70:150-152). The resulting cells were subjected to immunofluorescence microscopy using both p75$^+$ and P$_0^-$ antibodies (Kubu et al., 2000, Genomics 70:150-152) and the p75$^+$/P$_0^-$ cells identified as putative stem cells. All non-p75$^+$/P$_0^-$ cells were removed from the dish with a tungsten needle. The cultures of secondary NCSC clones were subjected to the clonogenic assay as described above.

Murine E13 cerebral cortices were dissected, the ventricular zone isolated, dissected free of the meninges and utilized as a source for the generation of clonal neurspheres. The resulting cells were dispersed by aspiration to produce single cells and cells expressing the heat shock antigen, CD24 as previously described (Rietze et al., 2001), and peanut agglutinin antigen (PNA) were sorted using a FASC Vantage SE cell sorter at a low gate (CD24$^{low}$/PNA$^{low}$), and the cells were subjected to immunofluoresence microscopy using an antibody against CD24 (Rietze et al., 2001, Nature 412:736-739). Double-positive cells (2×10$^3$/ml) were plated in suspension as described (Reynolds et al., 1992, J. Neurosci. 12:4565-4574; Reynolds et al., 1992, Science 255:1707-1710) and secondary neurospheres generated 14 days later by isolating single spheres followed by trypsin digestion of each sphere. Cells obtained from the sphere were placed in suspension culture at a clonal cell seed density and colonies selected.

Transfection and Adenoviral Transduction of NIH 3T3 Cells

β-galactosidase vector control and FGF1R136K mutant (a gift from Dr. W. H. Burgess; as described in International Patent Publication No. WO 03/052378) NIH 3T3 cell transfectants were obtained using methods previously described (Small et al., 2001, J. Biol. Chem. 276:32022-32030), and adenoviral vectors expressing S100A13:Myc and the constitutively active form of Notch1 were also prepared as described elsewhere herein and also in Hardy et al. (1997, J. Virol. 71:1842-1849) and Mandinova et al. (2003, J. Cell Sci. 116:2687-2696). The p65 Syt1 and p40 Syt1 constructs (LaVallee et al.,1998, J. Biol. Chem. 273:22217-22223) as well as the FGFR136K mutant construct were subcloned in the multiple cloning site of the adenovirus shuttle vector, pAdlox, and NIH 3T3 cells were transduced by incubation in serum-free DMEM with approximately 103 PFU as previously described (Mandinova et al., 2003, J. Cell Sci. 116:2687-2696).

Thrombin Stimulation and Immunoblot Analysis of FGF1 Release

FGF1R136K NIH 3T3 cell transfectants or adenovirally-transduced NIH 3T3 cells were washed with DMEM containing 5 units/ml of heparin (Sigma) and stimulated with either 10 µg/ml α-thrombin (a gift from Dr. J. Fenton) or 5 µM TRAP (Sigma) at 37° C. for different periods of time. Control cells were incubated in the absence of thrombin for the same time period. Conditioned media were collected at each time period, filtered, and concentrated as previously described (Jackson et al., 1992, Proc. Natl. Acad. Sci. U.S.A. 89:10691-10695). The concentrates were resolved by SDS-PAGE and subjected to immunoblot analysis using a rabbit antibody against either FGF1 (Jackson et al., 1992), Syt1 (LaVallee et al.,1998, J. Biol. Chem. 273:22217-22223) or Myc (Oncogene). The heat shock-induced release of FGF1 was performed at 42° C. for 110 minutes as previously described (Jackson et al., 1992). Cell viability was assessed by measuring lactate dehydrogenase activity in the conditioned medium after filtration as disclosed previously elsewhere herein (published as Mandinova et al., 2003, J. Cell Sci. 116:2687-2696), and total cell lysates were obtained and processed for immunoblot analysis as described (Landriscina et al., 2001, J. Biol. Chem. 276:22544-22552).

Stable FGF1R136K NIH 3T3 cell transfectants were pre-incubated with either 100 ng/ml pertussis toxin (PTX) or 10 ng/ml cholera toxin (CT) for 60 minutes at 37° C. in DMEM containing 10% BCS. After pre-incubation, the cells were washed, stimulated with 10 µg/ml of thrombin for different periods of time in the presence of either 100 ng/ml PTX or 10 ng/ml CT, conditioned medium collected, and subjected to immunoblot analysis as described above.

Nuclear Run-on Transcription and RT-PCR Analysis

Approximately either 1×10$^7$ Swiss or NIH 3T3 cells were harvested and washed using ice-cold 50 mM sodium phosphate buffer, pH 7.0 containing 15 mM NaCl. Cell pellets were lysed in 4 ml of ice-cold 10 mM Tris-HCl, pH 7.5, containing 3 mM CaCl$_2$, 3 mM MgCl$_2$, 10 mM NaCl, and 0.5% NP-40. The nuclear pellet was resuspended in glycerol storage buffer (50 mM Tris-HCl, pH 8.3 containing 40% glycerol, 5 mM MgCl$_2$ and 0.1 mM EDTA), the nuclei were snap frozen, and stored in liquid nitrogen. For run-on transcription, 200 µl aliquots of the frozen nuclei were added to 200 µl of reaction buffer (10 mM Tris-HCl, pH 8.3 containing 5 mM MgCl$_2$, 300 mM KCl, 5 mM DTT, 1 mM each of ATP, CTP, and GTP, 40 units of RNase inhibitor and 100 µCi of [$^{32}$P]UTP (800 Ci/mmol; Amersham), and incubated at 30° C. for 30 minutes. The mixture was treated with 100 units of RNase-free DNase I for 30 minutes at 30° C. and then incubated with 400 µl of 20 mM Tris-HCl, pH 7.5, containing 2% SDS, 10 mM EDTA, 200 mg/ml proteinase K for 30 minutes at 42° C. Following phenol/CHCl3 extraction, the labelled transcripts were precipitated with isopropanol and dissolved in 50 µl of 10 mM TES, pH 7.5, containing 10 mM EDTA and 0.2% SDS. Linearized plasmid constructs (0.4 µg/dot) containing either the fgf1 or gapdh cDNA were alkali denatured and immobilized onto a Hybond-N$^+$ membrane (Amersham). Hybridization was performed in 1 ml of ULTRA Hyb (Ambion), with 5×10$^6$ cpm of radiolabeled RNA and yeast RNA (10 µg/ml) for 18 hours with shaking at 50° C. Membranes were washed twice with washing buffer (2×SSC containing 0.1% SDS) at 50° C. and analyzed using a phosphoimager (Molecular Dynamics).

The plasmids containing 500 bp from the coding sequences of the gapdh and fgf1 genes were prepared as follows: a portion of the gapdh and fgf1 cDNA sequences were amplified by RT-PCR from RNA derived from sJ1 NIH 3T3 cell transfectants using primers and conditions previously described (Small et al., 2003). DNA fragments were cloned into pCR 2.1 TOPO vector (Invitrogen).

RT-PCR was performed using total RNA from insert-less vector control and sJ1 NIH 3T3 cell transfectants isolated using the RNeasy kit (Qiagen) according to the manufacturer's protocol. The following primers were utilized: FGF1 (coding sequence):

(Sense)
5'-ATGGCTGAAGGGGAGATCACAACC-3',      (SEQ ID NO:5)

(Antisense)
5'-CGCGCTTACAGCTCCCGTTC-3',          (SEQ ID NO:6)

FGF1.A: (Sense)
5'-CCCAAAGCCAAGAAGCCACC-3',          (SEQ ID NO:30)

FGF1.B: (Sense)
5'-CGGACTTCATTCCCGTCTTGTG-3',        (SEQ ID NO:31)

FGF1.C: (Sense)
5'-CCTCTGAGCCCCCTGGGT-3',            (SEQ ID NO:32)

FGF1.G: (Sense)
5'-CTCTAGGAAGTAGAAGGCAGGTT-3'.       (SEQ ID NO:33)

RT-PCR was performed with 1 µg RNA using the Platinum Taq One Step RT-PCR kit (Invitrogen) as follows: RT (30 minutes at 50° C.), PCR (40 cycles at 94° C. for 15 seconds, at 58° C. for 30 seconds and 72° C. for 1 minute). All amplified cDNA was visualized with ethidium bromide followed by 1.5% agarose gel electrophoresis. RT-PCR analysis of fgf and gapdh was performed as previously described elsewhere herein. RT-PCR analysis of stem cell RNA was performed as previously described (Verdi et al., 1994, Neuron 13:1359-1372; Verdi et al., 1996, Neuron 16:515-527) using primers generating amplification products of Nucleostemin from 894 to 1304 of the mouse cDNA (sense: Nucleostemin 894 5'-CAA ATG TGG GGA AAA GCA GTG TCA-3' [SEQ ID NO:34] and antisense: Nucleostemin 1304 5'-GCA GGG GGA TGG CAA TAG TAA CC-3' [SEQ ID NO:35]); Bmi1 from 242 to 632 of mouse cDNA (sense: Bmi 242 5'-AAT TAG TCC CAG GGC TTT TCA A-3' [SEQ ID NO:36] and antisense: Bmi 632 5'-GGG CCA TTT CTT CTC CAG GTA T-3' [SEQ ID NO:37]), and Nestin from 320-748 (sense: Nestin 320 5'-CA ACC TTG CCG AAG AGC TGG-3' [SEQ ID NO:38] and antisense: Nestin 720 5'-TCT AAG CGA CTC TCC GAG CGC-3' [SEQ ID NO:39]). Each reaction product was measured as a ratio relative to the amplification product of actin and samples were run in triplicate. All RT-PCR experiments were performed at least three times from separate stem cell isolations.

Dual Luciferase Reporter Assay

Insert-less vector control and sJ1 NIH 3T3 cell transfectants (approximately 3×10$^4$) were plated on fibronectin-coated (10 µg/cm$^2$) cell culture dishes and the cells were transiently transfected at approximately 50% confluency with 500 ng of a luciferase construct containing four tandem copies of the CBF1 response element (Small et al., 2001, J. Biol. Chem. 276:32022-32030).

Cotransfection with 100 ng of the TK Renilla (Promega) construct was used as an internal control for transfection efficiency using Fugene 6 (Roche), according to the manufacturer's instructions. Cells were treated with or without 10, 20 or 40 µM α-thrombin or 10, 20, or 40 nM TRAP for 12 hours before and 48 hours after transfection, harvested 48 hours after the transfection and luciferase/renilla activity measured using the Dual Luciferase Reporter Assay System (Promega). Each experiment was performed in triplicate.

DNA Synthesis Assay

A combination of ($^3$H)-thymidine autoradiography and immunohistochemistry was used to evaluate the levels of DNA synthesis in Swiss 3T3 cells expressing a dominant-negative FGFR1 mutant. Swiss 3T3 cells were plated at 50% confluency on glass coverslips precoated with fibronectin (10 µg/cm$^2$) for 24 hours. The cells were transfected with the pCS2 vector expressing a dominant-negative X. laevis FGFR1 deletion mutant lacking the FGFR1 intracellular domain (a gift from Dr. R. Friesel) using the Fugene 6 reagent (Roche). After 24 hours, the medium was changed to DMEM containing 0.25% BCS and following a 48 hour incubation in low BCS, the cells were stimulated with either 10 µg/ml of α-thrombin, 10% BCS or 10 ng/ml of recombinant FGF1 plus 10 units/ml of heparin. After stimulation for 24 hours, ($^3$H)-thymidine (NEN; 1 µCi/ml) was added to the medium and cells were incubated for 12 hours and fixed with 4% neutral formaldehyde. The cells were immunostained for the X. laevis FGFR1 protein using a monoclonal antibody against the extracellular domain of the X. laevis FGFR1 (a gift from Dr. R. Friesel) and with an immunoperoxidase-conjugated goat anti-mouse IgG secondary antibody. Immuno-stained cells were processed for radioautography as previously described (Prudovsky et al., 1991, Dev. Biol. 144:232-239). The percentage of ($^3$H)-labeled nuclei among the dnFGFR1-positive and dnFGFR1-negative cells was quantitated using an inverted Olympus microscope.

The Synthesis of Jagged1, Thrombin Cleavage and Automated Edman Microsequencing

A plasmid containing human Jagged1 (Zimrin et al., 1996, J. Biol. Chem. 271:32499-32502) was in vitro transcribed and in vitro translated in the presence of a ($^{35}$S)-Met/Cys protein-labeling mixture (Amersham) using the T7-coupled reticulocyte lysate system according to the manufacturer's instructions (Promega) in a total volume of 50 µl. After 60 minutes incubation at 30° C., 0.05% DTT was added, half of the reaction mixture incubated with 10 µg α-thrombin for 15 minutes at 37° C., and the reaction stopped by boiling in the presence of SDS-PAGE sample buffer. The samples were resolved by 12% SDS-PAGE, transferred to a nitrocellulose membrane, and analyzed by autoradiography. The bands corresponding to the thrombin cleavage products were excised and subjected to automated Edman microsequencing (Applied Bio Sciences). The products of each cycle were collected prior to resolution by HPLC, added to liquid scintillation fluid (Beckman) and the ($^{35}$S) samples quantitated by liquid scintillation spectroscopy (Beckman).

The Results of the Experiments disclosed are now described.

Thrombin Cleaves Jagged1

The data disclosed previously elsewhere herein, e.g., Example 1, demonstrates that the non-transmembrane form of Jagged1 (sJ1) represses Notch-mediated CSL1-dependent transcription and induces a transformed phenotype by the non-classical release of FGF1. (These results are now published in Small et al., 2003, J. Biol. Chem. 278:16405-16413).

Figure 8A:
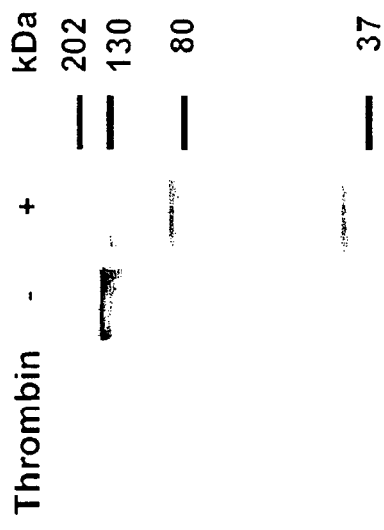
FIG. 8A is an autoradiography depicting in vitro translated human Jagged1 cleaved by α-thrombin. Briefly, the full-length human Jagged1 transcript was in vitro translated in the presence of a ($^{35}$S)-Met/Cys mixture and the translation product was incubated with or without 1 μg of α-thrombin for 15 minutes at 37° C.
Figure 8B:
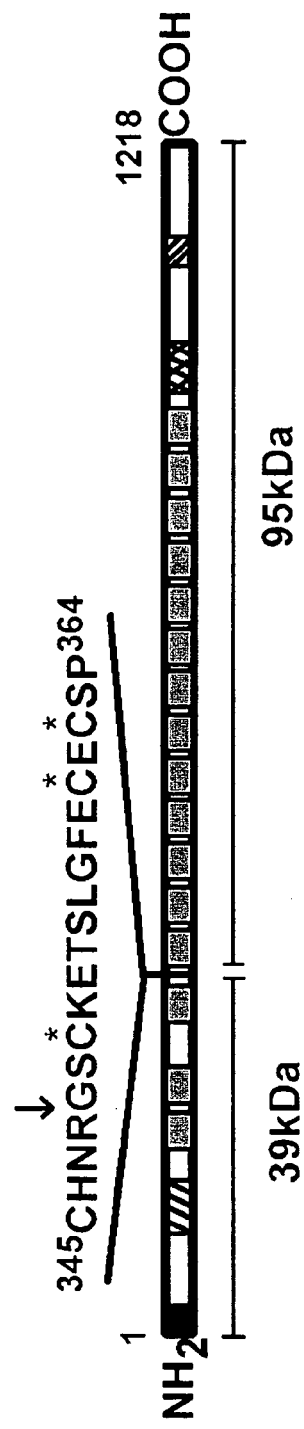
FIG. 8B is a schematic diagram of Jagged1 depicting the position of the α-thrombin cleavage site. The Jagged1 amino acid sequence between residues 345 and 364 is depicted in context with the thrombin cleavage site (arrow) between the third and the fourth EGF repeats. Asterisks depicts Cys residues utilized in the identification of the NH2-terminal α-thrombin cleavage product using automated Edman chemistry of the (35S)-Cys/Met-labeled Jagged1 translation product.

In an attempt to further define this pathway and the role that sJ1 might play in the regulation of cell proliferation, it was assessed if the Jagged1 translation product was susceptible to proteolytic cleavage by thrombin. Examination of human Jagged1 amino acid sequence revealed two putative thrombin cleavage sites within the extracellular domain of Jagged1. In order to assess Jagged1 as a thrombin substrate, full-length Jagged1 was in vitro transcribed and translated in the presence of a ($^{35}$S)-Cys/Met mixture and the 134 kDa Jagged1 translation product incubated either with or without thrombin. Radiographic analysis of the reaction products revealed cleavage of the full-length Jagged1 protein into 39 kDa and 95 kDa fragments (FIG. 8A). Because the size of these fragments was consistent with a Jagged1 cleavage site between residues R348 and G349 (FIG. 8B) and eliminated position R113 and G114 from further consideration as a thrombin cleavage site, we sought to confirm the identity of this putative site. The Jagged1 transcript was translated in vitro in the presence of ($^{35}$S)-Cys, resolved by SDS-PAGE, the 95 kDa fragment excised, subjected to automated Edman chemistry and the products of each cycle monitored by liquid scintillation spectroscopy. We observed ($^{35}$S)-Cys radioactivity in cycles 2, 3, 12 and 14 which agrees with the position of Cys at residues 351, 360 and 362 but not in the cycles corresponding to either residues 352 through 359 or in the cycles corresponding to residues 361 and 363 (FIG. 8B). These analyses suggest that thrombin is able to cleave Jagged1 between residues R348 and G349 which is located between EGF repeats 3 and 4 (Shimizu et al., 1999, J. Biol. Chem. 274:32961-32969), and this cleavage yields an amino terminal fragment with a molecular mass of approximately 39 kDa. The ability of thrombin to cleave Jagged1 may be specific since thrombin was unable to proteolytically modify the in vitro translation product of the Delta1 transcript.

Thrombin Rapidly Induces the Non-Classical Release of FGF1

FGF1 is released from cells in response to cellular stress as a non-covalent S100A13 heterotetramer complexed to the extravesicular p40 domain of Syt1 (Landriscina et al., 2001, J. Biol. Chem. 276:22544-22552). The release of this multiprotein complex involves the copper-dependent assembly (Landriscina et al., 2001, J. Biol. Chem. 276:25549-25557) of the individual components of the complex near the inner surface of the plasma membrane (Prudovsky et al., 2002, J. Cell. Biol. 158:201-208) and requires at least 90 minutes of exposure to in vitro cellular stress (Jackson et al., 1992, Proc. Natl. Acad. Sci. U.S.A. 89:10691-10695). The identification of agents which would facilitate non-classical FGF1 release with more rapid kinetics was undertaken, and since the data disclosed elsewhere herein demonstrated that the expression of sJ1 enabled the constitutive non-classical release of FGF1 at 37° C., and that thrombin is able to cleave Jagged1 in its extracellular domain, thrombin was evaluated as a potential inducer of FGF1 release in vitro.

Since FGF1 is known to be susceptible to thrombin cleavage at residue 136 (Erzurum et al., 2003, J. Vasc. Surg. 37:1075-1081), a thrombin-resistant FGF1 mutant (FGF1R136K; described in International Patent Publication No. WO03/052378, which is incorporated by reference in its entirety herein) was used and stable FGF1R136K NIH 3T3 cell transfectants were produced. FGF1 immunoblot analysis revealed the presence of the FGF1R136K mutant in media conditioned by heat shock (FIG. 9A) and like wild type FGF1 (Jackson et al., 1992, Proc. Natl. Acad. Sci. U.S.A. 89:10691-10695), the appearance of the FGF1R136K mutant required at least 90 minutes of exposure to temperature stress (42° C.) to visualize this signal. However, the addition of thrombin to the FGF1R136K NIH 3T3 cell transfectants at 37° C. demonstrated the rapid and sustained appearance of the FGF1R136K mutant in the extracellular compartment (FIG. 9A). Further, the release of the FGF1R136K mutant was dependent on the concentration of thrombin with a maximal response at 10 μg/ml, whereas thrombin was unable to induce the export of FGF2, the signal peptide-less structural homolog of FGF1. These data suggest that, unlike the stress-induced FGF1 release pathway (Ananyeva et al., 1997, Arterioscler. Thromb. Vasc. Biol. 17:445-453; Jackson et al., 1992, Proc. Natl. Acad. Sci. U.S.A. 89:10691-10695; Mouta et al., 2001, Growth Factors 18:277-285; Shin et al., 1996, Biochim. Biophys. Acta. 1312:27-38), thrombin is able to induce the release of FGF1 under non-stress conditions with rapid kinetics in vitro.

Further, it was assessed whether thrombin was able to direct the export of S100A13 and p40 Syt1, two components of the non-classical stress-induced FGF1 release pathway described in Landriscina et al. (2001, J. Biol. Chem. 276: 22544-22552). As shown in FIG. 9A, S100A13 immunoblot analysis of medium conditioned at 37° C. from NIH 3T3 cells co-expressing both S100A13 and the FGF1R136K mutant revealed the presence of S100A13 in the extracellular compartment with kinetics similar to that observed with FGF1.

In order to determine whether p40 Syt1 is also released in response to thrombin, p40 Syt1 was adenovirally transduced into FGF1R136K NIH 3T3 cell transfectants, and as shown in FIG. 9A, Syt1 immunoblot analysis revealed the presence of p40 Syt1 in the extracellular compartment with kinetics similar to that observed with both FGF1 and S100A13 (FIG. 9A). Thus, like the non-classical stress-induced FGF1 export pathway (Ananyeva et al., 1997, Arterioscler. Thromb. Vasc. Biol. 17:445-453; Jackson et al., 1992, Proc. Natl. Acad. Sci. U.S.A. 89:10691-10695; Mouta et al., 2001, Growth Factors 18:277-285; Shin et al., 1996, Biochim. Biophys. Acta. 1312: 27-38), the release of FGF1 in response to thrombin also exports the individual polypeptide components of the FGF1 multiprotein complex but with more rapid kinetics.

The Role of Protease-Activated Receptor (PAR)1-Mediated Signaling in the Thrombin-Induced Release of FGF1

Figure 9C:
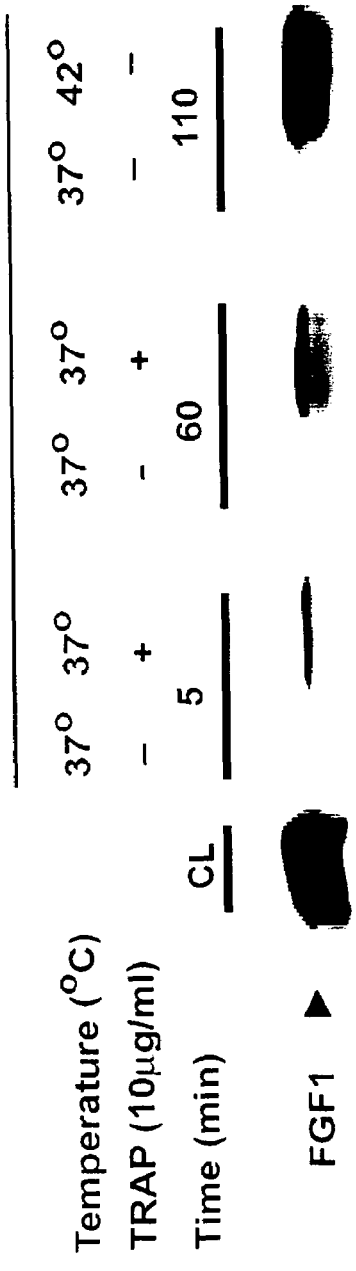
FIG. 9C demonstrates that FGF1 release is induced by TRAP.

It is well established that thrombin mediates its biological responses predominantly through the activation of PARs (see, e.g., Brass et al., 1997, Thromb. Haemost. 78:234-241; Coughlin, 1993, Thromb. Haemost. 70:184-187; Hou et al., 1998, Br. J. Haematol. 101:1-9; Jamieson, 1997, Thromb. Haemost. 78:242-246; Ishihara et al., 1997, Nature 386:502-506; Kahn et al., 1998, Nature 394:690-694; Rasmussen et al., 1991, FEBS Lett. 288:123-128; Vu et al., 1991, Cell 64:1057-1068), which are expressed by a variety of cell types (Algermissen et al., 2000, Arch Dermatol. Res. 292:488-495). The activation of these G protein-coupled receptors occurs through a proteolytic modification in the amino-terminal domain of the receptor (Vu et al., 1991, Cell 64:1057-1068). Since PAR1 signaling is coupled to pertussis toxin (PTX)-sensitive inhibition of adenylate cyclase (Brass et al., 1991, J. Biol. Chem. 266:958-965), and the thrombin receptor agonist peptide (TRAP) is able to activate PAR1 independent of a proteolytic cleavage event (Herbert et al., 1994, Biochem. J. 303: 227-231), it was assessed whether the thrombin-induced release of the thrombin-resistant FGF1R136K mutant was sensitive to PTX and also whether TRAP was able to mimic the ability of thrombin to induce the release of the FGF1R136K mutant. As shown in FIG. 9B, PTX was able to repress the release of the FGFR1R136K mutant in response to thrombin, whereas TRAP, like thrombin, was able to induce and sustain the export of both the thrombin-resistant FGF1R136K mutant (FIG. 9C) and wild type FGF1.

Figure 9D:
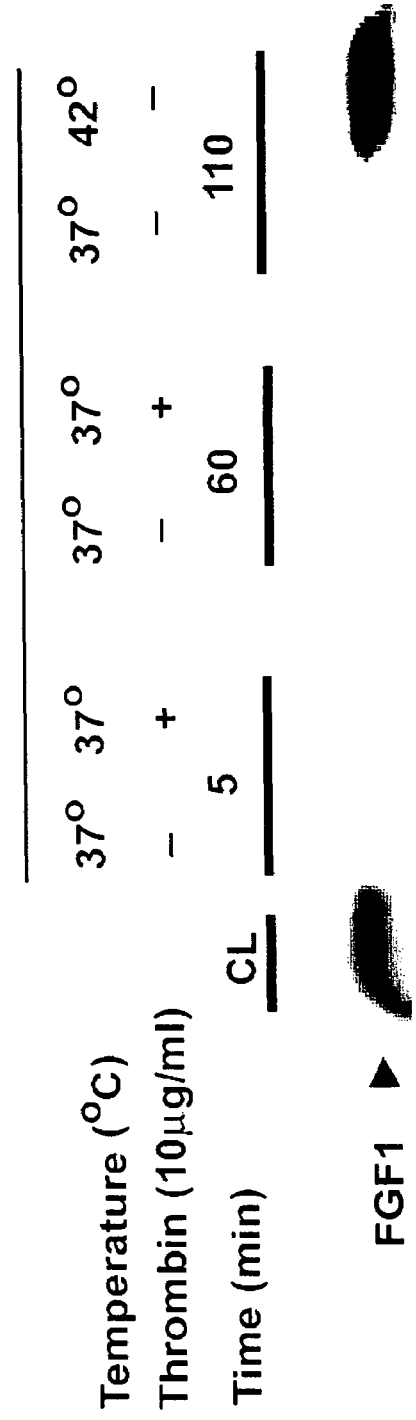
FIG. 9D demonstrates that thrombin did not induce FGF1 release in PAR1 null cells.

An alternative approach to evaluate the role of PAR1 in the thrombin induced release of FGF1 was also applied that utilized cells obtained from the PAR1 null mouse (Connolly et al., 1996, Nature 381:516-519). The PAR1 null cells were adenovirally-transduced with the FGF1R136K mutant and as shown in FIG. 9D, thrombin was unable to induce the export of the FGF1R136K mutant. However, the adenovirally-transduced FGF1R136K PAR1 null cells were able to export the FGFR1136K mutant in response to temperature stress (42° C.), suggesting that the PAR1 null cells were not defective in mediating the stress-induced non-classical export of FGF1.

Thrombin and sJ1 Enhance FGF1.A Transcription

Figure 10B:
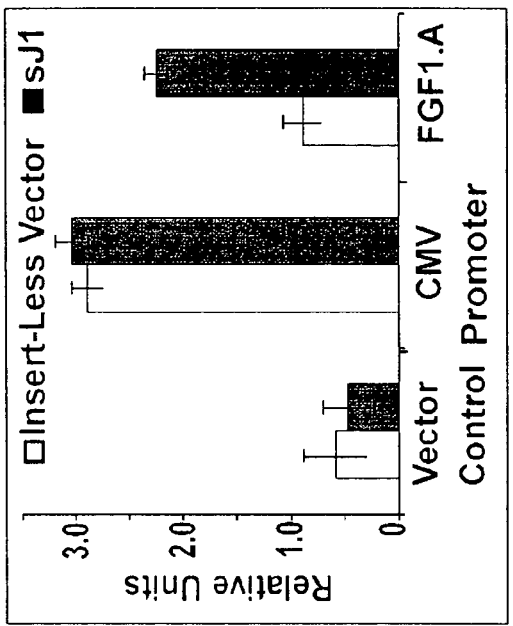
FIG. 10B demonstrates FGF1.A promoter activity in sJ1 NIH 3T3 cell transfectants. Briefly, the corresponding 1.8 Kbp region of the FGF1.A promoter was cloned into a firefly luciferase reporter gene plasmid. The luciferase activity of the FGF1.A reporter construct, a positive control (CMV promoter) and a negative control (promoter-less construct) in both insert-less and sJ1 NIH 3T3 cell transfectants was evaluated by Dual Luciferase Reporter Assay (Promega) with *Renilla* SV40 serving as an internal transfection control. The bar graphs represent the normalized ratio of the luciferase to *Renilla* activity±the standard error of the mean.
Figure 10A:
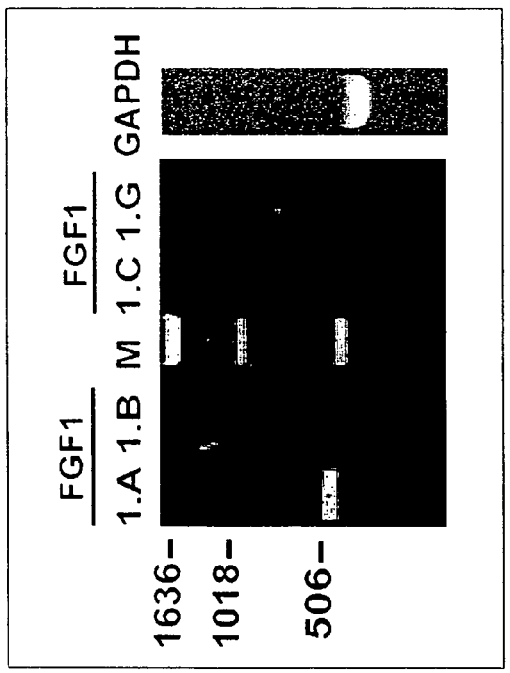
FIG. 10A demonstrates that FGF1.A transcription is induced by sJ1. The presence of the four murine FGF1 transcripts in sJ1 and NIH3T3 cell transfectants was determined by RT-PCR using primers specific for 5'-untranslated region of either the FGF1.A, FGF1.B, FGF1.C or FGF1.G transcripts. RT-PCR using primers specific for murine GAPDH served as a control.

The murine FGF1 gene is unusual in that it is transcribed from at least 4 promoters (FGF1.A, 1.B, 1.C and 1.G), and these transcripts are expressed in the mouse in a cell- and tissue-specific manner (Chiu et al., 2001, Prog. Nucleic Acid Res. Mol. Biol. 70:155-174). Since these promoters generate four mRNAs that encode the same open-reading frame yet differ in their 5'UTR (Madiai et al., 1999, J. Biol. Chem. 274:11937-11944) and since the expression of sJ1 in the NIH 3T3 cell induces the expression of the FGF1 transcript as demonstrated elsewhere herein, studies where undertaken to identify which promoter was functional in the sJ1 NIH 3T3 cell transfectants. Taking advantage of the sequence-based differences at the 5'UTR of the FGF1 transcripts, RT-PCR analyses was performed using primers specific for each 5'UTR. As shown in FIG. 10A, the results demonstrated that only the FGF1.A promoter was activated upon suppression of the Notch1 signaling pathway by the expression of sJ1, while transcripts from the FGF1.B, FGF1.C and FGF1.G promoters were not detectable.

In order to confirm the sJ1-dependent function of the FGF1.A promoter, the corresponding 1.8 Kbp region (Madiai et al., 1999, J. Biol. Chem. 274:11937-11944) was cloned into a promoter-less firefly luciferase reporter vector and FGF1.A-driven firefly luciferase activity was evaluated in both insert-less vector and sJ1 NIH 3T3 cell transfectants. A significant increase in the FGF1.A-driven promoter activity was detected in the sJ1 NIH 3T3 cell transfectants but not in the insert-less vector control NIH 3T3 cell transfectants (FIG. 10B). These data suggest that the repression of Notch signaling by sJ1 induces the expression of the FGF1.A transcript.

Figure 10C:
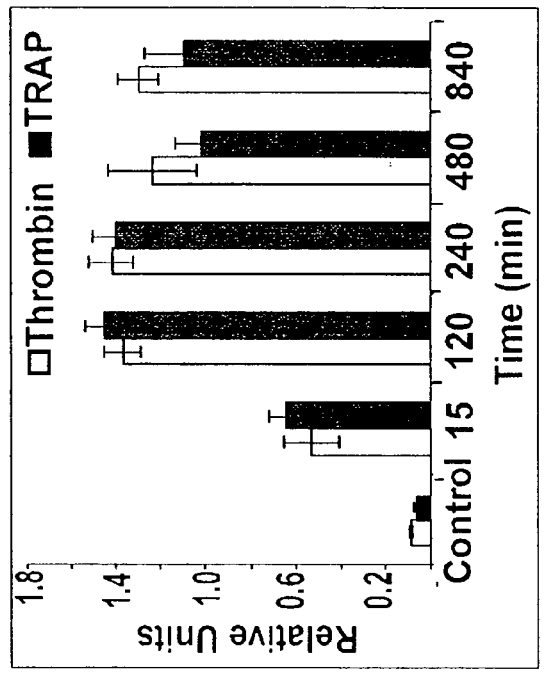
FIG. 10C demonstrates FGF1 expression is induced by thrombin and TRAP. The expression of the FGF1 transcript in α-thrombin- and TRAP-treated Swiss 3T3 cells was evaluated by nuclear run-on analysis. Briefly, cells were harvested at different time intervals after the addition of either 10 μg/ml α-thrombin or 5 μM TRAP, nuclei isolated, and the transcription rate for fgf1 gene determined as described elsewhere herein. The bar graphs represent the normalized ratio of ($^{35}$P)-labeled FGF1 transcript to the GAPDH transcript±the standard error of the mean.

Since thrombin is able to proteolytically cleave Jagged1, it was assessed whether thrombin was able to induce the transcription of the FGF1 mRNA. The expression of the FGF1 transcript in NIH 3T3 and Swiss 3T3 cells in response to thrombin was analyzed by nuclear run-on, and stimulation of either cell line with thrombin was able to induce the expression of the FGF I transcript (FIG. 10C). The FGF1 mRNA was initially detected 15 minutes after the addition of thrombin, steadily increased over time and reached a plateau by 2 hours (FIG. 10C). In addition, the PAR1 agonist, TRAP, was also able to induce the transcription of FGF1 mRNA with similar kinetics (FIG. 10C). These data suggest that both sJ1 expression and PAR1 signaling are able to specifically induce the expression of the FGF1 transcript.

Figure 11A:
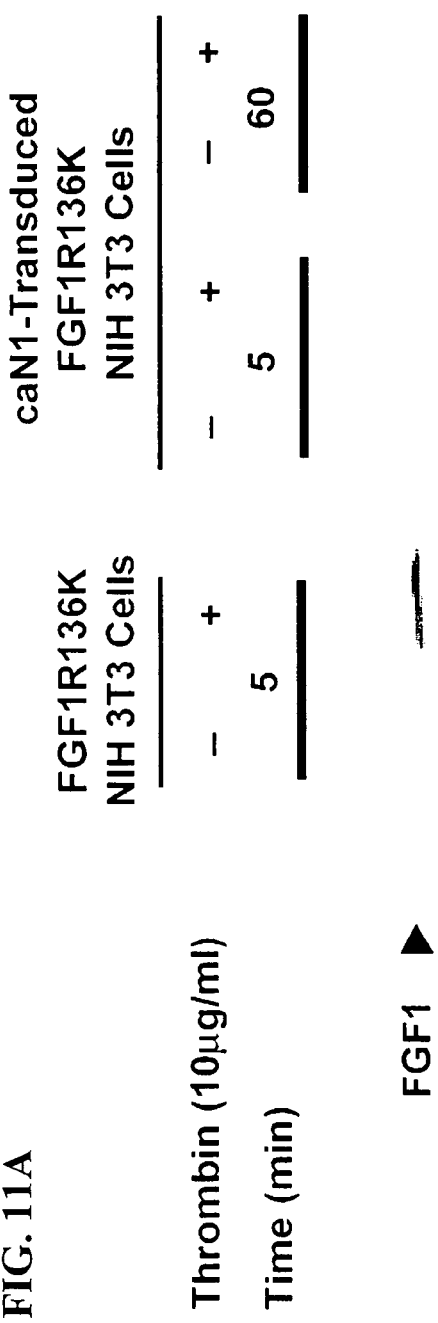
FIG. 11A demonstrates that thrombin-induced release of FGF1 is repressed by the expression of constitutively active (ca) Notch1. FGF1R136K NIH 3T3 cell transfectants were adenovirally transduced with caNotch1 and the levels of the FGF1 mutant in media conditioned by the addition of α-thrombin (10 μg/ml) assessed using FGF1 immunoblot analysis of control and transduced cells.
Figure 11B:
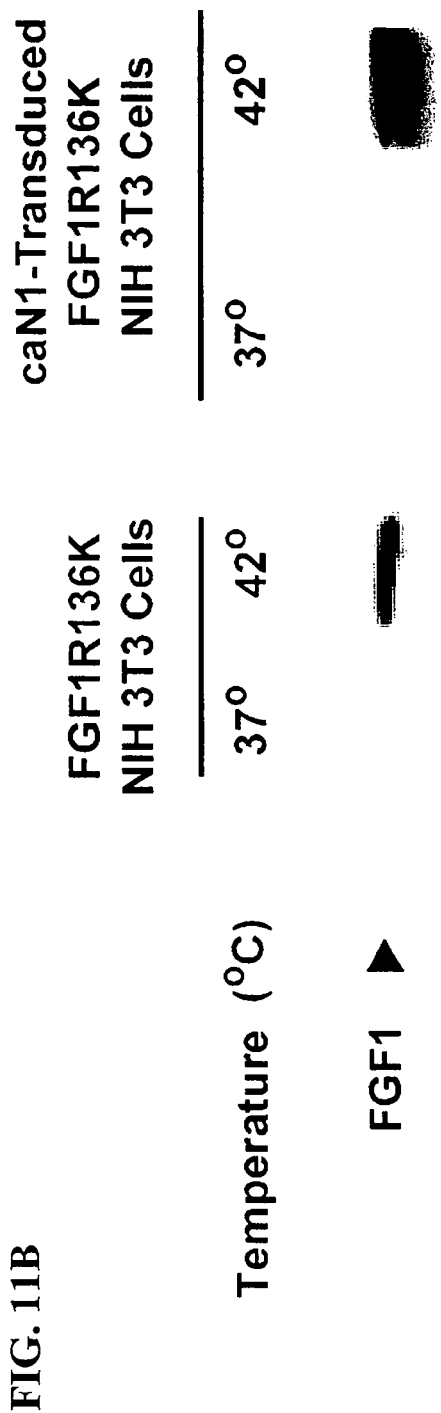
FIG. 11B demonstrates that the stress-induced release of FGF1 is not repressed by the expression of caNotch1. Analysis is identical to that described in FIG. 11A except that the response of FGF1R136K release to heat shock (42° C., 110 minutes) is depicted.

Functional Notch1 Inhibits the Thrombin-Induced Non-Classical Release of FGF1, and Thrombin and sJ1 Antagonize CSL-Dependent Signaling It was determined whether Notch signaling played a role in the thrombin-induced release of FGF1 and utilized NIH 3T3 cells where endogenous Notch signaling was maximized. Specifically, FGF1R136K NIH 3T3 cell transfectants were adenovirally transduced with either constitutively active Notch 1 (caN1) or β-galactosidase vector control and stimulated with thrombin. As shown in FIG. 1A, thrombin was able to stimulate the release of the FGF1R136K mutant from control cells, yet thrombin was unable to initiate the release of the FGF1R136K mutant from those cells with elevated Notch1 signaling (FIG. 11A). The expression of caN1 in the FGF1R136K NIH 3T3 cell transfectants did not affect the stress-induced non-classical FGF1 release pathway since these cells were able to export the FGF1R136K mutant in response to heat shock (FIG. 11B). These data suggest that the induction of FGF1 release by thrombin may be dependent on the down-regulation of Notch signaling and may involve the proteolytic cleavage of Jagged1 by thrombin.

Figure 11C:
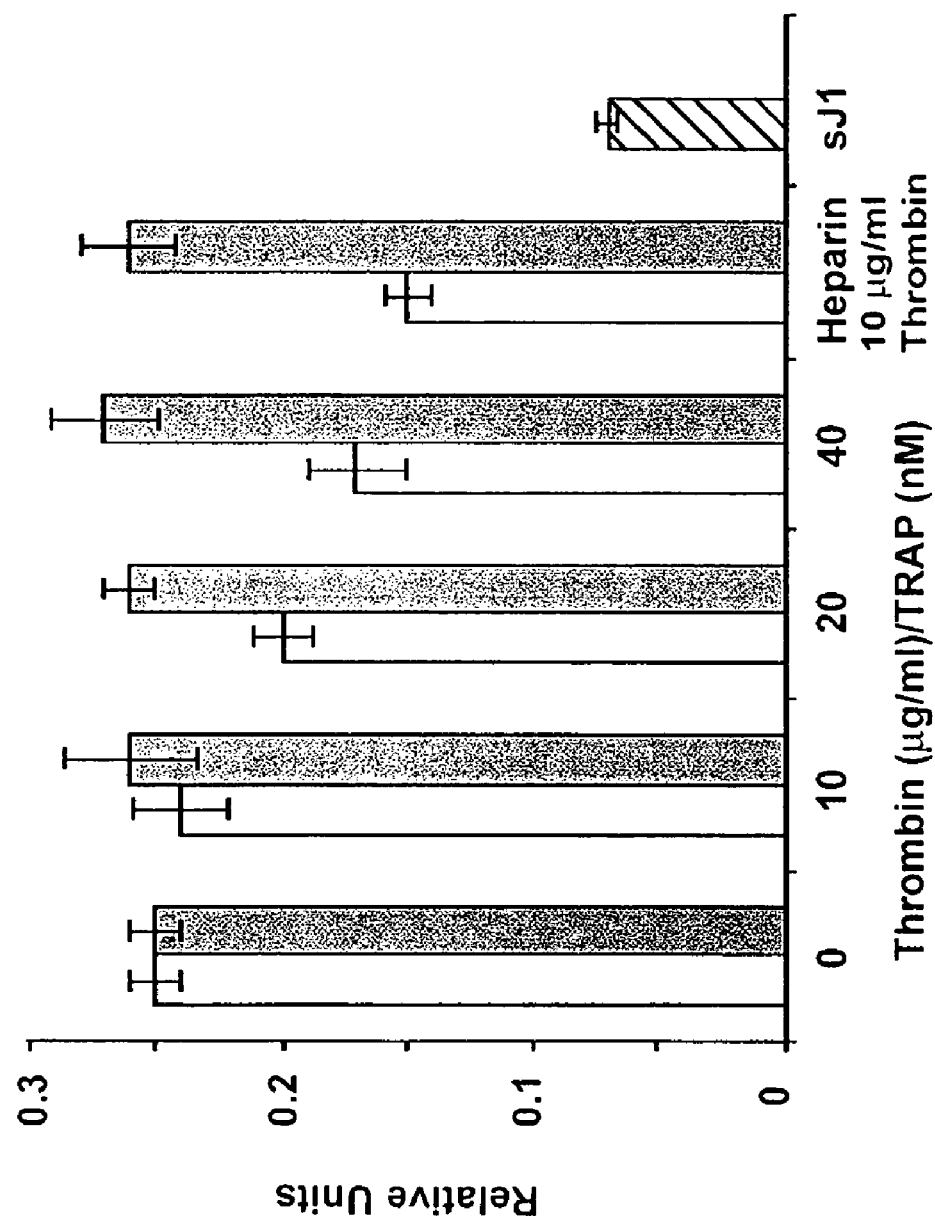
FIG. 11C demonstrates that thrombin attenuates CSL-dependent transcription in FGF1R136K NIH 3T3 cell transfectants. The Dual Luciferase Reporter Assay was utilized to assess CSL1-mediated transcription as described in Small et al. (2001, J. Biol. Chem. 278:16405-16413). The bar graphs represent the ratio of luciferase to *Renilla* activity, ±the standard error of the mean as a function of the concentration of α-thrombin, TRAP and the results from sJ1 NIH 3T3 cell transfectants served as a control.

Because the ability of Notch1 to up-regulate the transcription of a CSL1-luciferase reporter construct in NIH 3T3 cells can be significantly repressed either by the addition of exogenous FGF1 or by the expression of sJ1 which enables the non-classical release of FGF1 (Small et al., 2003, J. Biol. Chem. 278:16405-16413), and since thrombin is able to cleave Jagged1 in its extracellular domain, it was assessed whether thrombin and TRAP may also be able to attenuate CSL1-mediated signaling. While the treatment of the full-length Jagged1 NIH 3T3 cell transfectants with thrombin was able to reduce the level of Notch-dependent CSL1 activity in a dose-dependent manner, TRAP was unable to affect CSL1-dependent transcription (FIG. 11C). However, thrombin was only able to attenuate CSL1-dependent transcription to approximately 75% of the control level (FIG. 11C). In contrast, sJ1 expression (FIG. 11C) and the addition of 10 ng/ml of exogenous FGF1 were both able to repress CSL1-dependent transcription to approximately 25% of the control level.

Since thrombin is able to proteolytically inactivate FGF1 (Erzurum et al., 2003, J. Vasc. Surg. 37:1075-1081), and heparin is able to protect FGF1 from proteolytic inactivation (Rosengart et al., 1988, Biochem. Biophys. Res. Commun. 152:432-440), it was examined whether heparin was able to potentiate the repression of CSL1-dependent transcription by thrombin. Indeed, the addition of heparin (5 units/ml) to the full-length Jagged1 NIH 3T3 cell transfectants in the presence of thrombin (10 μg/ml) was able to potentiate the thrombin-dependent repression of CSL1-dependent transcription (FIG. 11C). In contrast, heparin either by itself or in the presence of 10 μM TRAP (FIG. 11C) was ineffective in altering CSL1-dependent transcription in the full-length Jagged1 NIH 3T3 cell transfectants. These data suggest that heparin is able to accentuate the repression of CSL1-dependent transcription mediated thrombin and it is likely this response is due to the protection of FGF1 by heparin against proteolytic inactivation in the extracellular compartment.

The Mitogenic Activity of Thrombin is FGFR1-Dependent

Figure 11D:
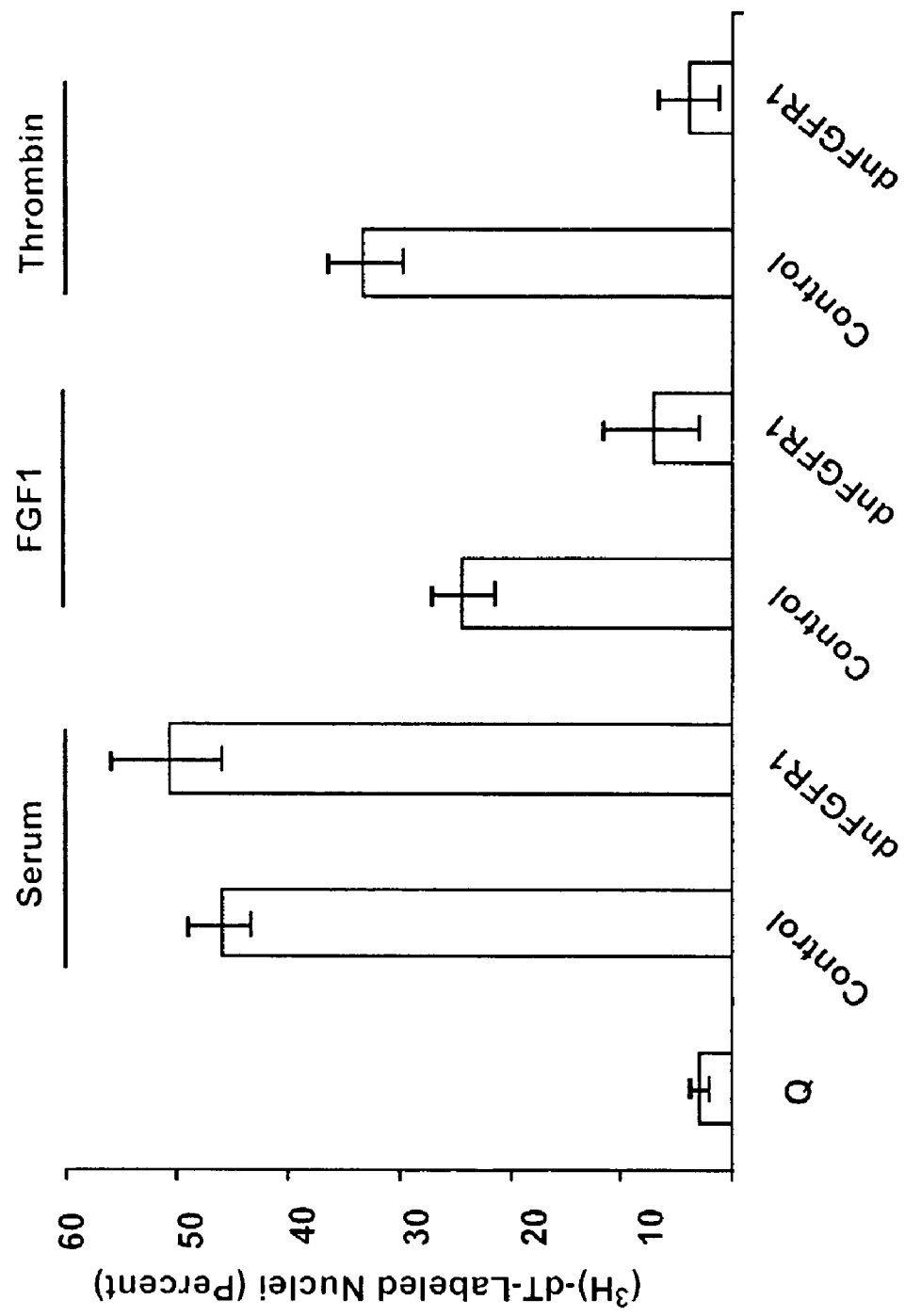
FIG. 11D demonstrates that the expression of a dominant-negative (dn) FGFR1 mutant inhibited thrombin-induced DNA synthesis in Swiss 3T3 cells. Briefly, quiescent Swiss 3T3 cells transiently transfected with a FGFR1 deletion mutant lacking the intracellular domain were stimulated with either 10% BCS (serum), 10 μg/ml of α-thrombin or 10 ng/ml of FGF1 plus 10 units/ml of heparin for 36 hours. DNA synthesis in control and dnFGFR1-positive cells was determined using ($^3$H)-thymidine incorporation as described elsewhere herein.

Since the expression of a dominant-negative (dn) FGFR1 construct attenuates the FGF1-dependent transformed phenotype exhibited by sJ1 NIH 3T3 cell transfectants as disclosed previously elsewhere herein, it was assessed whether the thrombin-induced release of FGF1 into the extracellular compartment may be responsible for the mitogenic activity of thrombin. Swiss 3T3 cell was used for this study since, unlike the NIH 3T3 cell, it exhibits a low level of apoptosis and endogenous DNA synthesis in response to serum deprivation. Thus, a dominant-negative (dn) FGFR1 construct was expressed in Swiss 3T3 cells and their proliferative index measured in the presence and absence of exogenous thrombin. As shown in FIG. 11D, the expression of dnFGFR1 not only reduced the ability of exogenous FGF1 to induce the appearance of replicating nuclei by approximately 70%, but dnFGFR1 expression also decreased the DNA synthesis frequency in the presence of thrombin to a level consistent with a quiescent cellular phenotype. Since both sJ1, and thrombin induces the non-classical release of FGF1 and the expression of the dnFGFR1 construct inhibits the transformed phenotype exhibited by the sJ1 NIH 3T3 cell transfectants, all as disclosed previously elsewhere herein, it is likely that the mitogenic activity of thrombin is not only dependent on the presence of FGF1 in the extracellular compartment but that this activity may involve the ability of thrombin to proteolytically modify Jagged1.

Neural Crest Stem Cells (NCSC) Express the FGF1.A Transcript in Response to Thrombin, TRAP and the Non-Transmembrane Form of Jagged1

Figure 12B:
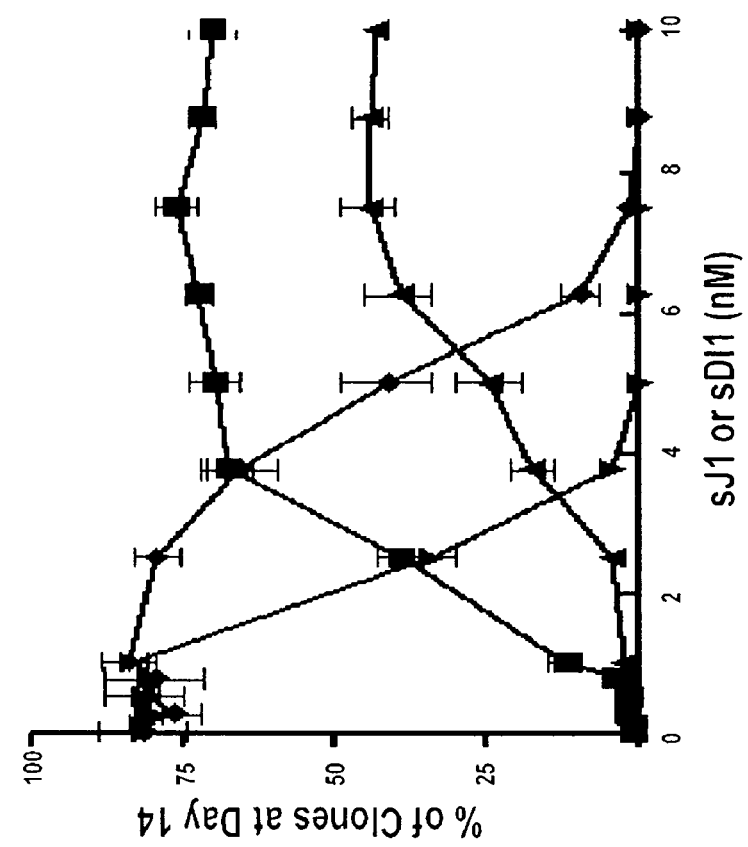
FIG. 12B demonstrates that glial differentiation is induced by sJ1 after neurogenic potential is lost in response to sJ1. Clonogenic differentiation assays of murine NCSC populations were assessed by maintaining the cells in Morrison media supplemented with increasing concentrations of either sJ1 or sDl1. The results are presented as the number of colonies at day 14 (mean±standard deviation for at least three experiments) originating from three independent cell isolations as function of concentration of sJ1 and sDl1 using two assays of ligand sensitivity: the percentage of glial-only clones (■-■; ▲-▲) and the percentage of neuron-containing clones (♦-♦; ▼-▼) produced after 14 days of ligand exposure. Legend: (▲-▲)sJ1/Glial, (▼-▼) sDl1/Glial (♦-♦) sJ1/Neural and (▼-▼) sJDl1/Neural.
Figure 12A:
FIG. 12A depicts an RT-PCR analysis of FGF1.A mRNA expression. Briefly, populations of murine NCSC were treated for 48 hours in Morrison media supplemented with either 7.5 nM sJ1, 5.0 nM sDl1, 10 μg/ml of α-thrombin or 5 μg/ml TRAP, and the steady-state levels of the FGF1.A mRNA were measured using RT-PCR as described elsewhere herein.

It was determined whether the function of thrombin as disclosed, for the first time, elsewhere herein, was also relevant to the growth of stem cells. Since both Jagged1 and Delta1 have been implicated in the regulation of neural crest cell growth and differentiation (Morrison et al., 2000, Cell 101:499-510), populations of murine NCSC were examined for their ability to express the FGF1.A transcript. As shown in FIG. 12A, populations of NCSC do not express the FGF1.A transcript. However, the addition of either thrombin or sJ1 induced the expression of the FGF1.A transcript, suggesting that, like the NIH 3T3 cell, NCSC populations are able to modify the steady-state levels of the FGF1.A transcript (FIG. 12A). In addition, the thrombin receptor agonist, TRAP, was also able to do so (FIG. 12A) suggesting that the ability of thrombin to upregulate the expression of the FGF1.A mRNA can proceed through the proteolytic cleavage of either Jagged1 or PAR1. This effect appears to be specific for Jagged1 since sDl1 did not influence the steady-state levels of the FGF1.A transcript (FIG. 12A). Because the transient expression of a dnFGFR1 mutant in the NCSC population inhibited the mitogenic activity of both thrombin and sJ1, these data suggest, as more fully disclosed below, that the mitogenic activity of thrombin may prove useful for the expansion of neural crest stem cells in vitro.

Thrombin and sJ1 Enhance the Self-Renewal of Neural Crest Stem Cells

Because the function of thrombin and fibrin have been implicated in regulation of tissue and organ repair (Strukova, S. M., 2001, Biochemistry 66:8-18) including neurogenesis (Hirose et al., 2000, Ann. Surg. 232:272-280; Martinez-Gonzalez et al., 2003, Circ. Res. 92:96-103; Matras et al., 1973, J. Maxillofac. Surg. 1:236-247), and the novel finding that addition of sJ1, thrombin and TRAP was able to induce the expression of the FGF1.A transcript in NCSC populations, it was investigated whether thrombin and sJ1 could modify the self-renewal potential of NCSC populations. Previously, it was reported that the activation of Notch by Dl1 leads to an immediate loss of NCSC neurogenic potential and differentiation into Schwann cells (Kubu et al., 2002, Dev. Biol. 244:199-214; Morrison et al., 2000, Cell 101:499-510). Since exposure of soluble Delta1 (sDl1) to populations of NCSC results in an immediate loss (24 hours) of neurogenic potential (Morrison et al., 2000, Cell 101:499-510), it was assessed whether sJ1 may also induce a similar irreversible loss in the presence of the neurogenic instructive factor, bone morphogenetic protein 2 (BMP2). Surprisingly, not only did the neurogenic potential of sJ1 contrast with sDl1 (Morrison et al., 2000, Cell 101:499-510), but neuronal differentiation was as pronounced as observed in control cells (Table 1). While, increasing the time of exposure of NCSC populations to sJ1 prior to the addition of BMP2 resulted in the retention of neurogenic potential for seven days (Table 1), increasing the level of sJ1 had little effect on eliminating the neurogenic potential.

TABLE 1

|  |  | Glial-Only | Neuron-Only | Neuron-Containing |
|---|---|---|---|---|
| No addition | 24 hrs; BMP2 | 0.4 ± 0.7% | 57.4 ± 13.3% | 77.0 ± 15.2% |
| sDl1 | 24 hrs; BMP2 | 57.8 ± 9.9% | 0% | 7.0 ± 5.7% |
| sJ1 | 24 hrs; BMP2 | 0% | 54.4 ± 8.4%* | 71.4 ± 6.2%* |
| No addition | 72 hrs; BMP2 | 4.0 ± 3.4% | 34.3 ± 4.1% | 75.7 ± 8.0% |
| sJ1 | 72 hrs; BMP2 | 0.8 ± 1.4%* | 42.8 ± 6.6%* | 74.8 ± 16.3%* |
| No addition | 120 hrs; BMP2 | 3.1 ± 2.9% | 16.7 ± 5.9% | 81.3 ± 11.9% |
| sJ1 | 120 hrs; BMP2 | 5.82 ± 3.4%* | 13.43 ± 6.5%* | 52.01 ± 14.1%* |
| No addition | 168 hrs; BMP2 | 2.5 ± 2.7% | 3.8 ± 2.3% | 72.6 ± 7.6% |
| sJ1 | 168 hrs; BMP2 | 13.3 ± 4.5%* | 6.5 ± 1.3%* | 35.03 ± 9.1% |

NCSC Retain Neurogenic capacity in the presence of sJ1. A clonogenic differentiation assay was performed using mouse NSCS populations as described previously (Kubu et al., 2002, Dev. Biol. 244:199-214; Stemple et al., 1992, Cell 71:973-985). The cells were incubated in Stemple media (Stemple et al., 1992) with or without 5 nM sDl1 or 7.5 nM sJ1 for the time periods set forth in Table 1. After the initial incubation period, cells were washed and neuronal differentiation was challenged in the presence of 1 ng/ml BMP2 for an additional seven days. The resulting clones were fixed and stained for detection of neural crest markers. The data disclosed in Table 1 is presented as the percentage of glial-only, neuron-only, and neuron colonies containing either smooth muscle or glial markers as the mean±standard deviation (SD) of three experiments originating from three independent cell isolations. Note the retention of neurogenic differentiation capacity in sJ1-treated cells (*=p<0.01) compared with the sDl1-treated cells.

Because these results are consistent with the observations that Notch signaling attenuates neurogenic differentiation while maintaining a stem cell-like phenotype (Campos-Ortega, J. A., 1993, J. Neurobiol. 24:1305-1327; Campos-Ortega, J. A., 1995, Mol. Neurobiol. 10:75-89), the clonogenic differentiation of primary NCSC populations isolated from explants of E10 rat neural tubes was examined to assess the dosage sensitivity of these cells to the Notch ligands, sJ1 and sDl1. Despite being unable to rapidly eliminate neurogenic potential, it was observed that sJ1 was capable of inducing gliogenic differentiation of the NCSC population over the two week period of the differentiation assay (FIG. 12B). However, at all concentrations tested, sJ1 never produced the same robust instructive gliogenic differentiation response as observed with sDl1 (FIG. 12B).

Figure 12C:
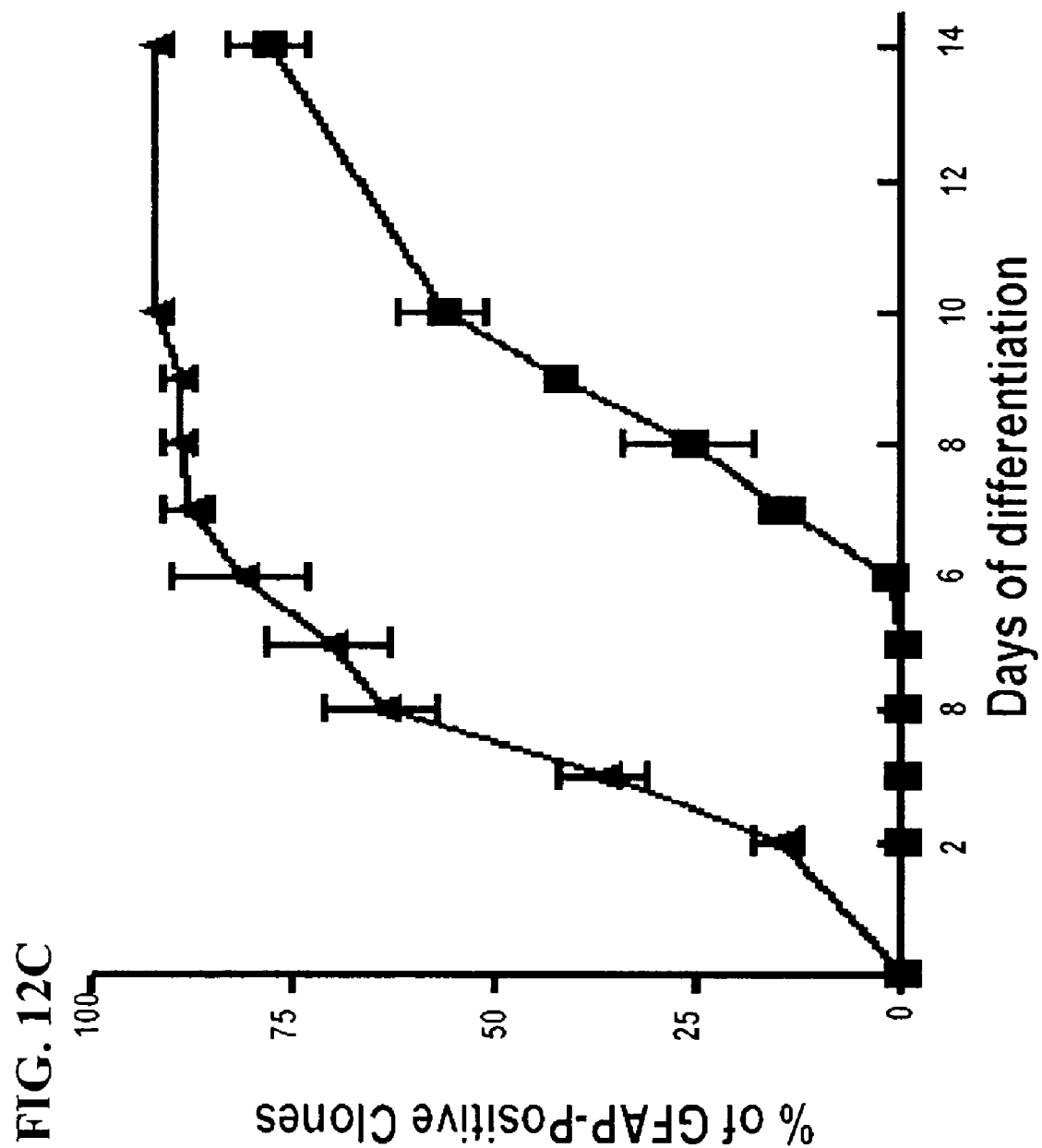
FIG. 12C demonstrates that the onset of GFAP induction in sDl1- and sJ1-treated NCSC was concurrent with the loss of neurogenic potential. Clonogenic differentiation assays of NCSC populations was assessed by maintaining the cells in Morrison media supplemented with either 7.5 nM sJ1 (■-■) or 5 nM sDl1 (▲-▲). The onset of gliogenic differentiation was determined by GFAP immunohistochemistry. Results are presented as the percentage of GFAP-positive clones (mean±standard deviation of three experiments). A long lag in the production of GFAP-positive progeny in the sJ1-treated NCSC clones was observed.

Since sJ1 enabled the retention of NCSC neurogenic potential over a 7 day period of exposure (Table 1), glial fibrillary acidic protein (GFAP) immunoreactivity was utilized as a measure of the onset of glial-specific clonogenic differentiation (Morrison et al., 1999, Cell 96:737-749; Stemple et al., 1992, Cell 71:973-985). Instead of examining the NCSC progeny after 14 days, developing clones were examined beginning at day 2 in order to determine the time period when gliogenic differentiation was initiated. As previously reported (Morrison et al., 2000, Cell 101:499-510), after 48 hours of exposure to sDl1, GFAP immunoreactive cells were detected in NCSC populations (FIG. 12C). In contrast, GFAP-immunoreactive cells were infrequently detected in the populations treated with sJ1 prior to day 7 and then only a moderate percentage of the colony (23±5) expressed the glial-specific protein at day 7 (FIG. 12C). Without wishing to be bound by any particular theory, these data suggest that gliogenic differentiation may result from the loss of neurogenic potential and that Notch activation may not serve to instruct gliogenesis as much as it may eliminate neurogenesis as a possible outcome.

ing strategy was employed by assessing clonal cell density growth of the NCSC populations in the presence of either thrombin, sJ1, sDl1, or TRAP. Using p75 immunoreactivity to identify the putative secondary NCSC populations as well as a clonogenic differentiation assay to determine the differentiation profiles for these secondary stem cell populations (Kubu et al., 2002, Dev. Biol. 244:199-214; Morrison et al., 2000, Cell 101:499-510), an enhancement in overall numbers of secondary clones established from either sJ1-, TRAP-, or thrombin-treated founder clones was observed, but not in response to sDl1 was detected. Indeed, the differentiation profiles of the resulting clones demonstrated that 86.8±2.1% and 74.1±9% of the clones established in the presence of either thrombin or sJ1, respectively, were trifatent (neurons, glial, and smooth muscle progeny) compared to 0.5%±0.7, 58.3%±7 ($P<0.025$), 56.9%±6 for those that originated in either the sDl1, TRAP or control NCSC populations, respectively (Table 2). These data suggest that unlike thrombin and sJ1, the presence of TRAP was less efficient in its ability to retain the multipotentiality of NCSC populations while still enabling the non-trifatent expansion of this population of cells, whereas the presence of sDl1 was unable to do either.

TABLE 2

| NCSCs | Secondary NSSC/ Founder | N | G | Sm | N + G | N + Sm | G + Sm | N + G + Sm |
|---|---|---|---|---|---|---|---|---|
| Control | 16.1 ± 2.9 | 2.3 ± 2.8 | 2.9 ± 0.2 | 7.4 ± 2.0 | 13.6 ± 2.3 | 8.5 ± 3.5 | 8.0 ± 3.9 | 56.9 ± 6.02 |
| sJ1 | 26.2 ± 6 | 0 | 7.8 ± 1.4 | 6.2 ± 1.0 | 7.0 ± 5.6 | 1.5 ± 1.7 | 3.4 ± 2.8 | 74.1 ± 9.1* |
| Thrombin (Thr) | 36.8 ± 6.3 | 0 | 0 ± 0 | 2.6 ± 1.01 | 3.93 ± 3.8 | 4.5 ± 2.1 | 2.0 ± 2.1 | 86.8 ± 2.1* |
| sDl1 | 0.6 ± 1.0 | 0 | 72 ± 6.4 | 20.5 ± 6.5 | 0 | 0 | 3.4 ± 2.8 | 0.5 ± 0.7 |
| TRAP | 24.4 ± 6.1 | 2.5 ± 2.3 | 1.3 ± 1.1 | 8.6 ± 3.3 | 15.3 ± 5.0 | 7.6 ± 1.0 | 6.6 ± 3.4 | 58.3 ± 7.2 |
| dnFGRF1 | 8.1 ± 1.5 | 7.9 ± 2.2 | 6.4 ± 1.7 | 15.9 ± 3.2 | 11.7 ± 11.6 | 8.8 ± 2.6 | 10.3 ± 9.5 | 39.8 ± 12.1** |
| dnFGFR1 + Thr | 13.5 ± 2.9 | 5.9 ± 1.7 | 1.7 ± 3.1 | 24.13 ± 1.4 | 9.8 ± 3.2 | 5.5 ± 1.5 | 6.9 ± 8.3 | 46.0 ± 13.6** |
| dnFGFR1 + sJ1 | 13.5 ± 4.7 | 0 | 9.3 ± 2.7 | 16.4 ± 8.5 | 7.2 ± 4.5 | 6.2 ± 7.0 | 10.3 ± 6.3 | 48.0 ± 11.8** |

Thrombin Mimics the Ability of sJ1 to Enhance Stamatozenesis, The Clonal Expansion of Stem Cell Populations Without Loss of Differentiation Potential Because, surprisingly, thrombin is able to mediate the non-classical release of FGF1, and because members of the FGF gene family are well recognized as neural cell mitogens (Mascarelli et al., 2001, J. Soc. Biol. 195:101-106; Sieber-Blum, M., 1998, Biochem. Cell. Biol. 76:1039-1050), and, as demonstrated for the first time herein, thrombin is able to upregulate the expression of the FGF1. A transcript in NCSC populations, it was determined whether thrombin could enable NCSC expansion. An art-recognized system was utilized that was previously employed to demonstrate that sDl1-induced Notch signaling is able to instruct gliogenic differentiation (Kubu et al., 2002; Morrison et al., 2000, Cell 101:499-510). Specifically, clonogenic differentiation and serial subcloning assays were performed using NCSC clones incubated with either thrombin, sDl1, sJ1 or TRAP. After 7 days of expansion, unlike the NCSC populations treated with sDl1 (0±0%), the vast majority (84±7%) of the NCSC clones treated with sJ1 did not express either gliogenic or neurogenic differentiation markers. Furthermore, these cells retained the expression of the stem cell markers, p75 and Nestin, and similar undifferentiated NCSC clones were also present in the cells treated with either thrombin (75±11%) or TRAP (39±13%).

In order to confirm that the p75+/Nestin+NCSC populations were indeed multipotential stem cells, a serial subclon- Table 2 demonstrates that thrombin and sJ1 expand clonal neural stem cells in vitro. Clonogenic NCSC differentiation outcomes are depicted in Table 2. Briefly, presented are the number of colonies with the resulting differentiation profiles (mean±SD of three experiments resulting from individual NCSC isolations). Note the statistically significant increase in the production of trifatent progeny from secondary stem cells isolated from sJ1 and thrombin NCSC founders after ten days of expansion (*=$p \leq 0.05$; **no significant difference between control (no addition) and dnFGFR1-transduced NCSC in their ability to produce trifatent (neurons (N), glial (G), and smooth muscle (Sm)) progeny within a single clone. Although significant changes in the number of secondary NCSC were observed in response to sJ1, TRAP and thrombin, these changes were independent of plating efficiency (44±6 for all conditions).

A genetic approach was used to determine whether thrombin, TRAP, or sJ1 were able to promote cell cycle progression in the NCSC population. Thus, a dnFGFR1 construct was expressed in the NSC cells and the clonogenic differentiation assay conducted in the presence of either sJ1, thrombin or no additional supplement. Interestingly, NCSC populations expressing dnFGFR1 demonstrated a significant reduction in their response to either sJ1, TRAP, or thrombin (Table 2) both in their ability to produce secondary stem cells at day 7 as well as the trifatent potential of the secondary stem cell population. Two additional interesting observations were also evident in these clonogenic analyses (Table 2). First, in spite of the increase in secondary subclones in the NCSC population treated with the thrombin receptor agonist, TRAP, the ability to generate trifatent clones was equivalent to controls, suggesting that perhaps thrombin has two dissectible functions: (i) to promote non-classical FGF1 release (PAR1-mediated) and (ii) to promote sJ1-induced signals to maintain the undifferentiated pluripotency of the NCSC populations (Notch-mediated). The expression of the dnFGFR1 mutant in this system confirms this premise since it also significantly reduces but does not eliminate these responses (Table 2). Second, the actions of sDl1 (Table 2) were the opposite of those for sJ1, and this is consistent with biochemical analysis (FIG. 11A) demonstrating the lack of thrombin-induced non-classical FGF1 release in the presence of constitutively active Notch1.

Figure 13A:
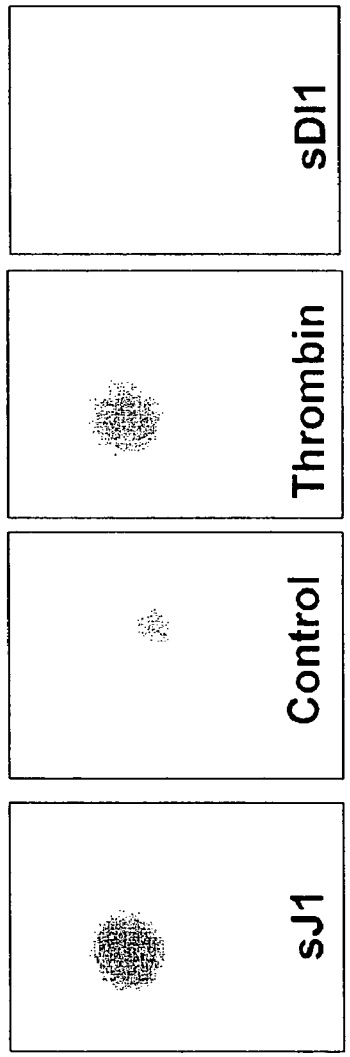
FIGS. 13A and 13B demonstrate that the size of primary clonal neurosphere is increased with sJ1 and thrombin. Clonal NCSC neurospheres were generated and allowed to expand for 10 days in either 7.5 nM sJ1, 5 nM sD1, 5 μg/ml α-thrombin, and no additive (control) (FIG. 13A) as described elsewhere herein. Clonal NCSC neurospheres were generated in a feeder-layer coculture system using a monolayer of stable full-length (FL) Jagged1 NIH 3T3 cell transfectants or insert-less NIH 3T3 cell transfectants and treated with either 5 μg/ml thrombin or without further supplementation (control) (FIG. 13B). The results are presented as representative photomicrographs of the spheres obtained under each condition after 14 days of treatment.

In addition, in both the clonogenic differentiation assays and the serial subcloning experiments, sJ1 could not maintain pluripotency in the presence of sDl1. This observation was further examined using an art-recognized cortical neurosphere model (Reynolds et al., 1992, J. Neurosci. 12:4565-4574; Reynolds et al., 1992, Science 255:1707-1710). The E14 prefrontal ventricular zone was dissected and plated at a clonal neurosphere-forming density in the presence of either sJ1, sDl1, thrombin, TRAP or no supplementation. After 2 weeks, the clones were dissociated to single cells and secondary spheres were generated using standard media with no supplementation (Reynolds et al., 1992, J. Neurosci. 12:4565-4574). While control spheres formed 12±8 secondary spheres per primary sphere, primary spheres originating in the presence of either thrombin, TRAP or sJ1 produced significantly more secondary clones (thrombin: 55±14; sJ1: 64±11; TRAP: 53±7). In contrast, sDl1 was unable to generate secondary stem cell spheres (sDl1: 3±3), an observation consistent with the literature (Hitoshi et al., 2002, Genes Dev. 16:846-858). These changes in secondary stem cell generation cannot be attributed to the size of the primary spheres, since despite the observation that sJ1 and thrombin produced the largest spheres (FIG. 13A), the total cell numbers were slightly less than 2-fold over the control yet the change in secondary stem cell generation exceeded 5-fold (Table 3).

TABLE 3

| Neurospheres | Secondary Spheres (SP) | Cells/Founder (F) | F/SP × 10² |
|---|---|---|---|
| Control | 12 ± 8 | 276 ± 108 | 4.3% |
| sJ1 | 55 ± 14 | 527 ± 170* | 10%* |
| Thrombin | 64 ± 11 | 488 ± 166* | 13%* |
| TRAP | 53 ± 7 | 407 ± 143* | 13%* |
| sDl1 | 3 ± 3 | 150 ± 69* | 2.0% |

Table 3 sets forth data demonstrating that secondary stem cell formation is enhanced by thrombin and sJ1 at day 10. Secondary spheres (SP) are formed from the dissociation of founder (F) spheres. The data presented are the number of colonies (mean±SD of three experiments). (*=p≦0.05).

Figure 13B:
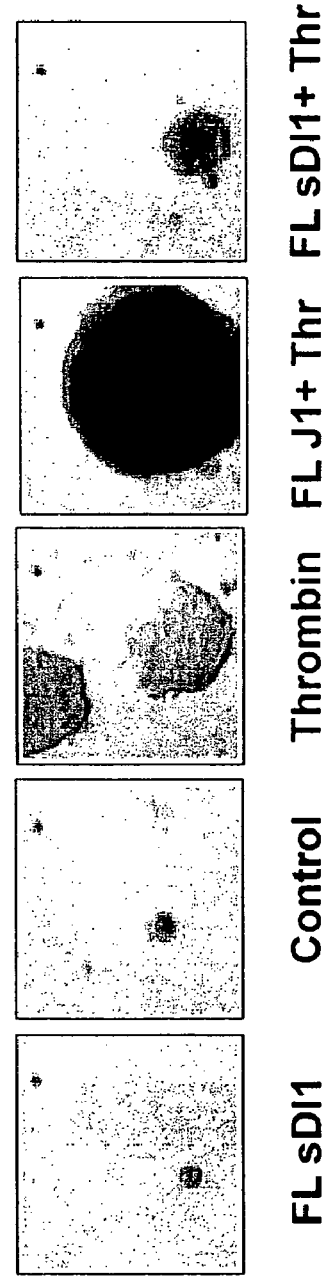

To further evaluate the activity of thrombin as a modifier of Jagged1, the clonal expansion studies were repeated using NSC populations cultured in the presence of a viable full-length Jagged1 NIH 3T3 cell transfectant feeder layer. Surprisingly, the addition of thrombin to this co-culture system resulted in an exaggeration of the size of the NSC colonies (FIG. 13B) over the controls. Because the introduction of a full-length Delta1 NIH 3T3 cell transfectant feeder layer failed to induce a similar thrombin-dependent effect on NSC colony size, it is likely that the cleavage of Jagged1 but not Delta1 by thrombin was responsible for this effect.

Figure 13C:
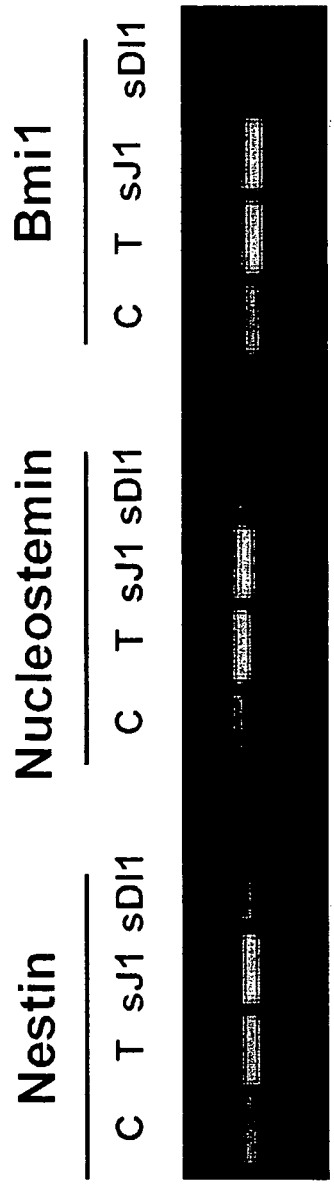
FIG. 13C demonstrates that thrombin and sJ1 lead to the retention of neural stem cell markers during neurosphere expansion. Clonal neurospheres were generated in the presence of either 5 μg/ml α-thrombin, 7.5 nM sJ1, 5 nM sDl1 or no supplement (control) and expanded for 14 days. RT-PCR was used to determine the steady-state mRNA level for three markers of neural stem cells (Nestin, Nucleostemin and Bmi1). An increase in the expression of all three transcripts compared to control was observed.
Figure 13D:
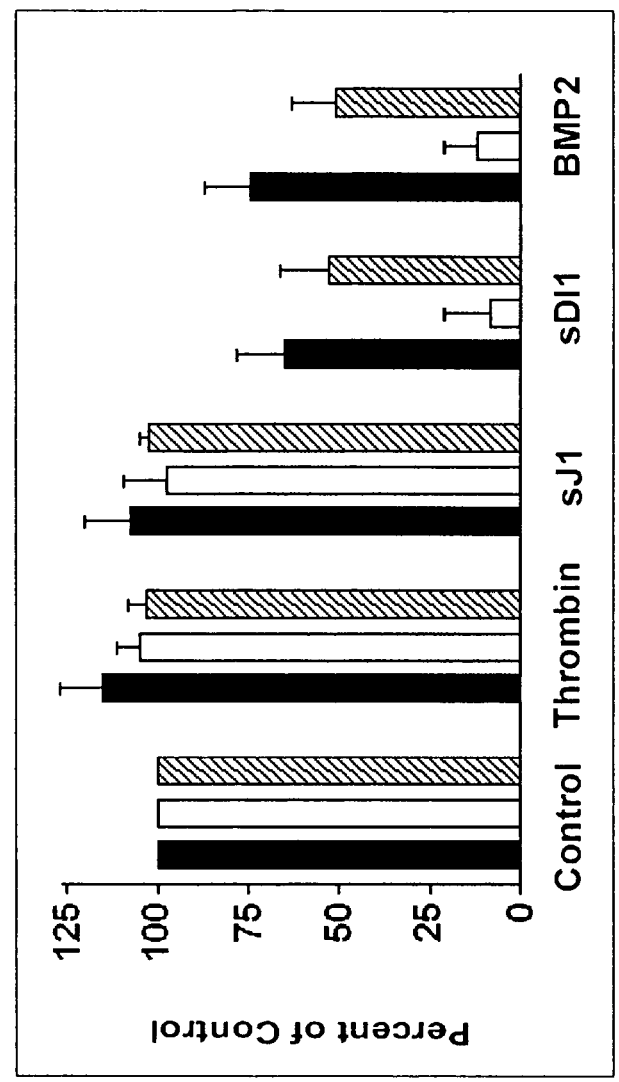
FIG. 13D demonstrates that the retention of stem cell markers is the result of an increase in the percentage of expressing cells. Approximately $5 \times 10^2$ NCSC were plated in Morrison media supplemented with either 7.5 nM sJ1, 5 μg/ml α-thrombin, 5 nM sD1, 2 ng/ml BMP2 or no additive (control) for 48 hours. The results are presented as the percent of control (mean±standard deviation of three RT-PCR experiments) performed in triplicate. No change in the steady-state level mRNA levels of the three markers relative to actin was observed.

To demonstrate that thrombin and sJ1 also facilitated NCSC self-renewal, RT-PCR analysis was utilized to examine the expression of three transcripts linked to the self-renewal process: Nestin, Nucleostemin, and Bmi1. As shown in FIG. 13C, the relative expression of all three transcripts was elevated in the primary and secondary neurosphere cultures established and maintained in the presence of either thrombin or sJ1 but neither in the presence of sDl1 nor in the controls. In order to assess the possibility that either sJ1 or thrombin was able to induce the expression of these genes, 200 individual p75$^+$/myelin protein $(P_0)^-$ neural crest stem cells were grown in the presence of either thrombin, sJ1, or sDl1 for 24 and 48 hours and subjected to RT-PCR analyses. As shown in FIG. 13D, while the levels of these three transcripts were sharply decreased in the sDl1-treated NCSC populations, they displayed no significant change in response to any other condition. These data suggest that the increase in the steady-state levels of these transcripts may have been the result of an increase in the number of cells and not the level of transcript per cell.

The Dosage Sensitivity of NCSC Populations to Instructive Differentiation Signals is Maintained by Thrombin and sJ1

It is well established that quantitative changes in the dosage sensitivity of NCSC populations occur in vitro and in vivo during NCSC self-renewal (Kubu et al., 2002, Dev. Biol. 244:199-214; White et al., 1999, Development 126:4351-4363; White et al., 2001, Neuron 29:57-71). In order to resolve whether it was possible to clonally expand stem cell populations without the loss of qualitative or quantitative differentiation potential, it was evaluated whether NCSC population expansion in either a thrombin or a sJ1 environment was able to maintain the quantitative dosage sensitivity of the NCSC populations to instructive differentiation factors. NCSC clones were expanded with either thrombin, TRAP, or sJ1 for 18 days, the clones dissociated to a clonal density every 6 days to minimize cell-cell interactions, and the p75+/$P_0^-$ cells identified. The dosage sensitivity of secondary NCSC populations to both BMP2 and sDl1 was evaluated using the clonogenic differentiation assay to quantitate the production of neuron-only clones (BMP2) and glial-only clones (sDl1) after day 18.

Figure 14A:
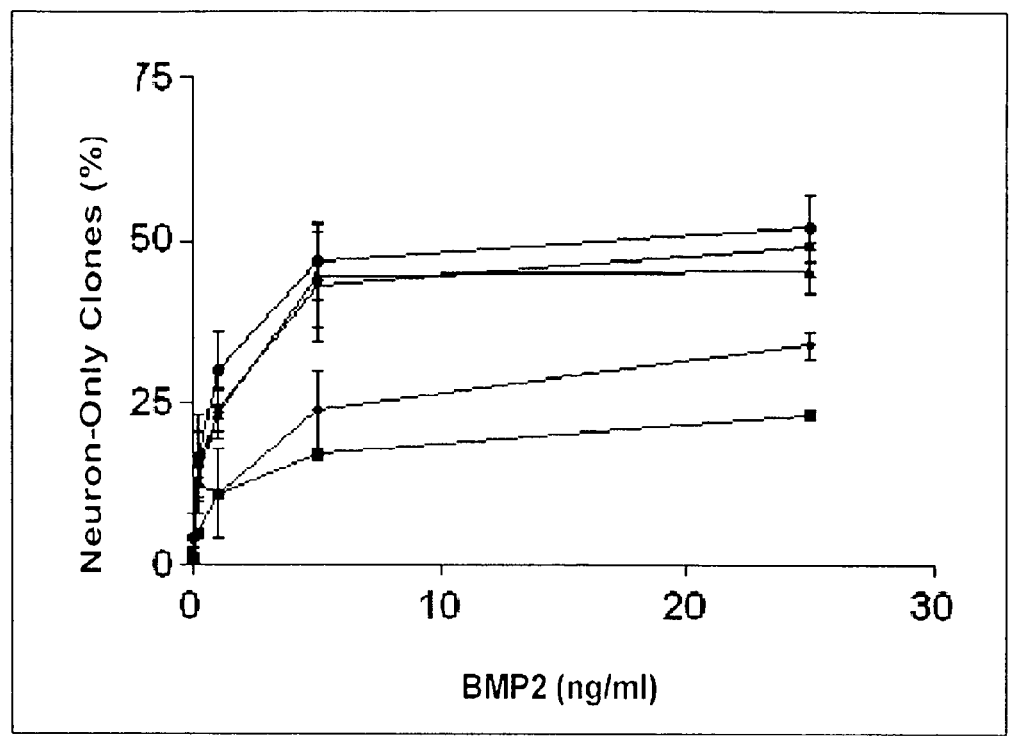
FIG. 14A demonstrates that founder NCSC populations expanded in either sJ1 or thrombin retain maximal dosage sensitivity to BMP2. Clonogenic differentiation assays of secondary P75$^+$/P$_0^-$ NCSC populations were assayed in Morrison media as a function of the concentration of the neurogenic differentiation factor, BMP2, and the generation of Neuron-only clones was assessed 14 days after the addition of BMP2. The results are presented as the percent of neuron-only colonies (mean±standard deviation of three experiments) originating from distinct NCSC isolations.
Figure 14B:
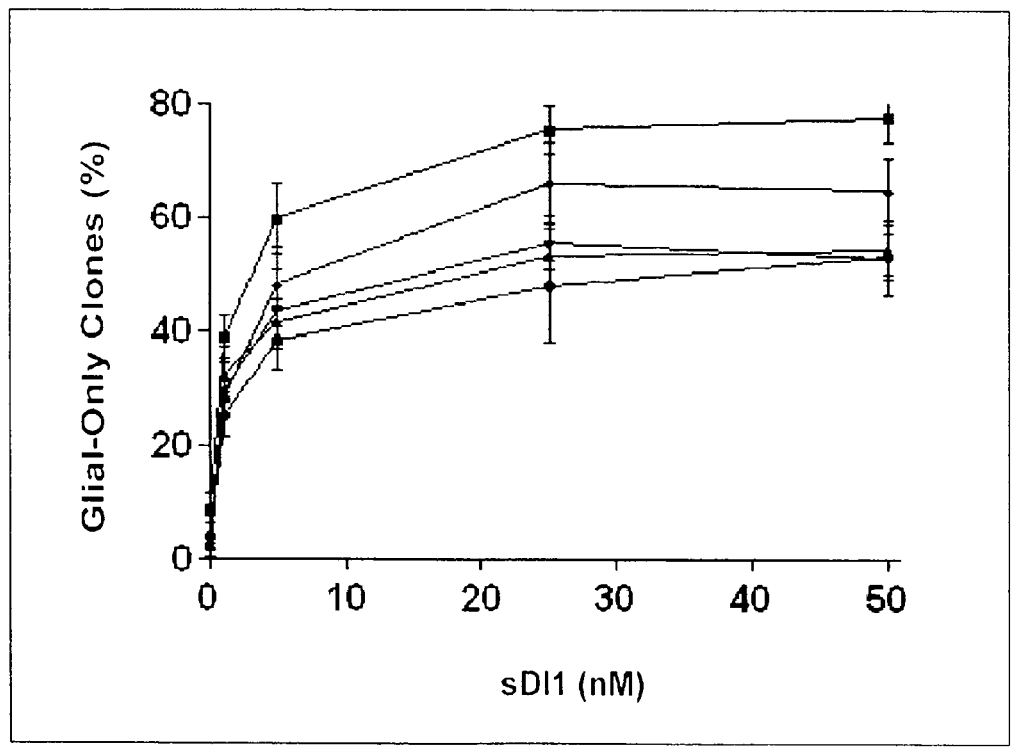
FIG. 14B demonstrates that secondary NCSC populations originating from founder NCSC populations do not display a gliogenic bias when expanded in either sJ1 or thrombin. Clonogenic differentiation assays of secondary P75$^+$/P$_0^-$ NCSC were preformed in Morrison media supplemented with increasing concentrations of the gliogenic differentiation factor, sDl1 and the generation of Glial-only clones was assessed 14 days after the addition of sDl1. The results are presented as the percentage of glial-only colonies (mean±standard deviation of three experiments) originating from distinct NCSC isolations. It was observed that the secondary stem cells originating from the founder populations grown in control media exhibit a shift in dosage sensitivity to both neurogenic and gliogenic differentiation signals compared to the freshly isolated primary NCSC founders. This is not observed in secondary stem cells originating from founders grown in the presence of either sJ1 or thrombin.

As previously demonstrated (Kubu et al., 2002, Dev. Biol. 244:199-214), secondary stem cells under control conditions (FIGS. 14A and 14B) or in the presence of 5 μM TRAP (FIGS. 14A and 14B) exhibited a shift from a neurogenic to gliogenic differentiation bias. In contrast, this shift in sensitivity to instructive differentiation signals was not observed when the primary clones were maintained in the presence of either sJ1 or thrombin (FIGS. 14A and 14B). These data suggest that the dosage sensitivity of NCSC populations maintained in the presence of either sJ1 or thrombin was similar to isolated NCSC populations in vitro, and that the function of thrombin in this regard is to proteolytically modify Jagged1 since the presence of TRAP was not effective. Thus, without wishing to be bound by any particular theory, the data disclosed herein establish the first "clonal" expansion of a non-embryonic stem cell population without influencing the differentiated character of the expanded population, a process termed "stamatogenesis".

Discussion

Stem cells persist throughout adult life by a self-renewal process in numerous tissues including the peripheral and central nervous systems. This raises the intriguing possibility that common mechanisms may regulate self-renewal in stem cell populations. While several genes have been implicated in the self-renewal process, such as Nanog (Cavaleri et al., 2003, Cell 113:551-552; Hirata et al., 2001, EMBO J. 20:4454-4466; Mitsui et al., 2003, Cell 113:631-642), and Bmil (Molofsky et al., 2003, Nature 425:962-967; Raaphorst, F. M., 2003, Trends Immunol. 24:522-524), it is unclear how these genes function in either the activation or expansion of stem cell populations. However, it is anticipated that receptor-mediated signaling systems which regulate cell fate, survival, migration, proliferation, differentiation and apoptosis may ultimately provide access to mechanisms responsible for cellular self-renewal. The data disclosed herein demonstrate the involvement of non-classical FGF1 export and its role as a Notch antagonist in the process of stem cell self-renewal. In addition, these data merge the fields of hemostasis and thrombosis with stem cell biology since thrombin appears to be the common denominator between the nonclassical export of FGF1 and the antagonism of classical Notch signaling. This surprising observation was unanticipated, but now makes possible numerous therapeutic approaches to a wide plethora of previously untreatable diseases and conditions.

Tissue injury induced by stress as a result of physical trauma, infection, metabolism (acidosis, hypoxia, etc.) or inflammation is often, if not always, accompanied by a thrombotic event (Taubman et al., 1999, Thromb. Haemost. 82:801-805). In this situation, thrombin may play a critical role to not only form a temporary extracellular matrix (fibronectin-adsorbed fibrin) but also to signal the PAR1-dependent transcription of the FGF1.A mRNA and the translation and non-classical export of FGF 1, an established regulator of cell survival (Renaud et al., 1994, J. Cell. Physiol. 158:435-443). Indeed, within the central and peripheral nervous systems, the availability of FGF1 as a neurotrophic and angiogenic factor may play a fundamental role in the repair process and there has been a report, albeit controversial, of central nervous system repair using the surgical implantation of FGF1 and fibrin (Cheng et al., 1996, Science 273:510-513). Thrombin ensures the release of FGF1 by its ability to also cleave Jagged1, an event which antagonizes classical Notch signaling (Small et al., 2003, J. Biol. Chem. 278:16405-16413), and this may enable the target cell to remain in an undifferentiated state during FGFR1-mediated signaling. It is interesting to note that FGF1 also contains a thrombin cleavage site (Erzurum et al., 2003, J. Vasc. Surg. 37:1075-1081), but this proteolytic event is inhibited by heparin (Rosengart et al., 1988, Biochem. Biophys. Res. Commun. 152:432-440). Thus, the data disclosed herein suggest that the saturation of cell-associated heparin-like, heparan sulfate proteoglycan sites by extracellular FGF1 may assure that excess FGF1 will be proteolytically inactivated by thrombin (Erzurum et al., 2003, J. Vasc. Surg. 37:1075-1081; Lobb, R. R., 1988, Biochemistry 27:2572-2578). The release of FGF1 is a critical outcome, since thrombin and/or sJ1 have little mitogenic activity when neural stem cells or NIH 3T3 cells express a dominant negative form of FGFR1. This latter finding is supported by previous findings that FGF is required for the expansion of clonal neurospheres and NCSC populations (Reynolds et al., 1992, J. Neurosci. 12:4565-4574; Reynolds et al., 1992, Science 255:1707-1710; Stemple et al., 1992, Cell 71:973-985). However, a hallmark of this system is that thrombin and/or sJ1 preserve cells in an undifferentiated state during cell proliferation.

These observations present a potential paradox within the current literature regarding Notch signaling and embryogenesis because there is no study linking the enzymatic activity of thrombin to any aspect of developmental biology. Thus, it is unlikely that the proteolytic modification of Jagged1 by thrombin plays a role during development. This would therefore limit the stamatogenic functions of thrombin to the modification of post-developmental adult stem cells but does not eliminate the possibility of a similar proteolytic mechanism using a developmentally regulated protease to accomplish a similar task. Indeed, the observation that PAR1 is one of eight genes upregulated in embryonic, mammary, neurosphere and hematopoietic stem populations (Dontu et al., 2003, Genes Dev 17:1253-1270) supports this premise.

It is also interesting that sJ1 and sDl1 induce distinctive phenotypic outcomes. Whereas sJ1:Notch interactions enable stamatogenesis, sDl1:Notch associations lead to an immediate loss of neurogenic potential. Delta1 and Jagged1 have been previously observed to differentially regulate Notch signaling during human lymphoid differentiation (Jaleco et al., 2001, J. Exp. Med. 194:991-1002), and Delta1 but not Jagged1, is able to repress the differentiation of human cord blood-derived progenitors of the B cell lineage (Jaleco et al., 2001, J. Exp. Med. 194:991-1002). Likewise, Delta1, but not Jagged1, is able to promote the in vitro development of human cord blood-derived progenitor cells with a T cell/natural killer cell phenotype (Jaleco et al., 2001, J. Exp. Med. 194:991-1002), and sJ1 is able to promote the clonal expansion of hematopoietic stem cells in vitro (Vas et al., 2004, J. Leukoc. Biol., in press). The expression of sDl1 and sJ1 also exhibit similar yet disparate phenotypes in the NIH 3T3 cell including the modification of Src-dependent signaling (Trifonova et al., J. Biol. Chem., 2004, in press). Thus, it appears that sJ1 and sDl1 induce different cell fate decisions in NCSC populations. Because dnFGFR1 expression abrogates the ability of sJ1 to facilitate self-renewal, and non-classical FGF1 release is dependent upon the repression of classical Notch signaling as demonstrated elsewhere herein, these data suggest that the soluble form of Delta1 may be able to enhance Notch activity in NCSC populations while the non-transmembrane form of Jagged1 is able to suppress Notch signaling in these cells. Indeed, RT-PCR analyses of Notch down-stream effectors demonstrate a suppression of the steady-state levels of HEY and Deltex transcripts in sJ1—but not sDl1-treated NCSC populations and these results agree with the differences mediated by sJ1 and sDl1 to induce gliogenesis. Since Notch signaling plays a vital role in neurogenesis (Anderson, D. J., 1997, Trends Genet. 13:276-280; Cau et al., 2000, Development 127:2323-2332) and the ontogeny of other organ systems (Del Amo et al., 1992, Development 115:737-744), the data disclosed herein suggest that the repression of Notch activity may result in a diminished population of neural stem cells, whereas constitutively active Notch signaling may result in a loss of the stem cell pool itself and terminal differentiation into glia. Thus, without wishing to be bound by any particular theory, the levels of Notch signaling may be paramount in regulating the undifferentiated expansion of multipotential neural stem cells, and thrombin and/or sJ1, may be one of the key elements in this process that enable stamatogenesis to occur. The data disclosed herein further suggest that since gliogenic differentiation may be concurrent with the loss of neurogenic potential, gliogenic differentiation may not be an instructive event but rather a default state when neurogenic potential is lost.

It is interesting that while TRAP enables the release of FGF1, it does not enable the stamatogenic expansion of these cells. Since TRAP also induces PAR1-mediated (Coughlin, S. R., 1993, Thromb Haemost 70:184-187; Scarborough et al., 1992, J. Biol. Chem. 267:13146-13149) and FGF1-dependent DNA synthesis (FIG. 11D), the data disclosed herein suggest that the activation of PAR1 is a critical component for the induction of the stamatogenic event and that the modification of Jagged1 by thrombin may play a supportive role in the modification of stem clonal expansion. Since TRAP does not mimic the full potential of either thrombin or sJ1 to enable maximal stem cell expansion, it is likely that PAR1 signaling is an important component for the initiation of FGFR1-dependent DNA synthesis, but stamatogenesis requires both PAR1 signaling and the cleavage of Jagged 1. Although sJ1 and FGF1 are both Notch receptor signaling antagonists (Baron, 2003, Semin. Cell Dev. Biol. 14:113-119) and the simple addition of an exogenous source of FGF does not, by itself, promote maximal stem cell expansion in vitro (Weissman et al., 2001, Annu. Rev. Cell. Dev. Biol. 17:387-403), it is very likely that sJ1 may also provide other unknown functions to achieve maximal stamatogenic potential independently of FGFR signaling. The fact that Morrison media is supplemented with exogenous FGF2 but does not enable stamatogenesis to occur is consistent with this premise.

The surprising ability of thrombin to stimulate the rapid non-classical release of FGF1 is also noteworthy since it appears to utilize the stress-induced mechanism involving the function of S100A13 (Landriscina et al., 2001b, J. Biol. Chem. 276:22544-22552) and the alternative translation product (Bagala et al., 2003, Biochem. Biophys. Res. Commun. 310:1041-1047) of the p65 Syt1 transcript (LaVallee et al., 1998, J. Biol. Chem. 273:22217-22223). Since the stress-induced pathway for FGF1 export exhibits slower kinetics (Jackson et al., 1992, Proc. Natl. Acad. Sci. U.S.A. 89:10691-10695), the data disclosed herein suggest that the thrombin-dependent release of FGF1 may be utilized to rapidly establish low levels of FGF1 in the extracellular compartment to function primarily as a cell survival factor in vivo. This event would be the consequence of a cellular stress involving the activation of either the intrinsic or extrinsic coagulation pathways which would provide for fibrin deposition as well as a source of thrombin at the stress site. Since fibrin is able to associate with fibronectin (Niewiarowska et al., 1984, J. Biol. Chem. 259:6181-6187), fibrin may also serve as a transportable extracellular matrix for stem cell migration. However, should the time period of the initial stress be extended beyond this immediate-early phase by additional physiologic and/or pathophysiologic stress (acidosis, hypoxia, and the like), it is likely that the non-classical export of FGF1 is further maintained by the function of the stress-induced pathway (Ananyeva et al., 1997, Arterioscler. Thromb. Vasc. Biol. 17:445-453; Jackson et al., 1992, Proc. Natl. Acad. Sci. U.S.A. 89:10691-10695; Mouta et al., 2001, Growth Factors 18:277-285; Shin et al., 1996, Biochim. Biophys. Acta. 1312: 27-38). The data disclosed herein further suggest that in this situation, the function of FGF1 in the extracellular compartment may be to promote and sustain the cell cycle and enable the target cell to enter S-phase (Zhan et al., 1993, J. Biol. Chem. 268:9611-9620). This implies that the function of PAR1 signaling may be limited to the modification of immediate-early events and that the modification of Jagged1 by thrombin may occur after this event when cell-cell contacts are being modified. Further, the ability of constitutively active Notch1 to repress the thrombin-induced non-classical release of FGF1 and the ability of sJ1 expression to enable the continual release of FGF1 over prolonged time periods as disclosed elsewhere herein, argue that non-classical FGF1 export mediated by PAR1 and sJ1 may be temporally- and spatially-linked. Indeed, the failure of PAR1 null cells to release FGF1 in response to thrombin versus the ability of the PAR1 null cells to release FGF1 in response to temperature stress, supports this premise.

It is generally accepted that as stem cells transition through the self-renewal process, they appear qualitatively similar in vivo and in vitro and maintain their basic properties of self-renewal and multilineage differentiation by their abilities to respond to instructive differentiation signals (Morrison et al., 2001, Curr. Opin. Cell. Biol. 13:666-672). Unlike the hematopoietic (Guidos, C. J., 2002, Semin. Immunol. 14:395-404; Krause, D. S., 2002, Oncogene 21:3262-3269; Maillard et al., 2003, Immunity 19:781-791; Maillard et al, 2003, Immunity 18:587-589) or neuropoietic systems (Shah et al., 1997, Proc. Natl. Acad. Sci. U.S.A. 94:11369-11374; Shah et al., 1996, Cell 85:331-343), no abrupt restriction in self-renewal potential is observed; rather, there may be a bias in the differentiation outcome mediated through changes in responsivity to instructive differentiation signals. This shift in bias is likely to occur through cell-cell communication more so than from instructive signals derived from either the stroma or surrounding tissue where instructive differentiation signals originate.

Thus, changes in classical Notch signaling may bias NCSC populations toward a gliogenic differentiation program and, in contrast, the generation of sJ1 appears to either reset or repress this outcome. In clonal neural crest and cortical neurosphere assays, sJ1 allows for the expansion of trifatent stem cells at the expense of bipotential and unipotential differentiation. Instructive differentiation factors such as BMP2 or Delta1, which restrict the self-renewal potential of stem cells may do so by either eliminating or overriding the sJ1 signal. Since the data disclosed herein suggest that the activity of sDl1 appears to be dominant over sJ1, it may be that as stem cells self-renew, a slight shift in factor responsivity occurs in either cells (symmetric) or their progeny (asymmetric). As this process continues, each subsequent stem cell is slightly different until a particular phenotypic outcome is lost due to lowering its ability to respond to a particular instructive differentiation factor. Thus, expanding stem cell populations may maintain their self-renewal potential when analyzed in vitro where one can manipulate the concentrations of ligand, but this potential may be lost in vivo. However, the process of stem cell renewal may be attenuated by the repression of classical Notch signaling by the serial passage of the stem cell populations in vitro (Kubu et al., 2000, Genomics 70:150-152) or by the generation of sJ1. Indeed, it has been demonstrated that the total abrogation of Notch signaling results in a loss in the maintenance of neural stem cell populations and this event appears to be independent of HES or HEY transcription (Hitoshi et al., 2002, Genes Dev. 16:846-858). Because the activation of Notch signaling may enable a similar event by instructing the differentiation of neural stem cells into glia (Furukawa et al., 2000, Neuron 26:383-394; Gaiano et al., 2000, Neuron 26:395-404; Morrison et al., 2000, Cell 101:499-510), the data disclosed herein suggest that a threshold of endogenous Notch signaling may be paramount for neural stem cell maintenance. Rather, exaggerated Notch signaling may result in the loss of neurogenic potential and differentiation into glia, whereas repressed Notch signaling may result in cell proliferation by enabling the non-classical release of FGF1 by the target stem cell. Thus, the data disclosed herein suggest that repression of Notch signaling by sJ1 will enable long-term expansion of adult stem cell populations without altering either their responsiveness to instructive differentiation signals, multipotentiality or stamatogenic potential.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for producing a population of pluripotent stem cells, said method comprising expanding a stem cell wherein said cell is contacted with an effective amount of a factor selected from the group consisting of thrombin, soluble Jagged1 (sJ1), and thrombin receptor-activated peptide (TRAP), and combinations thereof, thereby producing a population of pluripotent stem cells, wherein said stem cell is selected from the group consisting of a neural stem cell and a neural crest stem cell.

2. A method for obtaining a clonally expanded stem cell, said method comprising obtaining a stem cell from a human, administering a differentiation inhibiting amount of at least one inhibitor of Notch-signaling selected from the group consisting of thrombin, soluble Jagged 1 (sJ1), and thrombin receptor-activated peptide (TRAP) to said stem cell; allowing said cell to proliferates, thereby obtaining a clonally expanded stem cell, wherein said stem cell is selected from the group consisting of a neural stem cell and a neural crest stem cell.

3. A method for expanding a multipotent stem cell without detectable loss of multipotentiality, said method comprising growing a multipotent stem cell wherein said cell is contacted with a differentiation inhibiting amount of thrombin, thereby expanding a multipotent stem cell without detectable loss of multipotentiality, wherein said stem cell is selected from the group consisting of a neural stem cell and a neural crest stem cell.

4. The method of claim 3, further comprising contacting said cell with a differentiation inhibiting amount of sJ1.

5. The method of claim 4, said method further comprising contacting said cell with a differentiation inhibiting amount of TRAP.

6. The method of claim 3, said method further comprising contacting said cell with a differentiation inhibiting amount of TRAP.

7. A kit for producing a population of pluripotent stem cells, without detectable loss of pluripotency, said kit comprising an effective amount of thrombin, said kit further comprising sJ1, said kit further comprising an applicator and an instructional material for the use of said kit.

8. A kit for expanding a pluripotent stem cell without detectable loss of pluripotency, said kit comprising a differentiation inhibiting amount of thrombin, said kit further comprising thrombin receptor-activated peptide (TRAP), said kit further comprising an applicator and an instructional material for the use of said kit.

* * * * *

```
                              SEQUENCE LISTING

<160> NUMBER OF SEQ ID NOS: 39

<210> SEQ ID NO 1
<211> LENGTH: 1218
<212> TYPE: PRT
<213> ORGANISM: Homo sapiens
<220> FEATURE:
<221> NAME/KEY: MISC_FEATURE
<223> OTHER INFORMATION: Full-length Jagged1

<400> SEQUENCE: 1

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300
```

```
Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
```

-continued

```
                725                 730                 735
Gly Thr Thr Cys Asn Ile Ala Arg Asn Ser Ser Cys Leu Pro Asn Pro
            740                 745                 750
Cys His Asn Gly Gly Thr Cys Val Val Asn Gly Glu Ser Phe Thr Cys
            755                 760                 765
Val Cys Lys Glu Gly Trp Glu Gly Pro Ile Cys Ala Gln Asn Thr Asn
            770                 775                 780
Asp Cys Ser Pro His Pro Cys Tyr Asn Ser Gly Thr Cys Val Asp Gly
785                 790                 795                 800
Asp Asn Trp Tyr Arg Cys Glu Cys Ala Pro Gly Phe Ala Gly Pro Asp
                805                 810                 815
Cys Arg Ile Asn Ile Asn Glu Cys Gln Ser Ser Pro Cys Ala Phe Gly
            820                 825                 830
Ala Thr Cys Val Asp Glu Ile Asn Gly Tyr Arg Cys Val Cys Pro Pro
            835                 840                 845
Gly His Ser Gly Ala Lys Cys Gln Glu Val Ser Gly Arg Pro Cys Ile
            850                 855                 860
Thr Met Gly Ser Val Ile Pro Asp Gly Ala Lys Trp Asp Asp Cys
865                 870                 875                 880
Asn Thr Cys Gln Cys Leu Asn Gly Arg Ile Ala Cys Ser Lys Val Trp
                885                 890                 895
Cys Gly Pro Arg Pro Cys Leu Leu His Lys Gly His Ser Glu Cys Pro
            900                 905                 910
Ser Gly Gln Ser Cys Ile Pro Ile Leu Asp Asp Gln Cys Phe Val His
            915                 920                 925
Pro Cys Thr Gly Val Gly Glu Cys Arg Ser Ser Ser Leu Gln Pro Val
            930                 935                 940
Lys Thr Lys Cys Thr Ser Asp Ser Tyr Tyr Gln Asp Asn Cys Ala Asn
945                 950                 955                 960
Ile Thr Phe Thr Phe Asn Lys Glu Met Met Ser Pro Gly Leu Thr Thr
                965                 970                 975
Glu His Ile Cys Ser Glu Leu Arg Asn Leu Asn Ile Leu Lys Asn Val
            980                 985                 990
Ser Ala Glu Tyr Ser Ile Tyr Ile Ala Cys Glu Pro Ser Pro Ser Ala
            995                1000                1005
Asn Asn Glu Ile His Val Ala Ile Ser Ala Glu Asp Ile Arg Asp
            1010                1015                1020
Asp Gly Asn Pro Ile Lys Glu Ile Thr Asp Lys Ile Ile Asp Leu
            1025                1030                1035
Val Ser Lys Arg Asp Gly Asn Ser Ser Leu Ile Ala Ala Val Ala
            1040                1045                1050
Glu Val Arg Val Gln Arg Arg Pro Leu Lys Asn Arg Thr Asp Phe
            1055                1060                1065
Leu Val Pro Leu Leu Ser Ser Val Leu Thr Val Ala Trp Ile Cys
            1070                1075                1080
Cys Leu Val Thr Ala Phe Tyr Trp Cys Leu Arg Lys Arg Arg Lys
            1085                1090                1095
Pro Gly Ser His Thr His Ser Ala Ser Glu Asp Asn Thr Thr Asn
            1100                1105                1110
Asn Val Arg Glu Gln Leu Asn Gln Ile Lys Asn Pro Ile Glu Lys
            1115                1120                1125
His Gly Ala Asn Thr Val Pro Ile Lys Asp Tyr Glu Asn Lys Asn
            1130                1135                1140
```

Ser Lys Met Ser Lys Ile Arg Thr His Asn Ser Glu Val Glu Glu
    1145                1150                1155

Asp Asp Met Asp Lys His Gln Gln Lys Ala Arg Phe Gly Lys Gln
    1160                1165                1170

Pro Ala Tyr Thr Leu Val Asp Arg Glu Glu Lys Pro Pro Asn Gly
    1175                1180                1185

Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 2
<211> LENGTH: 3657
<212> TYPE: DNA
<213> ORGANISM: Homo sapiens
<220> FEATURE:
<221> NAME/KEY: misc_feature
<223> OTHER INFORMATION: Full-length Jagged1

<400> SEQUENCE: 2

| | | |
|---|---|---|
| atgcgttccc cacggacrcg cggccggtcc gggcgccccc taagcctcct gctcgccctg | 60 |
| ctctgtgccc tgcgagccaa ggtgtgtggg gcctcgggtc agttcgagtt ggagatcctg | 120 |
| tccatgcaga acgtgaacgg ggagctgcag aacgggaact gctgcggcgg cgcccggaac | 180 |
| ccggagacc gcaagtgcac ccgcgacgag tgtgacacat acttcaaagt gtgcctcaag | 240 |
| gagtatcagt cccgcgtcac ggccgggggg ccctgcagct tcggctcagg gtccacgcct | 300 |
| gtcatcgggg gcaacacctt caacctcaag gccagccgcg gcaacgaccg caaccgcatc | 360 |
| gtgctgcctt tcagtttcgc ctggccgagg tcctatacgt gcttgtggac ggcgtgggat | 420 |
| tccagtaatg acaccgttca acctgacagt attattgaaa aggcttctca ctcgggcatg | 480 |
| atcaaccccca gccggcagtg gcagacgctg aagcagaaca cgggcgttgc ccactttgag | 540 |
| tatcagatcc gcgtgaccctg tgatgactac tactatggct ttggctgyaa taagttctgc | 600 |
| cgccccagag atgacttctt tggacactat gcctgtgacc agaatggcaa caaaacttgc | 660 |
| atggaaggct ggatgggccc cgaatgtaac agagctattt gccgacaagg ctgcagtcct | 720 |
| aagcatgggt cttgcaaact cccaggtgac tgcaggtgcc agtayggctg gcaaggcctg | 780 |
| tactgtgata gtgcatccc acacccggga tgcgtccacg gcatctgtaa tgagccctgg | 840 |
| cagtgcctct gtgagaccaa ctggggcggc cagctctgtg acaaagatct caattactgt | 900 |
| gggactcatc agccgtgtct caacggggga acttgtagca acacaggccc tgacaaatat | 960 |
| cagtgttcct gccctgaggg gtattcagga cccaactgtg aaattgctga gcacgcctgc | 1020 |
| ctctctgatc cctgtcacaa cagaggcagc tgtaaggaga cctccctggg ctttgagtgt | 1080 |
| gagtgttccc caggctggac cggccccaca tgctctacaa acattgatga ctgttctcct | 1140 |
| aataactgtt cccacggggg cacctgccag gacctggtta acggatttaa gtgtgtgtgc | 1200 |
| ccccacagt ggactgggaa aacgtgccag ttagatgcaa atgaatgtga ggccaaacct | 1260 |
| tgtgtaaacg ccaaatcctg taagaatctc attgccagct actactgcga ctgtcttccc | 1320 |
| ggctggatgg gtcagaattg tgacataaat attaatgact gccttggcca gtgtcagaat | 1380 |
| gacgcctcct gtcgggattt ggttaatggt tatcgctgta tctgtccacc tggctatgca | 1440 |
| ggcgatcact gtgagagaga catcgatgaa tgtgccagca ccccctgttt gaatgggggt | 1500 |
| cactgtcaga atgaaatcaa cagattccag tgtctgtgtc ccactggttt ctctggaaac | 1560 |

```
ctctgtcagc tggacatcga ttattgtgag cctaatccct gccagaacgg tgcccagtgc    1620
tacaaccgtg ccagtgacta tttctgcaag tgccccgagg actatgaggg caagaactgc    1680
tcacacctga agaccactg ccgcacgacc cctgtgaag tgattgacag ctgcacagtg      1740
gccatggctt ccaacgacac acctgaaggg gtgcggtata tttcctccaa cgtctgtggt    1800
cctcacggga agtgcaagag tcagtcggga ggcaaattca cctgtgactg taacaaaggc    1860
ttcacgggaa catactgcca tgaaaatatt aatgactgtg agagcaaccc ttgtagaaac    1920
ggtggcactt gcatcgatgg tgtcaactcc tacaagtgca tctgtagtga cggctgggag    1980
ggggcctact gtgaaaccaa tattaatgac tgcagccaga cccctgcca caatgggggc     2040
acgtgtcgcg acctggtcaa tgacttctac tgtgactgta aaatgggtg aaaggaaag     2100
acctgccact cacgtgacag tcagtgtgat gaggccacgt gcaacaacgg tggcacctgc   2160
tatgatgagg gggatgcttt taagtgcatg tgtcctggcg gctgggaagg aacaacctgt   2220
aacatagccc gaaacagtag ctgcctgccc aaccctgcc ataatggggg cacatgtgtg    2280
gtcaacggcg agtcctttac gtgcgtctgc aaggaaggct gggagggggcc catctgtgct  2340
cagaatacca tgactgcag ccctcatccc tgttacaaca gcggcacctg tgtggatgga    2400
gacaactggt accggtgcga atgtgccccg ggttttgctg ggccccgactg cagaataaac 2460
atcaatgaat gccagtcttc accttgtgcc tttggagcga cctgtgtgga tgagatcaat   2520
ggctaccggt gtgtctgccc tccagggcac agtggtgcca agtgccagga agtttcaggg  2580
agaccttgca tcaccatggg gagtgtgata ccagatgggg ccaaatggga tgatgactgt  2640
aatacctgcc agtgcctgaa tggacggatc gcctgctcaa aggtctggtg tggccctcga  2700
ccttgcctgc tccacaaagg gcacagcgag tgccccagcg gcagagctg catccccatc   2760
ctggacgacc agtgcttcgt ccaccccctgc actggtgtgg gcgagtgtcg gtcttccagt 2820
ctccagccgg tgaagacaaa gtgcacctct gactcctatt accaggataa ctgtgcgaac  2880
atcacattta cctttaacaa ggagatgatg tcaccaggtc ttactacgga gcacatttgc  2940
agtgaattga ggaatttgaa tattttgaag aatgtttccg ctgaatattc aatctacatc  3000
gcttgcgagc cttcccccttc agcgaacaat gaaatacatg tggccatttc tgctgaagat 3060
atacgggatg atgggaaccc gatcaaggaa atcactgaca aaataatcga tcttgttagt  3120
aaacgtgatg gaaacagctc gctgattgct gccgttgcag aagtaagagt tcagaggcgg  3180
cctctgaaga acagaacaga tttccttgtt cccttgctga gctctgtctt aactgtggct  3240
tggatctgtt gcttggtgac ggccttctac tggtgcctgc ggaagcggcg gaagccgggc  3300
agccacacac actcagcctc tgaggacaac accaccaaca acgtgcggga gcagctgaac  3360
cagatcaaaa accccattga gaacatggg gccaacacgg tccccatcaa ggattacgag   3420
aacaagaact ccaaaatgtc taaaataagg acacacaatt ctgaagtaga agaggacgac  3480
atggacaaac accagcagaa agcccggttt ggcaagcagc ggcgtatac gctggtagac   3540
agagaagaga agcccccaa cggcacgccg acaaaacacc caaactggac aaacaaacag   3600
gacaacagag acttggaaag tgcccagagc ttaaaccgaa tggagtacat cgtatag     3657
```

<210> SEQ ID NO 3
<211> LENGTH: 1067
<212> TYPE: PRT
<213> ORGANISM: Homo sapiens
<220> FEATURE:
<221> NAME/KEY: MISC_FEATURE
<223> OTHER INFORMATION: Solube Jagged1

<400> SEQUENCE: 3

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415
```

```
Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
            435                 440                 445

Ile Asn Ile Asn Asp Cys Leu Gly Gln Cys Gln Asn Asp Ala Ser Cys
            450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
            485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
            515                 520                 525

Cys Glu Pro Asn Pro Cys Gln Asn Gly Ala Gln Cys Tyr Asn Arg Ala
            530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
            565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
            610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
            645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
            690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
            725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
            820                 825                 830
```

```
Ala Thr Cys Val Asp Glu Ile Asn Gly Tyr Arg Cys Val Cys Pro Pro
        835                 840                 845
Gly His Ser Gly Ala Lys Cys Gln Glu Val Ser Gly Arg Pro Cys Ile
    850                 855                 860
Thr Met Gly Ser Val Ile Pro Asp Gly Ala Lys Trp Asp Asp Cys
865                 870                 875                 880
Asn Thr Cys Gln Cys Leu Asn Gly Arg Ile Ala Cys Ser Lys Val Trp
            885                 890                 895
Cys Gly Pro Arg Pro Cys Leu Leu His Lys Gly His Ser Glu Cys Pro
        900                 905                 910
Ser Gly Gln Ser Cys Ile Pro Ile Leu Asp Asp Gln Cys Phe Val His
    915                 920                 925
Pro Cys Thr Gly Val Gly Glu Cys Arg Ser Ser Leu Gln Pro Val
    930                 935                 940
Lys Thr Lys Cys Thr Ser Asp Ser Tyr Tyr Gln Asp Asn Cys Ala Asn
945                 950                 955                 960
Ile Thr Phe Thr Phe Asn Lys Glu Met Met Ser Pro Gly Leu Thr Thr
            965                 970                 975
Glu His Ile Cys Ser Glu Leu Arg Asn Leu Asn Ile Leu Lys Asn Val
        980                 985                 990
Ser Ala Glu Tyr Ser Ile Tyr Ile Ala Cys Glu Pro Ser Pro Ser Ala
    995                 1000                1005
Asn Asn  Glu Ile His Val Ala  Ile Ser Ala Glu Asp  Ile Arg Asp
    1010                1015                1020
Asp Gly  Asn Pro Ile Lys Glu  Ile Thr Asp Lys Ile  Ile Asp Leu
    1025                1030                1035
Val Ser  Lys Arg Asp Gly Asn  Ser Ser Leu Ile Ala  Ala Val Ala
    1040                1045                1050
Glu Val  Arg Val Gln Arg Arg  Pro Leu Lys Asn Arg  Thr Asp
    1055                1060                1065

<210> SEQ ID NO 4
<211> LENGTH: 3201
<212> TYPE: DNA
<213> ORGANISM: Homo sapiens
<220> FEATURE:
<221> NAME/KEY: misc_feature
<223> OTHER INFORMATION: Soluble Jagged1

<400> SEQUENCE: 4
atgcgttccc cacggacrcg cggccggtcc gggcgccccc taagcctcct gctcgccctg      60
ctctgtgccc tgcgagccaa ggtgtgtggg gcctcgggtc agttcgagtt ggagatcctg     120
tccatgcaga acgtgaacgg ggagctgcag aacgggaact gctgcggcgg cgcccggaac     180
ccgggagacc gcaagtgcac ccgcgacgag tgtgacacat acttcaaagt gtgcctcaag     240
gagtatcagt cccgcgtcac ggccgggggg ccctgcagct cggctcagg tccacgcct      300 gtcatcgggg gcaacacctt caacctcaag gccagccgcg gcaacgaccg caaccgcatc     360
gtgctgcctt tcagtttcgc ctggccgagg tcctatacgt tgcttgtgga ggcgtgggat     420
tccagtaatg acaccgttca acctgacagt attattgaaa aggcttctca ctcgggcatg     480 atcaaccca gccggcagtg gcagacgctg aagcagaaca cggcgttgc ccactttgag     540 tatcagatcc gcgtgacctg tgatgactac tactatggct ttggctgyaa taagttctgc     600
cgccccagag atgacttctt tggacactat gcctgtgacc agaatggcaa caaaacttgc     660
atggaaggct ggatgggccc cgaatgtaac agagctattt gccgacaagg ctgcagtcct     720
```

-continued

```
aagcatgggt cttgcaaact cccaggtgac tgcaggtgcc agtayggctg gcaaggcctg     780
tactgtgata agtgcatccc acacccggga tgcgtccacg gcatctgtaa tgagccctgg     840
cagtgcctct gtgagaccaa ctggggcggc cagctctgtg acaaagatct caattactgt     900
gggactcatc agccgtgtct caacggggga acttgtagca acacaggccc tgacaaatat     960
cagtgttcct gccctgaggg gtattcagga cccaactgtg aaattgctga gcacgcctgc    1020
ctctctgatc cctgtcacaa cagaggcagc tgtaaggaga cctccctggg ctttgagtgt    1080
gagtgttccc caggctggac cggccccaca tgctctacaa acattgatga ctgttctcct    1140
aataactgtt cccacggggg cacctgccag gacctggtta acggatttaa gtgtgtgtgc    1200
cccccacagt ggactgggaa aacgtgccag ttagatgcaa atgaatgtga ggccaaacct    1260
tgtgtaaacg ccaaatcctg taagaatctc attgccagct actactgcga ctgtcttccc    1320
ggctggatgg gtcagaattg tgacataaat attaatgact gccttggcca gtgtcagaat    1380
gacgcctcct gtcgggattt ggttaatggt tatcgctgta tctgtccacc tggctatgca    1440
ggcgatcact gtgagagaga catcgatgaa tgtgccagca cccctgtttt gaatgggggt    1500
cactgtcaga atgaaatcaa cagattccag tgtctgtgtc ccactggttt ctctggaaac    1560
ctctgtcagc tggacatcga ttattgtgag cctaatccct gccagaacgg tgcccagtgc    1620
tacaaccgtg ccagtgacta tttctgcaag tgccccgagg actatgaggg caagaactgc    1680
tcacacctga agaccactg ccgcacgacc ccctgtgaag tgattgacag ctgcacagtg    1740
gccatggctt ccaacgacac acctgaaggg gtgcggtata tttcctccaa cgtctgtggt    1800
cctcacggga agtgcaagag tcagtcggga ggcaaattca cctgtgactg taacaaaggc    1860
ttcacgggaa catactgcca tgaaaatatt aatgactgtg agagcaaccc ttgtagaaac    1920
ggtggcactt gcatcgatgg tgtcaactcc tacaagtgca tctgtagtga cggctgggag    1980
ggggcctact gtgaaaccaa tattaatgac tgcagccaga cccctgcca caatgggggc    2040
acgtgtcgcg acctggtcaa tgacttctac tgtgactgta aaaatgggtg gaaaggaaag    2100
acctgccact cacgtgacag tcagtgtgat gaggccacgt gcaacaacgg tggcacctgc    2160
tatgatgagg gggatgcttt taagtgcatg tgtcctggcg gctgggaagg aacaacctgt    2220
aacatagccc gaaacagtag ctgcctgccc aaccccctgcc ataatggggg cacatgtgtg    2280
gtcaacggcg agtcctttac gtgcgtctgc aaggaaggct gggagggggcc catctgtgct    2340
cagaatacca atgactgcag ccctcatccc tgttacaaca gcggcacctg tgtggatgga    2400
gacaactggt accggtgcga atgtgccccg ggttttgctg ggcccgactg cagaataaac    2460
atcaatgaat gccagtcttc accttgtgcc tttggagcga cctgtgtgga tgagatcaat    2520
ggctaccggt gtgtctgccc tccagggcac agtggtgcca agtgccagga gtttcaggg    2580
agaccttgca tcaccatggg gagtgtgata ccagatgggg ccaaatggga tgatgactgt    2640
aatacctgcc agtgcctgaa tggacggatc gcctgctcaa aggtctggtg tggccctcga    2700
ccttgcctgc tccacaaagg gcacagcgag tgccccagcg ggcagagctg catcccatc    2760
ctggacgacc agtgcttcgt ccaccctgc actggtgtgg gcgagtgtcg gtcttccagt    2820
ctccagccgg tgaagacaaa gtgcacctct gactcctatt accaggataa ctgtgcgaac    2880
atcacatta cctttaacaa ggagatgatg tcaccaggtc ttactacgga gcacatttgc    2940
agtgaattga ggaatttgaa tattttgaag aatgtttccg ctgaatattc aatctacatc    3000
gcttgcgagc cttcccctc agcgaacaat gaaatacatg tggccatttc tgctgaagat    3060
```

-continued atacgggatg atgggaaccc gatcaaggaa atcactgaca aaataatcga tcttgttagt    3120
aaacgtgatg gaaacagctc gctgattgct gccgttgcag aagtaagagt tcagaggcgg    3180
cctctgaaga acagaacaga t    3201

<210> SEQ ID NO 5
<211> LENGTH: 24
<212> TYPE: DNA
<213> ORGANISM: Artificial sequence
<220> FEATURE:
<223> OTHER INFORMATION: FGF1(s)

<400> SEQUENCE: 5
atggctgaag gggagatcac aacc    24

<210> SEQ ID NO 6
<211> LENGTH: 20
<212> TYPE: DNA
<213> ORGANISM: Artificial sequence
<220> FEATURE:
<223> OTHER INFORMATION: FGF1(as)

<400> SEQUENCE: 6
cgcgcttaca gctcccgttc    20

<210> SEQ ID NO 7
<211> LENGTH: 20
<212> TYPE: DNA
<213> ORGANISM: Artificial sequence
<220> FEATURE:
<223> OTHER INFORMATION: FGF2(s)

<400> SEQUENCE: 7
atggctgcca gcggcatcac    20

<210> SEQ ID NO 8
<211> LENGTH: 25
<212> TYPE: DNA
<213> ORGANISM: Artificial sequence
<220> FEATURE:
<223> OTHER INFORMATION: FGF2(as)

<400> SEQUENCE: 8
gaagaaacag tatggccttc tgtcc    25

<210> SEQ ID NO 9
<211> LENGTH: 21
<212> TYPE: DNA
<213> ORGANISM: Artificial sequence
<220> FEATURE:
<223> OTHER INFORMATION: FGF3(s)

<400> SEQUENCE: 9
gcctgatctg gcttctgctg c    21

<210> SEQ ID NO 10
<211> LENGTH: 22
<212> TYPE: DNA
<213> ORGANISM: Artificial sequence
<220> FEATURE:
<223> OTHER INFORMATION: FGF3(as)

<400> SEQUENCE: 10
gcagctgggt gcttggaggt gg    22

```
<210> SEQ ID NO 11
<211> LENGTH: 16
<212> TYPE: DNA
<213> ORGANISM: Artificial sequence
<220> FEATURE:
<223> OTHER INFORMATION: FGF4(s)

<400> SEQUENCE: 11
accacaggga cgactg                                                     16

<210> SEQ ID NO 12
<211> LENGTH: 20
<212> TYPE: DNA
<213> ORGANISM: Artificial sequence
<220> FEATURE:
<223> OTHER INFORMATION: FGF4(as)

<400> SEQUENCE: 12
cataccgggg tacgcgtagg                                                 20

<210> SEQ ID NO 13
<211> LENGTH: 27
<212> TYPE: DNA
<213> ORGANISM: Artificial sequence
<220> FEATURE:
<223> OTHER INFORMATION: FGF6(s)

<400> SEQUENCE: 13
gggccattaa ttctgaccac gtgcctg                                         27

<210> SEQ ID NO 14
<211> LENGTH: 30
<212> TYPE: DNA
<213> ORGANISM: Artificial sequence
<220> FEATURE:
<223> OTHER INFORMATION: FGF6(as)

<400> SEQUENCE: 14
ggtccttata tcctggggag gaagtgagtg                                      30

<210> SEQ ID NO 15
<211> LENGTH: 21
<212> TYPE: DNA
<213> ORGANISM: Artificial sequence
<220> FEATURE:
<223> OTHER INFORMATION: FGF7(s)

<400> SEQUENCE: 15
cacggatcct gccaactctg c                                               21

<210> SEQ ID NO 16
<211> LENGTH: 23
<212> TYPE: DNA
<213> ORGANISM: Artificial sequence
<220> FEATURE:
<223> OTHER INFORMATION: FGF7(as)

<400> SEQUENCE: 16
ccacaattcc aactgccacg gtc                                             23

<210> SEQ ID NO 17
<211> LENGTH: 22
<212> TYPE: DNA
<213> ORGANISM: Artificial sequence
<220> FEATURE:
<223> OTHER INFORMATION: FGF8(s)
```

```
<400> SEQUENCE: 17
ctctgcctcc aagccaggta ag                                          22

<210> SEQ ID NO 18
<211> LENGTH: 23
<212> TYPE: DNA
<213> ORGANISM: Artificial sequence
<220> FEATURE:
<223> OTHER INFORMATION: FGF8(as)

<400> SEQUENCE: 18
gctgatgctg gcgcgtcttg gag                                         23

<210> SEQ ID NO 19
<211> LENGTH: 22
<212> TYPE: DNA
<213> ORGANISM: Artificial sequence
<220> FEATURE:
<223> OTHER INFORMATION: FGF9(s)

<400> SEQUENCE: 19
ggtgaagttg ggagctattt cg                                          22

<210> SEQ ID NO 20
<211> LENGTH: 25
<212> TYPE: DNA
<213> ORGANISM: Artificial sequence
<220> FEATURE:
<223> OTHER INFORMATION: FGF9(as)

<400> SEQUENCE: 20
catagtatct ccttccggtg tccac                                       25

<210> SEQ ID NO 21
<211> LENGTH: 21
<212> TYPE: DNA
<213> ORGANISM: Artificial sequence
<220> FEATURE:
<223> OTHER INFORMATION: FGF10(s)

<400> SEQUENCE: 21
cacattgtgc ctcagccttt c                                           21

<210> SEQ ID NO 22
<211> LENGTH: 24
<212> TYPE: DNA
<213> ORGANISM: Artificial sequence
<220> FEATURE:
<223> OTHER INFORMATION: FGF10(as)

<400> SEQUENCE: 22
cctctattct ctctttcagc ttac                                        24

<210> SEQ ID NO 23
<211> LENGTH: 18
<212> TYPE: DNA
<213> ORGANISM: Artificial sequence
<220> FEATURE:
<223> OTHER INFORMATION: FGFR1(s)

<400> SEQUENCE: 23
aggccagccc caaccttg                                               18

<210> SEQ ID NO 24
<211> LENGTH: 21
```

```
<212> TYPE: DNA
<213> ORGANISM: Artificial sequence
<220> FEATURE:
<223> OTHER INFORMATION: FGFR1(VT+as)

<400> SEQUENCE: 24
ggagtcagct gacactgtta c                                          21

<210> SEQ ID NO 25
<211> LENGTH: 20
<212> TYPE: DNA
<213> ORGANISM: Artificial sequence
<220> FEATURE:
<223> OTHER INFORMATION: FGFR1(VT-as)

<400> SEQUENCE: 25
cactggagtc agctgacacc                                            20

<210> SEQ ID NO 26
<211> LENGTH: 23
<212> TYPE: DNA
<213> ORGANISM: Artificial sequence
<220> FEATURE:
<223> OTHER INFORMATION: FGFR2(s)

<400> SEQUENCE: 26
tccttcagtt tagttgagga tac                                        23

<210> SEQ ID NO 27
<211> LENGTH: 21
<212> TYPE: DNA
<213> ORGANISM: Artificial sequence
<220> FEATURE:
<223> OTHER INFORMATION: FGFR2(as)

<400> SEQUENCE: 27
gcagctttca gaaccttgag g                                          21

<210> SEQ ID NO 28
<211> LENGTH: 21
<212> TYPE: DNA
<213> ORGANISM: Artificial sequence
<220> FEATURE:
<223> OTHER INFORMATION: FGFR3(s)

<400> SEQUENCE: 28
caagtgctaa atgcctccca c                                          21

<210> SEQ ID NO 29
<211> LENGTH: 18
<212> TYPE: DNA
<213> ORGANISM: Artificial sequence
<220> FEATURE:
<223> OTHER INFORMATION: FGFR3(as)

<400> SEQUENCE: 29
gcagagtatc acagctgc                                              18

<210> SEQ ID NO 30
<211> LENGTH: 20
<212> TYPE: DNA
<213> ORGANISM: Artificial sequence
<220> FEATURE:
<223> OTHER INFORMATION: FGF1.A(s)

<400> SEQUENCE: 30
```

-continued

```
cccaaagcca agaagccacc                                              20

<210> SEQ ID NO 31
<211> LENGTH: 22
<212> TYPE: DNA
<213> ORGANISM: Artificial sequence
<220> FEATURE:
<223> OTHER INFORMATION: FGF1.B(s)

<400> SEQUENCE: 31
cggacttcat tcccgtcttg tg                                           22

<210> SEQ ID NO 32
<211> LENGTH: 18
<212> TYPE: DNA
<213> ORGANISM: Artificial sequence
<220> FEATURE:
<223> OTHER INFORMATION: FGF1.C(s)

<400> SEQUENCE: 32
cctctgagcc ccctgggt                                                18

<210> SEQ ID NO 33
<211> LENGTH: 23
<212> TYPE: DNA
<213> ORGANISM: Artificial sequence
<220> FEATURE:
<223> OTHER INFORMATION: FGF1.G(s)

<400> SEQUENCE: 33
ctctaggaag tagaaggcag gtt                                          23

<210> SEQ ID NO 34
<211> LENGTH: 24
<212> TYPE: DNA
<213> ORGANISM: Artificial sequence
<220> FEATURE:
<223> OTHER INFORMATION: Nucleostemin 894(s)

<400> SEQUENCE: 34
caaatgtggg gaaaagcagt gtca                                         24

<210> SEQ ID NO 35
<211> LENGTH: 23
<212> TYPE: DNA
<213> ORGANISM: Artificial sequence
<220> FEATURE:
<223> OTHER INFORMATION: Nucleostemin 1304(as)

<400> SEQUENCE: 35 gcaggggat ggcaatagta acc                                           23

<210> SEQ ID NO 36
<211> LENGTH: 22
<212> TYPE: DNA
<213> ORGANISM: Artificial sequence
<220> FEATURE:
<223> OTHER INFORMATION: Bmi 242(s)

<400> SEQUENCE: 36
aattagtccc agggcttttc aa                                           22

<210> SEQ ID NO 37
<211> LENGTH: 22
<212> TYPE: DNA
<213> ORGANISM: Artificial sequence
```

```
<220> FEATURE:
<223> OTHER INFORMATION: Bmi 632(as)

<400> SEQUENCE: 37
gggccatttc ttctccaggt at                                              22

<210> SEQ ID NO 38
<211> LENGTH: 20
<212> TYPE: DNA
<213> ORGANISM: Artificial sequence
<220> FEATURE:
<223> OTHER INFORMATION: Nestin 320(s)

<400> SEQUENCE: 38
caaccttgcc gaagagctgg                                                 20

<210> SEQ ID NO 39
<211> LENGTH: 21
<212> TYPE: DNA
<213> ORGANISM: Artificial sequence
<220> FEATURE:
<223> OTHER INFORMATION: Nestin 720(as)

<400> SEQUENCE: 39
tctaagcgac tctccgagcg c                                               21
```